(12) United States Patent
Ben Khaled et al.

(10) Patent No.: US 12,234,468 B2
(45) Date of Patent: Feb. 25, 2025

(54) METHOD FOR DECREASING THE ALKALOID CONTENT OF A TOBACCO PLANT

(71) Applicant: BRITISH AMERICAN TOBACCO (INVESTMENTS) LIMITED, London (GB)

(72) Inventors: Sara Ben Khaled, London (GB); Francisco Anastacio De Abreu E Lima, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 0 days.

(21) Appl. No.: 17/310,160

(22) PCT Filed: Jan. 23, 2020

(86) PCT No.: PCT/GB2020/050153
§ 371 (c)(1),
(2) Date: Jul. 22, 2021

(87) PCT Pub. No.: WO2020/152466
PCT Pub. Date: Jul. 30, 2020

(65) Prior Publication Data
US 2022/0090112 A1 Mar. 24, 2022

(30) Foreign Application Priority Data
Jan. 23, 2019 (GB) ..................................... 1900940

(51) Int. Cl.
*C12N 15/82* (2006.01)
*A24B 15/10* (2006.01)

(52) U.S. Cl.
CPC .......... *C12N 15/8243* (2013.01); *A24B 15/10* (2013.01); *C12N 15/8218* (2013.01)

(58) Field of Classification Search
None
See application file for complete search history.

(56) References Cited

U.S. PATENT DOCUMENTS 7,798,153 B2 * 9/2010 Lawrence, Jr. ........ A24B 15/10
 131/352
9,066,538 B2 * 6/2015 Chen ....................... A24B 3/12
(Continued)

FOREIGN PATENT DOCUMENTS

EP 2292773 A1 3/2011
WO 2011080674 A2 7/2011
(Continued)

OTHER PUBLICATIONS

Moldoveanu et al. 2016 "Nicotine Analysis in Several Non-Tobacco Plant Materials" Contributions to Tobacco & Nicotine Research (formerly Beitrage zur Tabakforschung International) 27(2):54-59 (Year: 2016).*
(Continued)

*Primary Examiner* — Matthew R Keogh
*Assistant Examiner* — Rebecca Stephens

(57) ABSTRACT

The present invention provides a method for modulating (e.g. decreasing) the alkaloid content of a plant (e.g. a tobacco plant), the method comprising modifying said plant by modulating the activity or expression of at least one gene encoding a SOUL haem-binding protein. The present invention also provides for the use of at least one gene encoding a SOUL haem-binding protein for modulating the alkaloid content of a plant, as well as tobacco cells, plants, plant propagation materials, harvested leaves, processed tobaccos, or tobacco products obtainable in accordance with the invention.

15 Claims, 31 Drawing Sheets
Specification includes a Sequence Listing.

(56) References Cited

U.S. PATENT DOCUMENTS

| | | |
|---|---|---|
| 2007/0039067 A1 | 2/2007 | Feldmann et al. |
| 2008/0202538 A1 | 8/2008 | Li et al. |
| 2016/0237447 A1 | 8/2016 | Abad et al. |
| 2017/0088852 A1 | 3/2017 | Dangoor et al. |
| 2017/0121722 A1 | 5/2017 | Anand et al. |

FOREIGN PATENT DOCUMENTS

| | | |
|---|---|---|
| WO | 2015054106 A1 | 4/2015 |
| WO | 2016124932 A1 | 8/2016 |
| WO | 2018067985 A1 | 4/2018 |
| WO | 2018116164 A1 | 6/2018 |

OTHER PUBLICATIONS

Freire et al., "Preliminary structural characterization of human SOUL, a haem-binding protein", Acta Crystallographica, F65, pp. 723-726, 2009.

Hanselmann et al., "Haem oxygenase-1 : a novel player in cutaneous wound repair and psoriasis?", Biochem. J., vol. 353, pp. 459-466, 2001.

Lewis et al., "Three nicotine demethylase genes mediate nornicotine biosynthesis in Nicotiana tabacum L.: Functional characterization of the CYP82E10 gene", Phytochemistry, vol. 71, pp. 1988-1998, 2010.

Rushton et al., "Tobacco Transcription Factors: Novel Insights into Transcriptional Regulation in the Solanaceae 1[C] [W][OA]", Plant Physiology, vol. 147, pp. 280-295, May 2008.

Siminszky et al., "Conversion of nicotine to nornicotine in Nicotiana tabacum is mediated by CYP82E4, a cytochrome P450 monooxygenase", Proc Natl Acad Sci USA, vol. 102, No. 41, pp. 1-15, Oct. 2005.

Turner et al., "The Jasmonate Signal Pathway", The Plant Cell, Supplement 2002, pp. S153-S164, 2002.

Venkatasalam, Shanmugabalaji, "Plastoglobules—a new destination for recombinant proteins produced in transplastomic plants and characterization of plastidial At-SOUL heme binding protein", Laboratory of Plant Physiology, Institute of Biology, University of Neuchatel, pp. 1-120, 2012.

Voelckel et al., "Herbivore-induced ethylene burst reduces fitness costs of jasmonate-and oral secretion-induced defenses in Nicotiana attenuata", Oecologia, vol. 127, pp. 274-280, 2001.

Xu et al., "Biochemical and molecular characterizations of nicotine demethylase in tobacco", Physiologia Plantarum, vol. 129, pp. 307-319, 2007.

Database Uniprot, "Heme-binding-like protein At3g10130, chloroplastic isofrom X1", EBI accession No. XP_009761729.1, 4 pages, May 10, 2017.

Database Uniprot, "Heme-binding-like protein At3g10130, chloroplastic", EBI accession No. XP_016481155.1, 3 pages, Apr. 12, 2017.

Dias et al., "The First Structure from the SOUL/HBP Family of Heme-binding Proteins, Murine P22HBP," Journal of Biological Chemistry, vol. 281, No. 42, pp. 31553-31561 (2006).

Fortunato et al., "Evolution of the SOUL Heme-Binding Protein Superfamily Across Eukarya," Journal of Molecular Evolution, vol. 82, pp. 279-290 (2016).

Fortunato et al., Abstract—"Evolution of the SOUL Heme-Binding Protein Superfamily Across Eukarya," Journal of Molecular Evolution, vol. 82, pp. 279-290 (2016).

NCBI Reference Sequence: XM_016581144.1, "Predicted: Nicotiana tabacum heme-binding-like protein At3g10130, chloroplastic (LOC107762761), transcript variant X1, mRNA," GenBank, May 3, 2016, 2 pages.

* cited by examiner

Nitab4.5_0013616g0010.2 protein sequence (SEQ ID No. 1):

MLGKYGFDFNGASQSFNTLAEYLFGKNTKKESMAMTTPVITRRTQSDGEKMEMTTSVITKR
VEDQGKWRMSFVMPSKYGSDLPLPKDSSVTIKEVPRKTVAVVAFSGFVTDEEVKARESRL
CAALKGDAEFRVKDGASIEVAQYNPPFTLPFTRRNEISLEVERKQE

FIG. 5

Nitab4.5_0013616g0010.2 genomic sequence (SEQ ID No. 2):

TAATATTGTGACTTTAAACAGCCTTACTTTGCGGCGGAGGCTACAATGCTTGGGAAATA
TGGGTTTGATTTTAATGGTGCATCTCAATCCTTCAACACATTGGCAGAGTACTTGTTTGG
TAAGGTAGTTAAAGGTACTTATAGAGAGTCAAACTTAGATCGCCTCCAACCACATTGTAA
TGGTGTTCTTCTTTGGTTATGTTCTCTTTCTTGATGATTTCCAGAACACAAAGAAGGAAA
GTATGGCGATGACAACACCCGTAATCACTCGTAGAACTCAATCTGATGGGGAGAAGAT
GGAAATGACTACTTCAGTGATAACTAAAGGGTACAGATCGTCTTCTGGTCATTCCTTTT
TCCCTTTTAGTTCTTGTGCTGTGTATATTTACTACGTCATTCGTGACATATGGTTTGGTTA
CTAATGCGCATGCATTTTGTATGACATGGTGTTACTCAAAATATTAACTGCTAATCTATT
GAAGTTGAGTCACCACATAACTTGGGAAATGGTAAATGAAAAACTACTCTAAAATGACC
ACAGGTCGTCAAATGGAAATACAGACTTCACTGATTCTATTGAAAAGAAACATCATCTGG
TTACCTATCACAAGGAAAACATTTAAGCTCTTGATCTGGAATTGATAAAGAGGACATGT
GCTTTAGATTGAGATTTGAGGATCTTTCAATTGTATGCTAGGCCTATACGCCGGGGGAT
GGGGGTACATATAAAACGTAAACATTCTGGATGCTTATAGTTTAAACCTGTAATACTCTC
AGATAGTATTGCAAATCCATATCTGGGAGAGTGGAAACTGTTAGATTCCAGGTTTGATTA
TGTTGCATGGATCCTTCAAACAAGTGTGACATGGGTGTGGGTACTTCTTGCAGGTTCTT
CAAAGTATACTAATAATTAGGAAAAAATGCACAAAACTCCTATCAGATACTTACACACA
CACAAACACACACATGGTATATACCTATAGGTTTGTCCATATAATGCGATATCTAATC
TTAGTCTAGAACAAGTGTCGAATGGAATAACAGTCACAAAGAACGATCTTCTTAATGATA
AAGGTTATGGTACGAATAAAATATACACCCCTATATAAACGATAACACATTTTCTTGTAAT
TCTTAAGTTAATTTCTGAGAATAACATTTTGTAACATAAAAAACCAATTTTATGTGAAAAT
GGGCCCTCCATATAGATTGGCATCCTATAAGAATTCTTTACTCCCAGAAACCTTGAAAC
CGGATTTAGTCCATTCTAGAAAAGAAAAACTCATTTTAGCTTGATGTATGATCCTATGTT
ATAGGGCTTAAACCCAGAAGAAAAAAGATAAACATTGTGTATATAGTTTTTGTATTTCG
GAATGTCGTGCGCACATATTTTCACCAAAAAATATACCCACTGGAATTTCATTAAGAATT
TCATTAGGTGGAAGATCAAGGAAAGTGGAGGATGTCCTTTGTCATGCCCTCAAAGTATG
GTTCGGACTTGCCACTACCAAAGGATTCCTCCGTAACTATCAAGGAGGTGCCTAGGAAA
ACTGTCGCCGTTGTTGCTTTTCAGGTTTGTGATTTCAGATTTAGCATGTCAATATAAA
GTTCTATTTTATATGATGATGATATGAGTTGAGCTTATCGAAAGAAGTGAGGATTCATAG
CGCCGACCCCAACTTTGTGGGACTGAGGCATAGTTGTTGCTGTTAATACAAAGTTCTAG
ACAGATTTGCATTAAAGTTTATTTGAAATTCAATATCCTAGTAATTGGAAGCCGAGCTCT
GTCTCATTGGTCTATAGAAGTAAATCTTGTTTAAGTTTACTTAGTGCTTTATTGATAGCTT
CTCTTGTTTTGATATGAGAGAAACTTGCATCTAGTTGTATTTCTGTGCCTTTCCTTTGAC
GTGCTATATGCCTGTTGTGGTAGATAGCAATTTCCATTCAGAGTTCAAAAGCAAAACAT
TTAGGAATTCTATTTTCAAGTTTTATATCCTAACTTAGCTAGCTTTCTCCCATTTGATTCA
CCAAAGGTTTTGTGACTGATGAAGAAGTTAAAGCCCGAGAATCAAGACTATGTGCTGCG
TTAAAGGGAGATGCAGAGTTTCGGGTAAAAGATGGTGCCTCGATAGAAGTTGCACAGG
TATATTCGTAGAACCATTTCAATAGTACTTGTAATTCCTGGGGAACAGATTTTGGCCT
AGTGTAACCCCAAGTGACATACTAGTTGTGTTTTTTTATACTTCTGCTTGCAGTATAAT
CCACCATTCACTCTTCCATTCACACGTCGGAATGAGATTAGCCTGGAAGTTGAAAGGAA
ACAGGAATAGCTAGTCAGGGTGCAACATCTTGCAGATAAATCCGTGCACTGATATATAG
AAACCAGTGAAGCAAAACATATATGGCGTAAATATTGTGTTGATACTCCTTGTATA
TATATATGTATATATATATTTGGTGATTGCTTGACATTTTGGTAACAAGGTTATGTA
CATGCACAGAAATGTAAGGTCACTTATGCTTCAACTCTGAATATAATAACACTGTCTTTA
ATACTCTTCTCGATCCTC

FIG. 6

Nitab4.5_0013616g0010.2 coding sequence (SEQ ID No. 3):

ATGCTTGGGAAATATGGGTTTGATTTTAATGGTGCATCTCAATCCTTCAACACATTGGCA
GAGTACTTGTTTGGTAAGAACACAAGAAGGAAAGTATGGCGATGACAACACCCGTAAT
CACTCGTAGAACTCAATCTGATGGGGAGAAGATGGAAATGACTACTTCAGTGATAACTA
AAAGGGTGGAAGATCAAGGAAAGTGGAGGATGTCCTTTGTCATGCCCTCAAAGTATGG
TTCGGACTTGCCACTACCAAAGGATTCCTCCGTAACTATCAAGGAGGTGCCTAGGAAAA
CTGTCGCCGTTGTTGCTTTTCAGGTTTTGTGACTGATGAAGAAGTTAAAGCCCGAGAA
TCAAGACTATGTGCTGCGTTAAAGGGAGATGCAGAGTTTCGGGTAAAAGATGGTGCCT
CGATAGAAGTTGCACAGTATAATCCACCATTCACTCTTCCATTCACACGTCGGAATGAG
ATTAGCCTGGAAGTTGAAAGGAAACAGGAATAG

FIG. 7

Nitab4.5_0000652g0130.2 protein sequence (SEQ ID No. 4):

MGMILGKICVETPKYELIQSTADYEIRKYPASVIAQVTYDPTQFKGNKDGGFMLLANYIGALG
NPQNAKPETIAMTAPVITKSSEKIAMTAPVVTKNGDGESNMVTMQFILPAKYTKAEEAPKPL
DERVMIKEEGERKFGVVQFSGTASDKAVKEKVENLRKCLERDGYKIIGDYELARYNPPWTIP
PFKTNEVMIPVE

FIG. 8

Nitab4.5_0000652g0130.2 genomic sequence (SEQ ID No. 5):

CTGATTTCGTAATGCAGATTGGTTTAACCTTTTACAGAGCAAGTCAATTTTAACGGCGAT
ACTAAAATTACTGTGTGCACAAATAGTGCACAAACTATTCCTGTATAGGTTTATCTCCAC
CAGCTTATGGTGTAAACGTGGCAAAACAAACTCCACAGCATACTTCCCTGATCTGCCGC
CACTCATTTTGCAGCAAACAAAACCCCTTTCCCAAGTCTTCTGATCGTCTCTTTCCGAAT
TCCCACATGAAACTTCCTCTTTTCTTCCCTTATATGTAACAATTCACAGCCCCCATTTACT
ATCAAAACATTCTCAAATTCCATTTTCAATAACTAATTTCCCATTCCATCACAAAAATGGG
CATGATTTTGGGTAAGATCTGTGTGGAAACACCAAAATACGAGTTGATTCAATCTACAG
CTGACTACGAAATCCGCAAATACCCAGCATCTGTTATAGCACAAGTCACATATGATCCA
ACCCAGTTCAAAGGAAACAAAGACGGTGGGTTTATGCTATTAGCCAATTACATCGGCGC
ACTGGGCAATCCTCAAAACGCTAAGCCTGAAACAATCGCCATGACAGCTCCTGTAATCA
CCAAATCGTCCGAAAAAATCGCGATGACTGCACCAGTAGTGACTAAGAATGGTGACGG
AGAGAGCAATATGGTGACGATGCAGTTTATTTTACCTGCAAAGTATACAAAAGCTGAAG
AGGCACCTAAGCCGTTGGATGAGAGTGATGATTAAAGAAGAAGGTGAAAGGAAGTT
TGGTGTGGTGCAGTTTAGTGGGACTGCAAGTGATAAAGCGGTAAAAGAGAAGTGGAG
AATTTAAGGAAATGTTTAGAGAGATGGGTATAAGATAATTGGTGATTATGAGTTGGCT
AGGTATAATCCTCCTTGGACAATTCCTCCATTTAAGACCAATGAAGTTATGATTCCAGTT
GAGTGAGCTGAAATGGTGTAGTAAAGAAAACATGAGACTGCTGTGAAGCTAGCTCGT
GACATGAACCTACTTTATCTGGTGTTTATTATTGAATTGTGTATTTCTTGTTTATATGTTTA
CGCTGTTGACAATGTCTTTGCATACACTAGTGTCAATTATTCATAGTTATAATTAGCACAT
ATTTTGTCTTATTTTATACTTTGCCATAGTAAAGCAGTAAAACTGATGCAGTTTTGCAAG
CATCTAATGTG

FIG. 9

Nitab4.5_0000652g0130.2 coding sequence (SEQ ID No. 6):

ATGGGCATGATTTTGGGTAAGATCTGTGTGGAAACACCAAAATACGAGTTGATTCAATC
TACAGCTGACTACGAAATCCGCAAATACCCAGCATCTGTTATAGCACAAGTCACATATG
ATCCAACCCAGTTCAAAGGAAACAAAGACGGTGGGTTTATGCTATTAGCCAATTACATC
GGCGCACTGGGCAATCCTCAAAACGCTAAGCCTGAAACAATCGCCATGACAGCTCCTG
TAATCACCAAATCGTCCGAAAAAATCGCGATGACTGCACCAGTAGTGACTAAGAATGGT
GACGGAGAGAGCAATATGGTGACGATGCAGTTTATTTTACCTGCAAAGTATACAAAAGC

FIG. 10

TGAAGAGGCACCTAAGCCGTTGGATGAGAGTGATGATTAAAGAAGAAGGTGAAAGG
AAGTTTGGTGTGGTGCAGTTTAGTGGGACTGCAAGTGATAAAGCGGTAAAAGAGAAAG
TGGAGAATTTAAGGAAATGTTTAGAGAGATGGGTATAAGATAATTGGTGATTATGAG
TTGGCTAGGTATAATCCTCCTTGGACAATTCCTCCATTTAAGACCAATGAAGTTATGATT
CCAGTTGAGTGA

FIG. 10 (Continued)

Nitab4.5_0001140g0220.2 protein sequence (SEQ ID No. 7):

MQGVMNFFTRLSFFLILVSKLSNGHWTNNLKLDFYPPTCNRIECPNYDLIQSGKDYEIRRYN
SSMWMSTAPIDDINLYSATRTGFLRLFDYIQGKNSYQEKIEMTAPVITQVKPSDGPFCASSF
VVSFYVPKKNQPNPPPAKGLHVQKWSNTYVAVRQFGGFVADVDVAKEAAALSASIADTKW
AAAVEKSHAADNTTMYTVAGYNSPFEFKDRVNEIWFTFDLDKASAI

FIG. 11

Nitab4.5_0001140g0220.2 genomic sequence (SEQ ID No. 8):

TACCAATTCATTCTGGTCAGTTCATCTCTTTCCCTATAATTTCTGCTGCAATTAAACCACC
AAAAAGAAACAAAGATGCAGGGCGTTATGAATTTCTTCACGAGGCTATCTTTCTTTCTC
ATCCTTGTTTCTAAATTAAGCAATGGGCATTGGACAAACAATTTGAAATTGGATTTCTAT
CCTCCAACCTGTAACCGAATTGAGTGCCCAAATTATGACTTGATTCAATCTGGTAAAGA
CTATGAAATTCGTCGTTACAATTCATCCATGTGGATGTCTACTGCACCCATTGATGATAT
TAATCTTTATTCCGCCACCAGAACTGGTTTCCTCAGGTATCTATGGTTTTTTTCTTCTTT
TTGGTCATGAATTCCTTTCGGTGTGTTGCATATTGGATACGTTAGCTACTGTGCAATA
CCAATTAAAGCATGTCTGTTTTCTGTCCAAGATTCCTTAAGAAAACAACTAAGGGTTACT
TACATTTCAATCAATTGAAATTAATCGACTATTAAAAGAAGAAGAAGAAAAAAAAAGATA
GTTATCTGTAAACGATTTGACTTATATGCTGATAATGTAAAGTATTCAATTCAACTTTT
TCAAGCACGTAACCTGCGTGGTTTTTCAAGATAGTAATCTCACTTTTTATGGATGAATAC
TAATCTCACTTTTTATGGATATGATTATTGAAAGCGTAAAAGTTCTTTTGCACTGTTAGTC
AGTAGAATATTTTCGGGTGAGCTTGGTTTTTATACTCAAAATGTTAGTGTATCTATTCGC
GAAAACATAAAAGGGGTCGTTGTGAACTTTGCCTTGGCAGGCTATTCGATTACATTCAA
GGGAAGAACAGTTACCAGGAGAAAATAGAGATGACAGCTCCAGTTATCACTCAAGTAAA
ACCAAGTGATGGACCATTTTGTGCATCTTCATTTGTTGTGAGCTTCTATGTACCAAAGAA
GAACCAACCAAATCCTCCTCCAGCTAAAGGCCTTCACGTCCAAAAATGGAGCAATACTT
ATGTGGCCGTCAGGCAATTCGGCGGATTTGTAGCTGATGTTGATGTTGCAAAAGAAGCT
GCTGCTTTGAGTGCTAGTATTGCTGACACTAAATGGGCAGCTGCTGTTGAAAAAGCCA
TGCTGCAGATAACACTACCATGTATACAGTGGCGGGATACAACTCTCCATTTGAGTTCA
AGGACAGAGTTAATGAGATTTGGTTTACTTTTGATTTGGACAAAGCATCTGCCATTTGAG
AGGCTCTTATTCTGGACTCTTTAACATTTCAGGAGACATGAAACTATCTTATTTTCTTGG
GTTTGTATTATTAAACAGCAGTTTTGTATGACCACAACGCTACATTATATAGCAAATAA
GATAGGTTGTATAATACAATCTGATTCTGAGGATTTAGTGGTTAAGATACCTCTTTCAAG
ACCTTTCAAAATAATCCGATATATATGGAAAGGGCTAGACCATATTGAGTTTATTGTAT
GTACGCAGTTTTACCTTCCATTT

FIG. 12

Nitab4.5_0001140g0220.2 coding sequence (SEQ ID No. 9):

ATGCAGGGCGTTATGAATTTCTTCACGAGGCTATCTTTCTTTCTCATCCTTGTTTCTAAA
TTAAGCAATGGGCATTGGACAAACAATTTGAAATTGGATTTCTATCCTCCAACCTGTAAC
CGAATTGAGTGCCCAAATTATGACTTGATTCAATCTGGTAAAGACTATGAAATTCGTCGT
TACAATTCATCCATGTGGATGTCTACTGCACCCATTGATGATATTAATCTTTATTCCGCC
ACCAGAACTGGTTTCCTCAGGCTATTCGATTACATTCAAGGGAAGAACAGTTACCAGGA
GAAAATAGAGATGACAGCTCCAGTTATCACTCAAGTAAAACCAAGTGATGGACCATTTT
GTGCATCTTCATTTGTTGTGAGCTTCTATGTACCAAAGAAGAACCAACCAAATCCTCCTC

FIG. 13

```
CAGCTAAAGGCCTTCACGTCCAAAAATGGAGCAATACTTATGTGGCCGTCAGGCAATTC
GGCGGATTTGTAGCTGATGTTGATGTTGCAAAGAAGCTGCTGCTTTGAGTGCTAGTAT
TGCTGACACTAAATGGGCAGCTGCTGTTGAAAAAGCCATGCTGCAGATAACACTACCA
TGTATACAGTGGCGGGATACAACTCTCCATTTGAGTTCAAGGACAGAGTTAATGAGATT
TGGTTTACTTTTGATTTGGACAAAGCATCTGCCATTTGA
```

FIG. 13 (Continued)

Nitab4.5_0003235g0060.2 protein sequence (SEQ ID No. 10):

```
MATSQLSDLIFRPSLHRRTNFRQCHPTSVFLTPPKNIKTKTLKYDRKIKWLIKFSLVDKQSPT
KKPTVDMNQLVEFLYEDLPHLFDDQGIDRKAYDDYVKFRDPITKHDSIDGYLFNIAMLKQLF
KPDFQLHWAKQTGPYEITTRWTMVMKFILLPWKPELVFTGTSVMGVNPETNKFNSHVDYW
DSIKNNDYFSVEGLLEVIKQLRIYKTPDLETPSYQILRRTATYEVRKYDPFIVVETEGDKLAGN
RGFNDVAGYIFGKNSATEKIPMTTPVFTQAFDAEKSKVSIQIVLPSDKSLSSLPAPNQEGISL
RKTEGGIAAALKFSGKPTDDVVREKEKQLRSSLIKDGLKPQSDCMLARYNDPGRTWKFIMR
NEVLIWLEDFKLD
```

FIG. 14

Nitab4.5_0003235g0060.2 genomic sequence (SEQ ID No. 11):

```
AATGGCCACCTCACAACTTTCCGACCTCATTTTCCGGCCATCACTTCACAGGCGAACCA
ATTTCCGGCAATGCCACCCTACTTCAGTCTTTCTCACTCCTCCAAAAAATATCAAAACAA
AAACTCTTAAATATGACAGAAAATTAAGTGGTTAATTAAGTTTAGTTTAGTTGATAAACA
GAGCCCAACCAAAAAACCAACAGTTGATATGAACCAATTAGTGGAATTTTTATATGAGGA
TTTACCTCATCTTTTTGATGATCAAGGTATTGATCGTAAGGCATATGATGATTATGTGAA
GTTTAGGGATCCAATTACAAAACATGATTCAATTGATGGCTATTTGTTTAATATTGCCAT
GTTGAAACAGTTGTTTAAGCCTGATTTTCAGCTGCATTGGGCTAAACAGGTTAGTATTTC
TACCCTTCTTGTTAATTGGTTAGTTAAACTTCCTTTGTTGGGAGCATGGCGTAATTAGTA
GTTGCCAACGGGTTCAAGCCATGAAAACCGACTCTTGCATAAATGCGAGGTAGGTCCA
AATGATCGAATTGTAGTTCTTAACAATAGTAGGTCGAGATGATCGAATGGAAATGACAAT
TTTTACATGGCATATTTTCATACATTCTGGTCTTCAGTCTCTTACATAAATTAAGAACATT
GAAATAATATGTCAAGGAGTCGTTTGAACATTATTTTTTTCCTTCTATCCAAAAGACGTA
TTTTCAAGCCATGTTTGGTTATCAAATTGGACTGAACTTTTGTGTTTTTTTTTTTTTGAAA
ATGAGTTTTAAGTTTGAAGTAAAAATTCACTTTCTCTTACAAACTGTAATATTTTTTCAA
GTGAAATACATGTCCAAACATAACTTTAAATTTCAAATATTATTTTTCAACTTAACTCCGA
TCCAAACACTACTTTGTTTTCTTTTAGAAATCACATTTTTATGTCCTAAGCGTCTACTAAA
TGTCTCATCCGAAGCTCATGAGACTATCAACAACTGTGACCATCACCTTCATCGATATAT
TTTCACAGTGAATTTCTACACTATAAATGAAATTAACAGGCTATAAGATGTCAAACTCGT
TATGTAGATCAATTGTTGTAAGTCAATATAACCTAATTGTTCAACTATCTATACGTTATCA
GTTTACATAATCTTTACCTGTAGTTTAACTTCTATTAACTGTTTAGTGTATATAGTTGTAA
CGTATAACTGTCTAAACTTCATGTTAATGATAGCATTTACTTGTAGATGATATTATTCATT
TATCTTGTTCGTTAGTGATTAAATTTTGATCACTCTTCTAAGCTTTCTACCGTTAATGCTG
GTCGATAAAAATTCCTTCAAAAGTTCACTAGTACGTTAAGCACTTAAGCCTAGACAGTTG
ACATTAATAGACTACTAATACTCACATGATAGACAAAACTATTTTATAATTTGCTGATTAT
ATATAATAATCATGTCATGACCAATTATATATGGAATTATCAATACAATCACAATTCACAT
CATTATGTGAGGCTAATTCCACTACTAGAAAACTGTCAAAAAGCATCCAGAGCATACC
GACAGAAATTGATTGGAAATAATACCGACTGACATCGGTCAGAAACGAAGTAAATTGGT
CGAAAATATCAAATAACAAATTGTAAATAAAAATACCGACCGCAATTAGTAGAAAAATGT
GATCCCACAAAAAGAAAGTTTACTTTATCTGACACTGTTAAAATTTTCGACCGATTACG
GTCGGAAATGATCAATTTTTTACCAAAGCCCGATCAGACTTGCATACTATCAAATATAG
GTTTTAGAAGTTTATTTTTCTTTTTAGATTTGTATCGAATTAAGTTAGATTTGTGTCGAATT
AGATTTGCCCGGAGATAATGAAATTAAAATTAATCAAAAGAAAGTTCAGAATAGAAAAAC
TTAACCAACCTCGATATTTAAATTATAACTTATACTTAAATTAAAAGAATTTAAAAAGAAAA
```

FIG. 15

```
AAAAAACAAATGAGGGACCTGCAATAAATCACAACCAATCCTTTCTATGGTCAATATTTA
TTACACGTAAGCCAAAGACATCCTTTTACAACATGCAAACTAAAACATCACTACTAAAA
ACAAATGGCCACCTCACAACTTTCCGACCTCATTTTCCGGCCATCACTTCACCGGCGCA
CCACTTTCCGGCAATGCCACCCTACTTCAGTCTTTCTCACTCCTCCAAAAAATATCAAAA
CAAAAACTCTTAAATATGACAGAAAAATCAAGTGTTTAATTAAGTTTAGTTTAGTTGATAA
ACAGAGCCCAACCAAAAAACCAACAGTTGATATGAACCAATTAGTGGAATTTTTATATGA
GGATTTGCCTCATCTTTTGATGATCAAGGTATTGATCGTAAGGCATATGATGATTATGT
GAAGTATAGGGATCCAATTACAAACATGATTCAATTGATGGCTATTTGTTAATATTGC
AATGTTGAAACAGTTGTTAGGCCTGATTTTCAGCTGCATTGGGCTAAACAGGTTAGCA
TTTCTGCAGTTTCTTGTGAATTGGTTGTGTGGCTATGAGGTGCCTAAAGTAAAAATAGCA
CGGGCTAGCCAATTTTCGGATTGGTAATTGAAAATAGTCAACGTTTGCAAAGTCATTG
AAAAATAGCCACTATTTTGCTGCAACATGGAAAGTTACAACATAATATACTGGAGATTAG
TGCACATGTGTATGAACTTTCAGCATAATATACTGGAGATTGGAGGAGCACATGTGTAT
GAACTTTCAGCACCATGATATTATGCTGGAACTCCAGTATATTATGCTGGAAGTTCATAG
GTAAAAAATTCGAACTCCAGTATATTATGCTGGAATATTTTCGGATTTTGAATAGGGTTT
TCGTTCAGATTTATCTTTACATGAAAAGTGGCTAAGTTTTGATTACTTTTGAAAATGTGGC
TATTTTTTAATTACCACTTGTAAATCTGACTATTTTTGAATTTAACCCGTGCCTAAAAGAT
GGAGTAGGATTTAAGTTATATACGCCGTCATGTAAAGGTTATTATTATACTCAGTGGATA
TAAACTTGTGGGTTGATTACAATATTTAGCAGATTACTAGTTAATACTTACTAGAGATTAA
CATGTAATTACTAGTTAATAAGTGACCTCATTGTTTAAATATTTTTATACCATTAATGGAT
AGAATTTCAACTCTAAAGGATAACTATACCTAATATAGGTGACTATTAGGGTGCCTAAGA
AGCCACCACACTAATTGTCCTTAGAAAGTTGTATTAGTAATCTGGATAACAAGGCAGATT
ACCTATTACGACAAGTTAAAATATACCGATAGTGTGTGTATATAAGTTAAATAAATTGGTT
GTTTAAACTCTCTGTTTTTTATCGCTTTTCGTTCTTCTTATTATGTTTTCGGTTGGTTTAA
GGTGTTGCACAAATATTCAAGAACATAGTATCACCCTTATACATAGTACATTTACTGCTC
TTTGAATATCAGTCCACTGTTTGTTAAATGCAGAGGCACAGATGAACTGATGAACTGCTT
CTGATTGTTAAGTGTGTCATTTCATTAAGTGAAGAATTTTACATGTTGAGTATTATGTAG
TTTGGTATTGGGGCAGAAGTTGCATCTAATCTGTTTGTTTTGTGCTACTAAACTTAATTG
CGTATTAGTGTCTCATGGTTTTGCATATCCATTTAAGGATACCGATACATGTAGTGTACT
ATGTAGGTTCTCTTTTTCAAAATTTAGTTTGGAAACAGCCTCTCTATCCTCACAAGATAG
GGGTAAGGTCTGCGTATATGCTACCCTCCCCAGATCCCACGGTGTGGGATAATACTGG
GTATGTTATTGTTGTTGTTGTAGTTTGGTATTGGAGCAGAAGTTTTATTTAATCATTTAAT
CAGTTTGCTTTGAGCTACTAAACTTGTATTTTTAAGGAATGTGATGCATAGATTATGCATT
TGAATCTTTTGAGTGATTGAGTTTGTTGTAGACAGGACCCTATGAAATAACTACAAGGTG
GACAATGGTAATGAAGTTCATTCTTCTTCCATGGAAACCTGAATTAGTCTTCACCGGCAC
TTCTGTTATGGGCGTCAATCCTGAAACAAACAAATTTAACAGCCATGTGGTTTGATTCTT
CACTCTTCCTCGACGCGAATTCAAATTTTTAGATTGCTTTGCGAATTAGTCACCGACTCT
TTGTTGAAATCTATAGGACTACTGGGATTCAATTAAGAATAACGATTATTTTCTGTAGAA
GGTCTGCTGGAGGTCATAAAACAGGTGCGCGTTCGAACTGTTTTAGTTTATGCTTTTAA
TTAAATTCTTGGACTGTTGGGATAAACCGGCCCAATGATACTCTTAACATGGTGTGATAT
TGTCCGCTTGGGGCCAAGCCCGCACGGTTTTCACTAAAAGGGCTCGTACCATTAAGAG
ATCCTTACACCTTATATAAGCTCCCAATATTTTCAGCTACCAATGTCGCCTTATTATGA
TTTGAGAATACAAATCTTGGGCAGTTAAGGATTTACAAGACTCCGGATTTGGAAACACC
TAGTTATCAGATATTAAGAAGAACAGCAACTTACGAGGTTTGTAGTATTTATGTTATAAC
ATCGTATTTTCAAGCTAAGAACTTCTATATTAGGCGTACATTTTATTTGGTTTGCGCTAC
TTTTAGCTGAACTGATGCACTAGGACGTTTAGATTTATGATGTGGAATGGTCACAACTTT
CATTGGTGCAATACAGGTCAGGAAATATGATCCGTTTATAGTTGTAGAAACAGAAGGTG
ACAAACTCGCAGGAAATAGAGGTTTCAATGATGTTGCGGGGTGAGATAAGTTGACTATT
TTTTTTAAAAGAAAAAACTTCTGTGATGTTTTCTGATTTAGATTGGTAGACTGTTAACTC
GTCTTAATATAGGTACATATTTGGCAAAAATTCAGCGACAGAGAAGATACCGATGACTA
CTCCTGTCTTCACTCAGGCATTCGATGCTGAAAAATCTAAAGTGTCAATCCAGATAGTTC
TTCCATCGGATAAATCTTTGAGCAGGTAACACTTAACACGTTGTATTAATAATATACAAG
AAAACATCTCACACTGAGTGAAAACAGTATGGAATCTTTAAATATTCTTAGCACTGATCT
GATTATACTTTTTGACAATATGGTTTCACATTTTAACAATTTGTTGAAACTTAGTGGCTTT
TCATATATATAAGTCATCATAAGCATCGCCCGCCTATGTGTAAGAGTTGGACTTTAGTCC
```

FIG. 15 (Continued)

```
TTTTCTTTGTTCAAATGAGACCTATGGAAATTATTGCCTTATTCTTAACAGCTTACCAGCT
CCCAATCAAGAAGGTATAAGCTTAAGGAAAACGGAAGGAGGCATCGCTGCTGCATTAA
AATTTAGTGGAAAACCAACTGATGATGTTGTTCGAGAAAAGGAGAAACAACTCAGATCA
AGTCTTATTAAGGACGGTCTCAAACCTCAATCGGATTGCATGCTTGCTCGCTACAATGA
TCCTGGTCGAACGTGGAAGTTTATAATGGTATATTCTATGTACTGATAATGTTCCTTTC
ATTGCATTCCTGCTTAAGTTCTTCTTTTGCTTTAGACTTTAGAAAAGGAATCTTCTTTTG
CTCTTTCTATTTCTGTTTTCAATTATCAGTGCCTTCATTACCAAGGGCGGAGCTAGTATA
CTATGTACGGTTTCGGCAGAACCCACTAACTTTAGCTGAAACCATGTATTTTGTTAAAAA
ATAAAACCACTCAATGTGTATAAATAATTTATTCAGAACCCAGTAAGTCAGCCTTTCTAT
AATAAGACCCCATAAACTTAAAATCTTAGCTCGGCCTCTGTTCACTACTGAATATTTTGA
TATTCCAACTAGTTTGAGATTGAGGCATAGGTGATTGATTGATCAATAAAATTAGTTTGA
CATTATGTTGGTATATTATCTACTGCTAATATTTTCTCATCTGATGGAAGGTTTTTGTTG
GTGTTTGCATTATATTTTATGATCCTTTGGGTGACAAGAGTGGGTTGCTCTAGTGGTGA
GCACCCTCCACTTCCAACCAAGAGGTTGTGAGTTCGAGTCACCCCAAGAACAAGGTGG
GGAGTTCTTGTCGGGAGGGAGCCGAGGGTCTATCGAAACAGCCTTCTACCCCAGGG
TAGGGGTAAGGTCTGCGTACACACTACCTTCCCCATACCCCACTAGTTCCCCATACCCC
ACTAGTGGGATTATACTGGGTTGTTGTTGTAGTGTTCTTATCACTTCTTAAAGTCA
TTGTGTGTCTAATCTATTTGTTTTCTGTTTGGATTTTGCAGAGGAATGAAGTTCTTATA
TGGCTTGAGGATTTCAAGCTGGATTAAGCTCCCATTCTCAAAATTGCTGAGAGTTTCAT
GAGTGAAAAACAGGAGAGATTCACAAGCAAGACAGTTTAGAAAATGTTCTTATACTG
AACAGATCCAAAAGCTATGAAATTAGGTTACTGTATTTTGTATCTCAAAATATTTAGAGA
TTTTGACAAATATATGGCTTGTACATAGCACAGAATGCTTGTGCTGAACACTACTAAACT
GATTTCTCTTGTGCACTGCACCAAATATTGTTAGAGCTGTAGTTCTATG
```

FIG. 15 (Continued)

Nitab4.5_0003235g0060.2 coding sequence (SEQ ID No. 12):

```
ATGGCCACCTCACAACTTTCCGACCTCATTTTCCGGCCATCACTTCACAGGCGAACCAA
TTTCCGGCAATGCCACCCTACTTCAGTCTTTCTCACTCCTCCAAAAAATATCAAAACAAA
AACTCTTAAATATGACAGAAAATTAAGTGGTTAATTAAGTTTAGTTTAGTTGATAAACAG
AGCCCAACCAAAAAACCAACAGTTGATATGAACCAATTAGTGGAATTTTATATGAGGAT
TTACCTCATCTTTTTGATGATCAAGGTATTGATCGTAAGGCATATGATGATTATGTGAAG
TTTAGGGATCCAATTACAAAACATGATTCAATTGATGGCTATTGTTTAATATTGCCATGT
TGAAACAGTTGTTTAAGCCTGATTTTCAGCTGCATTGGGCTAAACAGACAGGACCCTAT
GAAATAACTACAAGGTGGACAATGGTAATGAAGTTCATTCTTCTTCCATGGAAACCTGAA
TTAGTCTTCACCGGCACTTCTGTTATGGGCGTCAATCCTGAAACAAACAAATTTAACAGC
CATGTGGACTACTGGGATTCAATTAAGAATAACGATTATTTTCTGTAGAAGGTCTGCTG
GAGGTCATAAAACAGTTAAGGATTTACAAGACTCCGGATTTGGAAACACCTAGTTATCA
GATATTAAGAAGAACAGCAACTTACGAGGTCAGGAAATATGATCCGTTTATAGTTGTAG
AAACAGAAGGTGACAAACTCGCAGGAAATAGAGGTTTCAATGATGTTGCGGGGTACATA
TTTGGCAAAATTCAGCGACAGAGAAGATACCGATGACTACTCCTGTCTTCACTCAGGC
ATTCGATGCTGAAAAATCTAAAGTGTCAATCCAGATAGTTCTTCCATCGGATAAATCTTT
GAGCAGCTTACCAGCTCCCAATCAAGAAGGTATAAGCTTAAGGAAAACGGAAGGAGGC
ATCGCTGCTGCATTAAAATTTAGTGGAAAACCAACTGATGATGTTGTTCGAGAAAGGA
GAAACAACTCAGATCAAGTCTTATTAAGGACGGTCTCAAACCTCAATCGGATTGCATGC
TTGCTCGCTACAATGATCCTGGTCGAACGTGGAAGTTTATAATGAGGAATGAAGTTCTT
ATATGGCTTGAGGATTTCAAGCTGGATTAA
```

FIG. 16

Nitab4.5_0004868g0020.2 protein sequence (SEQ ID No. 13):

MGMILGKITVETPKYELIQSTADYEIRKYPASVIAQVTYDPTQFKGNKDGGFMLLANYIGALG
NPQNAKPEKIAMTAPVITKSSEKIAMTAPVVTKSGDGENNMVTMQFILPAKYTKAEEAPKPL

FIG. 17

DERVVVKEEGERKFGVVQFSGTASDKVVKEKVENLRKCLERDGYKIIGDFELARYNPPWTI
PPFKTNEVMIPVE

FIG. 17 (Continued)

Nitab4.5_0004868g0020.2 genomic sequence (SEQ ID No. 14):

CTCCACCAGCTTATGGTGCAAACGTGGCAAAACAAACTCCACAGCAGTTCCCTCATCTA
CCGCCATTCATTTTGCAGCAATCAAAAACCCCTTTCCCAAGTTCTCTCTTCCTCTCTTTC
CGATTTCCCACAAGAAACTTCCTCTTCTCTCCCCTTATATGTAACAAATTCACAGCCTCC
ATTTACTATCAAAACATTCTCAAATTCCATTCCCAATAACTAATTTTCGTTCCATCAAAAT
GGGCATGATTTTGGGGAAAATCACTGTGGAAACACCAAAATACGAATTGATTCAATCTA
CAGCTGACTACGAAATCCGCAAATACCCAGCATCTGTTATAGCACAAGTCACATATGAT
CCAACCCAGTTCAAAGGAAACAAAGACGGTGGGTTTATGCTATTAGCCAATTACATCGG
CGCACTTGGCAATCCTCAAAACGCTAAGCCTGAAAAATCGCCATGACAGCTCCTGTAA
TCACCAAATCGTCCGAAAAATCGCGATGACTGCACCAGTGGTGACTAAGAGTGGTGA
TGGAGAGAACAATATGGTGACGATGCAGTTTATTTTACCAGCAAAGTATACAAAAGCTG
AAGAGGCACCTAAGCCGTTGGATGAAAGGGTGGTGGTTAAAGAAGAAGGGGAAAGAAA
GTTTGGTGTGGTGCAGTTTAGTGGGACTGCAAGTGATAAAGTGGTTAAAGAGAAAGTG
GAGAATTTAAGGAAATGTTTGGAGAGAGATGGGTATAAGATAATTGGTGATTTTGAGTT
GGCTCGGTATAATCCTCCTTGGACAATTCCTCCATTTAAGACCAATGAAGTTATGATTCC
AGTTGAGTGAGCTGAAAATGGTGTATTAAAGAAAAATATGAGACGGCTGTGAAGCTAGC
TTGTAACCTACTTTATCTGGTGTTTATTAGTATTGAATTGTGTATTTCTGTTTATATGTT
TACGTTGTTGACAATGTCTTTGCATACCCTAGCTAGTGTCAATTATCATAGTTAATTAG
CACATATTTTAGCTCAATTTTATACTTTGCCATAGTAAAGTAGTAAAACCAATGTGGTTTT
GCAAGCACCTAATGTGGTAAGTCCTTACTCTCTGTTTTCATTTCACACTCTTCTCTCTG
TCCATTTCTGCCAGTATAAGTGCTTCTTCTGTCAATACCCGGTGAATCATGTAAGGGCC
CTGTTAGTTGGGTAAAAATTTTCCTTTTGCTTCATCTTTATGTGATAAGATTCGCTTTAGC
ACCAATTGCCCCAGCATGAATTTCCTTGATCTGACCTTTTTGTTGAAAAATCTTGCCATT
CTGTTCTAGTAGAGTTGACCGTGACATACTACATTCATTCTCTTTTCATCAATGAGAGCT
AGTTGTTCATACTGGCTTCGTACCAATTCCTCGTCGCTGAGCTCGGTTTCTTGTATGATT
CTTAAAGAAGGAATTTCTACTTCGGCGGAAATAACGACTTCAGTACCATAAACTAGTAG
GTAGGGAGTTGCCCCATTTGATGTACGAACTGTGGTACGATACCCCGAGTAAGAAAAT
GGTAGATTATGATGCCATTATTTGTAATTGTTCACCATTTCCCTCAATATCTTTTTGATGT
TCTTGTTGGCGGCTTCCACGGCTTCGTTCATTTGCGACCTGTACGCTATAGAGTTCCTA
TGCTTGATCTTGAATGTTTCACACATGGCTTCATCAAATTGCTATTGAGA

FIG. 18

Nitab4.5_0004868g0020.2 coding sequence (SEQ ID No. 15):

ATGGGCATGATTTTGGGGAAAATCACTGTGGAAACACCAAAATACGAATTGATTCAATC
TACAGCTGACTACGAAATCCGCAAATACCCAGCATCTGTTATAGCACAAGTCACATATG
ATCCAACCCAGTTCAAAGGAAACAAAGACGGTGGGTTTATGCTATTAGCCAATTACATC
GGCGCACTTGGCAATCCTCAAAACGCTAAGCCTGAAAAATCGCCATGACAGCTCCTG
TAATCACCAAATCGTCCGAAAAATCGCGATGACTGCACCAGTGGTGACTAAGAGTGGT
GATGGAGAGAACAATATGGTGACGATGCAGTTTATTTTACCAGCAAAGTATACAAAAGC
TGAAGAGGCACCTAAGCCGTTGGATGAAAGGGTGGTGGTTAAAGAAGAAGGGGAAAGA
AAGTTTGGTGTGGTGCAGTTTAGTGGGACTGCAAGTGATAAAGTGGTTAAAGAGAAAGT
GGAGAATTTAAGGAAATGTTTGGAGAGAGATGGGTATAAGATAATTGGTGATTTTGAGT
TGGCTCGGTATAATCCTCCTTGGACAATTCCTCCATTTAAGACCAATGAAGTTATGATTC
CAGTTGAGTGA

FIG. 19

Nitab4.5_0006614g0010.2 protein sequence (SEQ ID No. 16):

MQAVMNFFMRLAFFLILVSKLSNGYSTNHLQPQKLGFYPPTCNRIECPNYDLIQSGKDYEIR
LYNSSMWMSTAPIDDINLYSATRTGFLRLFDYIQGKNSYQEKIEMTAPVITQVKPSDGPFCA
SSFVVSFYVPKKNQPNPPPAKGLHVQIWSNTYVAVRQFGGFVADVDVAKEAAALSASIADT
KWAAAVEKSHAADNTTMYTVAGYNSPFEFKDRVNEIWFTFDLDKASAI

FIG. 20

Nitab4.5_0006614g0010.2 genomic sequence (SEQ ID No. 17):

AAACCTCTGGACACCCCTCATTGATTTTCTTTTTCTTTTATGCATGAGGAAATTAGTTC
ATTCGGGTCACTTCATTCTCTCTCCGTATAATTTCTAGGAACTAAAACACTAAAAAGAAA
CAAAAGATGCAGGCTGTTATGAATTTCTTCATGAGGCTAGCTTTCTTTCTGATCCTCGTT
TCTAAATTGAGCAATGGGTATTCGACAAACCACTTGCAGCCACAGAAGTTGGGTTTCTA
TCCTCCAACCTGTAACCGAATTGAGTGCCCAATTATGACTTAATTCAATCTGGAAAAGA
CTATGAAATTCGTCTTTATAATTCATCCATGTGGATGTCTACTGCACCCATTGATGATATT
AACCTTTATTCCGCCACCAGAACTGGTTTCCTCAGGTTAATATTATATTCCCTCTTTCTC
CCACTAGTTCCCTTTTACATCAGTTATCTGTATCTATTGTTTTTTTTTTCAATTCCTTTC
TATTTGTTGCATATTTGATAAGTTAGCTACACTGTGCAACACCAACTAAAGCATGTGTGT
TTGCTTTCCAAGATTCCTCAAAAAAAAAAAAAAAAAAACAAGGGACTTAATTAAAGGTTT
ACTTACATCTCAATCAATTGAAAATAATCGACTATTAAAAGGAAAAAAAAATTATGTCTT
GCCAGGTTACATTGAAGCAGGTTGCTGCCAGTTACCAATTTACAATTATATTGCTAGTTA
TCTGTAACTGATTTGATTTATATGTACTGAAATGCATAGTATTTAATCTAGATTGTTAAA
GCAAATACCTGCCTTATTTTACAAGTTACTAATCTCCCTTTTTACGGTTAGTTATCGTGTT
ATTATTGAGTTGACTTGATAGTGTAAAAGTGATCTTTTCCACTGTCAGTATTTAGAAGTTA
TTTTATGTGAACTTAATCTTTATACTTAAGATGTTAGCCTATCCATTTGCAAAACATAAAA
AACAGTTGTTGTAAACTTTGCCTTGGCAGGCTATTCGATTACATTCAAGGGAAGAACAG
TTACCAGGAGAAAATAGAGATGACAGCTCCAGTTATCACTCAAGTAAAACCAAGTGATG
GACCATTTTGTGCATCTTCATTTGTTGTGAGCTTCTACGTACCAAAGAAGAACCAACCAA
ATCCTCCTCCAGCTAAAGGCCTTCACGTCCAAATATGGAGCAATACTTATGTCGCCGTC
AGGCAATTCGGCGGATTTGTAGCTGATGTTGATGTTGCAAAAGAAGCTGCTGCTTTGAG
TGCTAGTATTGCTGACACTAAATGGGCAGCAGCCGTTGAAAAAGCCATGCTGCAGATA
ACACTACGATGTATACAGTGGCGGGATACAACTCTCCTTTTGAGTTCAAGGACAGAGTT
AATGAGATTTGGTTTACATTTGATTTGGACAAAGCATCTGCCATTTGATTCTGGACTCTT
TAACATTTCAGGAGACATGAAACTATCTTATTTTCTTGGTTTGTATTACTATTAAACAACA
GTTTTGTATGACCACAATGCTACATTATATAGATAGAAAATAAGATAGGTTGTACAATAC
AATTTGATTCTGAGGATTTAGTGGTTAAGATACCTCTTTCAAGACCTTTCAAAATAATCCA
ATATATATGGAAAAGGGCTTAGACCATATTGAGTTTATTGTATGCAGTT

FIG. 21

Nitab4.5_0006614g0010.2 coding sequence (SEQ ID No. 18):

ATGCAGGCTGTTATGAATTTCTTCATGAGGCTAGCTTTCTTTCTGATCCTCGTTTCTAAA
TTGAGCAATGGGTATTCGACAAACCACTTGCAGCCACAGAAGTTGGGTTTCTATCCTCC
AACCTGTAACCGAATTGAGTGCCCAATTATGACTTAATTCAATCTGGAAAAGACTATGA
AATTCGTCTTTATAATTCATCCATGTGGATGTCTACTGCACCCATTGATGATATTAACCTT
TATTCCGCCACCAGAACTGGTTTCCTCAGGCTATTCGATTACATTCAAGGGAAGAACAG
TTACCAGGAGAAAATAGAGATGACAGCTCCAGTTATCACTCAAGTAAAACCAAGTGATG
GACCATTTTGTGCATCTTCATTTGTTGTGAGCTTCTACGTACCAAAGAAGAACCAACCAA
ATCCTCCTCCAGCTAAAGGCCTTCACGTCCAAATATGGAGCAATACTTATGTCGCCGTC
AGGCAATTCGGCGGATTTGTAGCTGATGTTGATGTTGCAAAAGAAGCTGCTGCTTTGAG
TGCTAGTATTGCTGACACTAAATGGGCAGCAGCCGTTGAAAAAGCCATGCTGCAGATA

FIG. 22

ACACTACGATGTATACAGTGGCGGGATACAACTCTCCTTTTGAGTTCAAGGACAGAGTT
AATGAGATTTGGTTTACATTTGATTTGGACAAAGCATCTGCCATTTGA

FIG. 22 (Continued)

Nitab4.5_0006991g0050.2 protein sequence (SEQ ID No. 19):

MATSQLSGHIFRSSLHRRTIFRQCHPTSVFLTPPKNIKTKPLKYDRKFKWLIKFSLVDKQTPT
KKPTVDMKQLVEFLYEDLPHLFDDQGIDRKAYDDYVKFRDPITKHDSIDGYLFNIAMLKQLF
RPDFQLHWAKQTGPYEITTRWTMVMKFILLPWKPELVFTGTSVMGVNPETNKFNSHVDYW
DSIKNNEYFSLEGLLEVIKQLRIYKTPDLETPSYQILRRTATYEVRKYDPFIVVETEGDKLAGN
RGFNDVAGYIFGKNAATEKIPMTTPVFTQAFDAEKSKVSIQIVLPSDKSLNSLPAPNQEGISIR
KTEGGIAAALKFSGKPTDDIVREKEKQLRSSLIKDGLKPQSGCMLARYNDPGRTWKFIMRN
EVLIWLEDFKLD

FIG. 23

Nitab4.5_0006991g0050.2 genomic sequence (SEQ ID No. 20):

ACTAAAACCAAATGGCCACCTCACAACTTTCCGGCCACATTTTCCGGTCATCACTTCAC
CGGCGCACCATTTTCCGGCAATGCCACCCAACTTCAGTCTTCCTTACTCCCCAAAAAA
TATCAAAACAAAACCTCTTAAATATGACAGAAATTCAAGTGGTTAATAAAGTTTAGTTTA
GTTGATAAACAGACCCCAACAAAAAACCAACAGTTGATATGAAACAATTAGTTGAATTT
TTATATGAGGATTTACCTCATTTATTTGATGATCAAGGTATTGATCGAAAGGCATATGAT
GATTATGTGAAGTTTAGAGATCCAATTACAAAACATGATTCAATTGATGGCTATTTGTTTA
ATATTGCCATGTTGAAACAGTTGTTTAGGCCTGATTTTCAGCTGCATTGGGCTAAACAG
GTTAGCATTTCTACAGTTTCTTGTTAATTGGTTAGTTAAACTGCTGTTTGTTTAACTTTCT
TACTTGGATTTAAGTTTACGGGAGCCTTGGCGTAACTGGTAAAGTTGATGTCATGTCAC
CAAAAGGTCATGAGTTCGAGCAGTGGAAACAACCTCTTGCAGAAATGCAGTATAAAGCT
GCATACAATAGACCTTTGTGGTCCAGCCCTTTTCCGGACCCCGCGCATAGCGGGAGCT
TATGCACTGGGCTGTCTTTTTTCCTCGGATTTTAAGTTATGTTCAATGATGGTGTGAAA
TTATTTTACTCTAATTAATGTGTGTCGTAGAGATAATGTAATCACCTCATAATTGACCTGA
CTGTGTAAATAATTTTATATCGTCGGTGCATAAAACGAAAGGTCCACAATCACTTAGAGT
ACCATGTTACAAATAAATGTTTATCATCAAGAATCACTTAGAATTACCTTGCGATATGATT
GTGTATTTGCACTGTCAGTGCCTAAAACTTAAGCGTCACGCCTATAATACAATTATTAAT
GCTTATTATAGGGAATCACTTGGAATTGCCTTACGATATGATTGTGTATTTGCATTGTTA
GTGCCTGAAACTTAAAGGTCTGCGAACATATTACCTTTAGCCGAGGGTCTATCGAAATA
ACTCTCTACTTGCACAAGGTAGGGGTAAGGTCTGCGTATATACTAATCTCCCTAGACCC
CGCTTGTGGGATTACACTGGGTTTATTGTTGTTGTTGTGCCTAAAGCTTAAGCACCATAT
CTATTATACAGTTACAATTGAATCACTTGGACTACCTTAATTGTGTATTAGTGTCTCATGG
TTTTGTAAATCTATTTATGGATACCGATACATGTAGTGTACTATGTAGGTTCTCTCTTTCA
AAATTTAGTTTGGTGTCAGAAGTCTTATTCAATCATTTAATCTATTTGCTTTGGCCGAGG
GTCCATCGGAAACGGTCTCTCTACCTTCTCAAGGTAAAGGTAAGGTCTGCGTACACACT
ACCCTTCCGAGACCCCACTCGTGGTATTACACTGTGGTATTACACTGAATTTATTATTGT
TGTTGTAGTCAGTTTGCTTTGTGCTATTAAACTTGTATTTCTAAGGAATGTGATACATAAA
TTATGCCTTGAATTTTTGAGTGATTGAGTTTGTTGTAGACAGGGCCCTATGAAATAACTA
CAAGATGGACTATGGTGATGAAGTTCATTCTTCTTCCATGGAAACCTGAATTAGTCTTCA
CTGGCACTTCTGTTATGGGCGTCAATCCTGAAACAAACAAGTTAACAGCCATGTGGTT
TGATTCTTCACTCTTCCTCGACGCAAATTCAAATTTATTAGATTGCTTTGCAGATTAGTCA
CCGACTCTTGTTGAAATCTATAGGACTACTGGGATTCAATTAAGAATAACGAATATTTTT
CCCTGGAAGGTCTGCTCGAGGTCATAAAACAGGTGCGCGCTCGAACTGTTTTAGTTTAT
GTTTCTTGAACTGTTGGACTAAACCAGCGCAAAGATACTCTTATCATGGTGTGATATTGT
CTGCTTTGGGCCAAATTCGCGCGGTTTTCCCTATGAGGCCTCACACCATTGGGAGATCT
CTACACCTTATATATAGGCTCTCAATCTTATCAACTACCAATGTGGCTTTATTATAATTTG
AGAACACAAATTTTGGGCAGTTAAGGATTTACAAGACTCCGGACCTGGAAACGCCTAGT
TATCAGATACTAAGAAGAACAGCAACTTACGAGGTTTGTCATATTTATGTTTACAGCGTT

FIG. 24

GTACTTCAAGCTAAGAACTTCTATATTAGGCGTACATTTTTATTGGGTTTGCGCTACTTTT
AGCTGAACTGATGCACTAGGACGTTTAGATTTATGATGTGGAATGGTCACAATTATCATT
TATGTAATACAGGTCAGGAAATATGATCCGTTTATAGTTGTTGAAACAGAAGGTGACAAA
CTCGCAGGAAATAGAGGTTTCAATGATGTTGCAGGGTGAGATAAGTTGACCCTTTTTCT
TTAAAATCTTCTGTGGTGTTTTCTGATTTAGATTGGCGGACCATTAACTCGTCTTAATATA
GGTACATATTTGGGAAAAATGCTGCAACAGAGAAGATACCGATGACTACTCCTGTCTTC
ACTCAGGCATTTGATGCTGAAAAATCTAAAGTGTCAATCCAGATAGTTCTTCCATCGGAT
AAATCTTTGAACAGGTAACACGTTTTATTAATTAATAGACACGAAACATCTCACACCGA
GCGATCATATTGTACTTATTACAATATGAGTTCAAATTTTACATTCGTCGAAACTTAGTA
ATTCATATATATAATTCATAAGCATCGTTCGCCTCTGTGTAAGAGTTGGATTTTAGTTATT
TTCTTTGATCAAATGAGAATTATGGAAATTAAAGCTTTATTCTTAACAGCTTACCAGCTCC
CAATCAAGAAGGTATTAGCATAAGGAAGACAGAAGGAGGAATCGCGGCTGCACTAAAA
TTTAGTGGAAAGCCAACAGATGATATTGTTCGCGAAAAGGAGAAACAACTTAGATCCAG
TCTTATTAAGGACGGTCTCAAACCTCAATCGGGTTGTATGCTTGCTCGCTACAATGATC
CTGGTCGAACGTGGAAGTTTATAATGGTATACTTCTATGTACTGAATATCGTTCGTTTCA
TTGCATTCTTGTTTAAGTTCTTATTTTGTTTAGTATGAAGTGTCTCTTTAGAATGAGAAC
CTTGGCGTAACTGGTAAAGTTGCTGCTATGTGACCAGGAGGTCACGGGTTCGAGCCGT
GGAAACACCCTCTTGCAGAAATGTTGGGTAAGGCTGCGTACAATTGACCCTTGTGGTC
CGGCCCTTCCGCGGACCCCTCGTATAGCAGGAACTTAGTGCACCGGGCTTCCCTTTTA
GTCTGAAGTGTCTCTTTATCACTTTGTCATCTGGTGTCTAATCTATTTGTTTTTCTGTTTG
GATTTTTGCAGAGGAATGAAGTTCTTATATGGCTTGAGGATTTCAAGCTGGATTAACTCC
CATTCCAAAAATTGCTGAGATTTTCATGTATGTAAAACAGGAGAGATTCACAAGCAAAGA
CAGTTTAGAAAAATTCTTATACTGAAATGAAATTAGTTCTCAAAATGTTTAGAGATTTTGA
CAAATATATGACTTGTGCATAGCCACAAATGCTTGTGCTGAACTCACTTTACACTAAACA
AACTTCTATTGTGCATTACAAAGTTCGATGTGTTGATGGTGTAAATAATATTTGTCACTTG
TAAGGTAATTAATGGTAATTAAC

FIG. 24 (Continued)

Nitab4.5_0006991g0050.2 coding sequence (SEQ ID No. 21):

ATGGCCACCTCACAACTTTCCGGCCACATTTTCCGGTCATCACTTCACCGGCGCACCAT
TTTCCGGCAATGCCACCCAACTTCAGTCTTCCTTACTCCCCAAAAAATATCAAAACAAA
ACCTCTTAAATATGACAGAAATTCAAGTGGTTAATAAAGTTTAGTTTAGTTGATAAACAG
ACCCCAACAAAAAAACCAACAGTTGATATGAAACAATTAGTTGAATTTTTATATGAGGAT
TTACCTCATTTATTTGATGATCAAGGTATTGATCGAAAGGCATATGATGATTATGTGAAG
TTTAGAGATCCAATTACAAAACATGATTCAATTGATGGCTATTTGTTAATATTGCCATGT
TGAAACAGTTGTTTAGGCCTGATTTTCAGCTGCATTGGGCTAAACAGACAGGGCCTAT
GAAATAACTACAAGATGGACTATGGTGATGAAGTTCATTCTTCTTCCATGGAAACCTGAA
TTAGTCTTCACTGGCACTTCTGTTATGGGCGTCAATCCTGAAACAAACAAGTTTAACAGC
CATGTGGACTACTGGGATTCAATTAAGAATAACGAATATTTTCCCTGGAAGGTCTGCTC
GAGGTCATAAAACAGTTAAGGATTTACAAGACTCCGGACCTGGAAACGCCTAGTTATCA
GATACTAAGAAGAACAGCAACTTACGAGGTCAGGAAATATGATCCGTTTATAGTTGTTG
AAACAGAAGGTGACAAACTCGCAGGAAATAGAGGTTTCAATGATGTTGCAGGGTACATA
TTTGGGAAAAATGCTGCAACAGAGAAGATACCGATGACTACTCCTGTCTTCACTCAGGC
ATTTGATGCTGAAAAATCTAAAGTGTCAATCCAGATAGTTCTTCCATCGGATAAATCTTT
GAACAGCTTACCAGCTCCCAATCAAGAAGGTATTAGCATAAGGAAGACAGAAGGAGGA
ATCGCGGCTGCACTAAAATTTAGTGGAAAGCCAACAGATGATATTGTTCGCGAAAAGGA
GAAACAACTTAGATCCAGTCTTATTAAGGACGGTCTCAAACCTCAATCGGGTTGTATGC
TTGCTCGCTACAATGATCCTGGTCGAACGTGGAAGTTTATAATGAGGAATGAAGTTCTT
ATATGGCTTGAGGATTTCAAGCTGGATTAA

FIG. 25

Nitab4.5_0009023g0010.2 protein sequence (SEQ ID No. 22):

MLLCSPSSISAHNLSRNRTRPSPINSMAVDRSSSRVATTASQRRNGTSALEARISLVIALAS
QTSSLSQKLLTELAGETAKYVLPKRIFESRTLEEALMSVPDLETVKFNVLKRSDQYEIREVEP
YFVAEATMPGKYGFDFNGASQSFNTLAEYLFGKNTKKESMAMTTPVITRRTQSDGERMEM
TTPVITKRVEDQGKWRMSFVMPSKYGSDLPLPKDSSVTIKEVPRKTVAVVAFSGFVTDEEV
KARESRLRAALKGDAEFRVKDGASIEVAQYNPPFTLPFTRRNEISLEVEREQE

FIG. 26

Nitab4.5_0009023g0010.2 genomic sequence (SEQ ID No. 23):

ATGTGACATACACAGTATGTGATAAGGAATTAACCAAGTAATTCGGGGGCGACAAATAC
AAATATAGATGAACCACAATCCCCTTCTTTGAAGCACAGAATTTCAAAAGGAGTGAAACA
AACACTGTAACGTAGTTAAAGATGCTTCTGTGCTCACCTTCTTCCATTTCTGCTCACAAT
CTTAGCAGAAACAGAACCAGACCTTCGCCTATCAATTCTATGGCAGTTGACAGAAGCAG
CTCCCGCGTTGCCACAACTGCTTCGCAGCGGAGAAACGGCACGTCAGCTCTCGAAGCT
CGCATCTCCCTCGTCATCGCTCTCGCCTCCAAACCTCTTCTCTCTCAGAAACGTAA
TTTCTTCACTCCATTTCCTAATTCCTCATTTTAATCGGATTTTAAGCATTTCTCTCCCAATT
CTTTTTTTGATTTGTTTAAAACATTTCGTCCAGTGCTTCCAGGACTCTTTTAAGTCAGATT
AGAGAACTTCTTAGAAAAGAATTAATTTAGTTTAAGAGACTAATTATTTACCAGTGTTGGA
ATGAACTTGTGCTTGACGGCTAAAGCGGAACGGATATAAATGATTCTATGTAGTCCTCT
GGCTAGTTTAGGAATGAGAACCTAGTCAATTGACTAATTGAGTAATTGCTACTTATATTG
TTAAATTTTTATTGTTCGCAGTTCTGACGGAATTGGCTGGTGAAACCGCGAAATACGTG
TTACCGAAGAGGATATTCGAAAGTCGGACTTTAGAGGAAGCTTTGATGTCTGGTATTCT
TTCTCAATCTTTTCTATGATTGTTATATCCTCTATTTTAATAATAATGAGAATTTAGATGGT
TAAAAATAATGACTAGCTCCCATCGCTGTTATCTTCTTGAAGTGCCGGATCTGGAGACA
GTGAAATTCAATGTTTTGAAACGCAGTGATCAGTATGAAATAAGGGAAGTTGAGGTATTT
TCTCTATGATTCTATTTATAAATTACTAATGTTGTCATTCCTTTTTTTTTTCCCAGTAGA
GTCTAGATTTGTATGCATCCATTCTGCAACTTATCGGGGGAGTGGTTCCAGACGAGAG
AGGAGCAATATTTGACGGGAAAAAAAGGTTTAAACCTTCATTAAAAAAATGTTGAAGAT
AGAGGGCAAACTTGTTTTGAGAACACCTTTAGAATACTACTTACATAGATACAAATATTA
GGCAAAGATACGTTTATTATATTTGTTCACACCAGCTAAATATTCTCAAACAAAGATTAAT
CCTTTAGTTAGAATTTCTTGATATATGGTAGAATGCTCCGTCTCAGAAAGTAATCAAGGG
TACTAATACAAGAAAGCATTAGTTGGTAAAAGTTACTAGGCCATGTAATTAGATACAAGA
GACATTTGTGAAGATTTTGTTGTAACTTGATTCTACATAATGGGCCTTAGTTCATATTTGT
GTTTTCCCTTATTATGGTCATTAAAAAAAAAAAACACAAGTACCTGGGGATTGAAAATG
CAATTCTGAAAGGTACAATACATATGGAAGTGGAACTGGCACAACTGGAGACTGATAGT
TATAGTGGGGAGTCAGCATGTCTATCAATAAGAAAGAAAAGAAATAAACGAACCTGAA
AGAGATTTGGTATTCAAAAGTATTTTGGAAAAGAATGAAATTGACAGAAATAGACTAGTG
ATCACAAATCAGGAGTTTCCTCAATTTTGAGGAACATGTTATTGACTCGGTGTTAAAACA
TGATGAGAAAGCAGAGGTGCCAGTTTTTTGAAATAAACATATGATGTTCTAACTTTTGGT
TTGATAACCTAGAATTAAGCATATCATAAGCTCTTTCCATGAACATTAAAGCCCTGGATC
CTGATACTTGAAAGTCATTCATTCACAAATTGTTTTTGGCAGATCTACCTTTGTATTAAA
ATTGAATTCTGGACCATCAGTCACCCTGTTATTATGGTGCACATATTCTTCTTATGTGT
ATATGCTCTTATTCTTTGCTTTTCGGAAACAGCCTCTACCCCGGGTAGGGGTAAGGT
CTGCATACACACTACCCTCCCCAGACCCCATACACTGGTTGTTGTTGTTGTATATG
CTCTTAAATTCTTGTCCTCAGTTATTCCTAACCTCTCTTAATAGCATTTCTCTTGATTATA
GATATGCTGTATTATTAGAACTTTAATCACCGATATCTCTTTATGTTGTCATGTTGATAGT
TATTCTTTCCCTTCTTGTCCTCTTAACAATAACTCTGAGTTTTTATTTTTTATTTTGATAA
AGTTCATTATAAACTCTGAGTTAATTTATCTAAAGTAATATTGCGACTTTGAACAGCCTTA
CTTTGTTGCTGAGGCTACAATGCCTGGGAAGTATGGGTTTGACTTAATGGTGCATCTC
AATCCTTCAACACATTGGCTGAGTACTTGTTGGTAAGGTAGTTAAAGGTACTTATAGAG
AGTCAAACTTAGATCGCCTCCAACCACATTGTAATGGTGGTCTTCTTTGGCTCTGTTCTA

FIG. 27

```
TTTCTTGGTGATTTCCAGAACACGAAGAAGGAGAGCATGGCGATGACAACACCAGTTAT
CACTCGTAGAACTCAATCTGATGGGGAGAGGATGGAAATGACTACTCCAGTGATAACTA
AACGGGTACAGCTCTTCTACTGGTTGTTCCTTTTTCCCTTTAGTTCTTTTGCAATGTATAT
TTACTATGTCATTCGTGATATATGGTGTGGTTACTAATATGCTTGCATTTTTGTATGACAT
GGTGTTACTCAAAATATTAAACTGATAATATATTGAAGTTGAGTCACCACATAACTTGGG
AAATGGTAAATGAAGAACTACTCTAAAATGACCACATATCGTCAAATGGAAATACTGACT
TTACTACTGATTCTGTTGAAAAGAAACATCGTCTGATTACCTATCACTAGGAAAACATTT
AAGCTCTTGATTTAGAATTGATAAAAGATGACATGTGCTTTAGATTGAGATTTGAGGATC
TTTCAATTGTATGCTAGGCTTATACGCCAGCGGGGGTACATACAAAACGTAAACATTCT
GGTTGCTTAGAGTTTGAATCTGTACTACTCTAAGATAGTATTGCAAATTCTGAGAGAGTG
GAAACTGTTAGATTCCAGGTTTTATTATGTTGCATGGATCCTTCAAACGGGTGTGACATG
GGTGTGGGTACTTCTTGCAGGTTCTTCAAAGTAGAAAAGAAATGCACGAACTCCATCA
AATACTTACATACACATGGTGTACACCTATAGGTTTGTCCATATAATGCAGATGTTTA
ATCTTAGTCCAGAACAAGTGTCGAACGGAATAACAGTCACAAAGAACAATCTTCATAAT
GATAAAGATTATGGTCCGAATAAAATACACCCCCATATAAATGATAACACATTTTCTTGT
AATTCTTAAGTAGATCTCCGAGAATAACATTTTGTAACTTAAAAGACCAATTTTTTGTGAA
AATGGGCCCGCCGTATTGATTGGCATCCTATAAGAATTCCTTACTTCCAGAACCTTTGA
AACCAGAATTAGTCCATTCTAGAAAAGAAAAACTCAGTTTAGCTTGATGTCTGATCCTAT
GTTATAGTGCTTAACANNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNN
NNNNNNNNNNNNNNGATCCTACTCGTTATACGTCGCCTTAACACCCCCCCCCCCACCC
CCCCCCCCTCCTTTCTCCCCGCGCCGCGCCTCCACCACCACCAACAAACCTAGTAAA
ATCCCACAAGTGGAGTCTGGGGAGGTAGCGTGTATGCAGACCATACCCCTACTTGCGG
GAAGGTAGAGAGGATGTTTTCTAATTTGGAATGTCATGCGCTCATATTTTCACCAAAAT
TACACCCACTGGAATCTCATTAAGAATTTCATTAGGTGGAAGATCAAGGAAAGTGGAGG
ATGTCCTTTGTCATGCCCTCAAAGTATGGTTCAGACTTGCCACTACCAAAGGATTCCTC
CGTAACTATCAAGGAGGTGCCTAGGAAAACTGTCGCCGTTGTTGCTTTTCAGGTTTGT
GATTTCAGATTTTAGCATGTCAATATAAAGTTCTATTTTGTATGATGATGATATGAGTTGA
GCTTACAGAAAGAAGTGAGGATTCATAGCGCCGACCTCAACTTTGTGGGACTGAGGCG
TAGTTGTTGCTGCTAATATAAAATTCTAGACAGATTTGCATTTTAAGTTAATTTGAAATTC
AATATCCTAGTAATCGGAAAGCAGAGCTCTGTCTCATTGGTCTATGGAAGTAAATCTTGT
TTAAGTTTACTTAGTGCTTTATTGATAGCTTCTCTTGTTATGACATGAGAGAATTTTTCAT
CTAGTTGTATTTTCTGTGTTTTTCCTTTGATGTCCTATATGCCTGCTGTGGTAGATAGCA
```

FIG. 27 (Continued)

ATTTCCATTCAGAGTTCAAAAGCAAAAACATTTAGGAATTCTATTTTTGAAGTTTTACATC
CTAACTTAGCTAGTTTTCTCCCATTCGATTTCAACAAAGGTTTTGTGACTGATGAAGAAG
TTAAAGCCCGAGAATCAAGACTCCGTGCTGCGCTAAAGGGAGATGCAGAGTTTCGGGT
AAAAGATGGTGCCTCAATAGAAGTTGCACAGGTATATTCGTAGAACCATTTCAATAGTAC
TTGTAATTCTCCTGGGGAACATATTTTGGCCTAGTGTAACCCCCAAATGACATACTAGTT
GTGTGTTTTTTATACTTCTGCTTGCAGTATAATCCACCATTTACTCTTCCGTTCACACGTC
GGAATGAGATTAGCCTGGAAGTTGAAAGGGAACAGGAATAGCTAGTCAGTGTGCAGTA
TATTGCAGATAAATCCGTGCACTGATGAAACCAGAGAAACAAAACATATATGGTGTAAAT
AAATTATATATATATGTATATATATTTGGTGATTGCTTGACATTTTGGTAACAAGGTTA
TGTACATGCACAGAAATGTAAGGTCATTTATGCTTCAACTCTATAATAACACGTTGTCTT
TAATACTC

FIG. 27 (Continued)

Nitab4.5_0009023g0010.2 coding sequence (SEQ ID No. 24):

ATGCTTCTGTGCTCACCTTCTTCCATTTCTGCTCACAATCTTAGCAGAAACAGAACCAGA
CCTTCGCCTATCAATTCTATGGCAGTTGACAGAAGCAGCTCCCGCGTTGCCACAACTGC
TTCGCAGCGGAGAAACGGCACGTCAGCTCTCGAAGCTCGCATCTCCTCGTCATCGCT
CTCGCCTCCCAAACCTCTTCTCTCTCAGAAACTTCTGACGGAATTGGCTGGTGAAAC
CGCGAAATACGTGTTACCGAAGAGGATATTCGAAAGTCGGACTTTAGAGGAAGCTTTGA
TGTCTGTGCCGGATCTGGAGACAGTGAAATTCAATGTTTTGAAACGCAGTGATCAGTAT
GAAATAAGGGAAGTTGAGCCTTACTTTGTTGCTGAGGCTACAATGCCTGGGAAGTATGG
GTTTGACTTTAATGGTGCATCTCAATCCTTCAACACATTGGCTGAGTACTTGTTTGGTAA
GAACACGAAGAAGGAGAGCATGGCGATGACAACACCAGTTATCACTCGTAGAACTCAA
TCTGATGGGGAGAGGATGGAAATGACTACTCCAGTGATAACTAAACGGGTGGAAGATC
AAGGAAAGTGGAGGATGTCCTTTGTCATGCCCTCAAAGTATGGTTCAGACTTGCCACTA
CCAAAGGATTCCTCCGTAACTATCAAGGAGGTGCCTAGGAAAACTGTCGCCGTTGTTG
CTTTTTCAGGTTTTGTGACTGATGAAGAAGTTAAAGCCCGAGAATCAAGACTCCGTGCT
GCGCTAAAGGGAGATGCAGAGTTTCGGGTAAAAGATGGTGCCTCAATAGAAGTTGCAC
AGTATAATCCACCATTTACTCTTCCGTTCACACGTCGGAATGAGATTAGCCTGGAAGTT
GAAAGGGAACAGGAATAG

FIG. 28

300-nucleotide cDNA fragment (SEQ ID No. 25):
GTAAGAACACAAAGAAGGAAAGTATGGCGATGACAACACCCGTAATCACTCGTAGAACT
CAATCTGATGGGGAGAAGATGGAAATGACTACTTCAGTGATAACTAAAAGGGTGGAAGA
TCAAGGAAAGTGGAGGATGTCCTTTGTCATGCCCTCAAAGTATGGTTCGGACTTGCCAC
TACCAAAGGATTCCTCCGTAACTATCAAGGAGGTGCCTAGGAAAACTGTCGCCGTTGTT
GCTTTTTCAGGTTTTGTGACTGATGAAGAAGTTAAAGCCCGAGAATCAAGACTATGTGC
TGCGT

FIG. 29

TRV1 (SEQ ID No. 26):
GTCTCAGAAGACCAAAGGGCTATTGAGACTTTTCAACAAAGGGTAATTTCGGGAAACCT
CCTCGGATTCCATTGCCCAGCTATCTGTCACTTCATCGAAGGACAGTAGAAAGGAAG
GTGGCTCCTACAAATGCCATCATTGCGATAAAGGAAAGGCTATCATTCAAGATGCCTCT
GCCGACAGTGGTCCCAAAGATGGACCCCACCCACGAGGAGCATCGTGGAAAAAGAA
GACGTCCCAACCACGTCTTCAAAGCAAGTGGATTGATGTGACATCTCCACTGACGTAAG
GGATGACGCACAATCCCACTATCCTTCGCAAGACCCTTCTTCTATATAAGGAAGTTCATT
TCATTTGGAGAGGACAGCCCAAGCTTTCTAGAGGATCCATAAAACATTTCAATCCTTTGA
ACGCGGGTAGAACGTGCTAATTGGATTTTGGTGAGAACGCGGTAGAACGTACTTATCACC
TACAGTTTTATTTTGTTTTCTTTTTGGTTTAATCTATCCAGCTTAGTACCGAGTGGGGGA
AAGTGACTGGTGTGCCTAAAACCTTTTCTTTGATACTTTGTAAAATACATACAGATACA

FIG. 30

```
ATGGCGAACGGTAACTTCAAGTTGTCTCAATTGCTCAATGTGGACGAGATGTCTGCTGA
GCAGAGGAGTCATTTCTTTGACTTGATGCTGACTAAACCTGATTGTGAGATCGGGCAAA
TGATGCAAGAGTTGTTGTTGATAAAGTCGATGACATGATTAGAGAAAGAAAGACTAAA
GATCCAGTGATTGTTCATGAAGTTCTTTCTCAGAAGGAACAGAACAAGTTGATGGAAATT
TATCCTGAATTCAATATCGTGTTTAAAGACGACAAAAACATGGTTCATGGGTTTGCGGCT
GCTGAGCGAAAACTACAAGCTTTATTGCTTTTAGATAGAGTTCCTGCTCTGCAAGAGGT
GGATGACATCGGTGGTCAATGGTCGTTTTGGGTAACTAGAGGTGAGAAAAGGATTCATT
CCTGTTGTCCAAATCTAGATATTCGGGATGATCAGAGAGAAATTTCTCGACAGATATTTC
TTACTGCTATTGGTGATCAAGCTAGAAGTGGTAAGAGACAGATGTCGGAGAATGAGCTG
TGGATGTATGACCAATTTCGTGAAATATTGCTGCGCCTAACGCGGTTAGGTGCAATAA
TACATATCAGGGTTGTACATGTAGGGGTTTTCTGATGGTAAGAAGAAAGGCGCGCAGT
ATGCGATAGCTCTTCACAGCCTGTATGACTTCAAGTTGAAAGACTTGATGGCTACTATG
GTTGAGAAGAAAACTAAAGTGGTTCATGCTGCTATGCTTTTTGCTCCTGAAAGTATGTTA
GTGGACGAAGGTCCATTACCTTCTGTTGACGGTTACTACATGAAGAAGAACGGGAAGAT
CTATTTCGGTTTTGAGAAAGATCCTTCCTTTTCTTACATTCATGACTGGGAAGAGTACAA
GAAGTATCTACTGGGGAAGCCAGTGAGTTACCAAGGGAATGTGTTCTACTTCGAACCGT
GGCAGGTGAGAGGAGACACAATGCTTTTTTCGATCTACAGGATAGCTGGAGTTCCGAG
GAGGTCTCTATCATCGCAAGAGTACTACCGAAGAATATATATCAGTAGATGGGAAAGCA
TGGTTGTTGTCCCAATTTTCGATCTGGTCGAATCAACGCGAGAGTTGGTCAAGAAAGAC
CTGTTTGTAGAGAAACAATTCATGGACAAGTGTTTGGATTACATAGCTAGGTTATCTGAC
CAGCAGCTGACCATAAGCAATGTTAAATCATACTTGAGTTCAAATAATTGGGTCTTATTC
ATAAACGGGGCGGCCGTGAAGAACAAGCAAAGTGTAGATTCTCGAGATTTACAGTTGTT
GGCTCAAACTTTGCTAGTGAAGGAACAAGTGGCGAGACCTGTCATGAGGGAGTTGCGT
GAAGCAATTCTGACTGAGACGAAACCTATCACGTCATTGACTGATGTGCTGGGTTTAAT
ATCAAGAAAACTGTGGAAGCAGTTTGCTAACAAGATCGCAGTCGGCGGATTCGTTGGC
ATGGTTGGTACTCTAATTGGATTCTATCCAAAGAAGGTACTAACCTGGGCGAAGGACAC
ACCAAATGGTCCAGAACTATGTTACGAGAACTCGCACAAAACCAAGGTGATAGTATTTC
TGAGTGTTGTGTATGCCATTGGAGGAATCACGCTTATGCGTCGAGACATCCGAGATGG
ACTGGTGAAAAAACTATGTGATATGTTTGATATCAAACGGGGGGCCCATGTCTTAGACG
TTGAGAATCCGTGCCGCTATTATGAAATCAACGATTTCTTTAGCAGTCTGTATTCGGCAT
CTGAGTCCGGTGAGACCGTTTTACCAGATTTATCCGAGGTAAAAGCCAAGTCTGATAAG
CTATTGCAGCAGAAGAAAGAAATCGCTGACGAGTTTCTAAGTGCAAAATTCTCTAACTAT
TCTGGCAGTTCGGTGAGAACTTCTCCACCATCGGTGGTCGGTTCATCTCGAAGCGGAC
TGGGTCTGTTGTTGGAAGACAGTAACGTGCTGACCCAAGCTAGAGTTGGAGTTTCAAG
AAAGGTAGACGATGAGGAGATCATGGAGCAGTTTCTGAGTGGTCTTATTGACACTGAAG
CAGAAATTGACGAGGTTGTTTCAGCCTTTTCAGCTGAATGTGAAAGAGGGGAAACAAGC
GGTACAAGGTGTTGTGTAAACCTTTAACGCCACCAGGATTTGAGAACGTGTTGCCAGC
TGTCAAACCTTTGGTCAGCAAAGGAAAAACGGTCAAACGTGTCGATTACTTCCAAGTGA
TGGGAGGTGAGAGATTACCAAAAAGGCCGGTTGTCAGTGGAGACGATTCTGTGGACGC
TAGAAGAGAGTTTCTGTACTACTTAGATGCGGAGAGAGTCGCTCAAAATGATGAAATTA
TGTCTCTGTATCGTGACTATTCGAGAGGAGTTATTCGAACTGGAGGTCAGAATTACCCG
CACGGACTGGGAGTGTGGGATGTGGAGATGAAGAACTGGTGCATACGTCCAGTGGTC
ACTGAACATGCTTATGTGTTCCAACCAGACAAACGTATGGATGATTGGTCGGGATACTT
AGAAGTGGCTGTTTGGGAACGAGGTATGTTGGTCAACGACTTCGCGGTCGAAAGGATG
AGTGATTATGTCATAGTTTGCGATCAGACGTATCTTTGCAATAACAGGTAATAATCCTCT
CTCTTGATATTTTAAATTATAGAATTAATTAGTTTACTTTATTCTTTACTATATGATTTAAA
TAGTTTAATCTTGTTTTTGAGTAAACTATTCGATTTTGATATTTGTATTCGTCCTACAAAG
TTGGAAATACTGATGATATTTTCTTTTGAACGTGATACCTACCAATACTAATCTTACGGAA
TCTTTTAATAGAGCACTAATCAACATGGAACTAAAGACCAATTCTTAAGTGTCTCTGTTG
TACAGTTCATTTTAGTAGTGCGTTTAAGTATTATTATCTCCCTTCATGCGGGCAATTAT
GTAGATTAAAATCGAATTATATAAAATTTACATAAGTCTAAGTCTAGGGTCTCCAGCTA
ATTGTTATTTTTTAACGATGTTGACTAAAGCAATAACGACGTTGACTTGTGTTAAACAG
GTTGATCTTGGACAATTTAAGTGCCCTGGATCTAGGACCAGTTAACTGTTCTTTTGAATT
AGTTGACGGTGTACCTGGTTGTGGTAAGTCGACAATGATTGTCAACTCAGCTAATCCTT
GTGTCGATGTGGTTCTCTCTACTGGGAGAGCAGCAACCGACGACTTGATCGAGAGATT
```

FIG. 30 (Continued)

```
CGCGAGCAAAGGTTTTCCATGCAAATTGAAAAGGAGAGTGAAGACGGTTGATTCTTTTT
TGATGCATTGTGTCGATGGTTCTTTAACCGGAGACGTGTTGCATTTCGACGAAGCTCTC
ATGGCCCATGCTGGTATGGTGTACTTTTGCGCTCAGATAGCTGGTGCTAAACGATGTAT
CTGTCAAGGAGATCAGAATCAAATTTCTTTCAAGCCTAGGGTATCTCAAGTTGATTTGAG
GTTTTCTAGTCTGGTCGGAAAGTTTGACATTGTTACAGAAAAAGAGAAACTTACAGAAG
TCCAGCAGATGTGGCTGCCGTATTGAACAAGTACTATACTGGAGATGTCAGAACACATA
ACGCGACTGCTAATTCGATGACGGTGAGGAAGATTGTGTCTAAAGAACAGGTTTCTTTG
AAGCCTGGTGCTCAGTACATAACTTTCCTTCAGTCTGAGAAGAAGGAGTTGGTAAATTT
GTTGGCATTGAGGAAAGTGGCAGCTAAAGTGAGTACAGTACACGAGTCGCAAGGAGAG
ACATTCAAAGATGTAGTCCTAGTCAGGACGAAACCTACGGATGACTCAATCGCTAGAGG
TCGGGAGTACTTAATCGTGGCATTGTCGCGTCACACACAATCACTTGTGTATGAAACTG
TGAAAGAGGACGATGTAAGCAAAGAGATCAGGGAAAGTGCCGCGCTTACGAAGGCGG
CTTTGGCAAGATTTTTGTTACTGAGACCGTCTTATGACGGTTTCGGTCTAGGTTTGATG
TCTTTAGACATCATGAAGGGCCTTGCGCCGTTCCAGATTCAGGTACGATTACGGACTTG
GAGATGTGGTACGACGCTTTGTTTCCGGGAAATTCGTTAAGAGACTCAAGCCTAGACG
GGTATTTGGTGGCAACGACTGATTGCAATTTGCGATTAGACAATGTTACGATCAAAAGT
GGAAACTGGAAGACAAGTTTGCTGAAAAGAAACGTTTCTGAAACCGGTTATTCGTAC
TGCTATGCCTGACAAAAGGAAGACTACTCAGTTGGAGAGTTTGTTAGCATTGCAGAAAA
GGAACCAAGCGGCACCCGATCTACAAGAAATGTGCACGCGACAGTTCTAATCGAAGA
GACGATGAAGAAGCTGAAATCTGTTGTCTACGATGTGGGAAAATTCGGGCTGATCCTA
TTGTCAATAGAGCTCAAATGGAGAGATGGTGGAGAAATCAAAGCACAGCGGTACAGGC
TAAGGTAGTAGCAGATGTGAGAGAGTTACATGAAATAGACTATTCGTCTTACATGTATAT
GATCAAATCTGACGTGAAACCTAAGACTGATTTAACACCGCAATTTGAATACTCAGCTCT
ACAGACTGTTGTGTATCACGAGAAGTTGATCAACTCGTTGTTCGGTCCAATTTTCAAAGA
AATTAATGAACGCAAGTTGGATGCTATGCAACCACATTTTGTGTTCAACACGAGAATGA
CATCGAGTGATTTAAACGATCGAGTGAAGTTCTTAAATACGGAAGCGGCTTACGACTTT
GTTGAGATAGACATGTCTAAATTCGACAAGTCGGCAAATCGCTTCCATTTACAACTGCA
GCTGGAGATTTACAGGTTATTTGGGCTGGATGAGTGGGCGGCCTTCCTTTGGGAGGTG
TCGCACACTCAAACTACTGTGAGAGATATTCAAAATGGTATGATGGCGCATATTTGGTA
CCAACAAAGAGTGGAGATGCTGATACTTATAATGCAAATTCAGATAGAACACTGTGTG
CACTCTTGTCTGAATTACCATTGGAGAAAGCAGTCATGGTTACATATGGAGGAGATGAC
TCACTGATTGCGTTTCCTAGAGGAACGCAGTTTGTTGATCCGTGTCCAAAGTTGGCTAC
TAAGTGGAATTTCGAGTGCAAGATTTTTAAGTACGATGTCCCAATGTTTTGTGGGAAGTT
CTTGCTTAAGACGTCATCGTGTTACGAGTTCGTGCCAGATCCGGTAAAAGTTCTGACGA
AGTTGGGGAAAAAGAGTATAAAGGATGTGCAACATTTAGCCGAGATCTACATCTCGCTG
AATGATTCCAATAGAGCTCTTGGGAACTACATGGTGGTATCCAAACTGTCCGAGTCTGT
TTCAGACCGGTATTTGTACAAAGGTGATTCTGTTCATGCGCTTTGTGCGCTATGGAAGC
ATATTAAGAGTTTTACAGCTCTGTGTACATTATTCCGAGACGAAAACGATAAGGAATTGA
ACCCGGCTAAGGTTGATTGGAAGAAGGCACAGAGAGCTGTGTCAAACTTTTACGACTG
GTAATATGGAAGACAAGTCATTGGTCACCTTGAAGAAGAAGACTTTCGAAGTCTCAAAA
TTCTCAAATCTAGGGGCCATTGAATTGTTTGTGGACGGTAGGAGGAAGAGACCGAAGT
ATTTTCACAGAAGAAGAGAAACTGTCCTAAATCATGTTGGTGGGAAGAAGAGTGAACAC
AAGTTAGACGTTTTTGACCAAAGGGATTACAAAATGATTAAATCTTACGCGTTTCTAAAG
GTAGTAGGTGTACAACTAGTTGTAACATCACATCTACCTGCAGATACGCCTGGGTTCAT
TCAAATCGATCTGTTGGATTCGAGACTTACTGAGAAAGAAAGAGAGGAAAGACTATTC
AGAGATTCAAAGCTCGAGCTTGCGATAACTGTTCAGTTGCGCAGTACAAGGTTGAATAC
AGTATTTCCACACAGGAGAACGTACTTGATGTCTGGAAGGTGGGTTGTATTTCTGAGGG
CGTTCCGGTCTGTGACGGTACATACCCTTTCAGTATCGAAGTGTCGCTAATATGGGTTG
CTACTGATTCGACTAGGCGCCTCAATGTGGAAGAACTGAACAGTTCGGATTACATTGAA
GGCGATTTTACCGATCAAGAGGTTTTCGGTGAGTTCATGTCTTTGAAACAAGTGGAGAT
GAAGACGATTGAGGCGAAGTACGATGGTCCTTACAGACCAGCTACTACTAGACCTAAG
TCATTATTGTCAAGTGAAGATGTTAAGAGAGCGTCTAATAAGAAAAACTCGTCTTAATGC
ATAAAGAAATTTATTGTCAATATGACGTGTGTACTCAAGGGTTGTGTGAATGAAGTCACT
GTTCTTGGTCACGAGACGTGTAGTATCGGTCATGCTAACAAATTGCGAAAGCAAGTTGC
TGACATGGTTGGTGTCACACGTAGGTGTGCGGAAAATAATTGTGGATGGTTTGTCTGTG
```

FIG. 30 (Continued)

```
TTGTTATCAATGATTTTACTTTTGATGTGTATAATTGTTGTGGCCGTAGTCACCTTGAAAA
GTGTCGTAAACGTGTTGAAACAAGAATCGAGAAATTTGGAAACAAATTCGACGAAATC
AAGCTGAAAACATGTCTGCGACAGCTAAAAAGTCTCATAATTCGAAGACCTCTAAGAAG
AAATTCAAGAGGACAGAGAATTTGGGACACCAAAAAGATTTTAAGAGATGATGTTCCT
TTCGGGATTGATCGTTTGTTTGCTTTTTGATTTTATTTTATATTGTTATCTGTTTCTGTGTA
TAGACTGTTTGAGATTGGCGCTTGGCCGACTCATTGTCTTACCATAGGGAACGGACTT
TGTTTGTGTTGTTATTTTATTTGTATTTTATTAAAATTCTCAATGATCTGAAAAGGCCTCG
AGGCTAAGAGATTATTGGGGGGTGAGTAAGTACTTTTAAAGTGATGATGGTTACAAAGG
CAAAAGGGGTAAAACCCCTCGCCTACGTAAGCGTTATTACGCCCGGATCCCCGGGGA
GCTCGAATTCGCTGAAATCACCAGTCTCTCTACAAATCTATCTCTCTATTTTTCCA
TAAATAATGTGTGAGTAGTTTCCCGATAAGGGAAATTAGGGTTCTTATAGGGTTTCGCTC
ATGTGTTGAGCATATAAGAAACCCTTAGTATGTATTTGTATTTGTAAAATACTTCTATTAT
CAATAAAATTTCTAATTCCTAAAACCAAAATCCAGTACTAAAATCCAGATCTCCTAAAGTC
CCTATAGATCTTTGTCGTGAATATAAACCAGACACGAGACGACTAAACCTGGAGCCCAG
ACGCCGTTCGAAGCTAGAAGTACCGCTTAGGCAGGAGGCCGTTAGGGAAAGATGCTA
AGGCAGGGTTGGTTACGTTGACTCCCCCGTAGGTTTGGTTTAAATATGATGAAGTGGAC
GGAAGGAAGGAGGAAGACAAGGAAGGATAAGGTTGCAGGCCCTGTGCAAGGTAAGAA
GATGGAAATTTGATAGAGGTACGCTACTATACTTATACTATACGCTAAGGGAATGCTTGT
ATTTATACCCTATACCCCCTAATAACCCCTTATCAATTTAAGAAATAATCCGCATAAGCC
CCCGCTTAAAATTGGTATCAGAGCCATGAATAGGTCTATGACCAAAACTCAAGAGGAT
AAAACCTCACCAAAATACGAAAGAGTTCTTAACTCTAAAGATAAAAGATCTTTCAAGATC
AAAACTAGTTCCCTCACACCGGAGCATGCGATATCCTCGACCTGCAGGCATGCAAGCT
TGGCGTAATCATGGTCATAGCTGTTTCCTGTGTGAAATTGTTATCCGCTCACAATTCCAC
ACAACATACGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCCAA
AGACAAAGGGCGACATTCAACCGATTGAGGGAGGGAAGGTAAATATTGACGGAAATT
ATTCATTAAAGGTGAATTATCACCGTCACCGACTTGAGCCATTTGGGAATTAGAGCCAG
CAAAATCACCAGTAGCACCATTACCATTAGCAAGGCCGGAAACGTCACCAATGAAACCA
TCGATAGCAGCACCGTAATCAGTAGCGACAGAATCAAGTTTGCCTTTAGCGTCAGACTG
TAGCGCGTTTTCATCGGCATTTTCGGTCATAGCCCCCTTATTAGCGTTTGCCATCTTTTC
ATAATCAAAATCACCGGAACCAGAGCCACCACCGGAACCGCCTCCCTCAGAGCCGCCA
CCCTCAGAACCGCCACCCTCAGAGCCACCACCCTCAGAGCCGCCACCAGAACCACCA
CCAGAGCCGCCGCCAGCATTGACAGGAGGCCCGATCTAGTAACATAGATGACACCGC
GCGCGATAATTTATCCTAGTTTGCGCGCTATATTTTGTTTTCTATCGCGTATTAAATGTAT
AATTGCGGGACTCTAATCATAAAAACCCATCTCATAAATAACGTCATGCATTACATGTTA
ATTATTACATGCTTAACGTAATTCAACAGAAATTATATGATAATCATCGCAAGACCGGCA
ACAGGATTCAATCTTAAGAAACTTTATTGCCAAATGTTTGAACGATCGGGGATCATCCG
GGTCTGTGGCGGGAACTCCACGAAAATATCCGAACGCAGCAAGATATCGCGGTGCATC
TCGGTCTTGCCTGGGCAGTCGCCGCCGACGCCGTTGATGTGGACGCCGGGCCCGATC
ATATTGTCGCTCAGGATCGTGGCGTTGTGCTTGTCGGCCGTTGCTGTCGTAATGATATC
GGCACCTTCGACCGCCTGTTCCGCAGAGATCCCGTGGGCGAAGAACTCCAGCATGAG
ATCCCCGCGCTGGAGGATCATCCAGCCGGCGTCCCGGAAAACGATTCCGAAGCCCAA
CCTTTCATAGAAGGCGGCGGTGGAATCGAAATCTCGTGATGGCAGGTTGGGCGTCGCT
TGGTCGGTCATTTCGAACCCCAGAGTCCCGCTCAGAAGAACTCGTCAAGAAGGCGATA
GAAGGCGATGCGCTGCGAATCGGGAGCGGCGATACCGTAAAGCACGAGGAAGCGGTC
AGCCCATTCGCCGCCAAGCTCTTCAGCAATATCACGGGTAGCCAACGCTATGTCCTGA
TAGCGGTCCGCCACACCCAGCCGGCCACAGTCGATGAATCCAGAAAAGCGGCCATTTT
CCACCATGATATTCGGCAAGCAGGCATCGCCATGGGTCACGACGAGATCATCGCCGTC
GGGCATGCGCGCCTTGAGCCTGGCGAACAGTTCGGCTGGCGCGAGCCCTGATGCTC
TTCGTCCAGATCATCCTGATCGACAAGACCGGCTTCCATCCGAGTACGTGCTCGCTCG
ATGCGATGTTTCGCTTGGTGGTCGAATGGGCAGGTAGCCGGATCAAGCGTATGCAGCC
GCCGCATTGCATCAGCCATGATGGATACTTTCTCGGCAGGAGCAAGGTGAGATGACAG
GAGATCCTGCCCCGGCACTTCGCCCAATAGCAGCCAGTCCCTTCCCGCTTCAGTGACA
ACGTCGAGCACAGCTGCGCAAGGAACGCCCGTCGTGGCCAGCCACGATAGCCGCGCT
```

FIG. 30 (Continued)

```
GCCTCGTCCTGCAGTTCATTCAGGGCACCGGACAGGTCGGTCTTGACAAAAAGAACCG
GGCGCCCTGCGCTGACAGCCGGAACACGGCGGCATCAGAGCAGCCGATTGTCTGTT
GTGCCCAGTCATAGCCGAATAGCCTCTCCACCCAAGCGGCCGGAGAACCTGCGTGCA
ATCCATCTTGTTCAATCATGCGAAACGATCCAGATCCGGTGCAGATTATTTGGATTGAG
AGTGAATATGAGACTCTAATTGGATACCGAGGGGAATTTATGGAACGTCAGTGGAGCAT
TTTTGACAAGAAATATTTGCTAGCTGATAGTGACCTTAGGCGACTTTTGAACGCGCAATA
ATGGTTTCTGACGTATGTGCTTAGCTCATTAAACTCCAGAAACCCGCGGCTGAGTGGCT
CCTTCAACGTTGCGGTTCTGTCAGTTCCAAACGTAAAACGGCTTGTCCCGCGTCATCGG
CGGGGGTCATAACGTGACTCCCTTAATTCTCCGCTCATGATCAGATTGTCGTTTCCCGC
CTTCAGTTTAAACTATCAGTGTTTGACAGGATATATTGGCGGGTAAACCTAAGAGAAAA
GAGCGTTTATTAGAATAATCGGATATTTAAAAGGGCGTGAAAAGGTTTATCCGTTCGTC
CATTTGTATGTGCATGCCAACCACAGGGTTCCCCAGATCTGGCGCCGGCCAGCGAGAC
GAGCAAGATTGGCCGCCGCCCGAAACGATCCGACAGCGCGCCCAGCACAGGTGCGCA
GGCAAATTGCACCAACGCATACAGCGCCAGCAGAATGCCATAGTGGGCGGTGACGTC
GTTCGAGTGAACCAGATCGCGCAGGAGGCCCGGCAGCACCGGCATAATCAGGCCGAT
GCCGACAGCGTCGAGCGCGACAGTGCTCAGAATTACGATCAGGGGTATGTTGGGTTTC
ACGTCTGGCCTCCGGACCAGCCTCCGCTGGTCCGATTGAACGCGCGGATTCTTTATCA
CTGATAAGTTGGTGGACATATTATGTTTATCAGTGATAAAGTGTCAAGCATGACAAAGTT
GCAGCCGAATACAGTGATCCGTGCCGCCTGGACCTGTTGAACGAGGTCGGCGTAGA
CGGTCTGACGACACGCAAACTGGCGGAACGGTTGGGGGTTCAGCAGCCGGCGCTTTA
CTGGCACTTCAGGAACAAGCGGGCGCTGCTCGACGCACTGGCCGAAGCCATGCTGGC
GGAGAATCATACGCATTCGGTGCCGAGAGCCGACGACGACTGGCGCTCATTTCTGATC
GGGAATGCCCGCAGCTTCAGGCAGGCGCTGCTCGCCTACCGCGATGGCGCGCGCATC
CATGCCGGCACGCGACCGGGCGCACCGCAGATGGAAACGGCCGACGCGCAGCTTCG
CTTCCTCTGCGAGGCGGGTTTTTCGGCCGGGGACGCCGTCAATGCGCTGATGACAATC
AGCTACTTCACTGTTGGGGCCGTGCTTGAGGAGCAGGCCGGCGACAGCGATGCCGGC
GAGCGCGGCGGCACCGTTGAACAGGCTCCGCTCTCGCCGCTGTTGCGGGCCGCGATA
GACGCCTTCGACGAAGCCGGTCCGGACGCAGCGTTCGAGCAGGGACTCGCGGTGATT
GTCGATGGATTGGCGAAAAGGAGGCTCGTTGTCAGGAACGTTGAAGGACCGAGAAAG
GGTGACGATTGATCAGGACCGCTGCCGGAGCGCAACCCACTCACTACAGCAGAGCCA
TGTAGACAACATCCCCTCCCCCTTTCCACCGCGTCAGACGCCCGTAGCAGCCCGCTAC
GGGCTTTTTCATGCCCTGCCCTAGCGTCCAAGCCTCACGGCCGCGCTCGGCCTCTCTG
GCGGCCTTCTGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCTGACGAGCATCAC
AAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCCGCTGCATAACCCTG
CTTCGGGGTCATTATAGCGATTTTTCGGTATATCCATCCTTTTCGCACGATATACAGG
ATTTTGCCAAAGGGTTCGTGTAGACTTTCCTTGGTGTATCCAACGGCGTCAGCCGGGC
AGGATAGGTGAAGTAGGCCCACCCGCGAGCGGGTGTTCCTTCTTCACTGTCCCTTATT
CGCACCTGGCGGTGCTCAACGGGAATCCTGCTCTGCGAGGCTGGCCGGCTACCGCCG
GCGTAACAGATGAGGGCAAGCGGATGGCTGATGAAACCAAGCCAACCAGGAAGGGCA
GCCCACCTATCAAGGTGTACTGCCTTCCAGACGAACGAAGAGCGATTGAGGAAAGGC
GGCGGCGGCCGGCATGAGCCTGTCGGCCTACCTGCTGGCCGTCGGCCAGGGCTACA
AAATCACGGGCGTCGTGGACTATGAGCACGTCCGCGAGCTGGCCCGCATCAATGGCG
ACCTGGGCCGCCTGGGCGGCCTGCTGAAACTCTGGCTCACCGACGACCCGCGCACGG
CGCGGTTCGGTGATGCCACGATCCTCGCCCTGCTGGCGAAGATCGAAGAGAAGCAGG
ACGAGCTTGGCAAGGTCATGATGGGCGTGGTCCGCCCGAGGGCAGAGCCATGACTTT
TTTAGCCGCTAAAACGGCCGGGGGTGCGCGTGATTGCCAAGCACGTCCCCATGCGC
TCCATCAAGAAGAGCGACTTCGCGGAGCTGGTGAAGTACATCACCGACGAGCAAGGCA
AGACCGAGCGCCTTTGCGACGCTCACCGGGCTGGTTGCCCTCGCCGCTGGGCTGGCG
GCCGTCTATGGCCCTGCAAACGCGCCAGAAACGCCGTCGAAGCCGTGTGCGAGACAC
CGCGGCCGCCGGCGTTGTGGATACCTCGCGGAAAACTTGGCCCTCACTGACAGATGA
```

FIG. 30 (Continued)

```
GGGGCGGACGTTGACACTTGAGGGGCCGACTCACCCGGCGCGGCGTTGACAGATGA
GGGGCAGGCTCGATTTCGGCCGGCGACGTGGAGCTGGCCAGCCTCGCAAATCGGCG
AAAACGCCTGATTTTACGCGAGTTTCCCACAGATGATGTGGACAAGCCTGGGGATAAGT
GCCCTGCGGTATTGACACTTGAGGGGCGCGACTACTGACAGATGAGGGGCGCGATCC
TTGACACTTGAGGGGCAGAGTGCTGACAGATGAGGGGCGCACCTATTGACATTTGAGG
GGCTGTCCACAGGCAGAAAATCCAGCATTTGCAAGGGTTTCCGCCCGTTTTCGGCCA
CCGCTAACCTGTCTTTTAACCTGCTTTTAAACCAATATTTATAAACCTTGTTTTTAACCAG
GGCTGCGCCTGTGCGCGTGACCGCGCACGCCGAAGGGGGTGCCCCCCCTTCTCG
AACCCTCCCGGCCCGCTAACGCGGGCCTCCCATCCCCCAGGGGCTGCGCCCTCGG
CCGCGAACGGCCTCACCCCAAAAATGGCAGCGCTGGCAGTCCTTGCCATTGCCGGGA
TCGGGGCAGTAACGGGATGGGCGATCAGCCCGAGCGCGACGCCCGGAAGCATTGAC
GTGCCGCAGGTGCTGGCATCGACATTCAGCGACCAGGTGCCGGGCAGTGAGGGCGG
CGGCCTGGGTGGCGGCCTGCCCTTCACTTCGGCCGTCGGGGCATTCACGGACTTCAT
GGCGGGGCCGGCAATTTTTACCTTGGGCATTCTTGGCATAGTGGTCGCGGGTGCCGT
GCTCGTGTTCGGGGGTGCGATAAACCCAGCGAACCATTTGAGGTGATAGGTAAGATTA
TACCGAGGTATGAAAACGAGAATTGGACCTTTACAGAATTACTCTATGAAGCGCCATAT
TTAAAAAGCTACCAAGACGAAGAGGATGAAGAGGATGAGGAGGCAGATTGCCTTGAAT
ATATTGACAATACTGATAAGATAATATATCTTTTATATAGAAGATATCGCCGTATGTAAGG
ATTTCAGGGGGCAAGGCATAGGCAGCGCGCTTATCAATATATCTATAGAATGGGCAAA
GCATAAAAACTTGCATGGACTAATGCTTGAAACCCAGGACAATAACCTTATAGCTTGTAA
ATTCTATCATAATTGGGTAATGACTCCAACTTATTGATAGTGTTTATGTTCAGATAATGC
CCGATGACTTTGTCATGCAGCTCCACCGATTTTGAGAACGACAGCGACTTCCGTCCCA
GCCGTGCCAGGTGCTGCCTCAGATTCAGGTTATGCCGCTCAATTCGCTGCGTATATCG
CTTGCTGATTACGTGCAGCTTTCCCTTCAGGCGGGATTCATACAGCGGCCAGCCATCC
GTCATCCATATCACCACGTCAAAGGGTGACAGCAGGCTCATAAGACGCCCCAGCGTCG
CCATAGTGCGTTCACCGAATACGTGCGCAACAACCGTCTTCCGGAGACTGTCATACGC
GTAAAACAGCCAGCGCTGGCGCGATTTAGCCCCGACATAGCCCCACTGTTCGTCCATT
TCCGCGCAGACGATGACGTCACTGCCCGGCTGTATGCGCGAGGTTACCGACTGCGGC
CTGAGTTTTTAAGTGACGTAAAATCGTGTTGAGGCCAACGCCCATAATGCGGGCTGTT
GCCCGGCATCAACGCCATTCATGGCCATATCAATGATTTTCTGGTGCGTACCGGGTT
GAGAAGCGGTGTAAGTGAACTGCAGTTGCCATGTTTTACGGCAGTGAGAGCAGAGATA
GCGCTGATGTCCGGCGGTGCTTTTGCCGTTACGCACCACCCCGTCAGTAGCTGAACAG
GAGGGACAGCTGATAGACACAGAAGCCACTGGAGCACCTCAAAAACACCATCATACAC
TAAATCAGTAAGTTGGCAGCATCACCCATAATTGTGGTTTCAAAATCGGCTCCGTCGAT
ACTATGTTATACGCCAACTTTGAAAACAACTTTGAAAAAGCTGTTTTCTGGTATTTAAGG
TTTTAGAATGCAAGGAACAGTGAATTGGAGTTCGTCTTGTTATAATTAGCTTCTTGGGGT
ATCTTTAAATACTGTAGAAAAGAGGAAGGAAATAATAAATGGCTAAAATGAGAATATCAC
CGGAATTGAAAAAACTGATCGAAAATACCGCTGCGTAAAAGATACGGAAGGAATGTCT
CCTGCTAAGGTATATAAGCTGGTGGGAGAAAATGAAAACCTATATTTAAAAATGACGGA
CAGCCGGTATAAAGGGACCACCTATGATGTGGAACGGGAAAAGGACATGATGCTATGG
CTGGAAGGAAAGCTGCCTGTTCCAAAGGTCCTGCACTTTGAACGGCATGATGGCTGGA
GCAATCTGCTCATGAGTGAGGCCGATGGCGTCCTTTGCTCGGAAGAGTATGAAGATGA
ACAAAGCCCTGAAAAGATTATCGAGCTGTATGCGGAGTGCATCAGGCTCTTTCACTCCA
TCGACATATCGGATTGTCCCTATACGAATAGCTTAGACAGCCGCTTAGCCGAATTGGAT
TACTTACTGAATAACGATCTGGCCGATGTGGATTGCGAAAACTGGGAAGAAGACACTCC
ATTTAAAGATCCGCGCGAGCTGTATGATTTTTAAAGACGGAAAAGCCCGAAGAGGAAC
TTGTCTTTTCCCACGGCGACCTGGGAGACAGCAACATCTTTGTGAAAGATGGCAAAGTA
AGTGGCTTTATTGATCTTGGGAGAAGCGGCAGGGCGGACAAGTGGTATGACATTGCCT
TCTGCGTCCGGTCGATCAGGGAGGATATCGGGAAGAACAGTATGTCGAGCTATTTTT
TGACTTACTGGGGATCAAGCCTGATTGGGAGAAAATAAATATTATATTTTACTGGATGA
ATTGTTTTAGTACCTAGATGTGGCGCAACGATGCCGGCGACAAGCAGGAGCGCACCGA
CTTCTTCCGCATCAAGTGTTTTGGCTCTCAGGCCGAGGCCCACGGCAAGTATTTGGGC
AAGGGGTCGCTGGTATTCGTGCAGGGCAAGATTCGGAATACCAAGTACGAGAAGGACG
GCCAGACGGTCTACGGGACCGACTTCATTGCCGATAAGGTGGATTATCTGGACACCAA
GGCACCAGGCGGGTCAAATCAGGAATAAGGGCACATTGCCCCGGCGTGAGTCGGGGC
```

FIG. 30 (Continued)

```
AATCCCGCAAGGAGGGTGAATGAATCGGACGTTTGACCGGAAGGCATACAGGCAAGAA
CTGATCGACGCGGGGTTTTCCGCCGAGGATGCCGAAACCATCGCAAGCCGCACCGTC
ATGCGTGCGCCCCGCGAAACCTTCCAGTCCGTCGGCTCGATGGTCCAGCAAGCTACG
GCCAAGATCGAGCGCGACAGCGTGCAACTGGCTCCCCCTGCCCTGCCCGCGCCATCG
GCCGCCGTGGAGCGTTCGCGTCGTCTCGAACAGGAGGCGGCAGGTTTGGCGAAGTCG
ATGACCATCGACACGCGAGGAACTATGACGACCAAGAAGCGAAAAACCGCCGGCGAG
GACCTGGCAAAACAGGTCAGCGAGGCCAAGCAGGCCGCGTTGCTGAAACACACGAAG
CAGCAGATCAAGGAAATGCAGCTTTCCTTGTTCGATATTGCGCCGTGGCCGGACACGA
TGCGAGCGATGCCAAACGACACGGCCCGCTCTGCCCTGTTCACCACGCGCAACAAGA
AAATCCCGCGCGAGGCGCTGCAAAACAAGGTCATTTTCCACGTCAACAAGGACGTGAA
GATCACCTACACCGGCGTCGAGCTGCGGGCCGACGATGACGAACTGGTGTGGCAGCA
GGTGTTGGAGTACGCGAAGCGCACCCCTATCGGCGAGCCGATCACCTTCACGTTCTAC
GAGCTTTGCCAGGACCTGGGCTGGTCGATCAATGGCCGGTATTACACGAAGGCCGAG
GAATGCCTGTCGCGCCTACAGGCGACGGCGATGGGCTTCACGTCCGACCGCGTTGGG
CACCTGGAATCGGTGTCGCTGCTGCACCGCTTCCGCGTCCTGGACCGTGGCAAGAAAA
CGTCCCGTTGCCAGGTCCTGATCGACGAGGAAATCGTCGTGCTGTTTGCTGGCGACCA
CTACACGAAATTCATATGGGAGAAGTACCGCAAGCTGTCGCCGACGGCCCGACGGATG
TTCGACTATTTCAGCTCGCACCGGGAGCCGTACCCGCTCAAGCTGGAAACCTTCCGCC
TCATGTGCGGATCGGATTCCACCCGCGTGAAGAAGTGGCGCGAGCAGGTCGGCGAAG
CCTGCGAAGAGTTGCGAGGCAGCGGCCTGGTGGAACACGCCTGGGTCAATGATGACC
TGGTGCATTGCAAACGCTAGGGCCTTGTGGGGTCAGTTCCGGCTGGGGGTTCAGCAG
CCAGCGCTTTACTGGCATTTCAGGAACAAGCGGGCACTGCTCGACGCACTTGCTTCGC
TCAGTATCGCTCGGGACGCACGGCGCGCTCTACGAACTGCCGATAAACAGAGGATTAA
AATTGACAATTGTGATTAAGGCTCAGATTCGACGGCTTGGAGCGGCCGACGTGCAGGA
TTTCCGCGAGATCCGATTGTCGGCCCTGAAGAAAGCTCCAGAGATGTTCGGGTCCGTT
TACGAGCACGAGGAGAAAAAGCCCATGGAGGCGTTCGCTGAACGGTTGCGAGATGCC
GTGGCATTCGGCGCCTACATCGACGGCGAGATCATTGGGCTGTCGGTCTTCAAACAGG
AGGACGGCCCCAAGGACGCTCACAAGGCGCATCTGTCCGGCGTTTTCGTGGAGCCCG
AACAGCGAGGCCGAGGGGTCGCCGGTATGCTGCTGCGGGCGTTGCCGGCGGGTTTAT
TGCTCGTGATGATCGTCCGACAGATTCCAACGGGAATCTGGTGGATGCGCATCTTCAT
CCTCGGCGCACTTAATATTTCGCTATTCTGGAGCTTGTTGTTTATTTCGGTCTACCGCCT
GCCGGGCGGGGTCGCGGCGACGGTAGGCGCTGTGCAGCCGCTGATGGTCGTGTTCA
TCTCTGCCGCTCTGCTAGGTAGCCCGATACGATTGATGGCGGTCCTGGGGGCTATTTG
CGGAACTGCGGGCGTGGCGCTGTTGGTGTTGACACCAAACGCAGCGCTAGATCCTGT
CGGCGTCGCAGCGGGCCTGGCGGGGCGGTTTCCATGGCGTTCGGAACCGTGCTGA
CCCGCAAGTGGCAACCTCCCGTGCCTCTGCTCACCTTTACCGCCTGGCAACTGGCGGC
CGGAGGACTTCTGCTCGTTCCAGTAGCTTTAGTGTTTGATCCGCCAATCCCGATGCCTA
CAGGAACCAATGTTCTCGGCCTGGCGTGGCTCGGCCTGATCGGAGCGGGTTTAACCTA
CTTCCTTTGGTTCCGGGGGATCTCGCGACTCGAACCTACAGTTGTTTCCTTACTGGGCT
TTCTCAGCCCCAGATCTGGGGTCGATCAGCCGGGGATGCATCAGGCCGACAGTCGGA
ACTTCGGGTCCCCGACCTGTACCATTCGGTGAGCAATGGATAGGGAGTTGATATCGT
CAACGTTCACTTCTAAAGAAATAGCGCCACTCAGCTTCCTCAGCGGCTTTATCCAGCGA
TTTCCTATTATGTCGGCATAGTTCTCAAGATCGACAGCCTGTCACGGTTAAGCGAGAAA
TGAATAAGAAGGCTGATAATTCGGATCTCTGCGAGGGAGATGATATTTGATCACAGGCA
GCAACGCTCTGTCATCGTTACAATCAACATGCTACCCTCCGCGAGATCATCCGTGTTTC
AAACCCGGCAGCTTAGTTGCCGTTCTTCCGAATAGCATCGGTAACATGAGCAAAGTCTG
CCGCCTTACAACGGCTCTCCCGCTGACGCCGTCCGGACTGATGGGCTGCCTGTATC
GAGTGGTGATTTTGTGCCGAGCTGCCGGTCGGGAGCTGTTGGCTGGCTGGTGGCAG
GATATATTGTGGTGTAAACAAATTGACGCTTAGACAACTTAATAACACATTGCGGACGTT
TTTAATGTACTGGGGTGGTTTTTCTTTTCACCAGTGAGACGGGCAACAGCTGATTGCCC
TTCACCGCCTGGCCCTGAGAGAGTTGCAGCAAGCGGTCCACGCTGGTTTGCCCCAGC
AGGCGAAAATCCTGTTTGATGGTGGTTCCGAAATCGGCAAAATCCCTTATAAATCAAAA
GAATAGCCCGAGATAGGGTTGAGTGTTGTTCCAGTTTGGAACAAGAGTCCACTATTAAA
GAACGTGGACTCCAACGTCAAAGGGCGAAAAACCGTCTATCAGGGCGATGGCCCACTA
CGTGAACCATCACCCAAATCAAGTTTTTGGGGTCGAGGTGCCGTAAAGCACTAAATCG
```

FIG. 30 (Continued)

GAACCCTAAAGGGAGCCCCGATTTAGAGCTTGACGGGGAAAGCCGGCGAACGTGGC
GAGAAAGGAAGGGAAGAAAGCGAAAGGAGCGGGCGCCATTCAGGCTGCGCAACTGTT
GGGAAGGGCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGACGTTGTAA
AACGACGGCCAGTGAATTCGAGCTCGGTACCCCCC

FIG. 30 (Continued)

TRV2 (SEQ ID No. 27):
GTCTCAGAAGACCAAAGGGCTATTGAGACTTTTCAACAAAGGGTAATTTCGGGAAACCT
CCTCGGATTCCATTGCCCAGCTATCTGTCACTTCATCGAAAGGACAGTAGAAAAGGAAG
GTGGCTCCTACAAATGCCATCATTGCGATAAAGGAAAGGCTATCATTCAAGATGCCTCT
GCCGACAGTGGTCCCAAAGATGGACCCCCACCCACGAGGAGCATCGTGGAAAAAGAA
GACGTCCCAACCACGTCTTCAAAGCAAGTGGATTGATGTGACATCTCCACTGACGTAAG
GGATGACGCACAATCCCACTATCCTTCGCAAGACCCTTCTTCTATATAAGGAAGTTCATT
TCATTTGGAGAGGACAGCCCAAGCTTTCTAGAGGATCCATAAACATTTCAATCCTTTGA
ACGCGGTAGAACGTGCTAATTGGATTTTGGTGAGAACGCGGTAGAACGTACTTATCACC
TACAGTTTTATTTTGTTTTTCTTTTGGTTTAATCTATCCAGCTTAGTACCGAGTGGGGA
AAGTGACTGGTGTGCCTAAAACCTTTTCTTTGATACTTTGTAAAATACATACAGATACA
ATGGCGAACGGTAACTTCAAGTTGTCTCAATTGCTCAATGTGGACGAGATGTCTGCTGA
GCAGAGGAGTCATTTCTTTGACTTGATGCTGACTAAACCTGATTGTGAGATCGGGCAAA
TGATGCAAAGAGTTGTTGTTGATAAAGTCGATGACATGATTAGAGAAAGAAAGACTAAA
GATCCAGTGATTGTTCATGAAGTTCTTTCTCAGAAGGAACAGAACAAGTTGATGGAAATT
TATCCTGAATTCAATATCGTGTTTAAAGACGACAAAAACATGGTTCATGGGTTTGCGGCT
GCTGAGCGAAAACTACAAGCTTTATTGCTTTTAGATAGAGTTCCTGCTCTGCAAGAGGT
GGATGACATCGGTGGTCAATGGTCGTTTGGGTAACTAGAGGTGAGAAAAGGATTCATT
CCTGTTGTCCAAATCTAGATATTCGGGATGATCAGAGAGAAATTTCTCGACAGATATTTC
TTACTGCTATTGGTGATCAAGCTAGAAGTGGTAAGAGACAGATGTCGGAGAATGAGCTG
TGGATGTATGACCAATTTCGTGAAAATATTGCTGCGCCTAACGCGGTTAGGTGCAATAA
TACATATCAGGGTTGTACATGTAGGGGTTTTTCTGATGGTAAGAAGAAAGGCGCGCAGT
ATGCGATAGCTCTTCACAGCCTGTATGACTTCAAGTTGAAAGACTTGATGGCTACTATG
GTTGAGAAGAAAACTAAAGTGGTTCATGCTGCTATGCTTTTGCTCCTGAAAGTATGTTA
GTGGACGAAGGTCCATTACCTTCTGTTGACGGTTACTACATGAAGAAGAACGGGAAGAT
CTATTTCGGTTTTGAGAAAGATCCTTCCTTTTCTTACATTCATGACTGGGAAGAGTACAA
GAAGTATCTACTGGGGAAGCCAGTGAGTTACCAAGGGAATGTGTTCTACTTCGAACCGT
GGCAGGTGAGAGGAGACACAATGCTTTTTTCGATCTACAGGATAGCTGGAGTTCCGAG
GAGGTCTCTATCATCGCAAGAGTACTACCGAAGAATATATATCAGTAGATGGGAAAGCA
TGGTTGTTGTCCCAATTTTCGATCTGGTCGAATCAACGCGAGAGTTGGTCAAGAAAGAC
CTGTTTGTAGAGAAACAATTCATGGACAAGTGTTTGGATTACATAGCTAGGTTATCTGAC
CAGCAGCTGACCATAAGCAATGTTAAATCATACTTGAGTTCAAATAATTGGGTCTTATTC
ATAAACGGGGCGGCCGTGAAGAACAAGCAAAGTGTAGATTCTCGAGATTTACAGTTGTT
GGCTCAAACTTTGCTAGTGAAGGAACAAGTGGCGAGACCTGTCATGAGGGAGTTGCGT
GAAGCAATTCTGACTGAGACGAAACCTATCACGTCATTGACTGATGTGCTGGGTTTAAT
ATCAAGAAAACTGTGGAAGCAGTTTGCTAACAAGATCGCAGTCGGCGGATTCGTTGGC
ATGGTTGGTACTCTAATTGGATTCTATCCAAAGAAGGTACTAACCTGGGCGAAGGACAC
ACCAAATGGTCCAGAACTATGTTACGAGAACTCGCACAAAACCAAGGTGATAGTATTTC
TGAGTGTTGTGTATGCCATTGGAGGAATCACGCTTATGCGTCGAGACATCCGAGATGG
ACTGGTGAAAAAACTATGTGATATGTTTGATATCAAACGGGGGCCCATGTCTTAGACG
TTGAGAATCCGTGCCGCTATTATGAAATCAACGATTTCTTTAGCAGTCTGTATTCGGCAT
CTGAGTCCGGTGAGACCGTTTTACCAGATTTATCCGAGGTAAAAGCCAAGTCTGATAAG
CTATTGCAGCAGAAGAAAGAAATCGCTGACGAGTTTCTAAGTGCAAAATTCTCTAACTAT
TCTGGCAGTTCGGTGAGAACTTCTCCACCATCGGTGGTCGGTTCATCTCGAAGCGGAC
TGGGTCTGTTGTTGGAAGACAGTAACGTGCTGACCCAAGCTAGAGTTGGAGTTTCAAG
AAAGGTAGACGATGAGGAGATCATGGAGCAGTTTCTGAGTGGTCTTATTGACACTGAAG
CAGAAATTGACGAGGTTGTTTCAGCCTTTTCAGCTGAATGTGAAAGAGGGGAAACAAGC

FIG. 31

```
GGTACAAAGGTGTTGTGTAAACCTTTAACGCCACCAGGATTTGAGAACGTGTTGCCAGC
TGTCAAACCTTTGGTCAGCAAAGGAAAACGGTCAAACGTGTCGATTACTTCCAAGTGA
TGGGAGGTGAGAGATTACCAAAAGGCCGGTTGTCAGTGGAGACGATTCTGTGGACGC
TAGAAGAGAGTTTCTGTACTACTTAGATGCGGAGAGAGTCGCTCAAAATGATGAAATTA
TGTCTCTGTATCGTGACTATTCGAGAGGAGTTATTCGAACTGGAGGTCAGAATTACCCG
CACGGACTGGGAGTGTGGGATGTGGAGATGAAGAACTGGTGCATACGTCCAGTGGTC
ACTGAACATGCTTATGTGTTCCAACCAGACAAACGTATGGATGATTGGTCGGGATACTT
AGAAGTGGCTGTTTGGGAACGAGGTATGTTGGTCAACGACTTCGCGGTCGAAAGGATG
AGTGATTATGTCATAGTTTGCGATCAGACGTATCTTTGCAATAACAGGTAATAATCCTCT
CTCTTGATATTTTTAAATTATAGAATTAATTAGTTTACTTTATTCTTTACTATATGATTTAAA
TAGTTTAATCTTGTTTTTGAGTAAACTATTCGATTTGATATTTGTATTCGTCCTACAAAG
TTGGAAATACTGATGATATTTTCTTTTGAACGTGATACCTACCAATACTAATCTTACGGAA
TCTTTTAATAGAGCACTAATCAACATGGAACTAAAGACCAATTCTTAAGTGTCTCTGTTG
TACAGTTCATTTTAGTAGTGCGTTTAAGTATTATTATCTCCCTTCATGCGGGGCAATTAT
GTAGATTAAAATCGAATTATATAAAATTTACATAAGTCTAAGTCTAGGGTCTCCAGCTA
ATTGTTATTTTTTTAACGATGTTGACTAAAGCAATAACGACGTTGACTTGTGTTAAACAG
GTTGATCTTGGACAATTTAAGTGCCCTGGATCTAGGACCAGTTAACTGTTCTTTTGAATT
AGTTGACGGTGTACCTGGTTGTGGTAAGTCGACAATGATTGTCAACTCAGCTAATCCTT
GTGTCGATGTGGTTCTCTACTGGGAGAGCAGCAACCGACGACTTGATCGAGAGATT
CGCGAGCAAAGGTTTTCCATGCAAATTGAAAAGGAGAGTGAAGACGGTTGATTCTTTTT
TGATGCATTGTGTCGATGGTTCTTTAACCGGAGACGTGTTGCATTCGACGAAGCTCTC
ATGGCCCATGCTGGTATGGTGTACTTTTGCGCTCAGATAGCTGGTGCTAAACGATGTAT
CTGTCAAGGAGATCAGAATCAAATTTCTTTCAAGCCTAGGGTATCTCAAGTTGATTTGAG
GTTTTCTAGTCTGGTCGGAAAGTTTGACATTGTTACAGAAAAAGAGAAACTTACAGAAG
TCCAGCAGATGTGGCTGCCGTATTGAACAAGTACTATACTGGAGATGTCAGAACACATA
ACGCGACTGCTAATTCGATGACGGTGAGGAAGATTGTGTCTAAAGAACAGGTTTCTTTG
AAGCCTGGTGCTCAGTACATAACTTTCCTTCAGTCTGAGAAGAAGGAGTTGGTAAATTT
GTTGGCATTGAGGAAAGTGGCAGCTAAAGTGAGTACAGTACACGAGTCGCAAGGAGAG
ACATTCAAAGATGTAGTCCTAGTCAGGACGAAACCTACGGATGACTCAATCGCTAGAGG
TCGGGAGTACTTAATCGTGGCATTGTCGCGTCACACACAATCACTTGTGTATGAAACTG
TGAAAGAGGACGATGTAAGCAAAGAGATCAGGGAAAGTGCCGCGCTTACGAAGGCGG
CTTTGGCAAGATTTTTTGTTACTGAGACCGTCTTATGACGGTTTCGGTCTAGGTTTGATG
TCTTTAGACATCATGAAGGGCCTTGCGCCGTTCCAGATTCAGGTACGATTACGGACTTG
GAGATGTGGTACGACGCTTTGTTTCCGGGAAATTCGTTAAGAGACTCAAGCCTAGACG
GGTATTTGGTGGCAACGACTGATTGCAATTTGCGATTAGACAATGTTACGATCAAAAGT
GGAAACTGGAAAGACAAGTTTGCTGAAAAAGAAACGTTTCTGAAACCGGTTATTCGTAC
TGCTATGCCTGACAAAAGGAAGACTACTCAGTTGGAGAGTTTGTTAGCATTGCAGAAAA
GGAACCAAGCGGCACCCGATCTACAAGAAATGTGCACGCGACAGTTCTAATCGAAGA
GACGATGAAGAAGCTGAAATCTGTTGTCTACGATGTGGGAAAAATTCGGGCTGATCCTA
TTGTCAATAGAGCTCAAATGGAGAGATGGTGGAGAAATCAAAGCACAGCGGTACAGGC
TAAGGTAGTAGCAGATGTGAGAGAGTTACATGAAATAGACTATTCGTCTTACATGTATAT
GATCAAATCTGACGTGAAACCTAAGACTGATTTAACACCGCAATTTGAATACTCAGCTCT
ACAGACTGTTGTGTATCACGAGAAGTTGATCAACTCGTTGTTCGGTCCAATTTTCAAAGA
AATTAATGAACGCAAGTTGGATGCTATGCAACCACATTTTGTGTTCAACACGAGAATGA
CATCGAGTGATTTAAACGATCGAGTGAAGTTCTTAAATACGGAAGCGGCTTACGACTTT
GTTGAGATAGACATGTCTAAATTCGACAAGTCGGCAAATCGCTTCCATTTACAACTGCA
GCTGGAGATTTACAGGTTATTTGGGCTGGATGAGTGGGCGGCCTTCCTTTGGGAGGTG
TCGCACACTCAAACTACTGTGAGAGATATTCAAAATGGTATGATGGCGCATATTTGGTA
CCAACAAAGAGTGGAGATGCTGATACTTATAATGCAAATTCAGATAGAACACTGTGTG
CACTCTTGTCTGAATTACCATTGGAGAAAGCAGTCATGGTTACATATGGAGGAGATGAC
TCACTGATTGCGTTTCCTAGAGGAACGCAGTTTGTTGATCCGTGTCCAAAGTTGGCTAC
TAAGTGGAATTTCGAGTGCAAGATTTTAAGTACGATGTCCCAATGTTTTGTGGGAAGTT
CTTGCTTAAGACGTCATCGTGTTACGAGTTCGTGCCAGATCCGGTAAAAGTTCTGACGA
AGTTGGGGAAAAAGAGTATAAAGGATGTGCAACATTTAGCCGAGATCTACATCTCGCTG
AATGATTCCAATAGAGCTCTTGGGAACTACATGGTGGTATCCAAACTGTCCGAGTCTGT
```

FIG. 31 (Continued)

```
TTCAGACCGGTATTTGTACAAAGGTGATTCTGTTCATGCGCTTTGTGCGCTATGGAAGC
ATATTAAGAGTTTTACAGCTCTGTGTACATTATTCCGAGACGAAAACGATAAGGAATTGA
ACCCGGCTAAGGTTGATTGGAAGAAGGCACAGAGAGCTGTGTCAAACTTTTACGACTG
GTAATATGGAAGACAAGTCATTGGTCACCTTGAAGAAGAAGACTTTCGAAGTCTCAAAA
TTCTCAAATCTAGGGGCCATTGAATTGTTTGTGGACGGTAGGAGGAAGAGACCGAAGT
ATTTTCACAGAAGAAGAGAAACTGTCCTAAATCATGTTGGTGGGAAGAAGAGTGAACAC
AAGTTAGACGTTTTTGACCAAAGGGATTACAAAATGATTAAATCTTACGCGTTTCTAAAG
GTAGTAGGTGTACAACTAGTTGTAACATCACATCTACCTGCAGATACGCCTGGGTTCAT
TCAAATCGATCTGTTGGATTCGAGACTTACTGAGAAAGAAAGAGAGGAAAGACTATTC
AGAGATTCAAAGCTCGAGCTTGCGATAACTGTTCAGTTGCGCAGTACAAGGTTGAATAC
AGTATTTCCACACAGGAGAACGTACTTGATGTCTGGAAGGTGGGTTGTATTTCTGAGGG
CGTTCCGGTCTGTGACGGTACATACCCTTTCAGTATCGAAGTGTCGCTAATATGGGTTG
CTACTGATTCGACTAGGCGCCTCAATGTGGAAGAACTGAACAGTTCGGATTACATTGAA
GGCGATTTTACCGATCAAGAGGTTTTCGGTGAGTTCATGTCTTTGAAACAAGTGGAGAT
GAAGACGATTGAGGCGAAGTACGATGGTCCTTACAGACCAGCTACTACTAGACCTAAG
TCATTATTGTCAAGTGAAGATGTTAAGAGAGCGTCTAATAAGAAAAACTCGTCTTAATGC
ATAAAGAAATTTATTGTCAATATGACGTGTGTACTCAAGGGTTGTGTGAATGAAGTCACT
GTTCTTGGTCACGAGACGTGTAGTATCGGTCATGCTAACAAATTGCGAAAGCAAGTTGC
TGACATGGTTGGTGTCACACGTAGGTGTGCGGAAAATAATTGTGGATGGTTTGTCTGTG
TTGTTATCAATGATTTTACTTTTGATGTGTATAATTGTTGTGGCCGTAGTCACCTTGAAAA
GTGTCGTAAACGTGTTGAAACAAGAAATCGAGAAATTTGGAAACAAATTCGACGAAATC
AAGCTGAAAACATGTCTGCGACAGCTAAAAAGTCTCATAATTCGAAGACCTCTAAGAAG
AAATTCAAAGAGGACAGAGAATTTGGGACACCAAAAAGATTTTAAGAGATGATGTTCCT
TTCGGGATTGATCGTTTGTTTGCTTTTTGATTTTATTTTATATTGTTATCTGTTTCTGTGTA
TAGACTGTTTGAGATTGGCGCTTGGCCGACTCATTGTCTTACCATAGGGGAACGGACTT
TGTTTGTGTTGTTATTTTATTTGTATTTTATTAAAATTCTCAATGATCTGAAAAGGCCTCG
AGGCTAAGAGATTATTGGGGGGTGAGTAAGTACTTTTAAAGTGATGATGGTTACAAAGG
CAAAAGGGGTAAAACCCCTCGCCTACGTAAGCGTTATTACGCCCGGATCCCCCGGGGA
GCTCGAATTCGCTGAAATCACCAGTCTCTCTACAAATCTATCTCTCTATTTTTTCCA
TAAATAATGTGTGAGTAGTTTCCCGATAAGGGAAATTAGGGTTCTTATAGGGTTTCGCTC
ATGTGTTGAGCATATAAGAAACCCTTAGTATGTATTTGTATTTGTAAAATACTTCTATTAT
CAATAAAATTTCTAATTCCTAAAACCAAAATCCAGTACTAAAATCCAGATCTCCTAAAGTC
CCTATAGATCTTTGTCGTGAATATAAACCAGACACGAGACGACTAAACCTGGAGCCCAG
ACGCCGTTCGAAGCTAGAAGTACCGCTTAGGCAGGAGGCCGTTAGGGAAAAGATGCTA
AGGCAGGGTTGGTTACGTTGACTCCCCGTAGGTTTGGTTTAAATATGATGAAGTGGAC
GGAAGGAAGGAGGAAGACAAGGAAGGATAAGGTTGCAGGCCCTGTGCAAGGTAAGAA
GATGGAAATTTGATAGAGGTACGCTACTATACTTATACTATACGCTAAGGGAATGCTTGT
ATTTATACCCTATACCCCCTAATAACCCCTTATCAATTTAAGAAATAATCCGCATAAGCC
CCCGCTTAAAAATTGGTATCAGAGCCATGAATAGGTCTATGACCAAAACTCAAGAGGAT
AAAACCTCACCAAAATACGAAAGAGTTCTTAACTCTAAAGATAAAAGATCTTTCAAGATC
AAAACTAGTTCCCTCACACCGGAGCATGCGATATCCTCGACCTGCAGGCATGCAAGCT
TGGCGTAATCATGGTCATAGCTGTTTCCTGTGTGAATTGTTATCCGCTCACAATTCCAC
ACAACATACGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCCAA
AGACAAAGGGCGACATTCAACCGATTGAGGGAGGGAAGGTAAATATTGACGGAAATT
ATTCATTAAAGGTGAATTATCACCGTCACCGACTTGAGCCATTTGGGAATTAGAGCCAG
CAAAATCACCAGTAGCACCATTACCATTAGCAAGGCCGGAAACGTCACCAATGAAACCA
TCGATAGCAGCACCGTAATCAGTAGCGACAGAATCAAGTTTGCCTTTAGCGTCAGACTG
TAGCGCGTTTTCATCGGCATTTTCGGTCATAGCCCCCTTATTAGCGTTTGCCATCTTTTC
ATAATCAAAATCACCGGAACCAGAGCCACCACCGGAACCGCCTCCCTCAGAGCCGCCA
CCCTCAGAACCGCCACCCTCAGAGCCACCACCCTCAGAGCCGCCACCAGAACCACCA
CCAGAGCCGCCGCCAGCATTGACAGGAGGCCCGATCTAGTAACATAGATGACACCGC
GCGCGATAATTTATCCTAGTTTGCGCGCTATATTTTGTTTTCTATCGCGTATTAAATGTAT
AATTGCGGGACTCTAATCATAAAAACCCATCTCATAAATAACGTCATGCATTACATGTTA
```

```
ATTATTACATGCTTAACGTAATTCAACAGAAATTATATGATAATCATCGCAAGACCGGCA
ACAGGATTCAATCTTAAGAAACTTTATTGCCAAATGTTTGAACGATCGGGGATCATCCG
GGTCTGTGGCGGGAACTCCACGAAAATATCCGAACGCAGCAAGATATCGCGGTGCATC
TCGGTCTTGCCTGGGCAGTCGCCGCCGACGCCGTTGATGTGGACGCCGGGCCCGATC
ATATTGTCGCTCAGGATCGTGGCGTTGTGCTTGTCGGCCGTTGCTGTCGTAATGATATC
GGCACCTTCGACCGCCTGTTCCGCAGAGATCCCGTGGGCGAAGAACTCCAGCATGAG
ATCCCCGCGCTGGAGGATCATCCAGCCGGCGTCCCGGAAAACGATTCCGAAGCCCAA
CCTTTCATAGAAGGCGGCGGTGGAATCGAAATCTCGTGATGGCAGGTTGGGCGTCGCT
TGGTCGGTCATTTCGAACCCCAGAGTCCCGCTCAGAAGAACTCGTCAAGAAGGCGATA
GAAGGCGATGCGCTGCGAATCGGGAGCGGCGATACCGTAAAGCACGAGGAAGCGGTC
AGCCCATTCGCCGCCAAGCTCTTCAGCAATATCACGGGTAGCCAACGCTATGTCCTGA
TAGCGGTCCGCCACACCCAGCCGGCCACAGTCGATGAATCCAGAAAGCGGCCATTTT
CCACCATGATATTCGGCAAGCAGGCATCGCCATGGGTCACGACGAGATCATCGCCGTC
GGGCATGCGCGCCTTGAGCCTGGCAACAGTTCGGCTGGCGCGAGCCCTGATGCTC
TTCGTCCAGATCATCCTGATCGACAAGACCGGCTTCCATCCGAGTACGTGCTCGCTCG
ATGCGATGTTTCGCTTGGTGGTCGAATGGGCAGGTAGCCGGATCAAGCGTATGCAGCC
GCCGCATTGCATCAGCCATGATGGATACTTTCTCGGCAGGAGCAAGGTGAGATGACAG
GAGATCCTGCCCGGCACTTCGCCCAATAGCAGCCAGTCCCTTCCCGCTTCAGTGACA
ACGTCGAGCACAGCTGCGCAAGGAACGCCCGTCGTGGCCAGCCACGATAGCCGCGCT
GCCTCGTCCTGCAGTTCATTCAGGGCACCGGACAGGTCGGTCTTGACAAAAGAACCG
GGCGCCCTGCGCTGACAGCCGGAACACGGCGGCATCAGAGCAGCCGATTGTCTGTT
GTGCCCAGTCATAGCCGAATAGCCTCTCCACCCAAGCGGCCGGAGAACCTGCGTGCA
ATCCATCTTGTTCAATCATGCGAAACGATCCAGATCCGGTGCAGATTATTTGGATTGAG
AGTGAATATGAGACTCTAATTGGATACCGAGGGGAATTTATGGAACGTCAGTGGAGCAT
TTTTGACAAGAAATATTTGCTAGCTGATAGTGACCTTAGGCGACTTTTGAACGCGCAATA
ATGGTTTCTGACGTATGTGCTTAGCTCATTAAACTCCAGAAACCCGCGGCTGAGTGGCT
CCTTCAACGTTGCGGTTCTGTCAGTTCCAAACGTAAAACGGCTTGTCCCGCGTCATCGG
CGGGGGTCATAACGTGACTCCCTTAATTCTCCGCTCATGATCAGATTGTCGTTTCCCGC
CTTCAGTTTAAACTATCAGTGTTTGACAGGATATATTGGCGGGTAAACCTAAGAGAAAA
GAGCGTTTATTAGAATAATCGGATATTTAAAGGGCGTGAAAAGGTTTATCCGTTCGTC
CATTTGTATGTGCATGCCAACCACAGGGTTCCCCAGATCTGGCGCCGGCCAGCGAGAC
GAGCAAGATTGGCCGCCGCCCGAAACGATCCGACAGCGCGCCCAGCACAGGTGCGCA
GGCAAATTGCACCAACGCATACAGCGCCAGCAGAATGCCATAGTGGGCGGTGACGTC
GTTCGAGTGAACCAGATCGCGCAGGAGGCCCGGCAGCACCGGCATAATCAGGCCGAT
GCCGACAGCGTCGAGCGCGACAGTGCTCAGAATTACGATCAGGGGTATGTTGGGTTTC
ACGTCTGGCCTCCGGACCAGCCTCCGCTGGTCCGATTGAACGCGCGGATTCTTTATCA
CTGATAAGTTGGTGGACATATTATGTTTATCAGTGATAAAGTGTCAAGCATGACAAAGTT
GCAGCCGAATACAGTGATCCGTGCCGCCCTGGACCTGTTGAACGAGGTCGGCGTAGA
CGGTCTGACGACACGCAAACTGGCGGAACGGTTGGGGGTTCAGCAGCCGGCGCTTTA
CTGGCACTTCAGGAACAAGCGGGCGCTGCTCGACGCACTGGCCGAAGCCATGCTGGC
GGAGAATCATACGCATTCGGTGCCGAGAGCCGACGACGACTGGCGCTCATTTCTGATC
GGGAATGCCCGCAGCTTCAGGCAGGCGCTGCTCGCCTACCGCGATGGCGCGCGCATC
CATGCCGGCACGCGACCGGGCGCACCGCAGATGGAAACGGCCGACGCGCAGCTTCG
CTTCCTCTGCGAGGCGGGTTTTCGGCCGGGGACGCCGTCAATGCGCTGATGACAATC
AGCTACTTCACTGTTGGGGCCGTGCTTGAGGAGCAGGCCGGCGACAGCGATGCCGGC
GAGCGCGGCGGCACCGTTGAACAGGCTCCGCTCTCGCCGCTGTTGCGGGCCGCGATA
GACGCCTTCGACGAAGCCGGTCCGGACGCAGCGTTCGAGCAGGGACTCGCGGTGATT
GTCGATGGATTGGCGAAAAGGAGGCTCGTTGTCAGGAACGTTGAAGGACCGAGAAAG
GGTGACGATTGATCAGGACCGCTGCCGGAGCGCAACCCACTCACTACAGCAGAGCCA
TGTAGACAACATCCCCTCCCCCTTTCCACCGCGTCAGACGCCCGTAGCAGCCCGCTAC
GGGCTTTTTCATGCCCTGCCCTAGCGTCCAAGCCTCACGGCCGCGCTCGGCCTCTCTG
GCGGCCTTCTGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCAC
```

FIG. 31 (Continued)

```
AAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTTCCGCTGCATAACCCTG
CTTCGGGGTCATTATAGCGATTTTTTCGGTATATCCATCCTTTTTCGCACGATATACAGG
ATTTTGCCAAAGGGTTCGTGTAGACTTTCCTTGGTGTATCCAACGGCGTCAGCCGGGC
AGGATAGGTGAAGTAGGCCCACCCGCGAGCGGGTGTTCCTTCTTCACTGTCCCTTATT
CGCACCTGGCGGTGCTCAACGGGAATCCTGCTCTGCGAGGCTGGCCGGCTACCGCCG
GCGTAACAGATGAGGGCAAGCGGATGGCTGATGAAACCAAGCCAACCAGGAAGGGCA
GCCCACCTATCAAGGTGTACTGCCTTCCAGACGAACGAAGAGCGATTGAGGAAAAGGC
GGCGGCGGCCGGCATGAGCCTGTCGGCCTACCTGCTGGCCGTCGGCCAGGGCTACA
AAATCACGGGCGTCGTGGACTATGAGCACGTCCGCGAGCTGGCCCGCATCAATGGCG
ACCTGGGCCGCCTGGGCGGCCTGCTGAAACTCTGGCTCACCGACGACCCGCGCACGG
CGCGGTTCGGTGATGCCACGATCCTCGCCCTGCTGGCGAAGATCGAAGAGAAGCAGG
ACGAGCTTGGCAAGGTCATGATGGGCGTGGTCCGCCCGAGGGCAGAGCCATGACTTT
TTTAGCCGCTAAAACGGCCGGGGGGTGCGCGTGATTGCCAAGCACGTCCCCATGCGC
TCCATCAAGAAGAGCGACTTCGCGGAGCTGGTGAAGTACATCACCGACGAGCAAGGCA
AGACCGAGCGCCTTTGCGACGCTCACCGGGCTGGTTGCCCTCGCCGCTGGGCTGGCG
GCCGTCTATGGCCCTGCAAACGCGCCAGAAACGCCGTCGAAGCCGTGTGCGAGACAC
CGCGGCCGCCGGCGTTGTGGATACCTCGCGGAAACTTGGCCCTCACTGACAGATGA
GGGGCGGACGTTGACACTTGAGGGGCCGACTCACCCGGCGCGGCGTTGACAGATGA
GGGGCAGGCTCGATTTCGGCCGGCGACGTGGAGCTGGCCAGCCTCGCAAATCGGCG
AAAACGCCTGATTTTACGCGAGTTTCCCACAGATGATGTGGACAAGCCTGGGGATAAGT
GCCCTGCGGTATTGACACTTGAGGGGCGCGACTACTGACAGATGAGGGGCGCGATCC
TTGACACTTGAGGGGCAGAGTGCTGACAGATGAGGGGCGCACCTATTGACATTTGAGG
GGCTGTCCACAGGCAGAAAATCCAGCATTTGCAAGGGTTTCCGCCCGTTTTTCGGCCA
CCGCTAACCTGTCTTTTAACCTGCTTTTAAACCAATATTTATAAACCTTGTTTTTAACCAG
GGCTGCGCCTGTGCGCGTGACCGCGCACGCCGAAGGGGGTGCCCCCCCTTCTCG
AACCCTCCCGGCCCGCTAACGCGGGCCTCCCATCCCCCAGGGGCTGCGCCCTCGG
CCGCGAACGGCCTCACCCCAAAAATGGCAGCGCTGGCAGTCCTTGCCATTGCCGGGA
TCGGGGCAGTAACGGGATGGGCGATCAGCCCGAGCGCGACGCCCGGAAGCATTGAC
GTGCCGCAGGTGCTGGCATCGACATTCAGCGACCAGGTGCCGGGCAGTGAGGGCGG
CGGCCTGGGTGGCGGCCTGCCCTTCACTTCGGCCGTCGGGGCATTCACGGACTTCAT
GGCGGGGCCGGCAATTTTTACCTTGGGCATTCTTGGCATAGTGGTCGCGGGTGCCGT
GCTCGTGTTCGGGGGTGCGATAAACCCAGCGAACCATTTGAGGTGATAGGTAAGATTA
TACCGAGGTATGAAAACGAGAATTGGACCTTTACAGAATTACTCTATGAAGCGCCATAT
TTAAAAAGCTACCAAGACGAAGAGGATGAAGAGGATGAGGAGGCAGATTGCCTTGAAT
ATATTGACAATACTGATAAGATAATATATCTTTTATATAGAAGATATCGCCGTATGTAAGG
ATTTCAGGGGGCAAGGCATAGGCAGCGCGCTTATCAATATATCTATAGAATGGGCAAA
GCATAAAAACTTGCATGGACTAATGCTTGAAACCCAGGACAATAACCTTATAGCTTGTAA
ATTCTATCATAATTGGGTAATGACTCCAACTTATTGATAGTGTTTTATGTTCAGATAATGC
CCGATGACTTTGTCATGCAGCTCCACCGATTTTGAGAACGACAGCGACTTCCGTCCCA
GCCGTGCCAGGTGCTGCCTCAGATTCAGGTTATGCCGCTCAATTCGCTGCGTATATCG
CTTGCTGATTACGTGCAGCTTTCCCTTCAGGCGGGATTCATACAGCGGCCAGCCATCC
GTCATCCATATCACCACGTCAAAGGGTGACAGCAGGCTCATAAGACGCCCAGCGTCG
CCATAGTGCGTTCACCGAATACGTGCGCAACAACCGTCTTCCGGAGACTGTCATACGC
GTAAAACAGCCAGCGCTGGCGCGATTTAGCCCCGACATAGCCCCACTGTTCGTCCATT
TCCGCGCAGACGATGACGTCACTGCCCGGCTGTATGCGCGAGGTTACCGACTGCGGC
CTGAGTTTTTAAGTGACGTAAAATCGTGTTGAGGCCAACGCCCATAATGCGGGCTGTT
GCCCGGCATCCAACGCCATTCATGGCCATATCAATGATTTTCTGGTGCGTACCGGGTT
GAGAAGCGGTGTAAGTGAACTGCAGTTGCCATGTTTTACGGCAGTGAGAGCAGAGATA
GCGCTGATGTCCGGCGGTGCTTTTGCCGTTACGCACCACCCGTCAGTAGCTGAACAG
GAGGGACAGCTGATAGACACAGAAGCCACTGGAGCACCTCAAAAACACCATCATACAC
TAAATCAGTAAGTTGGCAGCATCACCCATAATTGTGGTTTCAAAATCGGCTCCGTCGAT
ACTATGTTATACGCCAACTTTGAAAACAACTTTGAAAAGCTGTTTTCTGGTATTTAAGG
TTTTAGAATGCAAGGAACAGTGAATTGGAGTTCGTCTTGTTATAATTAGCTTCTTGGGGT
```

FIG. 31 (Continued)

```
ATCTTTAAATACTGTAGAAAAGAGGAAGGAAATAATAAATGGCTAAAATGAGAATATCAC
CGGAATTGAAAAAACTGATCGAAAAATACCGCTGCGTAAAAGATACGGAAGGAATGTCT
CCTGCTAAGGTATATAAGCTGGTGGGAGAAAATGAAAACCTATATTTAAAAATGACGGA
CAGCCGGTATAAAGGGACCACCTATGATGTGGAACGGGAAAAGGACATGATGCTATGG
CTGGAAGGAAAGCTGCCTGTTCCAAAGGTCCTGCACTTTGAACGGCATGATGGCTGGA
GCAATCTGCTCATGAGTGAGGCCGATGGCGTCCTTTGCTCGGAAGAGTATGAAGATGA
ACAAAGCCCTGAAAAGATTATCGAGCTGTATGCGGAGTGCATCAGGCTCTTTCACTCCA
TCGACATATCGGATTGTCCCTATACGAATAGCTTAGACAGCCGCTTAGCCGAATTGGAT
TACTTACTGAATAACGATCTGGCCGATGTGGATTGCGAAAACTGGGAAGAAGACACTCC
ATTTAAAGATCCGCGCGAGCTGTATGATTTTTAAAGACGGAAAAGCCCGAAGAGGAAC
TTGTCTTTTCCCACGGCGACCTGGGAGACAGCAACATCTTTGTGAAAGATGGCAAAGTA
AGTGGCTTTATTGATCTTGGGAGAAGCGGCAGGGCGGACAAGTGGTATGACATTGCCT
TCTGCGTCCGGTCGATCAGGGAGGATATCGGGAAGAACAGTATGTCGAGCTATTTTT
TGACTTACTGGGGATCAAGCCTGATTGGGAGAAAATAAATATTATATTTTACTGGATGA
ATTGTTTTAGTACCTAGATGTGGCGCAACGATGCCGGCGACAAGCAGGAGCGCACCGA
CTTCTTCCGCATCAAGTGTTTTGGCTCTCAGGCCGAGGCCCACGGCAAGTATTTGGGC
AAGGGGTCGCTGGTATTCGTGCAGGGCAAGATTCGGAATACCAAGTACGAGAAGGACG
GCCAGACGGTCTACGGGACCGACTTCATTGCCGATAAGGTGGATTATCTGGACACCAA
GGCACCAGGCGGGTCAAATCAGGAATAAGGGCACATTGCCCCGGCGTGAGTCGGGGC
AATCCCGCAAGGAGGTGAATGAATCGGACGTTTGACCGGAAGGCATACAGGCAAGAA
CTGATCGACGCGGGGTTTTCCGCCGAGGATGCCGAAACCATCGCAAGCCGCACCGTC
ATGCGTGCGCCCCGCGAAACCTTCCAGTCCGTCGGCTCGATGGTCCAGCAAGCTACG
GCCAAGATCGAGCGCGACAGCGTGCAACTGGCTCCCCCTGCCCTGCCCGCGCCATCG
GCCGCCGTGGAGCGTTCGCGTCGTCTCAACAGGAGGCGGCAGGTTTGGCGAAGTCG
ATGACCATCGACACGCGAGGAACTATGACGACCAAGAAGCGAAAAACCGCCGGCGAG
GACCTGGCAAAACAGGTCAGCGAGGCCAAGCAGGCCGCGTTGCTGAAACACACGAAG
CAGCAGATCAAGGAAATGCAGCTTTCCTTGTTCGATATTGCCGTGGCCGGACACGA
TGCGAGCGATGCCAAACGACACGGCCCGCTCTGCCCTGTTCACCACGCGCAACAAGA
AAATCCCGCGCGAGGCGCTGCAAAACAAGGTCATTTTCCACGTCAACAAGGACGTGAA
GATCACCTACACCGGCGTCGAGCTGCGGGCCGACGATGACGAACTGGTGTGGCAGCA
GGTGTTGGAGTACGCGAAGCGCACCCCTATCGGCGAGCCGATCACCTTCACGTTCTAC
GAGCTTTGCCAGGACCTGGGCTGGTCGATCAATGGCCGGTATTACACGAAGGCCGAG
GAATGCCTGTCGCGCCTACAGGCGACGGCGATGGGCTTCACGTCCGACCGCGTTGGG
CACCTGGAATCGGTGTCGCTGCTGCACCGCTTCCGCGTCCTGGACCGTGGCAAGAAAA
CGTCCCGTTGCCAGGTCCTGATCGACGAGGAAATCGTCGTGCTGTTTGCTGGCGACCA
CTACACGAAATTCATATGGGAGAAGTACCGCAAGCTGTCGCCGACGGCCCGACGGATG
TTCGACTATTTCAGCTCGCACCGGGAGCCGTACCCGCTCAAGCTGGAAACCTTCCGCC
TCATGTGCGGATCGGATTCCACCCGCGTGAAGAAGTGGCGCGAGCAGGTCGGCGAAG
CCTGCGAAGAGTTGCGAGGCAGCGGCCTGGTGGAACACGCCTGGGTCAATGATGACC
TGGTGCATTGCAAACGCTAGGGCCTTGTGGGTCAGTTCCGGCTGGGGGTTCAGCAG
CCAGCGCTTTACTGGCATTTCAGGAACAAGCGGGCACTGCTCGACGCACTTGCTTCGC
TCAGTATCGCTCGGGACGCACGGCGCGCTCTACGAACTGCCGATAAACAGAGGATTAA
AATTGACAATTGTGATTAAGGCTCAGATTCGACGGCTTGGAGCGGCCGACGTGCAGGA
TTTCCGCGAGATCCGATTGTCGGCCCTGAAGAAAGCTCCAGAGATGTTCGGGTCCGTT
TACGAGCACGAGGAGAAAAAGCCCATGGAGGCGTTCGCTGAACGGTTGCGAGATGCC
GTGGCATTCGGCGCCTACATCGACGGCGAGATCATTGGGCTGTCGGTCTTCAAACAGG
AGGACGGCCCCAAGGACGCTCACAAGGCGCATCTGTCCGGCGTTTTCGTGGAGCCCG
AACAGCGAGGCCGAGGGGTCGCCGGTATGCTGCTGCGGGCGTTGCCGGCGGGTTTAT
TGCTCGTGATGATCGTCCGACAGATTCCAACGGGAATCTGGTGGATGCGCATCTTCAT
CCTCGGCGCACTTAATATTTCGCTATTCTGGAGCTTGTTGTTTATTTCGGTCTACCGCCT
GCCGGGCGGGGTCGCGGCGACGGTAGGCGCTGTGCAGCCGCTGATGGTCGTGTTCA
TCTCTGCCGCTCTGCTAGGTAGCCCGATACGATTGATGGCGGTCCTGGGGGCTATTTG
CGGAACTGCGGGCGTGGCGCTGTTGGTGTTGACACCAAACGCAGCGCTAGATCCTGT
CGGCGTCGCAGCGGGCCTGGCGGGGCGGTTTCCATGGCGTTCGGAACCGTGCTGA
CCCGCAAGTGGCAACCTCCCGTGCCTCTGCTCACCTTTACCGCCTGGCAACTGGCGGC
```

```
CGGAGGACTTCTGCTCGTTCCAGTAGCTTTAGTGTTTGATCCGCCAATCCCGATGCCTA
CAGGAACCAATGTTCTCGGCCTGGCGTGGCTCGGCCTGATCGGAGCGGGTTTAACCTA
CTTCCTTTGGTTCCGGGGGATCTCGCGACTCGAACCTACAGTTGTTTCCTTACTGGGCT
TTCTCAGCCCCAGATCTGGGGTCGATCAGCCGGGGATGCATCAGGCCGACAGTCGGA
ACTTCGGGTCCCCGACCTGTACCATTCGGTGAGCAATGGATAGGGGAGTTGATATCGT
CAACGTTCACTTCTAAAGAAATAGCGCCACTCAGCTTCCTCAGCGGCTTTATCCAGCGA
TTTCCTATTATGTCGGCATAGTTCTCAAGATCGACAGCCTGTCACGGTTAAGCGAGAAA
TGAATAAGAAGGCTGATAATTCGGATCTCTGCGAGGGAGATGATATTTGATCACAGGCA
GCAACGCTCTGTCATCGTTACAATCAACATGCTACCCTCCGCGAGATCATCCGTGTTTC
AAACCCGGCAGCTTAGTTGCCGTTCTTCCGAATAGCATCGGTAACATGAGCAAAGTCTG
CCGCCTTACAACGGCTCTCCCGCTGACGCCGTCCCGGACTGATGGGCTGCCTGTATC
GAGTGGTGATTTTGTGCCGAGCTGCCGGTCGGGGAGCTGTTGGCTGGCTGGTGGCAG
GATATATTGTGGTGTAAACAAATTGACGCTTAGACAACTTAATAACACATTGCGGACGTT
TTTAATGTACTGGGGTGGTTTTTCTTTTCACCAGTGAGACGGGCAACAGCTGATTGCCC
TTCACCGCCTGGCCCTGAGAGAGTTGCAGCAAGCGGTCCACGCTGGTTTGCCCCAGC
AGGCGAAAATCCTGTTTGATGGTGGTTCCGAAATCGGCAAAATCCCTTATAAATCAAAA
GAATAGCCCGAGATAGGGTTGAGTGTTGTTCCAGTTTGGAACAAGAGTCCACTATTAAA
GAACGTGGACTCCAACGTCAAAGGGCGAAAAACCGTCTATCAGGGCGATGGCCCACTA
CGTGAACCATCACCCAAATCAAGTTTTTTGGGGTCGAGGTGCCGTAAAGCACTAAATCG
GAACCCTAAAGGGAGCCCCCGATTTAGAGCTTGACGGGGAAAGCCGGCGAACGTGGC
GAGAAAGGAAGGGAAGAAAGCGAAGGAGCGGGCGCCATTCAGGCTGCGCAACTGTT
GGGAAGGGCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGACGTTGTAA
AACGACGGCCAGTGAATTCGAGCTCGGTACCCCCC
```

FIG. 31 (Continued)

SEQUENCE LISTING

<160> NUMBER OF SEQ ID NOS: 27

<210> SEQ ID NO 1
<211> LENGTH: 167

```
<212> TYPE: PRT
<213> ORGANISM: Nicotiana tabacum

<400> SEQUENCE: 1

Met Leu Gly Lys Tyr Gly Phe Asp Phe Asn Gly Ala Ser Gln Ser Phe
1               5                   10                  15

Asn Thr Leu Ala Glu Tyr Leu Phe Gly Lys Asn Thr Lys Lys Glu Ser
                20                  25                  30

Met Ala Met Thr Thr Pro Val Ile Thr Arg Arg Thr Gln Ser Asp Gly
            35                  40                  45

Glu Lys Met Glu Met Thr Thr Ser Val Ile Thr Lys Arg Val Glu Asp
        50                  55                  60

Gln Gly Lys Trp Arg Met Ser Phe Val Met Pro Ser Lys Tyr Gly Ser
65                  70                  75                  80

Asp Leu Pro Leu Pro Lys Asp Ser Ser Val Thr Ile Lys Glu Val Pro
                85                  90                  95

Arg Lys Thr Val Ala Val Val Ala Phe Ser Gly Phe Val Thr Asp Glu
                100                 105                 110

Glu Val Lys Ala Arg Glu Ser Arg Leu Cys Ala Ala Leu Lys Gly Asp
            115                 120                 125

Ala Glu Phe Arg Val Lys Asp Gly Ala Ser Ile Glu Val Ala Gln Tyr
        130                 135                 140

Asn Pro Pro Phe Thr Leu Pro Phe Thr Arg Arg Asn Glu Ile Ser Leu
145                 150                 155                 160

Glu Val Glu Arg Lys Gln Glu
                165

<210> SEQ ID NO 2
<211> LENGTH: 2592
<212> TYPE: DNA
<213> ORGANISM: Nicotiana tabacum

<400> SEQUENCE: 2
taatattgtg actttaaaca gccttacttt gcggcggagg ctacaatgct tgggaaatat      60
gggtttgatt ttaatggtgc atctcaatcc ttcaacacat tggcagagta cttgtttggt     120
aaggtagtta aggtactta  tagagagtca aacttagatc gcctccaacc acattgtaat     180
ggtgttcttc tttggttatg ttctctttct tgatgatttc cagaacacaa agaaggaaag     240
tatggcgatg acaacacccg taatcactcg tagaactcaa tctgatgggg agaagatgga     300
aatgactact tcagtgataa ctaaaagggt acagatcgtc ttctggtcat tccttttttcc    360 cttttagttc ttgtgctgtg tatatttact acgtcattcg tgacatatgg tttggttact     420
aatgcgcatg catttttgta tgacatggtg ttactcaaaa tattaactgc taatctattg     480
aagttgagtc accacataac ttgggaaatg gtaaatgaaa actactctca aaatgaccac     540
aggtcgtcaa atggaaatac agacttcact gattctattg aaaagaaaca tcatctggtt    600
acctatcaca aggaaaacat ttaagctctt gatctggaat tgataaaaga ggacatgtgc     660
tttagattga gatttgagga tctttcaatt gtatgctagg cctatacgcc gggggatggg     720
ggtacatata aaacgtaaac attctggatg cttatagttt aaacctgtaa tactctcaga     780
tagtattgca aatccatatc tgggagagtg gaaactgtta gattccaggt ttgattatgt     840
tgcatggatc cttcaaacaa gtgtgacatg ggtgtgggta cttcttgcag gttcttcaaa     900
gtatactaat aattaggaaa aaaatgcaca aaactcctat cagatactta cacacacaca     960
aacacacaca catggtatat acctataggt ttgtccatat aatgcgatat ctaatcttag    1020
```

-continued

```
tctagaacaa gtgtcgaatg gaataacagt cacaaagaac gatcttctta atgataaagg      1080
ttatggtacg aataaaatat acacccctat ataaacgata acacattttc ttgtaattct      1140
taagttaatt tctgagaata acattttgta acataaaaaa ccaatttat gtgaaaatgg       1200 gccctccata tagattggca tcctataaga attcttact cccagaaacc ttgaaaccgg       1260
atttagtcca ttctagaaaa gaaaaactca ttttagcttg atgtatgatc ctatgttata      1320
gggcttaaac ccagaagaaa aaagataaa cattgtgtat atagttttg tatttcggaa        1380 tgtcgtgcgc acatattttc accaaaaaat atcccactg gaatttcatt aagaatttca       1440
ttaggtggaa gatcaaggaa agtggaggat gtcctttgtc atgccctcaa agtatggttc      1500
ggacttgcca ctaccaaagg attcctccgt aactatcaag gaggtgccta ggaaaactgt      1560
cgccgttgtt gcttttcag gtttgtgatt tcagatttta gcatgtcaat ataaagttct       1620
attttatatg atgatgatat gagttgagct tatcgaaaga agtgaggatt catagcgccg      1680
accccaactt tgtgggactg aggcatagtt gttgctgtta atacaaagtt ctagacagat      1740
ttgcattaaa gtttatttga aattcaatat cctagtaatt ggaagccgag ctctgtctca      1800
ttggtctata gaagtaaatc ttgtttaagt ttacttagtg cttattgat agcttctctt       1860 gttttgatat gagagaaact tgcatctagt tgtattttct gtgcctttcc tttgacgtgc      1920
tatatgcctg ttgtggtaga tagcaatttc cattcagagt tcaaaagcaa aaacatttag      1980
gaattctatt ttcaagtttt atatcctaac ttagctagct ttctcccatt tgattcacca     2040
aaggttttgt gactgatgaa gaagttaaag cccgagaatc aagactatgt gctgcgttaa     2100
agggagatgc agagtttcgg gtaaaagatg gtgcctcgat agaagttgca caggtatatt     2160
cgtagaacca tttcaatagt acttgtaatt ctcctgggga acagattttg gcctagtgta     2220
acccccaagt gacatactag ttgtgttttt tttatacttc tgcttgcagt ataatccacc     2280
attcactctt ccattcacac gtcggaatga gattagcctg gaagttgaaa ggaaacagga     2340
atagctagtc agggtgcaac atcttgcaga taaatccgtg cactgatata tagaaaccag     2400
tgaagcaaaa catatatggc gtaaatatat tgtgttgata tactccttgt atatatatat     2460
atgtatatat atatatttgg tgattgcttg acattttggt aacaaggtta tgtacatgca     2520
cagaaatgta aggtcactta tgcttcaact ctgaatataa taacactgtc tttaatactc     2580
ttctcgatcc tc                                                          2592
```

<210> SEQ ID NO 3
<211> LENGTH: 504
<212> TYPE: DNA
<213> ORGANISM: Nicotiana tabacum

<400> SEQUENCE: 3

```
atgcttggga aatatgggtt tgattttaat ggtgcatctc aatccttcaa cacattggca       60
gagtacttgt ttggtaagaa cacaaagaag gaaagtatgg cgatgacaac acccgtaatc     120
actcgtagaa ctcaatctga tggggagaag atggaaatga ctacttcagt gataactaaa     180
agggtggaag atcaaggaaa gtggaggatg tcctttgtca tgccctcaaa gtatggttcg     240
gacttgccac taccaaagga ttcctccgta actatcaagg aggtgcctag gaaaactgtc     300
gccgttgttg cttttcagg ttttgtgact gatgaagaag ttaaagcccg agaatcaaga     360
ctatgtgctg cgttaaaggg agatgcagag tttcgggtaa agatggtgc ctcgatagaa     420 gttgcacagt ataatccacc attcactctt ccattcacac gtcggaatga gattagcctg     480
```

```
gaagttgaaa ggaaacagga atag                                          504
```

<210> SEQ ID NO 4
<211> LENGTH: 199
<212> TYPE: PRT
<213> ORGANISM: Nicotiana tabacum

<400> SEQUENCE: 4

```
Met Gly Met Ile Leu Gly Lys Ile Cys Val Glu Thr Pro Lys Tyr Glu
1               5                   10                  15

Leu Ile Gln Ser Thr Ala Asp Tyr Glu Ile Arg Lys Tyr Pro Ala Ser
            20                  25                  30

Val Ile Ala Gln Val Thr Tyr Asp Pro Thr Gln Phe Lys Gly Asn Lys
        35                  40                  45

Asp Gly Gly Phe Met Leu Leu Ala Asn Tyr Ile Gly Ala Leu Gly Asn
    50                  55                  60

Pro Gln Asn Ala Lys Pro Glu Thr Ile Ala Met Thr Ala Pro Val Ile
65                  70                  75                  80

Thr Lys Ser Ser Glu Lys Ile Ala Met Thr Ala Pro Val Val Thr Lys
                85                  90                  95

Asn Gly Asp Gly Glu Ser Asn Met Val Thr Met Gln Phe Ile Leu Pro
            100                 105                 110

Ala Lys Tyr Thr Lys Ala Glu Glu Ala Pro Lys Pro Leu Asp Glu Arg
        115                 120                 125

Val Met Ile Lys Glu Glu Gly Glu Arg Lys Phe Gly Val Val Gln Phe
    130                 135                 140

Ser Gly Thr Ala Ser Asp Lys Ala Val Lys Glu Lys Val Glu Asn Leu
145                 150                 155                 160

Arg Lys Cys Leu Glu Arg Asp Gly Tyr Lys Ile Ile Gly Asp Tyr Glu
                165                 170                 175

Leu Ala Arg Tyr Asn Pro Pro Trp Thr Ile Pro Pro Phe Lys Thr Asn
            180                 185                 190

Glu Val Met Ile Pro Val Glu
        195
```

<210> SEQ ID NO 5
<211> LENGTH: 1204
<212> TYPE: DNA
<213> ORGANISM: Nicotiana tabacum

<400> SEQUENCE: 5

```
ctgatttcgt aatgcagatt ggtttaacct tttacagagc aagtcaattt taacggcgat   60
actaaaatta ctgtgtgcac aaatagtgca caaactattc ctgtataggt ttatctccac  120
cagcttatgg tgtaaacgtg gcaaaacaaa ctccacagca tacttccctg atctgccgcc  180
actcattttg cagcaaacaa aaccccttc ccaagtcttc tgatcgtctc tttccgaatt   240
cccacatgaa acttcctctt ttcttccctt atatgtaaca attcacagcc cccatttact  300
atcaaaacat tctcaaattc cattttcaat aactaatttc ccattccatc acaaaaatgg  360
gcatgatttt gggtaagatc tgtgtggaaa caccaaaata cgagttgatt caatctacag  420
ctgactacga aatccgcaaa tacccagcat ctgttatagc acaagtcaca tatgatccaa  480
cccagttcaa aggaaacaaa gacggtgggt ttatgctatt agccaattac atcggcgcac  540
tgggcaatcc tcaaaacgct aagcctgaaa caatcgccat gacagctcct gtaatcacca  600
aatcgtccga aaaaatcgcg atgactgcac cagtagtgac taagaatggt gacggagaga  660
```

```
gcaatatggt gacgatgcag tttattttac ctgcaaagta tacaaaagct gaagaggcac    720
ctaagccgtt ggatgagaga gtgatgatta agaagaagg tgaaggaag tttggtgtgg    780 tgcagtttag tgggactgca agtgataaag cggtaaaaga gaaagtggag aatttaagga    840
aatgtttaga gagagatggg tataagataa ttggtgatta tgagttggct aggtataatc    900
ctccttggac aattcctcca tttaagacca atgaagttat gattccagtt gagtgagctg    960
aaaatggtgt agtaaagaaa acatgagac tgctgtgaag ctagctcgtg acatgaacct    1020
actttatctg gtgtttatta ttgaattgtg tatttcttgt ttatatgttt acgctgttga   1080
caatgtcttt gcatacacta gtgtcaatta ttcatagtta taattagcac atattttgtc   1140
ttatttttat actttgccat agtaaagcag taaaactgat gcagttttgc aagcatctaa   1200
tgtg                                                                 1204

<210> SEQ ID NO 6
<211> LENGTH: 600
<212> TYPE: DNA
<213> ORGANISM: Nicotiana tabacum

<400> SEQUENCE: 6
atgggcatga ttttgggtaa gatctgtgtg gaaacaccaa atacgagtt gattcaatct     60 acagctgact acgaaatccg caaataccca gcatctgtta tagcacaagt cacatatgat   120
ccaacccagt tcaaaggaaa caaagacggt gggtttatgc tattagccaa ttacatcggc   180
gcactgggca atcctcaaaa cgctaagcct gaaacaatcg ccatgacagc tcctgtaatc   240
accaaatcgt ccgaaaaaat cgcgatgact gcaccagtag tgactaagaa tggtgacgga   300
gagagcaata tggtgacgat gcagtttatt ttacctgcaa agtatacaaa agctgaagag   360
gcacctaagc cgttggatga gagtgatg attaaagaag aaggtgaaag aagtttggt    420 gtggtgcagt ttagtgggac tgcaagtgat aaagcggtaa agagaaagt ggagaattta    480 aggaaatgtt tagagagaga tgggtataag ataattggtg attatgagtt ggctaggtat   540
aatcctcctt ggacaattcc tccatttaag accaatgaag ttatgattcc agttgagtga   600

<210> SEQ ID NO 7
<211> LENGTH: 230
<212> TYPE: PRT
<213> ORGANISM: Nicotiana tabacum

<400> SEQUENCE: 7

Met Gln Gly Val Met Asn Phe Phe Thr Arg Leu Ser Phe Phe Leu Ile
1               5                   10                  15

Leu Val Ser Lys Leu Ser Asn Gly His Trp Thr Asn Asn Leu Lys Leu
                20                  25                  30

Asp Phe Tyr Pro Pro Thr Cys Asn Arg Ile Glu Cys Pro Asn Tyr Asp
            35                  40                  45

Leu Ile Gln Ser Gly Lys Asp Tyr Glu Ile Arg Arg Tyr Asn Ser Ser
        50                  55                  60

Met Trp Met Ser Thr Ala Pro Ile Asp Asp Ile Asn Leu Tyr Ser Ala
65                  70                  75                  80

Thr Arg Thr Gly Phe Leu Arg Leu Phe Asp Tyr Ile Gln Gly Lys Asn
                85                  90                  95

Ser Tyr Gln Glu Lys Ile Glu Met Thr Ala Pro Val Ile Thr Gln Val
            100                 105                 110

Lys Pro Ser Asp Gly Pro Phe Cys Ala Ser Ser Phe Val Val Ser Phe
        115                 120                 125
```

```
Tyr Val Pro Lys Lys Asn Gln Pro Asn Pro Pro Ala Lys Gly Leu
130                 135                 140

His Val Gln Lys Trp Ser Asn Thr Tyr Val Ala Val Arg Gln Phe Gly
145                 150                 155                 160

Gly Phe Val Ala Asp Val Asp Val Ala Lys Glu Ala Ala Leu Ser
                165                 170                 175

Ala Ser Ile Ala Asp Thr Lys Trp Ala Ala Val Glu Lys Ser His
                180                 185                 190

Ala Ala Asp Asn Thr Thr Met Tyr Thr Val Ala Gly Tyr Asn Ser Pro
            195                 200                 205

Phe Glu Phe Lys Asp Arg Val Asn Glu Ile Trp Phe Thr Phe Asp Leu
        210                 215                 220

Asp Lys Ala Ser Ala Ile
225                 230

<210> SEQ ID NO 8
<211> LENGTH: 1522
<212> TYPE: DNA
<213> ORGANISM: Nicotiana tabacum

<400> SEQUENCE: 8
taccaattca ttctggtcag ttcatctctt tccctataat ttctgctgca attaaaccac      60 caaaagaaa caaagatgc agggcgttat gaatttcttc acgaggctat ctttctttct      120
catccttgtt tctaaattaa gcaatgggca ttggacaaac aatttgaaat tggatttcta      180
tcctccaacc tgtaaccgaa ttgagtgccc aaattatgac ttgattcaat ctggtaaaga      240
ctatgaaatt cgtcgttaca attcatccat gtggatgtct actgcaccca ttgatgatat      300
taatctttat tccgccacca gaactggttt cctcaggtat ctatggtttt ttttcttctt      360
tttggtcatg aattcctttc ggttgtgttg catatttgga tacgttagct actgtgcaat      420
accaattaaa gcatgtctgt tttctgtcca agattcctta agaaaacaac taagggttac      480
ttacatttca atcaattgaa attaatcgac tattaaaaga agaagaagaa aaaaaaaga      540 tagttatctg taaacgattt gactatata tgctgataat gtaaagtatt caattcaact      600
ttttcaagca cgtaaacctgc gtggtttttc aagatagtaa tctcactttt tatggatgaa      660
tactaatctc acttttatg gatatgatta ttgaaagcgt aaaagttctt ttgcactgtt      720
agtcagtaga atattttcgg gtgagcttgg tttttatact caaaatgtta gtgtatctat      780
tcgcgaaaac ataaaagggg tcgttgtgaa ctttgccttg gcaggctatt cgattacatt      840
caagggaaga acagttacca ggagaaaata gagatgacag ctccagttat cactcaagta      900
aaaccaagtg atggaccatt ttgtgcatct tcatttgttg tgagcttcta tgtaccaaag      960
aagaaccaac caaatcctcc tccagctaaa ggccttcacg tccaaaaatg gagcaatact    1020
tatgtggccg tcaggcaatt cggcggattt gtagctgatg ttgatgttgc aaaagaagct    1080
gctgctttga gtgctagtat tgctgacact aaatgggcag ctgctgttga aaaaagccat    1140
gctgcagata cactaccat gtatacagtg gcgggataca actctccatt tgagttcaag    1200
gacagagtta atgagatttg gtttactttt gatttggaca agcatctgc catttgagag    1260 gctcttattc tggactcttt aacatttcag gagacatgaa actatcttat tttcttgggt    1320
ttgtattatt aaacagcagt tttgtatgac cacaacgcta cattatatat agcaaataag    1380
ataggttgta taatacaatc tgattctgag gatttagtgg ttaagatacc tctttcaaga    1440
cctttcaaaa taatccgata tatatggaaa agggctagac catattgagt ttattgtatg    1500
```
tacgcagttt taccttccat tt                                                   1522

<210> SEQ ID NO 9
<211> LENGTH: 693
<212> TYPE: DNA
<213> ORGANISM: Nicotiana tabacum

<400> SEQUENCE: 9
atgcagggcg ttatgaattt cttcacgagg ctatctttct ttctcatcct tgtttctaaa    60
ttaagcaatg ggcattggac aaacaatttg aaattggatt tctatcctcc aacctgtaac   120
cgaattgagt gcccaaatta tgacttgatt caatctggta agactatga aattcgtcgt   180 tacaattcat ccatgtggat gtctactgca cccattgatg atattaatct ttattccgcc   240
accagaactg gtttcctcag gctattcgat tacattcaag gaagaacag ttaccaggag   300 aaaatagaga tgacagctcc agttatcact caagtaaaac caagtgatgg accattttgt   360
gcatcttcat ttgttgtgag cttctatgta ccaagaaga accaaccaaa tcctcctcca   420
gctaaaggcc ttcacgtcca aaaatggagc aatacttatg tggccgtcag gcaattcggc   480
ggatttgtag ctgatgttga tgttgcaaaa gaagctgctg ctttgagtgc tagtattgct   540
gacactaaat gggcagctgc tgttgaaaaa agccatgctg cagataacac taccatgtat   600
acagtggcgg gatacaactc tccatttgag ttcaaggaca gagttaatga gatttggttt   660
acttttgatt tggacaaagc atctgccatt tga                              693

<210> SEQ ID NO 10
<211> LENGTH: 386
<212> TYPE: PRT
<213> ORGANISM: Nicotiana tabacum

<400> SEQUENCE: 10

Met Ala Thr Ser Gln Leu Ser Asp Leu Ile Phe Arg Pro Ser Leu His
1               5                   10                  15

Arg Arg Thr Asn Phe Arg Gln Cys His Pro Thr Ser Val Phe Leu Thr
            20                  25                  30

Pro Pro Lys Asn Ile Lys Thr Lys Thr Leu Lys Tyr Asp Arg Lys Ile
        35                  40                  45

Lys Trp Leu Ile Lys Phe Ser Leu Val Asp Lys Gln Ser Pro Thr Lys
    50                  55                  60

Lys Pro Thr Val Asp Met Asn Gln Leu Val Glu Phe Leu Tyr Glu Asp
65                  70                  75                  80

Leu Pro His Leu Phe Asp Asp Gln Gly Ile Asp Arg Lys Ala Tyr Asp
                85                  90                  95

Asp Tyr Val Lys Phe Arg Asp Pro Ile Thr Lys His Asp Ser Ile Asp
            100                 105                 110

Gly Tyr Leu Phe Asn Ile Ala Met Leu Lys Gln Leu Phe Lys Pro Asp
        115                 120                 125

Phe Gln Leu His Trp Ala Lys Gln Thr Gly Pro Tyr Glu Ile Thr Thr
    130                 135                 140

Arg Trp Thr Met Val Met Lys Phe Ile Leu Pro Trp Lys Pro Glu
145                 150                 155                 160

Leu Val Phe Thr Gly Thr Ser Val Met Gly Val Asn Pro Glu Thr Asn
                165                 170                 175

Lys Phe Asn Ser His Val Asp Tyr Trp Asp Ser Ile Lys Asn Asn Asp
            180                 185                 190

```
Tyr Phe Ser Val Glu Gly Leu Leu Glu Val Ile Lys Gln Leu Arg Ile
            195                 200                 205

Tyr Lys Thr Pro Asp Leu Glu Thr Pro Ser Tyr Gln Ile Leu Arg Arg
        210                 215                 220

Thr Ala Thr Tyr Glu Val Arg Lys Tyr Asp Pro Phe Ile Val Val Glu
225                 230                 235                 240

Thr Glu Gly Asp Lys Leu Ala Gly Asn Arg Gly Phe Asn Asp Val Ala
                245                 250                 255

Gly Tyr Ile Phe Gly Lys Asn Ser Ala Thr Glu Lys Ile Pro Met Thr
            260                 265                 270

Thr Pro Val Phe Thr Gln Ala Phe Asp Ala Glu Lys Ser Lys Val Ser
        275                 280                 285

Ile Gln Ile Val Leu Pro Ser Asp Lys Ser Leu Ser Ser Leu Pro Ala
    290                 295                 300

Pro Asn Gln Glu Gly Ile Ser Leu Arg Lys Thr Glu Gly Gly Ile Ala
305                 310                 315                 320

Ala Ala Leu Lys Phe Ser Gly Lys Pro Thr Asp Asp Val Val Arg Glu
                325                 330                 335

Lys Glu Lys Gln Leu Arg Ser Ser Leu Ile Lys Asp Gly Leu Lys Pro
            340                 345                 350

Gln Ser Asp Cys Met Leu Ala Arg Tyr Asn Asp Pro Gly Arg Thr Trp
        355                 360                 365

Lys Phe Ile Met Arg Asn Glu Val Leu Ile Trp Leu Glu Asp Phe Lys
370                 375                 380

Leu Asp
385

<210> SEQ ID NO 11
<211> LENGTH: 6662
<212> TYPE: DNA
<213> ORGANISM: Nicotiana tabacum

<400> SEQUENCE: 11
aatggccacc tcacaacttt ccgacctcat tttccggcca tcacttcaca ggcgaaccaa     60
tttccggcaa tgccacccta cttcagtctt tctcactcct ccaaaaaata tcaaaacaaa    120
aactcttaaa tatgcagaa  aaattaagtg gttaattaag tttagtttag ttgataaaca    180
gagcccaacc aaaaaaccaa cagttgatat gaaccaatta gtggaatttt tatatgagga    240
tttacctcat cttttgatg  atcaaggtat tgatcgtaag gcatatgatg attatgtgaa    300
gtttagggat ccaattacaa acatgattc  aattgatggc tatttgttta atattgccat    360
gttgaaacag ttgtttaagc ctgattttca gctgcattgg gctaaacagg ttagtatttc    420 taccttctt  gttaattggt tagttaaact tcctttgttg ggagcatggc gtaattagta    480
gttgccaacg ggttcaagcc atgaaaaccg actcttgcat aaatgcgagg taggtccaaa    540
tgatcgaatt gtagttctta caatagtag  gtcgagatga tcgaatggaa atgacaattt    600
ttacatggca tattttcata cattctggtc ttcagtctct tacataaatt aagaacattg    660
aaataatatg tcaaggagtc gtttgaacat tattttttt  ccttctatcc aaaagacgta    720
ttttcaagcc atgtttggtt atcaaattgg actgaacttt tgtgtttttt tttttttga    780 aaatgagttt taagtttgaa gtaaaaattc acttttctctt acaaaactgt aatatttttt    840
caagtgaaat acatgtccaa acataacttt aaatttcaaa tattatttt  caacttaact    900 ccgatccaaa cactactttg ttttctttta gaaatcacat ttttatgtcc taagcgtcta    960
```

```
ctaaatgtct catccgaagc tcatgagact atcaacaact gtgaccatca ccttcatcga    1020
tatattttca cagtgaattt ctacactata aatgaaattt aacaggctat aagatgtcaa    1080
actcgttatg tagatcaatt gttgtaagtc aatataacct aattgttcaa ctatctatac    1140
gttatcagtt tacataatct ttacctgtag tttaacttct attaactgtt ttagtgtata    1200
tagttgtaac gtataactgt ctaaacttca tgttaatgat agcatttact tgtagatgat    1260
attattcatt tatcttgttc gttagtgatt aaattttgat cactcttcta agctttctac    1320
cgttaatgct ggtcgataaa aattccttca aaagttcact agtacgttaa gcacttaagc    1380
ctagacagtt gacattaata gactactaat actcacatga tagacaaaac tattttataa    1440
tttgctgatt atatataata atcatgtcat gaccaattat atatggaatt atcaatacaa    1500
tcacaattca catcattatg tgaggctaat tccactacta gaaaactgtc aaaaaagcat    1560
ccagagcata ccgacagaaa ttgattggaa ataataccga ctgacatcgg tcagaaacga    1620
agtaaattgg tcgaaaatat caaataacaa attgtaaata aaaataccga ccgcaattag    1680
tagaaaaatg tgatcccaca aaaagaaag tttactttat ctgacactgt taaaattttc     1740
gaccgattac ggtcggaaaa tgatcaattt tttaccaaag cccgatcaga cttgcatact    1800
atcaaatata ggttttagaa gtttattttt cttttagat ttgtatcgaa ttaagttaga     1860
tttgtgtcga attagatttg cccggagata atgaaattaa aattaatcaa agaaagttc     1920 agaatagaaa aacttaacca acctcgatat ttaaattata acttatactt aaattaaaag    1980
aatttaaaaa gaaaaaaaaa acaaatgagg gacctgcaat aaatcacaac caatcctttc    2040
tatggtcaat atttattaca cgtaagccaa agacatcctt ttacaacatg caaactaaaa    2100
acatcactac taaaaacaaa tggccacctc acaactttcc gacctcattt tccggccatc    2160
acttcaccgg cgcaccactt tccggcaatg ccaccctact tcagtctttc tcactcctcc    2220
aaaaaatatc aaaacaaaaa ctcttaaata tgacagaaaa atcaagtgtt taattaagtt    2280
tagtttagtt gataaacaga gcccaaccaa aaaaccaaca gttgatatga accaattagt    2340 ggaatttta tatgaggatt tgcctcatct ttttgatgat caaggtattg atcgtaaggc     2400
atatgatgat tatgtgaagt ataggggatcc aattacaaaa catgattcaa ttgatggcta    2460
tttgtttaat attgcaatgt tgaaacagtt gtttaggcct gattttcagc tgcattgggc    2520
taaacaggtt agcatttctg cagtttcttg tgaattggtt gtgtggctat gaggtgccta    2580
aagtaaaaat agcacgggct agccaatttt cggattggta attgaaaaat agtcaacgtt    2640
tgcaaagtca ttgaaaaata gccactattt tgctgcaaca tggaaagtta caacataata    2700
tactggagat tagtgcacat gtgtatgaac tttcagcata atatactgga gattggagga    2760
gcacatgtgt atgaacttc agcaccatga tattatgctg gaactccagt atattatgct     2820
ggaagttcat aggtaaaaaa ttcgaactcc agtatattat gctggaatat ttttcggatt    2880 ttaataggg ttttcgttca gatttatctt tacatgaaaa gtggctaagt tttgattact     2940
tttgaaaatg tggctatttt ttaattacca cttgtaaatc tgactatttt tgaatttaac    3000
ccgtgcctaa aagatggagt aggatttaag ttatatacgc cgtcatgtaa aggttattat    3060
tatactcagt ggatataaac ttgtgggttg attacaatat ttagcagatt actagttaat    3120
acttactaga gattaacatg taattactag ttaataagtg acctcattgt ttaaatattt    3180
ttataccatt aatggataga atttcaactc taaaggataa ctatacctaa tataggtgac    3240
tattagggtg cctaagaagc caccacacta attgtcctta gaaagttgta ttagtaatct    3300
ggataacaag gcagattacc tattacgaca agttaaaata taccgatagt gtgtgtatat    3360
```

```
aagttaaaata aattggttgt ttaaactctc tgttttttta tcgcttttcg ttcttcttat    3420
tatgttttcg gttggtttaa ggtgttgcac aaatattcaa gaacatagta tcacccttat    3480
acatagtaca tttactgctc tttgaatatc agtccactgt ttgttaaatg cagaggcaca    3540
gatgaactga tgaactgctt ctgattgttt aagtgtgtca tttcattaag tgaagaattt    3600
tacatgttga gtattatgta gtttggtatt ggggcagaag ttgcatctaa tctgtttgtt    3660
ttgtgctact aaacttaatt gcgtattagt gtctcatggt tttgcatatc catttaagga    3720
taccgataca tgtagtgtac tatgtaggtt ctcttttttca aaatttagtt tggaaacagc    3780
ctctctatcc tcacaagata gggggtaaggt ctgcgtatat gctaccctcc ccagatccca    3840
cggtgtggga taatactggg tatgttattg ttgttgttgt agtttggtat tggagcagaa    3900
gttttattta atcatttaat cagtttgctt tgagctacta aacttgtatt tttaaggaat    3960
gtgatgcata gattatgcat ttgaatcttt tgagtgattg agtttgttgt agacaggacc    4020
ctatgaaata actacaaggt ggacaatggt aatgaagttc attcttcttc catggaaacc    4080
tgaattagtc ttcaccggca cttctgttat gggcgtcaat cctgaaacaa acaaatttaa    4140
cagccatgtg gtttgattct tcactcttcc tcgacgcgaa ttcaaatttt tagattgctt    4200
tgcgaattag tcaccgactc tttgttgaaa tctataggac tactgggatt caattaagaa    4260
taacgattat ttttctgtag aaggtctgct ggaggtcata aaacaggtgc gcgttcgaac    4320
tgttttagtt tatgctttta attaaaattct tggactgttg ggataaaccg gcccaatgat    4380
actcttaaca tggtgtgata ttgtccgctt ggggccaagc ccgcacggtt ttcactaaaa    4440
gggctcgtac cattaagaga tccttacacc ttatatataa gctcccaata ttttcagcta    4500
ccaatgtcgc cttattatga tttgagaata caaatcttgg gcagttaagg atttacaaga    4560
ctccggattt ggaaacacct agttatcaga tattaagaag aacagcaact tacgaggttt    4620
gtagtattta tgttataaca tcgtattttc aagctaagaa cttctatatt aggcgtacat    4680
ttttatttgg tttgcgctac ttttagctga actgatgcac taggacgttt agatttatga    4740
tgtggaatgg tcacaacttt cattggtgca atacaggtca ggaaatatga tccgtttata    4800
gttgtagaaa cagaaggtga caaactcgca ggaaatagag gtttcaatga tgttgcgggg    4860
tgagataagt tgactatttt ttttaaaaga aaaaaacttc tgtgatgttt tctgatttag    4920
attggtagac tgttaactcg tcttaatata ggtacatatt tggcaaaaat tcagcgacag    4980
agaagatacc gatgactact cctgtcttca ctcaggcatt cgatgctgaa aaatctaaag    5040
tgtcaatcca gatagttctt ccatcggata aatcttgag caggtaacac ttaacacgtt    5100
gtattaataa tatacaagaa aacatctcac actgagtgaa aacagtatgg aatctttaaa    5160
tattcttagc actgatctga ttatacttttt tgacaatatg gtttcacatt ttaacaattt    5220
gttgaaactt agtggctttt catatatata agtcatcata agcatcgccc gcctatgtgt    5280
aagagttgga ctttagtcct tttctttgtt caaatgagac ctatggaaat tattgccttta    5340 ttcttaacag cttaccagct cccaatcaag aaggtataag cttaaggaaa acggaaggag    5400
gcatcgctgc tgcattaaaa tttagtggaa aaccaactga tgatgttgtt cgagaaaagg    5460
agaaacaact cagatcaagt cttattaagg acggtctcaa acctcaatcg gattgcatgc    5520
ttgctcgcta caatgatcct ggtcgaacgt ggaagtttat aatggtatat ttctatgtac    5580
tgataatgtt cctttcattg cattcctgct aagttcttc ttttgcttta gactttagaa    5640
aaaggaatct tcttttgctc tttctatttc tgttttcaat tatcagtgcc ttcattacca    5700
```

| | |
|---|---:|
| agggcggagc tagtatacta tgtacggttt cggcagaacc cactaacttt agctgaaacc | 5760 |
| atgtattttg ttaaaaaata aaaccactca atgtgtataa ataatttatt cagaacccag | 5820 |
| taagtcagcc ttttctataa taagaccccca taaacttaaa atcttagctc ggcctctgtt | 5880 |
| cactactgaa tattttgata ttccaactag tttgagattg aggcataggt gattgattga | 5940 |
| tcaataaaat tagtttgaca ttatgtttgg tatattatct actgctaata ttttctcatc | 6000 |
| tgatggaagg ttttgttgg tgtttgcatt atattttatg atcctttggg tgacaagagt | 6060 |
| gggttgctct agtggtgagc accctccact tccaaccaag aggttgtgag ttcgagtcac | 6120 |
| cccaagaaca aggtggggag ttcttgtcgg gagggagccg agggtctatc gaaaacagcc | 6180 |
| tttctacccc agggtagggg taaggtctgc gtacacacta ccttccccat accccactag | 6240 |
| ttccccatac cccactagtg ggattatact gggttgttgt tgttgtagtg ttctttatca | 6300 |
| cttcttaaag tcattgtgtg tctaatctat ttgtttttct gtttggattt ttgcagagga | 6360 |
| atgaagttct tatatggctt gaggatttca agctggatta agctcccatt ctcaaaattg | 6420 |
| ctgagagttt catgagtgaa aaacaggaga gattcacaag caaagacagt ttagaaaaat | 6480 |
| gttcttatac tgaacagatc caaaagctat gaaattaggt ttactgtatt ttgtatctca | 6540 |
| aaatatttag agatttgac aaatatatgg cttgtacata gcacagaatg cttgtgctga | 6600 |
| acactactaa actgatttct cttgtgcact gcaccaaata ttgttagagc tgtagttcta | 6660 |
| tg | 6662 |

<210> SEQ ID NO 12
<211> LENGTH: 1161
<212> TYPE: DNA
<213> ORGANISM: Nicotiana tabacum

<400> SEQUENCE: 12

| | |
|---|---:|
| atggccacct cacaactttc cgacctcatt ttccggccat cacttcacag gcgaaccaat | 60 |
| ttccggcaat gccaccctac ttcagtcttt ctcactcctc caaaaaatat caaaacaaaa | 120 |
| actcttaaat atgacagaaa aattaagtgg ttaattaagt ttagtttagt tgataaacag | 180 |
| agcccaacca aaaaaccaac agttgatatg aaccaattag tggaattttt atatgaggat | 240 |
| ttacctcatc ttttgatga tcaaggtatt gatcgtaagg catatgatga ttatgtgaag | 300 |
| tttagggatc caattacaaa acatgattca attgatggct attttgtttaa attgccatg | 360 |
| ttgaaacagt tgtttaagcc tgattttcag ctgcattggg ctaaacagac aggaccctat | 420 |
| gaaataacta caaggtggac aatggtaatg aagttcattc ttcttccatg gaaacctgaa | 480 |
| ttagtcttca ccggcacttc tgttatgggc gtcaatcctg aaacaaacaa atttaacagc | 540 |
| catgtggact actgggattc aattaagaat aacgattatt tttctgtaga aggtctgctg | 600 |
| gaggtcataa acagttaag gatttacaag actccggatt tggaaacacc tagttatcag | 660 |
| atattaagaa gaacagcaac ttacgaggtc aggaaatatg atccgtttat agttgtagaa | 720 |
| acagaaggtg acaaactcgc aggaaataga ggtttcaatg atgttgcggg gtacatattt | 780 |
| ggcaaaaatt cagcgacaga gaagataccg atgactactc ctgtcttcac tcaggcattc | 840 |
| gatgctgaaa atctcaaagt gtcaatccag atagttcttc catcggataa atctttgagc | 900 |
| agcttaccag ctcccaatca agaaggtata agcttaagga aaacggaagg aggcatcgct | 960 |
| gctgcattaa aatttagtgg aaaaccaact gatgatgttg ttcgagaaaa ggagaaacaa | 1020 |
| ctcagatcaa gtcttattaa ggacggtctc aaacctcaat cggattgcat gcttgctcgc | 1080 |
| tacaatgatc ctggtcgaac gtggaagttt ataatgagga atgaagttct tatatggctt | 1140 |

-continued gaggatttca agctggatta a                                         1161

<210> SEQ ID NO 13
<211> LENGTH: 199
<212> TYPE: PRT
<213> ORGANISM: Nicotiana tabacum

<400> SEQUENCE: 13

Met Gly Met Ile Leu Gly Lys Ile Thr Val Glu Thr Pro Lys Tyr Glu
1               5                   10                  15

Leu Ile Gln Ser Thr Ala Asp Tyr Glu Ile Arg Lys Tyr Pro Ala Ser
            20                  25                  30

Val Ile Ala Gln Val Thr Tyr Asp Pro Thr Gln Phe Lys Gly Asn Lys
        35                  40                  45

Asp Gly Gly Phe Met Leu Leu Ala Asn Tyr Ile Gly Ala Leu Gly Asn
    50                  55                  60

Pro Gln Asn Ala Lys Pro Glu Lys Ile Ala Met Thr Ala Pro Val Ile
65                  70                  75                  80

Thr Lys Ser Ser Glu Lys Ile Ala Met Thr Ala Pro Val Val Thr Lys
                85                  90                  95

Ser Gly Asp Gly Glu Asn Asn Met Val Thr Met Gln Phe Ile Leu Pro
            100                 105                 110

Ala Lys Tyr Thr Lys Ala Glu Glu Ala Pro Lys Pro Leu Asp Glu Arg
        115                 120                 125

Val Val Val Lys Glu Glu Gly Glu Arg Lys Phe Gly Val Val Gln Phe
    130                 135                 140

Ser Gly Thr Ala Ser Asp Lys Val Lys Glu Lys Val Glu Asn Leu
145                 150                 155                 160

Arg Lys Cys Leu Glu Arg Asp Gly Tyr Lys Ile Ile Gly Asp Phe Glu
                165                 170                 175

Leu Ala Arg Tyr Asn Pro Pro Trp Thr Ile Pro Pro Phe Lys Thr Asn
            180                 185                 190

Glu Val Met Ile Pro Val Glu
        195

<210> SEQ ID NO 14
<211> LENGTH: 1718
<212> TYPE: DNA
<213> ORGANISM: Nicotiana tabacum

<400> SEQUENCE: 14
ctccaccagc ttatggtgca acgtggcaa  acaaactcc  acagcagttc  cctcatctac      60
cgccattcat tttgcagcaa tcaaaaaccc ctttcccaag ttctctcttc ctctcttttcc    120 gatttcccac aagaaacttc ctcttctctc cccttatatg taacaaattc acagcctcca    180
tttactatca aaacattctc aaattccatt cccataact aattttttcgt tccatcaaaa     240 tgggcatgat tttggggaaa atcactgtgg aaacaccaaa atacgaattg attcaatcta    300
cagctgacta cgaaatccgc aaatacccag catctgttat agcacaagtc acatatgatc    360
caacccagtt caaggaaac aaagacggtg ggtttatgct attagccaat tacatcggcg     420
cacttggcaa tcctcaaaac gctaagcctg aaaaaatcgc catgacagct cctgtaatca    480
ccaaatcgtc cgaaaaaatc gcgatgactg caccagtggt gactaagagt ggtgatggag    540
agaacaatat ggtgacgatg cagttttattt taccagcaaa gtatacaaaa gctgaagagg    600
cacctaagcc gttggatgaa agggtggtgg ttaaagaaga aggggaaaga aagtttggtg    660

```
tggtgcagtt tagtgggact gcaagtgata aagtggttaa agagaaagtg gagaatttaa      720
ggaaatgttt ggagagagat gggtataaga taattggtga ttttgagttg gctcggtata      780
atcctccttg gacaattcct ccatttaaga ccaatgaagt tatgattcca gttgagtgag      840
ctgaaaatgg tgtattaaag aaaaatatga gacggctgtg aagctagctt gtgaacctac      900
tttatctggt gtttattagt attgaattgt gtatttcttg tttatatgtt tacgttgttg      960
acaatgtctt tgcatacct agctagtgtc aattattcat agttaattag cacatatttt      1020
agctcaattt tatactttgc catagtaaag tagtaaaacc aatgtggttt tgcaagcacc      1080
taatgtggta agtccttact ctctgttttt catttcacac tcttctctct gtccatttct      1140
gccagtataa gtgcttcttc tgtcaatacc cggtgaatca tgtaagggcc ctgttagttg      1200
ggtaaaaatt ttccttttgc ttcatcttta tgtgataaga ttcgctttag caccaattgc      1260
cccagcatga atttccttga tctgaccttt ttgttgaaaa atcttgccat tctgttctag      1320
tagagttgac cgtgacatac tacattcatt ctcttttcat caatgagagc tagttgttca      1380
tactggcttc gtaccaattc ctcgtcgctg agctcggttt cttgtatgat tcttaaagaa      1440
ggaatttcta cttcggcgga aataacgact tcagtaccat aaactagtag gtagggagtt      1500
gccccatttg atgtacgaac tgtggtacga taccccgagt aagaaaatgg tagattatga      1560
tgccattatt tgtaattgtt caccatttcc ctcaatatct ttttgatgtt cttgttggcg      1620
gcttccacgg cttcgttcat ttgcgacctg tacgctatag agttcctatg cttgatcttg      1680
aatgtttcac acatggcttc atcaaattgc tattgaga                              1718

<210> SEQ ID NO 15
<211> LENGTH: 600
<212> TYPE: DNA
<213> ORGANISM: Nicotiana tabacum

<400> SEQUENCE: 15
atgggcatga ttttggggaa atcactgtg gaaacaccaa atacgaatt gattcaatct         60 acagctgact acgaaatccg caaataccca gcatctgtta tagcacaagt cacatatgat      120
ccaacccagt tcaaggaaa caaagacggt gggtttatgc tattagccaa ttacatcggc      180
gcacttggca atcctcaaaa cgctaagcct gaaaaaatcg ccatgacagc tcctgtaatc      240
accaaatcgt ccgaaaaaat cgcgatgact gcaccagtgg tgactaagag tggtgatgga      300
gagaacaata tggtgacgat gcagtttatt ttaccagcaa agtatacaaa agctgaagag      360
gcacctaagc cgttggatga aagggtggtg gttaaagaag aagggggaag aaagtttggt      420
gtggtgcagt ttagtgggac tgcaagtgat aaagtggtta agagaaagt ggagaatta       480 aggaaatgtt tggagagaga tgggtataag ataattggtg attttgagtt ggctcggtat      540
aatcctcctt ggacaattcc tccatttaag accaatgaag ttatgattcc agttgagtga      600

<210> SEQ ID NO 16
<211> LENGTH: 233
<212> TYPE: PRT
<213> ORGANISM: Nicotiana tabacum

<400> SEQUENCE: 16

Met Gln Ala Val Met Asn Phe Phe Met Arg Leu Ala Phe Phe Leu Ile
1               5                   10                  15

Leu Val Ser Lys Leu Ser Asn Gly Tyr Ser Thr Asn His Leu Gln Pro
            20                  25                  30
```

```
Gln Lys Leu Gly Phe Tyr Pro Pro Thr Cys Asn Arg Ile Glu Cys Pro
             35                  40                  45

Asn Tyr Asp Leu Ile Gln Ser Gly Lys Asp Tyr Glu Ile Arg Leu Tyr
 50                  55                  60

Asn Ser Ser Met Trp Met Ser Thr Ala Pro Ile Asp Asp Ile Asn Leu
 65                  70                  75                  80

Tyr Ser Ala Thr Arg Thr Gly Phe Leu Arg Leu Phe Asp Tyr Ile Gln
                 85                  90                  95

Gly Lys Asn Ser Tyr Gln Glu Lys Ile Glu Met Thr Ala Pro Val Ile
            100                 105                 110

Thr Gln Val Lys Pro Ser Asp Gly Pro Phe Cys Ala Ser Ser Phe Val
            115                 120                 125

Val Ser Phe Tyr Val Pro Lys Lys Asn Gln Pro Asn Pro Pro Ala
130                 135                 140

Lys Gly Leu His Val Gln Ile Trp Ser Asn Thr Tyr Val Ala Val Arg
145                 150                 155                 160

Gln Phe Gly Gly Phe Val Ala Asp Val Asp Val Ala Lys Glu Ala Ala
                165                 170                 175

Ala Leu Ser Ala Ser Ile Ala Asp Thr Lys Trp Ala Ala Ala Val Glu
            180                 185                 190

Lys Ser His Ala Ala Asp Asn Thr Thr Met Tyr Thr Val Ala Gly Tyr
            195                 200                 205

Asn Ser Pro Phe Glu Phe Lys Asp Arg Val Asn Glu Ile Trp Phe Thr
            210                 215                 220

Phe Asp Leu Asp Lys Ala Ser Ala Ile
225                 230

<210> SEQ ID NO 17
<211> LENGTH: 1673
<212> TYPE: DNA
<213> ORGANISM: Nicotiana tabacum

<400> SEQUENCE: 17
aaaacctctg gacaccccct cattgatttt ctttttcttt tatgcatgag gaaattagtt      60
cattcgggtc acttcattct ctctccgtat aatttctagg aactaaaaca ctaaaaagaa     120
acaaaagatg caggctgtta tgaatttctt catgaggcta gctttctttc tgatcctcgt     180
ttctaaattg agcaatgggt attcgacaaa ccacttgcag ccacagaagt tgggtttcta     240
tcctccaacc tgtaaccgaa ttgagtgccc aaattatgac ttaattcaat ctggaaaaga     300
ctatgaaatt cgtctttata attcatccat gtggatgtct actgcaccca ttgatgatat     360
taacctttat ccgccaccag aactggtttt cctcaggtta atattatatt ccctctttct     420
cccactagtt cccttttaca tcagttatct gtatctattg ttttttttt ttcaattcct     480 ttctatttgt tgcatatttg ataagttagc tacactgtgc aacaccaact aaagcatgtg     540
tgtttgcttt ccaagattcc tcaaaaaaaa aaaaaaaaa acaagggact taattaaagg     600
tttacttaca tctcaatcaa ttgaaaataa tcgactatta aaggaaaaa aaaaattatg     660 tcttgccagg ttacattgaa gcaggttgct gccagttacc aatttacaat tatattgcta     720
gttatctgta actgatttga tttatatgta ctgaaaatgc atagtattta atctagattg     780
ttaaagcaaa tacctgcctt attttacaag ttactaatct ccctttttac ggttagttat     840
cgtgttatta ttgagttgac ttgatagtgt aaaagtgatc ttttccactg tcagtattta     900
gaagttattt tatgtgaact taatcttat acttaagatg ttagcctatc catttgcaaa     960
```

```
acataaaaaa cagttgttgt aaactttgcc ttggcaggct attcgattac attcaaggga    1020
agaacagtta ccaggagaaa atagagatga cagctccagt tatcactcaa gtaaaaccaa    1080
gtgatggacc attttgtgca tcttcatttg ttgtgagctt ctacgtacca agaagaacc     1140 aaccaaatcc tcctccagct aaaggccttc acgtccaaat atggagcaat acttatgtcg    1200
ccgtcaggca attcggcgga tttgtagctg atgttgatgt tgcaaaagaa gctgctgctt    1260
tgagtgctag tattgctgac actaaatggg cagcagccgt tgaaaaaagc catgctgcag    1320
ataacactac gatgtataca gtggcgggat acaactctcc ttttgagttc aaggacagag    1380
ttaatgagat ttggtttaca tttgatttgg acaaagcatc tgccatttga ttctggactc    1440
tttaacattt caggagacat gaaactatct tattttcttg gtttgtatta ctattaaaca    1500
acagttttgt atgaccacaa tgctacatta tatagataga aaataagata ggttgtacaa    1560
tacaatttga ttctgaggat ttagtggtta agataccttt ttcaagacct ttcaaaataa    1620
tccaatatat atggaaaagg cttagaccca tattgagttt attgtatgca gtt          1673
```

<210> SEQ ID NO 18
<211> LENGTH: 702
<212> TYPE: DNA
<213> ORGANISM: Nicotiana tabacum

<400> SEQUENCE: 18

```
atgcaggctg ttatgaattt cttcatgagg ctagctttct ttctgatcct cgtttctaaa     60
ttgagcaatg ggtattcgac aaaccacttg cagccacaga agttgggttt ctatcctcca    120
acctgtaacc gaattgagtg cccaaattat gacttaattc aatctggaaa agactatgaa    180
attcgtcttt ataattcatc catgtggatg tctactgcac ccattgatga tattaacctt    240
tattccgcca ccagaactgg tttcctcagg ctattcgatt acattcaagg gaagaacagt    300
taccaggaga aaatagagat gacagctcca gttatcactc aagtaaaaacc aagtgatgga    360 ccattttgtg catcttcatt tgttgtgagc ttctacgtac caagaagaa ccaaccaaat     420 cctcctccag ctaaaggcct tcacgtccaa atatggagca atacttatgt cgccgtcagg    480
caattcggcg gatttgtagc tgatgttgat gttgcaaaag aagctgctgc tttgagtgct    540
agtattgctg acactaaatg ggcagcagcc gttgaaaaaa gccatgctgc agataacact    600
acgatgtata cagtggcggg atacaactct ccttttgagt tcaaggacag agttaatgag    660
atttggttta catttgattt ggacaaagca tctgccattt ga                       702
```

<210> SEQ ID NO 19
<211> LENGTH: 386
<212> TYPE: PRT
<213> ORGANISM: Nicotiana tabacum

<400> SEQUENCE: 19

```
Met Ala Thr Ser Gln Leu Ser Gly His Ile Phe Arg Ser Ser Leu His
1               5                   10                  15

Arg Arg Thr Ile Phe Arg Gln Cys His Pro Thr Ser Val Phe Leu Thr
            20                  25                  30

Pro Pro Lys Asn Ile Lys Thr Lys Pro Leu Lys Tyr Asp Arg Lys Phe
        35                  40                  45

Lys Trp Leu Ile Lys Phe Ser Leu Val Asp Lys Gln Thr Pro Thr Lys
    50                  55                  60

Lys Pro Thr Val Asp Met Lys Gln Leu Val Glu Phe Leu Tyr Glu Asp
65                  70                  75                  80
```

| | | | | | | | | | | | |
|---|---|---|---|---|---|---|---|---|---|---|---|
| Leu | Pro | His | Leu | Phe | Asp | Asp | Gln | Gly | Ile | Asp | Arg | Lys | Ala | Tyr | Asp |
| | | | | 85 | | | | 90 | | | | 95 | | | |

Asp Tyr Val Lys Phe Arg Asp Pro Ile Thr Lys His Asp Ser Ile Asp
            100                 105                 110

Gly Tyr Leu Phe Asn Ile Ala Met Leu Lys Gln Leu Phe Arg Pro Asp
            115                 120                 125

Phe Gln Leu His Trp Ala Lys Gln Thr Gly Pro Tyr Glu Ile Thr Thr
130                 135                 140

Arg Trp Thr Met Val Met Lys Phe Ile Leu Leu Pro Trp Lys Pro Glu
145                 150                 155                 160

Leu Val Phe Thr Gly Thr Ser Val Met Gly Val Asn Pro Glu Thr Asn
                165                 170                 175

Lys Phe Asn Ser His Val Asp Tyr Trp Asp Ser Ile Lys Asn Asn Glu
            180                 185                 190

Tyr Phe Ser Leu Glu Gly Leu Leu Glu Val Ile Lys Gln Leu Arg Ile
            195                 200                 205

Tyr Lys Thr Pro Asp Leu Glu Thr Pro Ser Tyr Gln Ile Leu Arg Arg
            210                 215                 220

Thr Ala Thr Tyr Glu Val Arg Lys Tyr Asp Pro Phe Ile Val Val Glu
225                 230                 235                 240

Thr Glu Gly Asp Lys Leu Ala Gly Asn Arg Gly Phe Asn Asp Val Ala
                245                 250                 255

Gly Tyr Ile Phe Gly Lys Asn Ala Ala Thr Glu Lys Ile Pro Met Thr
            260                 265                 270

Thr Pro Val Phe Thr Gln Ala Phe Asp Ala Glu Lys Ser Lys Val Ser
            275                 280                 285

Ile Gln Ile Val Leu Pro Ser Asp Lys Ser Leu Asn Ser Leu Pro Ala
            290                 295                 300

Pro Asn Gln Glu Gly Ile Ser Ile Arg Lys Thr Glu Gly Gly Ile Ala
305                 310                 315                 320

Ala Ala Leu Lys Phe Ser Gly Lys Pro Thr Asp Ile Val Arg Glu
                325                 330                 335

Lys Glu Lys Gln Leu Arg Ser Ser Leu Ile Lys Asp Gly Leu Lys Pro
            340                 345                 350

Gln Ser Gly Cys Met Leu Ala Arg Tyr Asn Asp Pro Gly Arg Thr Trp
            355                 360                 365

Lys Phe Ile Met Arg Asn Glu Val Leu Ile Trp Leu Glu Asp Phe Lys
            370                 375                 380

Leu Asp
385

<210> SEQ ID NO 20
<211> LENGTH: 3736
<212> TYPE: DNA
<213> ORGANISM: Nicotiana tabacum

<400> SEQUENCE: 20
actaaaacca aatggccacc tcacaacttt ccggccacat tttccggtca tcacttcacc     60
ggcgcaccat tttccggcaa tgccacccaa cttcagtctt ccttactccc ccaaaaaata   120
tcaaaacaaa acctcttaaa tatgacagaa aattcaagtg ttaataaag tttagtttag    180 ttgataaaca gacccccaaca aaaaaaccaa cagttgatat gaaacaatta gttgaatttt   240
tatatgagga tttacctcat ttatttgatg atcaaggtat tgatcgaaag gcatatgatg   300
attatgtgaa gtttagagat ccaattacaa aacatgattc aattgatggc tatttgttta   360

```
atattgccat gttgaaacag ttgtttaggc ctgattttca gctgcattgg gctaaacagg    420
ttagcatttc tacagtttct tgttaattgg ttagttaaac tgctgtttgt ttaactttct    480
tacttggatt taagtttacg ggagccttgg cgtaactggt aaagttgatg tcatgtcacc    540
aaaaggtcat gagttcgagc agtggaaaca acctcttgca gaaatgcagt ataaagctgc    600
atacaataga ccttttgtggt ccagcccttt tccggacccc gcgcatagcg ggagcttatg    660
cactgggctg tctttttttc ctcggatttt aagttatgtt caatgatggt gtgaaattat    720
tttactctaa ttaatgtgtg tcgtagagat aatgtaatca cctcataatt gacctgactg    780
tgtaaataat tttatatcgt cggtgcataa aacgaaaggt ccacaatcac ttagagtacc    840
atgttacaaa taaatgttta tcatcaagaa tcacttagaa ttaccttgcg atatgattgt    900
gtatttgcac tgtcagtgcc taaaacttaa gcgtcacgcc tataatacaa ttattaatgc    960
ttattatagg gaatcacttg gaattgcctt acgatatgat tgtgtatttg cattgttagt   1020
gcctgaaact taaggtctg cgaacatatt acctttagcc gagggtctat cgaaataact   1080
ctctacttgc acaaggtagg ggtaaggtct gcgtatatac taatctccct agaccccgct   1140
tgtgggatta cactgggttt attgttgttg ttgtgcctaa agcttaagca ccatatctat   1200
tatacagtta caattgaatc acttggacta ccttaattgt gtattagtgt ctcatggttt   1260
tgtaaatcta tttatggata ccgatacatg tagtgtacta tgtaggttct ctctttcaaa   1320
atttagtttg gtgtcagaag tcttattcaa tcatttaatc tatttgcttt ggccgagggt   1380
ccatcggaaa cggtctctct accttctcaa ggtaaaggta aggtctgcgt acacactacc   1440
cttccgagac cccactcgtg gtattacact gtggtattac actgaattta ttattgttgt   1500
tgtagtcagt ttgctttgtg ctattaaact tgtatttcta aggaatgtga tacataaatt   1560
atgccttgaa ttttgagtg attgagttttg ttgtagacag ggccctatga aataactaca   1620
agatggacta tggtgatgaa gttcattctt cttccatgga aacctgaatt agtcttcact   1680
ggcacttctg ttatgggcgt caatcctgaa acaaacaagt ttaacagcca tgtggtttga   1740
ttcttcactc ttcctcgacg caaattcaaa tttattagat tgctttgcag attagtcacc   1800
gactcttgtt gaaatctata ggactactgg gattcaatta agaataacga atattttttcc   1860 ctggaaggtc tgctcgaggt cataaaacag gtgcgcgctc gaactgtttt agtttatgtt   1920
tcttgaactg ttggactaaa ccagcgcaaa gatactctta tcatggtgtg atattgtctg   1980
ctttgggcca aattcgcgcg gttttcccta tgaggcctca caccattggg agatctctac   2040
accttatata taggctctca atcttatcaa ctaccaatgt ggctttatta taatttgaga   2100
acacaaattt tgggcagtta aggatttaca agactccgga cctggaaacg cctagttatc   2160
agatactaag aagaacagca acttacgagg tttgtcatat ttatgtttac agcgttgtac   2220
ttcaagctaa gaacttctat attaggcgta cattttttatt gggtttgcgc tacttttagc   2280
tgaactgatg cactaggacg tttagattta tgatgtggaa tggtcacaat tatcatttat   2340
gtaatacagg tcaggaaata tgatccgttt atagttgttg aaacagaagg tgacaaactc   2400
gcaggaaata gaggtttcaa tgatgttgca gggtgagata agttgaccct ttttctttaa   2460
aatcttctgt ggtgttttct gatttagatt ggcggaccat taactcgtct taatataggt   2520
acatatttgg gaaaaatgct gcaacagaga agataccgat gactactcct gtcttcactc   2580
aggcatttga tgctgaaaaa tctaaagtgt caatccagat agttcttcca tcggataaat   2640
ctttgaacag gtaacacgtt ttattaatta atagacacga aaacatctca caccgagcga   2700
```

-continued

```
tcatattgta cttattacaa tatgagttca aattttttaca ttcgtcgaaa cttagtaatt    2760
catatatata attcataagc atcgttcgcc tctgtgtaag agttggattt tagttatttt    2820
ctttgatcaa atgagaatta tggaaattaa agctttattc ttaacagctt accagctccc    2880
aatcaagaag gtattagcat aaggaagaca gaaggaggaa tcgcggctgc actaaaattt    2940
agtggaaagc caacagatga tattgttcgc gaaaaggaga aacaacttag atccagtctt    3000
attaaggacg gtctcaaacc tcaatcgggt tgtatgcttg ctcgctacaa tgatcctggt    3060
cgaacgtgga agtttataat ggtatacttc tatgtactga atatcgttcg tttcattgca    3120
ttcttgttta agttcttatt ttgttttagt atgaagtgtc tctttagaat gagaaccttg    3180
gcgtaactgg taaagttgct gctatgtgac caggaggtca cgggttcgag ccgtggaaac    3240
accctcttgc agaaatgttg ggtaaggctg cgtacaattg acccttgtgg tccggccctt    3300
ccgcggaccc ctcgtatagc aggaacttag tgcaccgggc ttcccttta gtctgaagtg     3360 tctctttatc actttgtcat ctggtgtcta atctatttgt ttttctgttt ggattttgc     3420 agaggaatga agttcttata tggcttgagg atttcaagct ggattaactc ccattccaaa    3480
aattgctgag attttcatgt atgtaaaaca ggagagattc acaagcaaag acagtttaga    3540
aaaattctta tactgaaatg aaattagttc tcaaaatgtt tagagatttt gacaaatata    3600
tgacttgtgc atagccacaa atgcttgtgc tgaactcact ttacactaaa caaacttcta    3660
ttgtgcatta caaagttcga tgtgttgatg gtgtaaataa tatttgtcac ttgtaaggta    3720
attaatggta attaac                                                    3736
```

<210> SEQ ID NO 21
<211> LENGTH: 1161
<212> TYPE: DNA
<213> ORGANISM: Nicotiana tabacum

<400> SEQUENCE: 21

```
atggccacct cacaactttc cggccacatt ttccggtcat cacttcaccg gcgcaccatt      60
ttccggcaat gccacccaac ttcagtcttc cttactcccc caaaaatat caaaacaaaa      120 cctcttaaat atgacagaaa attcaagtgg ttaataaagt ttagtttagt tgataaacag     180
accccaacaa aaaaccaac agttgatatg aaacaattag ttgaatttt atatgaggat      240 ttacctcatt tatttgatga tcaaggtatt gatcgaaagg catatgatga ttatgtgaag    300
tttagagatc caattacaaa acatgattca attgatggct atttgtttaa tattgccatg    360
ttgaaacagt tgtttaggcc tgattttcag ctgcattggg ctaaacagac agggccctat    420
gaaataacta caagatggac tatggtgatg aagttcattc ttcttccatg gaaacctgaa    480
ttagtcttca ctggcacttc tgttatgggc gtcaatcctg aaacaaacaa gtttaacagc    540
catgtggact actgggattc aattaagaat aacgaatatt tttccctgga aggtctgctc    600
gaggtcataa acagttaag gatttacaag actccggacc tggaaacgcc tagttatcag    660
atactaagaa gaacagcaac ttacgaggtc aggaaatatg atccgtttat agttgttgaa    720
acagaaggtg acaaactcgc aggaaataga ggtttcaatg atgttgcagg gtacatattt    780
gggaaaaatg ctgcaacaga gaagataccg atgactactc ctgtcttcac tcaggcattt    840
gatgctgaaa atctaaagt gtcaatccag atagttcttc catcggataa atctttgaac    900
agcttaccag ctcccaatca agaaggtatt agcataagga agacagaagg aggaatcgcg    960
gctgcactaa aatttagtgg aaagccaaca gatgatattg ttcgcgaaaa ggagaaacaa    1020
cttagatcca gtcttattaa ggacggtctc aaacctcaat cgggttgtat gcttgctcgc    1080
```

```
tacaatgatc ctggtcgaac gtggaagttt ataatgagga atgaagttct tatatggctt    1140
gaggatttca agctggatta a                                              1161
```

<210> SEQ ID NO 22
<211> LENGTH: 299
<212> TYPE: PRT
<213> ORGANISM: Nicotiana tabacum

<400> SEQUENCE: 22

```
Met Leu Leu Cys Ser Pro Ser Ile Ser Ala His Asn Leu Ser Arg
1               5                   10                  15

Asn Arg Thr Arg Pro Ser Pro Ile Asn Ser Met Ala Val Asp Arg Ser
            20                  25                  30

Ser Ser Arg Val Ala Thr Thr Ala Ser Gln Arg Arg Asn Gly Thr Ser
        35                  40                  45

Ala Leu Glu Ala Arg Ile Ser Leu Val Ile Ala Leu Ala Ser Gln Thr
    50                  55                  60

Ser Ser Leu Ser Gln Lys Leu Leu Thr Glu Leu Ala Gly Glu Thr Ala
65                  70                  75                  80

Lys Tyr Val Leu Pro Lys Arg Ile Phe Glu Ser Arg Thr Leu Glu Glu
                85                  90                  95

Ala Leu Met Ser Val Pro Asp Leu Glu Thr Val Lys Phe Asn Val Leu
            100                 105                 110

Lys Arg Ser Asp Gln Tyr Glu Ile Arg Glu Val Glu Pro Tyr Phe Val
        115                 120                 125

Ala Glu Ala Thr Met Pro Gly Lys Tyr Gly Phe Asp Phe Asn Gly Ala
    130                 135                 140

Ser Gln Ser Phe Asn Thr Leu Ala Glu Tyr Leu Phe Gly Lys Asn Thr
145                 150                 155                 160

Lys Lys Glu Ser Met Ala Met Thr Thr Pro Val Ile Thr Arg Arg Thr
                165                 170                 175

Gln Ser Asp Gly Glu Arg Met Glu Met Thr Thr Pro Val Ile Thr Lys
            180                 185                 190

Arg Val Glu Asp Gln Gly Lys Trp Arg Met Ser Phe Val Met Pro Ser
        195                 200                 205

Lys Tyr Gly Ser Asp Leu Pro Leu Pro Lys Asp Ser Ser Val Thr Ile
    210                 215                 220

Lys Glu Val Pro Arg Lys Thr Val Ala Val Ala Phe Ser Gly Phe
225                 230                 235                 240

Val Thr Asp Glu Glu Val Lys Ala Arg Glu Ser Arg Leu Arg Ala Ala
                245                 250                 255

Leu Lys Gly Asp Ala Glu Phe Arg Val Lys Asp Gly Ala Ser Ile Glu
            260                 265                 270

Val Ala Gln Tyr Asn Pro Pro Phe Thr Leu Pro Phe Thr Arg Arg Asn
        275                 280                 285

Glu Ile Ser Leu Glu Val Glu Arg Glu Gln Glu
    290                 295
```

<210> SEQ ID NO 23
<211> LENGTH: 6324
<212> TYPE: DNA
<213> ORGANISM: Nicotiana tabacum
<220> FEATURE:
<221> NAME/KEY: misc_feature
<222> LOCATION: (3617)..(4958)
<223> OTHER INFORMATION: n is a, c, g, or t

<400> SEQUENCE: 23

```
atgtgacata cacagtatgt gataaggaat taaccaagta attcgggggc gacaaataca    60
aatatagatg aaccacaatc cccttctttg aagcacagaa tttcaaaagg agtgaaacaa   120
acactgtaac gtagttaaag atgcttctgt gctcaccttc ttccatttct gctcacaatc   180
ttagcagaaa cagaaccaga ccttcgccta tcaattctat ggcagttgac agaagcagct   240
cccgcgttgc cacaactgct tcgcagcgga gaaacggcac gtcagctctc gaagctcgca   300
tctccctcgt catcgctctc gcctcccaaa cctcttctct ctctcagaaa cgtaatttct   360
tcactccatt tcctaattcc tcattttaat cggattttaa gcatttctct cccaattctt   420
tttttgattt gtttaaaaca tttcgtccag tgcttccagg actcttttaa gtcagattag   480
agaacttctt agaaaagaat taatttagtt taagagacta attatttacc agtgttggaa   540
tgaacttgtg cttgacggct aaagcggaac ggatataaat gattctatgt agtcctctgg   600
ctagtttagg aatgagaacc tagtcaattg actaattgag taattgctac ttatattgtt   660
aaattttta ttgttcgcag ttctgacgga attggctggt gaaaccgcga atacgtgtt    720
accgaagagg atattcgaaa gtcggacttt agaggaagct ttgatgtctg gtattctttc   780
tcaatctttt ctatgattgt tatatcctct attttaataa taatgagaat ttagatggtt   840
aaaaataatg actagctccc atcgctgtta tcttcttgaa gtgccggatc tggagacagt   900
gaaattcaat gttttgaaac gcagtgatca gtatgaaata agggaagttg aggtattttc   960
tctatgattc tatttataaa ttactaatgt tgtcattcct tttttttttt tcccagtaga  1020
gtctagattt gtatgcatcc attctgcaac tttatcgggg gagtggttcc agacgagaga  1080
ggagcaatat ttgacgggaa aaaaaaggtt taaaccttca ttaaaaaaat gttgaagata  1140
gagggcaaac ttgttttgag aacacccttta gaatactact tacatagata caaatattag  1200
gcaaagatac gtttattata tttgttcaca ccagctaaat attctcaaac aaagattaat  1260
cctttagtta gaatttcttg atatatggta gaatgctccg tctcagaaag taatcaaggg  1320
tactaataca agaaagcatt agttggtaaa agttactagg ccatgtaatt agatacaaga  1380
gacatttgtg aagattttgt tgtaacttga ttctacataa tgggccttag ttcatatttg  1440
tgttttccct tattatggtc attaaaaaaa aaaaaacaca agtacctggg gattgaaaat  1500
gcaattctga aaggtacaat acatatggaa gtggaactgg cacaactgga gactgatagt  1560
tatagtgggg agtcagcatg tctatcaata agaaagaaaa agaaataaac gaacctgaaa  1620
gagatttggt attcaaaagt attttggaaa agaatgaaat tgcagaaaat agactagtga  1680
tcacaaatca ggagtttcct caattttgag gaacatgtta ttgactcggt gttaaaacat  1740
gatgagaaag cagaggtgcc agttttttga aataaacata tgatgttcta acttttggtt  1800
tgataaccta gaattaagca tatcataagc tcttttccatg aacattaaag ccctggatcc  1860
tgatacttga aagtcattca ttcacaaatt gttttttggc agatctacct ttgtattaaa  1920
attgaattct ggaccatcag tcaccctgtt atttatggtg cacatatttc ttcttatgtg  1980
tatatgctct tattctttgc ttttttcggaa acagcctcta ccccgggta ggggtaaggt   2040
ctgcatacac actaccctcc ccagaccccca tacactggtt gttgttgttg ttgtatatgc  2100
tcttaaattc ttgtcctcag ttattcctaa cctctcttaa tagcatttct cttgattata  2160
gatatgctgt attattagaa ctttaatcac cgatatctct ttatgttgtc atgttgatag  2220
ttattctttc ccttcttgtc ctcttaacaa taactctgag ttttttattt tttatttga   2280
```

```
taaagttcat tataaactct gagttaatttt atctaaagta atattgcgac tttgaacagc    2340
cttactttgt tgctgaggct acaatgcctg ggaagtatgg gtttgactttt aatggtgcat    2400 ctcaatcctt caacacattg gctgagtact tgtttggtaa ggtagttaaa ggtacttata    2460
gagagtcaaa cttagatcgc ctccaaccac attgtaatgg tggtcttctt tggctctgtt    2520
ctatttcttg gtgatttcca gaacacgaag aaggagagca tggcgatgac aacaccagtt    2580
atcactcgta gaactcaatc tgatggggag aggatggaaa tgactactcc agtgataact    2640
aaacgggtac agctcttcta ctggttgttc ctttttccct ttagttcttt tgcaatgtat    2700
atttactatg tcattcgtga tatatggtgt ggttactaat atgcttgcat ttttgtatga    2760
catggtgtta ctcaaaatat taaactgata atatattgaa gttgagtcac cacataactt    2820
gggaaatggt aaatgaagaa ctactctaaa atgaccacat atcgtcaaat ggaaatactg    2880
actttactac tgattctgtt gaaaagaaac atcgtctgat tacctatcac taggaaaaca    2940
tttaagctct tgatttagaa ttgataaaag atgacatgtg ctttagattg agatttgagg    3000
atctttcaat tgtatgctag gcttatacgc cagcgggggt acatacaaaa cgtaaacatt    3060
ctggttgctt agagtttgaa tctgtactac tctaagatag tattgcaaat tctgagagag    3120
tggaaactgt tagattccag gttttattat gttgcatgga tccttcaaac gggtgtgaca    3180
tgggtgtggg tacttcttgc aggttcttca agtagaaaaa gaaatgcacg aactcctatc    3240
aaatacttac atacacacat ggtgtacacc tataggtttg tccatataat gcagatgttt    3300
aatcttagtc cagaacaagt gtcgaacgga ataacagtca caaagaacaa tcttcataat    3360
gataaagatt atggtccgaa taaaatacac ccccatataa atgataacac attttcttgt    3420
aattcttaag tagatctccg agaataacat tttgtaactt aaaagaccaa ttttttgtga    3480
aaatgggccc gccgtattga ttggcatcct ataagaattc cttacttcca gaacctttga    3540
aaccagaatt agtccattct agaaaagaaa aactcagttt agcttgatgt ctgatcctat    3600
gttatagtgc ttaacannnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnnnnnnnn nnnnnnnnnn nnnnnnnnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
```

| | |
|---|---|
| nnnnnnnnnn nnnnnnnnnn nnnnnnnnnn nnnnnnnnnn nnnnnnnnnn nnnnnnnnnn | 4740 |
| nnnnnnnnnn nnnnnnnnnn nnnnnnnnnn nnnnnnnnnn nnnnnnnnnn nnnnnnnnnn | 4800 |
| nnnnnnnnnn nnnnnnnnnn nnnnnnnnnn nnnnnnnnnn nnnnnnnnnn nnnnnnnnnn | 4860 |
| nnnnnnnnnn nnnnnnnnnn nnnnnnnnnn nnnnnnnnnn nnnnnnnnnn nnnnnnnnnn | 4920 |
| nnnnnnnnnn nnnnnnnnnn nnnnnnnnnn nnnnnnnnga tcctactcgt tatacgtcgc | 4980 |
| cttaacaccc ccccccccca cccccccccc ctcctttctc ccccgcgccg cgcctccacc | 5040 |
| accaccaaca aacctagtaa aatcccacaa gtggagtctg gggaggtagc gtgtatgcag | 5100 |
| accatacccc tacttgcggg aaggtagaga ggatgttttt ctaatttgga atgtcatgcg | 5160 |
| ctcatatttt caccaaaatt acacccactg gaatctcatt aagaatttca ttaggtggaa | 5220 |
| gatcaaggaa agtggaggat gtcctttgtc atgccctcaa agtatggttc agacttgcca | 5280 |
| ctaccaaagg attcctccgt aactatcaag gaggtgccta ggaaaactgt cgccgttgtt | 5340 |
| gcttttcag gtttgtgatt tcagatttta gcatgtcaat ataaagttct attttgtatg | 5400 |
| atgatgatat gagttgagct tacagaaaga agtgaggatt catagcgccg acctcaactt | 5460 |
| tgtgggactg aggcgtagtt gttgctgcta atataaaatt ctagacagat ttgcatttta | 5520 |
| agttaatttg aaattcaata tcctagtaat cggaaagcag agctctgtct cattggtcta | 5580 |
| tggaagtaaa tcttgtttaa gtttacttag tgctttattg atagcttctc ttgttatgac | 5640 |
| atgagagaat ttttcatcta gttgtatttt ctgtgttttt cctttgatgt cctatatgcc | 5700 |
| tgctgtggta gatagcaatt tccattcaga gttcaaaagc aaaaacattt aggaattcta | 5760 |
| tttttgaagt tttacatcct aacttagcta gttttctccc attcgatttc aacaaaggtt | 5820 |
| ttgtgactga tgaagaagtt aaagcccgag aatcaagact ccgtgctgcg ctaaagggag | 5880 |
| atgcagagtt tcgggtaaaa gatggtgcct caatagaagt tgcacaggta tattcgtaga | 5940 |
| accatttcaa tagtacttgt aattctcctg gggaacatat tttggcctag tgtaaccccc | 6000 |
| aaatgacata ctagttgtgt gtttttttata cttctgcttg cagtataatc caccatttac | 6060 |
| tcttccgttc acacgtcgga atgagattag cctggaagtt gaaagggaac aggaatagct | 6120 |
| agtcagtgtg cagtatattg cagataaatc cgtgcactga tgaaaccaga gaaacaaaac | 6180 |
| atatatggtg taaataaatt atatatatat atgtatatat atttggtgat tgcttgacat | 6240 |
| tttggtaaca aggttatgta catgcacaga aatgtaaggt catttatgct tcaactctat | 6300 |
| aataacacgt tgtctttaat actc | 6324 |

<210> SEQ ID NO 24
<211> LENGTH: 900
<212> TYPE: DNA
<213> ORGANISM: Nicotiana tabacum

<400> SEQUENCE: 24

| | |
|---|---|
| atgcttctgt gctcaccttc ttccatttct gctcacaatc ttagcagaaa cagaaccaga | 60 |
| ccttcgccta tcaattctat ggcagttgac agaagcagct cccgcgttgc cacaactgct | 120 |
| tcgcagcgga gaaacggcac gtcagctctc gaagctcgca tctccctcgt catcgctctc | 180 |
| gcctcccaaa cctcttctct ctctcagaaa cttctgacgg aattggctgg tgaaaccgcg | 240 |
| aaatacgtgt taccgaagag gatattcgaa agtcggactt tagaggaagc tttgatgtct | 300 |
| gtgccggatc tggagacagt gaaattcaat gttttgaaac gcagtgatca gtatgaaata | 360 |
| agggaagttg agccttactt tgttgctgag gctacaatgc ctgggaagta tgggtttgac | 420 |

```
tttaatggtg catctcaatc cttcaacaca ttggctgagt acttgtttgg taagaacacg      480
aagaaggaga gcatggcgat gacaacacca gttatcactc gtagaactca atctgatggg      540
gagaggatgg aaatgactac tccagtgata actaaacggg tggaagatca aggaaagtgg      600
aggatgtcct ttgtcatgcc ctcaaagtat ggttcagact tgccactacc aaaggattcc      660
tccgtaacta tcaaggaggt gcctaggaaa actgtcgccg ttgttgcttt ttcaggtttt      720
gtgactgatg aagaagttaa agcccgagaa tcaagactcc gtgctgcgct aaagggagat      780
gcagagtttc gggtaaaaga tggtgcctca atagaagttg cacagtataa tccaccattt      840
actcttccgt tcacacgtcg gaatgagatt agcctggaag ttgaaaggga acaggaatag      900
```

```
<210> SEQ ID NO 25
<211> LENGTH: 300
<212> TYPE: DNA
<213> ORGANISM: Artificial Sequence
<220> FEATURE:
<223> OTHER INFORMATION: 300-nucleotide cDNA fragment

<400> SEQUENCE: 25
gtaagaacac aaagaaggaa agtatggcga tgacaacacc cgtaatcact cgtagaactc       60
aatctgatgg ggagaagatg gaaatgacta cttcagtgat aactaaaagg gtggaagatc      120
aaggaaagtg gaggatgtcc tttgtcatgc cctcaaagta tggttcggac ttgccactac      180
caaaggattc ctccgtaact atcaaggagg tgcctaggaa actgtcgcc gttgttgctt       240 tttcaggttt tgtgactgat gaagaagtta agcccgaga atcaagacta tgtgctgcgt       300
```

```
<210> SEQ ID NO 26
<211> LENGTH: 20150
<212> TYPE: DNA
<213> ORGANISM: Artificial Sequence
<220> FEATURE:
<223> OTHER INFORMATION: TRV RNA1

<400> SEQUENCE: 26
gtctcagaag accaaagggc tattgagact tttcaacaaa gggtaatttc gggaaacctc       60
ctcggattcc attgcccagc tatctgtcac ttcatcgaaa ggacagtaga aaaggaaggt      120
ggctcctaca aatgccatca ttgcgataaa ggaaaggcta tcattcaaga tgcctctgcc      180
gacagtggtc ccaaagatgg acccccaccc acgaggagca tcgtggaaaa agaagacgtc      240
ccaaccacgt cttcaaagca agtggattga tgtgacatct ccactgacgt aagggatgac      300
gcacaatccc actatccttc gcaagaccct tcttctatat aaggaagttc atttcatttg      360
gagaggacag cccaagcttt ctagaggatc cataaaacat ttcaatcctt tgaacgcggt      420
agaacgtgct aattggattt tggtgagaac gcggtagaac gtacttatca cctacagttt      480
tattttgttt ttcttttttgg tttaatctat ccagcttagt accgagtggg ggaaagtgac      540
tggtgtgcct aaaaccttt ctttgatact ttgtaaaaat acatacagat acaatggcga      600
acggtaactt caagttgtct caattgctca atgtggacga gatgtctgct gagcagagga      660
gtcatttctt tgacttgatg ctgactaaac ctgattgtga atcgggcaa atgatgcaaa      720 gagttgttgt tgataaagtc gatgacatga ttagagaaag aaagactaaa gatccagtga      780
ttgttcatga agttctttct cagaaggaac agaacaagtt gatggaaatt tatcctgaat      840
tcaatatcgt gtttaaagac gacaaaaaca tggttcatgg gtttgcggct gctgagcgaa      900
aactacaagc tttattgctt ttagatagag ttcctgctct gcaagaggtg gatgacatcg      960
gtggtcaatg gtcgttttgg gtaactagag gtgagaaaag gattcattcc tgttgtccaa     1020
```

-continued

```
atctagatat tcgggatgat cagagagaaa tttctcgaca gatatttctt actgctattg    1080
gtgatcaagc tagaagtggt aagagacaga tgtcggagaa tgagctgtgg atgtatgacc    1140
aatttcgtga aaatattgct gcgcctaacg cggttaggtg caataataca tatcagggtt    1200
gtacatgtag gggtttttct gatggtaaga agaaaggcgc gcagtatgcg atagctcttc    1260
acagcctgta tgacttcaag ttgaaagact tgatggctac tatggttgag aagaaaacta    1320
aagtggttca tgctgctatg cttttgctc ctgaaagtat gttagtggac gaaggtccat    1380
taccttctgt tgacggttac tacatgaaga agaacgggaa gatctatttc ggttttgaga    1440
aagatccttc cttttcttac attcatgact gggaagagta caagaagtat ctactgggga    1500
agccagtgag ttaccaaggg aatgtgttct acttcgaacc gtggcaggtg agaggagaca    1560
caatgctttt ttcgatctac aggatagctg gagttccgag gaggtctcta tcatcgcaag    1620
agtactaccg aagaatatat atcagtagat gggaaagcat ggttgttgtc ccaattttcg    1680
atctggtcga atcaacgcga gagttggtca agaaagacct gtttgtagag aaacaattca    1740
tggacaagtg tttggattac atagctaggt tatctgacca gcagctgacc ataagcaatg    1800
ttaaatcata cttgagttca aataattggg tcttattcat aaacggggcg gccgtgaaga    1860
acaagcaaag tgtagattct cgagatttac agttgttggc tcaaactttg ctagtgaagg    1920
aacaagtggc gagacctgtc atgagggagt tgcgtgaagc aattctgact gagacgaaac    1980
ctatcacgtc attgactgat gtgctgggtt taatatcaag aaaactgtgg aagcagtttg    2040
ctaacaagat cgcagtcggc ggattcgttg gcatggttgg tactctaatt ggattctatc    2100
caaagaaggt actaacctgg gcgaaggaca caccaaatgg tccagaacta tgttacgaga    2160
actcgcacaa aaccaaggtg atagtatttc tgagtgttgt gtatgccatt ggaggaatca    2220
cgcttatgcg tcgagacatc cgagatggac tggtgaaaaa actatgtgat atgtttgata    2280
tcaaacgggg ggcccatgtc ttagacgttg agaatccgtg ccgctattat gaaatcaacg    2340
atttctttag cagtctgtat tcggcatctg agtccggtga gaccgttta ccagatttat    2400 ccgaggtaaa agccagtct gataagctat tgcagcagaa gaaagaaatc gctgacgagt    2460
ttctaagtgc aaaattctct aactattctg gcagttcggt gagaacttct ccaccatcgg    2520
tggtcggttc atctcgaagc ggactgggtc tgttgttgga agacagtaac gtgctgaccc    2580
aagctagagt tggagtttca agaaaggtag acgatgagga gatcatggag cagtttctga    2640
gtggtcttat tgacactgaa gcagaaattg acgaggttgt ttcagccttt tcagctgaat    2700
gtgaaagagg ggaaacaagc ggtacaaagg tgttgtgtaa acctttaacg ccaccaggat    2760
ttgagaacgt gttgccagct gtcaaacctt tggtcagcaa aggaaaaacg gtcaaacgtg    2820
tcgattactt ccaagtgatg ggaggtgaga gattaccaaa aaggccggtt gtcagtggag    2880
acgattctgt ggacgctaga agagagtttc tgtactactt agatgcggag agagtcgctc    2940
aaaatgatga aattatgtct ctgtatcgtg actattcgag aggagttatt cgaactggag    3000
gtcagaatta cccgcacgga ctgggagtgt gggatgtgga gatgaagaac tggtgcatac    3060
gtccagtggt cactgaacat gcttatgtgt tccaaccaga caaacgtatg gatgattggt    3120
cgggatactt agaagtggct gtttgggaac gaggtatgtt ggtcaacgac ttcgcggtcg    3180
aaaggatgag tgattatgtc atagtttgcg atcagacgta tctttgcaat aacaggtaat    3240
aatcctctct cttgatattt ttaaattata gaattaatta gtttacttta ttctttacta    3300
tatgatttaa atagtttaat cttgtttttg agtaaactat tcgattttga tatttgtatt    3360
```

```
cgtcctacaa agttggaaat actgatgata ttttcttttg aacgtgatac ctaccaatac    3420
taatcttacg gaatctttta atagagcact aatcaacatg gaactaaaga ccaattctta    3480
agtgtctctg ttgtacagtt cattttagta gtgcgtttaa gtattattat ctcccttcat    3540
gcggggcaat tatgtagatt aaaatcgaaa ttatataaaa tttacataag tctaagtcta    3600
gggtctccag ctaattgtta ttttttttaac gatgttgact aaagcaataa cgacgttgac   3660
ttgtgttaaa caggttgatc ttggacaatt taagtgccct ggatctagga ccagttaact    3720
gttcttttga attagttgac ggtgtacctg gttgtggtaa gtcgacaatg attgtcaact    3780
cagctaatcc ttgtgtcgat gtggttctct ctactgggag agcagcaacc gacgacttga    3840
tcgagagatt cgcgagcaaa ggttttccat gcaaattgaa aaggagagtg aagacggttg    3900 attcttttt gatgcattgt gtcgatggtt ctttaaccgg agacgtgttg catttcgacg      3960
aagctctcat ggcccatgct ggtatggtgt acttttgcgc tcagatagct ggtgctaaac    4020
gatgtatctg tcaaggagat cagaatcaaa tttctttcaa gcctagggta tctcaagttg    4080
atttgaggtt ttctagtctg gtcggaaagt ttgacattgt tacagaaaaa agagaaactt    4140
acagaagtcc agcagatgtg gctgccgtat tgaacaagta ctatactgga gatgtcagaa    4200
cacataacgc gactgctaat tcgatgacgg tgaggaagat tgtgtctaaa gaacaggttt    4260
ctttgaagcc tggtgctcag tacataactt tccttcagtc tgagaagaag gagttggtaa    4320
atttgttggc attgaggaaa gtggcagcta aagtgagtac agtacacgag tcgcaaggag    4380
agacattcaa agatgtagtc ctagtcagga cgaaacctac ggatgactca atcgctagag    4440
gtcgggagta cttaatcgtg gcattgtcgc gtcacacaca atcacttgtg tatgaaactg    4500
tgaaagagga cgatgtaagc aaagagatca gggaaagtgc cgcgcttacg aaggcggctt    4560
tggcaagatt ttttgttact gagaccgtct tatgacggtt tcggtctagg tttgatgtct    4620
ttagacatca tgaagggcct tgcgccgttc cagattcagg tacgattacg gacttggaga    4680
tgtggtacga cgctttgttt ccgggaaatt cgttaagaga ctcaagccta gacgggtatt    4740
tggtggcaac gactgattgc aatttgcgat tagacaatgt tacgatcaaa agtggaaact    4800
ggaaagacaa gtttgctgaa aaagaaacgt ttctgaaacc ggttattcgt actgctatgc    4860
ctgacaaaag gaagactact cagttggaga gtttgttagc attgcagaaa aggaaccaag    4920
cggcacccga tctacaagaa aatgtgcacg cgacagttct aatcgaagag acgatgaaga    4980
agctgaaatc tgttgtctac gatgtgggaa aaattcgggc tgatcctatt gtcaatagag    5040
ctcaaatgga gagatggtgg agaaatcaaa gcacagcggt acaggctaag gtagtagcag    5100
atgtgagaga gttacatgaa atagactatt cgtcttacat gtatatgatc aaatctgacg    5160
tgaaacctaa gactgattta acaccgcaat ttgaatactc agctctacag actgttgtgt    5220
atcacgagaa gttgatcaac tcgttgttcg gtccaatttt caaagaaatt aatgaacgca    5280
agttggatgc tatgcaacca cattttgtgt tcaacacgag aatgcatcg agtgatttaa    5340 acgatcgagt gaagttctta aatacggaag cggcttacga ctttgttgag atagacatgt    5400
ctaaattcga caagtcggca aatcgcttcc atttacaact gcagctggag atttacaggt    5460
tatttgggct ggatgagtgg gcggccttcc tttgggaggt gtcgcacact caaactactg    5520
tgagagatat tcaaaatggt atgatggcgc atatttggta ccaacaaaag agtggagatg    5580
ctgatactta taatgcaaat tcagatagaa cactgtgtgc actcttgtct gaattaccat    5640
tggagaaagc agtcatggtt acatatggag gagatgactc actgattgcg tttcctagag    5700
gaacgcagtt tgttgatccg tgtccaaagt tggctactaa gtggaatttc gagtgcaaga    5760
```

```
tttttaagta cgatgtccca atgttttgtg ggaagttctt gcttaagacg tcatcgtgtt   5820
acgagttcgt gccagatccg gtaaaagttc tgacgaagtt ggggaaaaag agtataaagg   5880
atgtgcaaca tttagccgag atctacatct cgctgaatga ttccaataga gctcttggga   5940
actacatggt ggtatccaaa ctgtccgagt ctgtttcaga ccggtatttg tacaaaggtg   6000
attctgttca tgcgctttgt gcgctatgga agcatattaa gagttttaca gctctgtgta   6060
cattattccg agacgaaaac gataaggaat tgaacccggc taaggttgat tggaagaagg   6120
cacagagagc tgtgtcaaac ttttacgact ggtaatatgg aagacaagtc attggtcacc   6180
ttgaagaaga agactttcga agtctcaaaa ttctcaaatc taggggccat tgaattgttt   6240
gtggacggta ggaggaagag accgaagtat tttcacagaa gaagagaaac tgtcctaaat   6300
catgttggtg ggaagaagag tgaacacaag ttagacgttt ttgaccaaag ggattacaaa   6360
atgattaaat cttacgcgtt tctaaaggta gtaggtgtac aactagttgt aacatcacat   6420
ctacctgcag atacgcctgg gttcattcaa atcgatctgt tggattcgag acttactgag   6480
aaaagaaaga gaggaaagac tattcagaga ttcaaagctc gagcttgcga taactgttca   6540
gttgcgcagt acaaggttga atacagtatt tccacacagg agaacgtact tgatgtctgg   6600
aaggtgggtt gtatttctga gggcgttccg gtctgtgacg gtacataccc tttcagtatc   6660
gaagtgtcgc taatatgggt tgctactgat tcgactaggc gcctcaatgt ggaagaactg   6720
aacagttcgg attacattga aggcgatttt accgatcaag aggttttcgg tgagttcatg   6780
tctttgaaac aagtggagat gaagacgatt gaggcgaagt acgatggtcc ttacagacca   6840
gctactacta gacctaagtc attattgtca agtgaagatg ttaagagagc gtctaataag   6900
aaaaactcgt cttaatgcat aaagaaattt attgtcaata tgacgtgtgt actcaagggt   6960
tgtgtgaatg aagtcactgt tcttggtcac gagacgtgta gtatcggtca tgctaacaaa   7020
ttgcgaaagc aagttgctga catggttggt gtcacacgta ggtgtgcgga aaataattgt   7080
ggatggtttg tctgtgttgt tatcaatgat tttacttttg atgtgtataa ttgttgtggc   7140
cgtagtcacc ttgaaaagtg tcgtaaacgt gttgaaacaa gaaatcgaga atttggaaa    7200
caaattcgac gaaatcaagc tgaaaacatg tctgcgacag ctaaaaagtc tcataattcg   7260
aagacctcta agaagaaatt caaagaggac agagaatttg ggacaccaaa aagattttta   7320
agagatgatg ttccttccgg gattgatcgt ttgtttgctt tttgatttta ttttatattg   7380
ttatctgttt ctgtgtatag actgtttgag attggcgctt ggccgactca ttgtcttacc   7440
atagggaac ggactttgtt tgtgttgtta ttttatttgt attttattaa aattctcaat   7500
gatctgaaaa ggcctcgagg ctaagagatt attgggggt gagtaagtac ttttaaagtg   7560
atgatggtta caaaggcaaa aggggtaaaa cccctcgcct acgtaagcgt tattacgccc   7620
ggatccccg gggagctcga attcgctgaa atcaccagtc tctctctaca aatctatctc   7680
tctctatttt ttccataaat aatgtgtgag tagtttcccg ataagggaaa ttagggttct   7740
tatagggttt cgctcatgtg ttgagcatat aagaaaccct tagtatgtat ttgtatttgt   7800
aaaatacttc tattatcaat aaaatttcta attcctaaaa ccaaaatcca gtactaaaat   7860
ccagatctcc taaagtccct atagatcttt gtcgtgaata taaccagac acgagacgac    7920
taaacctgga gcccagacgc cgttcgaagc tagaagtacc gcttaggcag gaggccgtta   7980
gggaaaagat gctaaggcag ggttggttac gttgactccc ccgtaggttt ggtttaaata   8040
tgatgaagtg gacggaagga aggaggaaga caaggaagga taaggttgca ggccctgtgc   8100
```

```
aaggtaagaa gatggaaatt tgatagaggt acgctactat acttatacta tacgctaagg    8160
gaatgcttgt attttataccc tatcccccct aataacccct tatcaattta agaaataatc    8220
cgcataagcc cccgcttaaa aattggtatc agagccatga ataggtctat gaccaaaact    8280
caagaggata aaacctcacc aaaatacgaa agagttctta actctaaaga taaaagatct    8340
ttcaagatca aaactagttc cctcacaccg gagcatgcga tatcctcgac ctgcaggcat    8400
gcaagcttgg cgtaatcatg gtcatagctg tttcctgtgt gaaattgtta tccgctcaca    8460
attccacaca acatacgagc cggaagcata aagtgtaaag cctggggtgc ctaatgagtg    8520
agctaactca cattaattgc gttgcgctca ctgcccgctt tccagtcggg aaacctgtcg    8580
tgccagctgc attaatgaat cggccaacgc gcggggagag gcggtttgcg tattgggcca    8640
aagacaaaag gcgacattc aaccgattga gggagggaag gtaaatattg acggaaatta    8700
ttcattaaag gtgaattatc accgtcaccg acttgagcca tttgggaatt agagccagca    8760
aaatcaccag tagcaccatt accattagca aggccgaaaa cgtcaccaat gaaaccatcg    8820
atagcagcac cgtaatcagt agcgacagaa tcaagtttgc ctttagcgtc agactgtagc    8880
gcgttttcat cggcattttc ggtcatagcc cccttattag cgtttgccat cttttcataa    8940
tcaaaatcac cggaaccaga gccaccaccg gaaccgcctc cctcagagcc gcaccctca    9000 gaaccgccac cctcagagcc accaccctca gagccgccac cagaaccacc accagagccg    9060
ccgccagcat tgacaggagg cccgatctag taacatagat gacaccgcgc gcgataattt    9120
atcctagttt gcgcgctata ttttgttttc tatcgcgtat taaatgtata attgcgggac    9180
tctaatcata aaaacccatc tcataaataa cgtcatgcat tacatgttaa ttattacatg    9240
cttaacgtaa ttcaacagaa attatatgat aatcatcgca agaccggcaa caggattcaa    9300
tcttaagaaa ctttattgcc aaatgtttga acgatcgggg atcatccggg tctgtggcgg    9360
gaactccacg aaaatatccg aacgcagcaa gatatcgcgg tgcatctcgg tcttgcctgg    9420
gcagtcgccg ccgacgccgt tgatgtggac gccgggcccg atcatattgt cgctcaggat    9480
cgtggcgttg tgcttgtcgg ccgttgctgt cgtaatgata tcggcacctt cgaccgcctg    9540
ttccgcagag atcccgtggg cgaagaactc cagcatgaga tccccgcgct ggaggatcat    9600
ccagccggcg tcccggaaaa cgattccgaa gcccaacctt tcatagaagg cggcggtgga    9660
atcgaaatct cgtgatggca ggttgggcgt cgcttggtcg gtcatttcga accccagagt    9720
cccgctcaga agaactcgtc aagaaggcga tagaaggcga tgcgctgcga atcgggagcg    9780
gcgataccgt aaagcacgag gaagcggtca gcccattcgc cgccaagctc ttcagcaata    9840
tcacgggtag ccaacgctat gtcctgatag cggtccgcca cacccagccg gccacagtcg    9900
atgaatccag aaaagcggcc attttccacc atgatattcg gcaagcaggc atcgccatgg    9960
gtcacgacga gatcatcgcc gtcgggcatg cgcgccttga gcctggcgaa cagttcggct    10020
ggcgcgagcc cctgatgctc ttcgtccaga tcatcctgat cgacaagacc ggcttccatc    10080
cgagtacgtg ctcgctcgat gcgatgtttc gcttggtggt cgaatgggca ggtagccgga    10140
tcaagcgtat gcagccgccg cattgcatca gccatgatgg atactttctc ggcaggagca    10200
aggtgagatg acaggagatc ctgccccggc acttcgccca atagcagcca gtcccttccc    10260
gcttcagtga caacgtcgag cacagctgcg caaggaacgc ccgtcgtggc cagccacgat    10320
agccgcgctg cctcgtcctg cagttcattc agggcaccgg acaggtcggt cttgacaaaa    10380
agaaccgggc gcccctgcgc tgacagccgg aacacggcgg catcagagca gccgattgtc    10440
tgttgtgccc agtcatagcc gaatagcctc tccacccaag cggccggaga acctgcgtgc    10500
```

```
aatccatctt gttcaatcat gcgaaacgat ccagatccgg tgcagattat ttggattgag   10560
agtgaatatg agactctaat tggataccga ggggaattta tggaacgtca gtggagcatt   10620
tttgacaaga aatatttgct agctgatagt gaccttaggc gacttttgaa cgcgcaataa   10680
tggtttctga cgtatgtgct tagctcatta aactccagaa acccgcggct gagtggctcc   10740
ttcaacgttg cggttctgtc agttccaaac gtaaacggc ttgtcccgcg tcatcggcgg    10800
gggtcataac gtgactccct taattctccg ctcatgatca gattgtcgtt tcccgccttc   10860
agtttaaact atcagtgttt gacaggatat attggcgggt aaacctaaga gaaagagcg    10920 tttattagaa taatcggata tttaaaaggg cgtgaaaagg tttatccgtt cgtccatttg   10980
tatgtgcatg ccaaccacag ggttccccag atctggcgcc ggccagcgag acgagcaaga   11040
ttggccgccg cccgaaacga tccgacagcg cgcccagcac aggtgcgcag gcaaattgca   11100
ccaacgcata cagcgccagc agaatgccat agtgggcggt gacgtcgttc gagtgaacca   11160
gatcgcgcag gaggcccggc agcaccggca taatcaggcc gatgccgaca cgtcgagcg    11220 cgacagtgct cagaattacg atcaggggta tgttgggttt cacgtctggc ctccggacca   11280
gcctccgctg gtccgattga acgcgcggat tctttatcac tgataagttg gtggacatat   11340
tatgtttatc agtgataaag tgtcaagcat gacaaagttg cagccgaata cagtgatccg   11400
tgccgccctg gacctgttga acgaggtcgg cgtagacggt ctgacgacac gcaaactggc   11460
ggaacggttg ggggttcagc agccggcgct ttactggcac ttcaggaaca gcgggcgct    11520 gctcgacgca ctggccgaag ccatgctggc ggagaatcat acgcattcgg tgccgagagc   11580
cgacgacgac tggcgctcat ttctgatcgg gaatgcccgc agcttcaggc aggcgctgct   11640
cgcctaccgc gatggcgcgc gcatccatgc cggcacgcga ccgggcgcac cgcagatgga   11700
aacggccgac gcgcagcttc gcttcctctg cgaggcgggt ttttcggccg gggacgccgt   11760
caatgcgctg atgacaatca gctacttcac tgttggggcc gtgcttgagg agcaggccgg   11820
cgacagcgat gccggcgagc gcggcggcac cgttgaacag gctccgctct cgccgctgtt   11880 gcggccgcg atagacgcct tcgacgaagc cggtccggac gcagcgttcg agcagggact    11940
cgcggtgatt gtcgatggat tggcgaaaag gaggctcgtt gtcaggaacg ttgaaggacc   12000
gagaaagggt gacgattgat caggaccgct gccggagcgc aacccactca ctacagcaga   12060
gccatgtaga caacatcccc tccccctttc caccgcgtca gacgcccgta gcagcccgct   12120
acgggctttt tcatgccctg ccctagcgtc aagcctcac ggccgcgctc ggcctctctg    12180
gcggccttct ggcgctcttc cgcttcctcg ctcactgact cgctgcgctc ggtcgttcgg   12240
ctgcggcgag cggtatcagc tcactcaaag gcggtaatac ggttatccac agaatcaggg   12300
gataacgcag gaaagaacat gtgagcaaaa ggccagcaaa aggccaggaa ccgtaaaaag   12360
gccgcgttgc tggcgttttt ccataggctc cgcccccctg acgagcatca caaaaatcga   12420
cgctcaagtc agaggtggcg aaacccgaca ggactataaa gataccaggc gtttccccct   12480
ggaagctccc tcgtgcgctc tcctgttccg accctgccgc ttaccggata cctgtccgcc   12540
tttctccctt cggaagcgt ggcgctttc cgctgcataa ccctgcttcg ggtcattat     12600 agcgattttt tcggtatatc catccttttt cgcacgatat acaggatttt gccaaagggt   12660
tcgtgtagac tttccttggt gtatccaacg cgtcagccg gcaggatag gtgaagtagg    12720 cccacccgcg agcgggtgtt ccttcttcac tgtcccttat tcgcacctgg cggtgctcaa   12780
cgggaatcct gctctgcgag gctggccggc taccgccggc gtaacagatg agggcaagcg   12840
```

```
gatggctgat gaaaccaagc caaccaggaa gggcagccca cctatcaagg tgtactgcct    12900
tccagacgaa cgaagagcga ttgaggaaaa ggcggcggcg gccggcatga gcctgtcggc    12960
ctacctgctg gccgtcggcc agggctacaa aatcacgggc gtcgtggact atgagcacgt    13020
ccgcgagctg gcccgcatca atggcgacct gggccgcctg gcggcctgc tgaaactctg     13080
gctcaccgac gacccgcgca cggcgcggtt cggtgatgcc acgatcctcg ccctgctggc    13140
gaagatcgaa gagaagcagg acgagcttgg caaggtcatg atgggcgtgg tccgcccgag    13200
ggcagagcca tgactttttt agccgctaaa acggccgggg ggtgcgcgtg attgccaagc    13260
acgtccccat gcgctccatc aagaagagcg acttcgcgga gctggtgaag tacatcaccg    13320
acgagcaagg caagaccgag cgcctttgcg acgctcaccg ggctggttgc cctcgccgct    13380
gggctggcgg ccgtctatgg ccctgcaaac gcgccagaaa cgccgtcgaa gccgtgtgcg    13440
agacaccgcg gccgccggcg ttgtggatac ctcgcggaaa acttggccct cactgacaga    13500
tgaggggcgg acgttgacac ttgaggggcc gactcacccg gcgcggcgtt gacagatgag    13560
gggcaggctc gatttcggcc ggcgacgtgg agctggccag cctcgcaaat cggcgaaaac    13620
gcctgatttt acgcgagttt cccacagatg atgtggacaa gcctggggat aagtgccctg    13680
cggtattgac acttgagggg cgcgactact gacagatgag gggcgcgatc cttgacactt    13740
gaggggcaga gtgctgacag atgaggggcg caccctattga catttgaggg gctgtccaca    13800
ggcagaaaat ccagcatttg caagggtttc gcccgtttt tcggccaccg ctaacctgtc     13860
ttttaacctg cttttaaacc aatattata aaccttgttt ttaaccaggg ctgcgccctg      13920
tgcgcgtgac cgcgcacgcc gaaggggggt gccccccctt ctcgaaccct ccggccgc      13980
taacgcgggc ctcccatccc cagggggct gcgccctcg gccgcgaacg gcctcacccc      14040
aaaaatggca gcgctggcag tccttgccat tgccgggatc ggggcagtaa cgggatgggc    14100
gatcagcccg agcgcgacgc ccggaagcat tgacgtgccg caggtgctgg catcgacatt    14160
cagcgaccag gtgccgggca gtgagggcgg cggcctgggt ggcggcctgc ccttcacttc    14220
ggccgtcggg gcattcacgg acttcatggc ggggccggca attttttacct tgggcattct   14280
tggcatagtg gtcgcgggtg ccgtgctcgt gttcggggt gcgataaacc cagcgaacca     14340
tttgaggtga taggtaagat tataccgagg tatgaaaacg agaattggac ctttacagaa    14400
ttactctatg aagcgccata tttaaaaagc taccaagacg aagaggatga agaggatgag    14460
gaggcagatt gccttgaata tattgacaat actgataaga taatatatct tttatataga    14520
agatatcgcc gtatgtaagg atttcagggg gcaaggcata ggcagcgcgc ttatcaatat    14580
atctatagaa tgggcaaagc ataaaaactt gcatggacta atgcttgaaa cccaggacaa    14640
taaccttata gcttgtaaat tctatcataa ttgggtaatg actccaactt attgatagtg    14700
ttttatgttc agataatgcc cgatgacttt gtcatgcagc tccaccgatt ttgagaacga    14760
cagcgacttc cgtcccagcc gtgccaggtg ctgcctcaga ttcaggttat gccgctcaat    14820
tcgctgcgta tatcgcttgc tgattacgtg cagctttccc ttcaggcggg attcatacag    14880
cggccagcca tccgtcatcc atatcaccac gtcaaagggt gacagcaggc tcataagacg    14940
ccccagcgtc gccatagtgc gttcaccgaa tacgtgcgca acaaccgtct tccggagact    15000
gtcatacgcg taaaacagcc agcgctggcg cgatttagcc ccgacatagc cccactgttc    15060
gtccatttcc gcgcagacga tgacgtcact gcccggctgt atgcgcgagg ttaccgactg    15120
cggcctgagt ttttttaagtg acgtaaaatc gtgttgaggc caacgccat aatgcgggct    15180
gttgcccggc atccaacgcc attcatggcc atatcaatga ttttctggtg cgtaccgggt    15240
```

```
tgagaagcgg tgtaagtgaa ctgcagttgc catgttttac ggcagtgaga gcagagatag   15300
cgctgatgtc cggcggtgct tttgccgtta cgcaccaccc cgtcagtagc tgaacaggag   15360
ggacagctga tagacacaga agccactgga gcacctcaaa acaccatca tacactaaat   15420 cagtaagttg gcagcatcac ccataattgt ggtttcaaaa tcggctccgt cgatactatg   15480
ttatacgcca actttgaaaa caactttgaa aaagctgttt tctggtattt aaggttttag   15540
aatgcaagga acagtgaatt ggagttcgtc ttgttataat tagcttcttg gggtatcttt   15600
aaatactgta gaaagagga aggaaataat aaatggctaa aatgagaata tcaccggaat   15660
tgaaaaaact gatcgaaaaa taccgctgcg taaaagatac ggaaggaatg tctcctgcta   15720
aggtatataa gctggtggga gaaatgaaa acctatattt aaaaatgacg gacagccggt   15780
ataaagggac cacctatgat gtggaacggg aaaaggacat gatgctatgg ctggaaggaa   15840
agctgcctgt tccaaaggtc ctgcactttg aacggcatga tggctggagc aatctgctca   15900
tgagtgaggc cgatggcgtc ctttgctcgg aagagtatga agatgaacaa agccctgaaa   15960
agattatcga gctgtatgcg gagtgcatca ggctctttca ctccatcgac atatcggatt   16020
gtccctatac gaatagctta gacagccgct tagccgaatt ggattactta ctgaataacg   16080
atctggccga tgtggattgc gaaaactggg aagaagacac tccatttaaa gatccgcgcg   16140
agctgtatga ttttttaaag acggaaaagc ccgaagagga acttgtcttt tcccacggcg   16200
acctgggaga cagcaacatc tttgtgaaag atggcaaagt aagtggcttt attgatcttg   16260
ggagaagcgg cagggcggac aagtggtatg acattgcctt ctgcgtccgg tcgatcaggg   16320
aggatatcgg ggaagaacag tatgtcgagc tatttttga cttactgggg atcaagcctg   16380
attgggagaa aataaaatat tatatttac tggatgaatt gttttagtac ctagatgtgg   16440
cgcaacgatg ccggcgacaa gcaggagcgc accgacttct tccgcatcaa gtgttttggc   16500
tctcaggccg aggcccacgg caagtatttg gcaaggggt cgctggtatt cgtgcagggc   16560
aagattcgga ataccaagta cgagaaggac ggccagacgg tctacgggac cgacttcatt   16620
gccgataagg tggattatct ggacaccaag gcaccaggcg ggtcaaatca ggaataaggg   16680
cacattgccc cggcgtgagt cggggcaatc ccgcaaggag ggtgaatgaa tcggacgttt   16740
gaccggaagg catacaggca agaactgatc gacgcggggt tttccgccga ggatgccgaa   16800
accatcgcaa gccgcaccgt catgcgtgcg ccccgcgaaa ccttccagtc cgtcggctcg   16860
atggtccagc aagctacggc caagatcgag cgcgacagcg tgcaactggc tcccctgcc   16920 ctgcccgcgc atcggccgc cgtggagcgt tcgcgtcgtc tcgaacagga ggcggcaggt   16980
ttggcgaagt cgatgaccat cgacacgcga ggaactatga cgaccaagaa gcgaaaaacc   17040
gccggcgagg acctggcaaa acaggtcagc gaggccaagc aggccgcgtt gctgaaacac   17100
acgaagcagc agatcaagga aatgcagctt tccttgttcg atattgcgcc gtggccggac   17160
acgatgcgag cgatgccaaa cgacacggcc cgctctgccc tgttcaccac cgcaacaag   17220 aaaatcccgc gcgaggcgct gcaaaacaag gtcattttcc acgtcaacaa ggacgtgaag   17280
atcacctaca ccggcgtcga gctgcgggcc gacgatgacg aactggtgtg gcagcaggtg   17340
ttggagtacg cgaagcgcac ccctatcggc gagccgatca ccttcacgtt ctacgagctt   17400
tgccaggacc tgggctggtc gatcaatggc cggtattaca cgaaggccga ggaatgcctg   17460
tcgcgcctac aggcgacggc gatgggcttc acgtccgacc gcgttgggca cctggaatcg   17520
gtgtcgctgc tgcaccgctt ccgcgtcctg gaccgtggca agaaaacgtc ccgttgccag   17580
```

```
gtcctgatcg acgaggaaat cgtcgtgctg tttgctggcg accactacac gaaattcata  17640
tgggagaagt accgcaagct gtcgccgacg gcccgacgga tgttcgacta tttcagctcg  17700
caccgggagc cgtacccgct caagctggaa accttccgcc tcatgtgcgg atcggattcc  17760
acccgcgtga agaagtggcg cgagcaggtc ggcgaagcct gcgaagagtt gcgaggcagc  17820
ggcctggtgg aacacgcctg ggtcaatgat gacctggtgc attgcaaacg ctagggcctt  17880
gtggggtcag ttccggctgg gggttcagca gccagcgctt tactggcatt tcaggaacaa  17940
gcgggcactg ctcgacgcac ttgcttcgct cagtatcgct cgggacgcac ggcgcgctct  18000
acgaactgcc gataaacaga ggattaaaat tgacaattgt gattaaggct cagattcgac  18060
ggcttggagc ggccgacgtg caggatttcc gcgagatccg attgtcggcc ctgaagaaag  18120
ctccagagat gttcgggtcc gtttacgagc acgaggagaa aaagcccatg gaggcgttcg  18180
ctgaacggtt gcgagatgcc gtggcattcg gcgcctacat cgacggcgag atcattgggc  18240
tgtcggtctt caaacaggag gacgccccca aggacgctca aaggcgcat ctgtccggcg  18300 ttttcgtgga gcccgaacag cgaggccgag gggtcgccgg tatgctgctg cgggcgttgc  18360
cggcgggttt attgctcgtg atgatcgtcc gacagattcc aacgggaatc tggtggatgc  18420
gcatcttcat cctcggcgca cttaatattt cgctattctg gagcttgttg tttatttcgg  18480
tctaccgcct gccgggcggg gtcgcggcga cggtaggcgc tgtgcagccg ctgatggtcg  18540
tgttcatctc tgccgctctg ctaggtagcc cgatacgatt gatggcggtc ctgggggcta  18600
tttgcggaac tgcgggcgtg gcgctgttgg tgttgacacc aaacgcagcg ctagatcctg  18660
tcggcgtcgc agcgggcctg gcggggggcgg tttccatggc gttcggaacc gtgctgaccc  18720
gcaagtggca acctcccgtg cctctgctca cctttaccgc ctggcaactg gcggccggag  18780
gacttctgct cgttccagta gctttagtgt ttgatccgcc aatcccgatg cctacaggaa  18840
ccaatgttct cggcctggcg tggctcggcc tgatcggagc gggtttaacc tacttccttt  18900
ggttccgggg gatctcgcga ctcgaaccta cagttgtttc cttactgggc tttctcagcc  18960
ccagatctgg ggtcgatcag ccggggatgc atcaggccga cagtcggaac ttcgggtccc  19020
cgacctgtac cattcggtga gcaatggata ggggagttga tatcgtcaac gttcacttct  19080
aaagaaatag cgccactcag cttcctcagc ggctttatcc agcgatttcc tattatgtcg  19140
gcatagttct caagatcgac agcctgtcac ggttaagcga gaaatgaata agaaggctga  19200
taattcggat ctctgcgagg gagatgatat ttgatcacag gcagcaacgc tctgtcatcg  19260
ttacaatcaa catgctaccc tccgcgagat catccgtgtt tcaaacccgg cagcttagtt  19320
gccgttcttc cgaatagcat cggtaacatg agcaaagtct gccgccttac aacggctctc  19380
ccgctgacgc cgtcccggac tgatgggctg cctgtatcga gtggtgattt tgtgccgagc  19440
tgccggtcgg ggagctgttg gctggctggt ggcaggatat attgtggtgt aaacaaattg  19500
acgcttagac aacttaataa cacattgcgg acgttttaa tgtactgggg tggtttttct  19560
tttcaccagt gagacgggca acagctgatt gcccttcacc gcctggccct gagagagttg  19620
cagcaagcgg tccacgctgg tttgccccag caggcgaaaa tcctgtttga tggtggttcc  19680
gaaatcggca aaatccctta taaatcaaaa gaatagcccg ataggggtt gagtgttgtt  19740 ccagtttgga acaagagtcc actattaaag aacgtggact ccaacgtcaa agggcgaaaa  19800
accgtctatc agggcgatgg cccactacgt gaaccatcac ccaaatcaag tttttgggg  19860 tcgaggtgcc gtaaagcact aaatcggaac cctaaaggga gccccgatt tagagcttga  19920 cggggaaagc cggcgaacgt ggcgagaaag gaagggaaga aagcgaaagg agcgggcgcc  19980
```

| | |
|---|---|
| attcaggctg cgcaactgtt gggaagggcg atcggtgcgg gcctcttcgc tattacgcca | 20040 |
| gctggcgaaa gggggatgtg ctgcaaggcg attaagttgg gtaacgccag gttttccca | 20100 |
| gtcacgacgt tgtaaaacga cggccagtga attcgagctc ggtaccccc | 20150 |

<210> SEQ ID NO 27
<211> LENGTH: 20150
<212> TYPE: DNA
<213> ORGANISM: Artificial Sequence
<220> FEATURE:
<223> OTHER INFORMATION: TRV RNA2

<400> SEQUENCE: 27

| | |
|---|---|
| gtctcagaag accaaagggc tattgagact tttcaacaaa gggtaatttc gggaaacctc | 60 |
| ctcggattcc attgcccagc tatctgtcac ttcatcgaaa ggacagtaga aaggaaggt | 120 |
| ggctcctaca aatgccatca ttgcgataaa ggaaaggcta tcattcaaga tgcctctgcc | 180 |
| gacagtggtc ccaaagatgg accccaccc acgaggagca tcgtggaaaa agaagacgtc | 240 |
| ccaaccacgt cttcaaagca agtggattga tgtgacatct ccactgacgt aagggatgac | 300 |
| gcacaatccc actatccttc gcaagaccct tcttctatat aaggaagttc atttcatttg | 360 |
| gagaggacag cccaagcttt ctagaggatc cataaaacat ttcaatcctt tgaacgcggt | 420 |
| agaacgtgct aattggattt tggtgagaac gcggtagaac gtacttatca cctacagttt | 480 |
| tatttgttt ttcttttgg tttaatctat ccagcttagt accgagtggg ggaaagtgac | 540 |
| tggtgtgcct aaaacctttt ctttgatact ttgtaaaaat acatacagat acaatgcga | 600 |
| acggtaactt caagttgtct caattgctca atgtggacga gatgtctgct gagcagagga | 660 |
| gtcatttctt tgacttgatg ctgactaaac ctgattgtga atcgggcaa atgatgcaaa | 720 |
| gagttgttgt tgataaagtc gatgcacatga ttagagaaag aaagactaaa gatccagtga | 780 |
| ttgttcatga agttctttct cagaaggaac agaacaagtt gatggaaatt tatcctgaat | 840 |
| tcaatatcgt gtttaaagac gacaaaaaca tggttcatgg gtttgcggct gctgagcgaa | 900 |
| aactacaagc tttattgctt ttagatagag ttcctgctct gcaagaggtg gatgacatcg | 960 |
| gtggtcaatg gtcgttttgg gtaactgag gtgagaaaag gattcattcc tgttgtccaa | 1020 |
| atctagatat tcgggatgat cagagagaaa tttctcgaca gatatttctt actgctattg | 1080 |
| gtgatcaagc tagaagtggt aagagacaga tgtcggagaa tgagctgtgg atgtatgacc | 1140 |
| aatttcgtga aaatattgct gcgcctaacg cggttaggtg caataataca tatcagggtt | 1200 |
| gtacatgtag gggtttttct gatggtaaga agaaaggcgc gcagtatgcg atagctcttc | 1260 |
| acagcctgta tgacttcaag ttgaaagact tgatggctac tatggttgag aagaaaacta | 1320 |
| aagtggttca tgctgctatg cttttttgctc ctgaaagtat gttagtggac gaaggtccat | 1380 |
| taccttctgt tgacggttac tacatgaaga agaacgggaa gatctatttc ggttttgaga | 1440 |
| aagatccttc cttttcttac attcatgact gggaagagta caagaagtat ctactgggga | 1500 |
| agccagtgag ttaccaaggg aatgtgttct acttcgaacc gtggcaggtg agaggagaca | 1560 |
| caatgctttt ttcgatctac aggatagctg gagttccgag gaggtctcta tcatcgcaag | 1620 |
| agtactaccg aagaatatat atcagtagat gggaaagcat ggttgttgtc ccaattttcg | 1680 |
| atctggtcga atcaacgcga gagttggtca agaaagacct gtttgtagag aaacaattca | 1740 |
| tggacaagtg tttggattac atagctaggt tatctgacca gcagctgacc ataagcaatg | 1800 |
| ttaaatcata cttgagttca aataattggg tcttattcat aaacggggcg gccgtgaaga | 1860 |

```
acaagcaaag tgtagattct cgagatttac agttgttggc tcaaactttg ctagtgaagg    1920
aacaagtggc gagacctgtc atgagggagt tgcgtgaagc aattctgact gagacgaaac    1980
ctatcacgtc attgactgat gtgctgggtt aatatcaag aaaactgtgg aagcagtttg    2040
ctaacaagat cgcagtcggc ggattcgttg gcatggttgg tactctaatt ggattctatc    2100
caaagaaggt actaacctgg gcgaaggaca caccaaatgg tccagaacta tgttacgaga    2160
actcgcacaa aaccaaggtg atagtatttc tgagtgttgt gtatgccatt ggaggaatca    2220
cgcttatgcg tcgagacatc cgagatggac tggtgaaaaa actatgtgat atgtttgata    2280
tcaaacgggg ggcccatgtc ttagacgttg agaatccgtg ccgctattat gaaatcaacg    2340
atttctttag cagtctgtat tcggcatctg agtccggtga gaccgtttta ccagatttat    2400
ccgaggtaaa agccaagtct gataagctat tgcagcagaa gaaagaaatc gctgacgagt    2460
ttctaagtgc aaaattctct aactattctg gcagttcggt gagaacttct ccaccatcgg    2520
tggtcggttc atctcgaagc ggactgggtc tgttgttgga agacagtaac gtgctgaccc    2580
aagctagagt tggagtttca agaaaggtag acgatgagga gatcatggag cagtttctga    2640
gtggtcttat tgacactgaa gcagaaattg acgaggttgt ttcagccttt tcagctgaat    2700
gtgaaagagg ggaaacaagc ggtacaaagg tgttgtgtaa acctttaacg ccaccaggat    2760
ttgagaacgt gttgccagct gtcaaacctt tggtcagcaa aggaaaaacg gtcaaacgtg    2820
tcgattactt ccaagtgatg ggaggtgaga gattaccaaa aaggccggtt gtcagtggag    2880
acgattctgt ggacgctaga agagagtttc tgtactactt agatgcggag agagtcgctc    2940
aaaatgatga aattatgtct ctgtatcgta actattcgag aggagttatt cgaactggag    3000
gtcagaatta cccgcacgga ctgggagtgt gggatgtgga gatgaagaac tggtgcatac    3060
gtccagtggt cactgaacat gcttatgtgt tccaaccaga caaacgtatg gatgattggt    3120
cgggatactt agaagtggct gtttgggaac gaggtatgtt ggtcaacgac ttcgcggtcg    3180
aaaggatgag tgattatgtc atagtttgcg atcagacgta tctttgcaat aacaggtaat    3240
aatcctctct cttgatattt ttaaattata gaattaatta gtttacttta ttctttacta    3300
tatgatttaa atagtttaat cttgtttttg agtaaactat tcgattttga tatttgtatt    3360
cgtcctacaa agttggaaat actgatgata ttttcttttg aacgtgatac ctaccaatac    3420
taatcttacg gaatctttta atagagcact aatcaacatg gaactaaaga ccaattctta    3480
agtgtctctg ttgtacagtt catttttagta gtgcgtttaa gtattattat ctcccttcat    3540
gcggggcaat tatgtagatt aaaatcgaaa ttatataaaa tttacataag tctaagtcta    3600
gggtctccag ctaattgtta ttttttttaac gatgttgact aaaagcaataa cgacgttgac    3660 ttgtgttaaa caggttgatc ttggacaatt taagtgccct ggatctagga ccagttaact    3720
gttcttttga attagttgac ggtgtacctg gttgtggtaa gtcgacaatg attgtcaact    3780
cagctaatcc ttgtgtcgat gtggttctct ctactgggag agcagcaacc gacgacttga    3840
tcgagagatt cgcgagcaaa ggttttccat gcaaattgaa aaggagagtg aagacggttg    3900 attcttttt gatgcattgt gtcgatggtt ctttaaccgg agacgtgttg catttcgacg    3960
aagctctcat ggcccatgct ggtatggtgt acttttgcgc tcagatagct ggtgctaaac    4020
gatgtatctg tcaaggagat cagaatcaaa tttctttcaa gcctagggta tctcaagttg    4080
atttgaggtt ttctagtctg gtcggaaagt ttgacattgt tacagaaaaa agagaaactt    4140
acagaagtcc agcagatgtg gctgccgtat tgaacaagta ctatactgga gatgtcagaa    4200
cacataacgc gactgctaat tcgatgacgg tgaggaagat tgtgtctaaa gaacaggttt    4260
```

```
ctttgaagcc tggtgctcag tacataactt tccttcagtc tgagaagaag gagttggtaa    4320
atttgttggc attgaggaaa gtggcagcta aagtgagtac agtacacgag tcgcaaggag    4380
agacattcaa agatgtagtc ctagtcagga cgaaacctac ggatgactca atcgctagag    4440
gtcgggagta cttaatcgtg gcattgtcgc gtcacacaca atcacttgtg tatgaaactg    4500
tgaaagagga cgatgtaagc aaagagatca gggaaagtgc cgcgcttacg aaggcggctt    4560
tggcaagatt ttttgttact gagaccgtct tatgacggtt tcggtctagg tttgatgtct    4620
ttagacatca tgaagggcct tgcgccgttc cagattcagg tacgattacg gacttggaga    4680
tgtggtacga cgctttgttt ccgggaaatt cgttaagaga ctcaagccta dacgggtatt    4740
tggtggcaac gactgattgc aatttgcgat tagacaatgt tacgatcaaa agtggaaact    4800
ggaaagacaa gtttgctgaa aaagaaacgt ttctgaaacc ggttattcgt actgctatgc    4860
ctgacaaaag gaagactact cagttggaga gtttgttagc attgcagaaa aggaaccaag    4920
cggcacccga tctacaagaa aatgtgcacg cgacagttct aatcgaagag acgatgaaga    4980
agctgaaatc tgttgtctac gatgtgggaa aaattcgggc tgatcctatt gtcaatagag    5040
ctcaaatgga gagatggtgg agaaatcaaa gcacagcggt acaggctaag gtagtagcag    5100
atgtgagaga gttacatgaa atagactatt cgtcttacat gtatatgatc aaatctgacg    5160
tgaaacctaa gactgattta acaccgcaat ttgaatactc agctctacag actgttgtgt    5220
atcacgagaa gttgatcaac tcgttgttcg gtccaatttt caaagaaatt aatgaacgca    5280
agttggatgc tatgcaacca cattttgtgt tcaacacgag aatgcatcg agtgatttaa    5340 acgatcgagt gaagttctta aatacggaag cggcttacga ctttgttgag atagacatgt    5400
ctaaattcga caagtcggca aatcgcttcc atttacaact gcagctggag atttacaggt    5460
tatttgggct ggatgagtgg gcggccttcc tttgggaggt gtcgcacact caaactactg    5520
tgagagatat tcaaaatggt atgatggcgc atatttggta ccaacaaaag agtggagatg    5580
ctgatactta taatgcaaat tcagatagaa cactgtgtgc actcttgtct gaattaccat    5640
tggagaaagc agtcatggtt acatatgag gagatgactc actgattgcg tttcctagag    5700
gaacgcagtt tgttgatccg tgtccaaagt tggctactaa gtggaatttc gagtgcaaga    5760
tttttaagta cgatgtccca atgttttgtg ggaagttctt gcttaagacg tcatcgtgtt    5820
acgagttcgt gccagatccg gtaaaagttc tgacgaagtt ggggaaaaag agtataaagg    5880
atgtgcaaca tttagccgag atctacatct cgctgaatga ttccaataga gctcttggga    5940
actacatggt ggtatccaaa ctgtccgagt ctgtttcaga ccggtatttg tacaaaggtg    6000
attctgttca tgcgctttgt gcgctatgga agcatattaa gagttttaca gctctgtgta    6060
cattattccg agacgaaaac gataaggaat tgaacccggc taaggttgat tggaagaagg    6120
cacagagagc tgtgtcaaac ttttacgact ggtaatatgg aagacaagtc attggtcacc    6180
ttgaagaaga agactttcga agtctcaaaa ttctcaaatc tagggggccat tgaattgttt    6240 gtggacggta ggaggaagag accgaagtat tttcacagaa gaagagaaac tgtcctaaat    6300
catgttggtg ggaagaagag tgaacacaag ttagacgttt ttgaccaaag ggattacaaa    6360
atgattaaat cttacgcgtt tctaaaggta gtaggtac aactagttgt aacatcacat    6420
ctacctgcag atacgcctgg gttcattcaa atcgatctgt tggattcgag acttactgag    6480
aaaagaaaga gaggaaagac tattcagaga ttcaaagctc gagcttgcga taactgttca    6540
gttgcgcagt acaaggttga atacagtatt tccacacagg agaacgtact tgatgtctgg    6600
```

```
aaggtgggtt gtatttctga gggcgttccg gtctgtgacg gtacataccc tttcagtatc    6660
gaagtgtcgc taatatgggt tgctactgat tcgactaggc gcctcaatgt ggaagaactg    6720
aacagttcgg attacattga aggcgatttt accgatcaag aggttttcgg tgagttcatg    6780
tctttgaaac aagtggagat gaagacgatt gaggcgaagt acgatggtcc ttacagacca    6840
gctactacta gacctaagtc attattgtca agtgaagatg ttaagagagc gtctaataag    6900
aaaaactcgt cttaatgcat aaagaaattt attgtcaata tgacgtgtgt actcaagggt    6960
tgtgtgaatg aagtcactgt tcttggtcac gagacgtgta gtatcggtca tgctaacaaa    7020
ttgcgaaagc aagttgctga catggttggt gtcacacgta ggtgtgcgga aaataattgt    7080
ggatggtttg tctgtgttgt tatcaatgat tttactttg atgtgtataa ttgttgtggc    7140
cgtagtcacc ttgaaaagtg tcgtaaacgt gttgaaacaa gaaatcgaga atttggaaa    7200 caaattcgac gaaatcaagc tgaaaacatg tctgcgacag ctaaaaagtc tcataattcg    7260
aagacctcta agaagaaatt caagaggac agagaatttg ggacaccaaa aagattttta    7320
agagatgatg ttcctttcgg gattgatcgt ttgtttgctt tttgatttta ttttatattg    7380
ttatctgttt ctgtgtatag actgtttgag attggcgctt ggccgactca ttgtcttacc    7440
ataggggaac ggactttgtt tgtgttgtta ttttatttgt attttattaa aattctcaat    7500
gatctgaaaa ggcctcgagg ctaagagatt attgggggt gagtaagtac ttttaaagtg    7560
atgatggtta caaggcaaa aggggtaaaa cccctcgcct acgtaagcgt tattacgccc    7620 ggatccccg gggagctcga attcgctgaa atcaccagtc tctctctaca aatctatctc    7680 tctctattt ttccataaat aatgtgtgag tagtttcccg ataagggaaa ttagggttct    7740
tatagggttt cgctcatgtg ttgagcatat aagaaaccct tagtatgtat ttgtatttgt    7800
aaaatacttc tattatcaat aaaatttcta attcctaaaa ccaaaatcca gtactaaaat    7860
ccagatctcc taaagtccct atagatcttt gtcgtgaata taaaccagac acgagacgac    7920
taaacctgga gcccagacgc cgttcgaagc tagaagtacc gcttaggcag gaggccgtta    7980
gggaaaagat gctaaggcag ggttggttac gttgactccc ccgtaggttt ggtttaaata    8040
tgatgaagtg gacggaagga aggaggaaga caaggaagga taaggttgca ggccctgtgc    8100
aaggtaagaa gatggaaatt tgatagaggt acgctactat acttatacta tacgctaagg    8160
gaatgcttgt atttataccc tatacccct aataaccct tatcaattta agaaataatc    8220
cgcataagcc cccgcttaaa aattggtatc agagccatga ataggtctat gaccaaaact    8280
caagaggata aaacctcacc aaaatacgaa agagttctta actctaaaga taaaagatct    8340
ttcaagatca aaactagttc cctcacaccg gagcatgcga tatcctcgac ctgcaggcat    8400
gcaagcttgg cgtaatcatg gtcatagctg tttcctgtgt gaaattgtta tccgctcaca    8460
attccacaca acatacgagc cggaagcata agtgtaaag cctggggtgc ctaatgagtg    8520
agctaactca cattaattgc gttgcgctca ctgcccgctt tccagtcggg aaacctgtcg    8580
tgccagctgc attaatgaat cggccaacgc gcggggagag gcggtttgcg tattgggcca    8640
aagacaaaag gccgacattc aaccgattga gggagggaag gtaaatattg acggaaatta    8700
ttcattaaag gtgaattatc accgtcaccg acttgagcca tttgggaatt agagccagca    8760
aaatcaccag tagcaccatt accattagca aggccggaaa cgtcaccaat gaaaccatcg    8820
atagcagcac cgtaatcagt agcgacagaa tcaagtttgc ctttagcgtc agactgtagc    8880
gcgttttcat cggcattttc ggtcatagcc cccttattag cgtttgccat cttttcataa    8940
tcaaaatcac cggaaccaga gccaccaccg gaaccgcctc cctcagagcc gccaccctca    9000
```

```
gaaccgccac cctcagagcc accaccctca gagccgccac cagaaccacc accagagccg   9060
ccgccagcat tgacaggagg cccgatctag taacatagat gacaccgcgc gcgataattt   9120
atcctagttt gcgcgctata ttttgttttc tatcgcgtat taaatgtata attgcgggac   9180
tctaatcata aaaacccatc tcataaataa cgtcatgcat tacatgttaa ttattacatg   9240
cttaacgtaa ttcaacagaa attatatgat aatcatcgca agaccggcaa caggattcaa   9300
tcttaagaaa ctttattgcc aaatgtttga acgatcgggg atcatccggg tctgtggcgg   9360
gaactccacg aaaatatccg aacgcagcaa gatatcgcgg tgcatctcgg tcttgcctgg   9420
gcagtcgccg ccgacgccgt tgatgtggac gccgggcccg atcatattgt cgctcaggat   9480
cgtggcgttg tgcttgtcgg ccgttgctgt cgtaatgata tcggcacctt cgaccgcctg   9540
ttccgcagag atcccgtggg cgaagaactc cagcatgaga tccccgcgct ggaggatcat   9600
ccagccggcg tcccggaaaa cgattccgaa gcccaaccct tcatagaagg cggcggtgga   9660
atcgaaatct cgtgatggca ggttgggcgt cgcttggtcg gtcatttcga accccagagt   9720
cccgctcaga agaactcgtc aagaaggcga tagaaggcga tgcgctgcga atcgggagcg   9780
gcgataccgt aaagcacgag gaagcggtca gcccattcgc cgccaagctc ttcagcaata   9840
tcacgggtag ccaacgctat gtcctgatag cggtccgcca cacccagccg ccacagtcg    9900
atgaatccag aaaagcggcc attttccacc atgatattcg gcaagcaggc atcgccatgg   9960
gtcacgacga gatcatcgcc gtcgggcatg cgcgccttga gcctggcgaa cagttcggct  10020
ggcgcgagcc cctgatgctc ttcgtccaga tcatcctgat cgacaagacc ggcttccatc  10080
cgagtacgtg ctcgctcgat gcgatgtttc gcttggtggt cgaatgggca ggtagccgga  10140
tcaagcgtat gcagccgccg cattgcatca gccatgatgg atactttctc ggcaggagca  10200
aggtgagatg acaggagatc ctgccccggc acttcgccca atagcagcca gtcccttccc  10260
gcttcagtga caacgtcgag cacagctgcg caaggaacgc ccgtcgtggc cagccacgat  10320
agccgcgctg cctcgtcctg cagttcattc agggcaccgg acaggtcggt cttgacaaaa  10380
agaaccgggc gcccctgcgc tgacagccgg aacacggcgg catcagagca gccgattgtc  10440
tgttgtgccc agtcatagcc gaatagcctc tccacccaag cggccggaga acctgcgtgc  10500
aatccatctt gttcaatcat gcgaaacgat ccagatccgg tgcagattat ttggattgag  10560
agtgaatatg agactctaat tggataccga ggggaattta tggaacgtca gtggagcatt  10620
tttgacaaga aatatttgct agctgatagt gaccttaggc gacttttgaa cgcgcaataa  10680
tggtttctga cgtatgtgct tagctcatta aactccagaa acccgcgcct gagtggctcc  10740
ttcaacgttg cggttctgtc agttccaaac gtaaacggc ttgtcccgcg tcatcggcgg  10800
gggtcataac gtgactccct taattctccg ctcatgatca gattgtcgtt tccgccttc   10860
agtttaaact atcagtgttt gacaggatat attggcgggt aaacctaaga gaaaagagcg  10920
tttattagaa taatcggata tttaaaaggg cgtgaaaagg tttatccgtt cgtccatttg  10980
tatgtgcatg ccaaccacag ggttccccag atctggcgcc ggccagcgag acgagcaaga  11040
ttggccgccg cccgaaacga tccgacagcc cgcccagcac aggtgcgcag gcaaattgca  11100
ccaacgcata cagcgccagc agaatgccat agtgggcggt gacgtcgttc gagtgaacca  11160
gatcgcgcag gaggcccggc agcaccggca taatcaggcc gatgccgaca gcgtcgagcg  11220
cgacagtgct cagaattacg atcagggta tgttgggttt cacgtctggc ctccggacca  11280
gcctccgctg gtccgattga acgcgcggat tctttatcac tgataagttg gtggacatat  11340
```

```
tatgtttatc agtgataaag tgtcaagcat gacaaagttg cagccgaata cagtgatccg  11400
tgccgccctg gacctgttga acgaggtcgg cgtagacggt ctgacgacac gcaaactggc  11460
ggaacggttg ggggttcagc agccggcgct ttactggcac ttcaggaaca agcgggcgct  11520
gctcgacgca ctggccgaag ccatgctggc ggagaatcat acgcattcgg tgccgagagc  11580
cgacgacgac tggcgctcat ttctgatcgg gaatgcccgc agcttcaggc aggcgctgct  11640
cgcctaccgc gatggcgcgc gcatccatgc cggcacgcga ccgggcgcac cgcagatgga  11700
aacggccgac gcgcagcttc gcttcctctg cgaggcgggt ttttcggccg gggacgccgt  11760
caatgcgctg atgacaatca gctacttcac tgttggggcc gtgcttgagg agcaggccgg  11820
cgacagcgat gccggcgagc gcggcggcac cgttgaacag gctccgctct cgccgctgtt  11880
gcgggccgcg atagacgcct tcgacgaagc cggtccggac gcagcgttcg agcagggact  11940
cgcggtgatt gtcgatggat tggcgaaaag gaggctcgtt gtcaggaacg ttgaaggacc  12000
gagaaagggt gacgattgat caggaccgct gccggagcgc aacccactca ctacagcaga  12060
gccatgtaga caacatcccc tcccccttc caccgcgtca gacgcccgta gcagcccgct  12120
acgggctttt tcatgccctg ccctagcgtc caagcctcac ggccgcgctc ggcctctctg  12180
gcggcctcct ggcgctcttc cgcttcctcg ctcactgact cgctgcgctc ggtcgttcgg  12240
ctgcggcgag cggtatcagc tcactcaaag gcggtaatac ggttatccac agaatcaggg  12300
gataacgcag gaaagaacat gtgagcaaaa ggccagcaaa aggccaggaa ccgtaaaaag  12360
gccgcgttgc tggcgttttt ccataggctc cgcccccctg acgagcatca caaaaatcga  12420
cgctcaagtc agaggtggcg aaacccgaca ggactataaa gataccaggc gtttccccct  12480
ggaagctccc tcgtgcgctc tcctgttccg accctgccgc ttaccggata cctgtccgcc  12540
tttctccctt cgggaagcgt ggcgcttttc cgctgcataa ccctgcttcg ggtcattat  12600 agcgattttt tcggtatatc catcctttt cgcacgatat acaggatttt gccaagggt  12660 tcgtgtagac tttccttggt gtatccaacg cgtcagccg gcaggatag gtgaagtagg  12720 cccacccgcg agcgggtgtt ccttcttcac tgtcccttat tcgcacctgg cggtgctcaa  12780
cgggaatcct gctctgcgag gctggccggc taccgccggc gtaacagatg agggcaagcg  12840
gatggctgat gaaaccaagc caaccaggaa gggcagccca cctatcaagg tgtactgcct  12900
tccagacgaa cgaagagcga ttgaggaaaa ggcggcggcg gccggcatga gcctgtcggc  12960
ctacctgctg gccgtcggcc agggctacaa aatcacgggc gtcgtggact atgagcacgt  13020
ccgcgagctg gcccgcatca atggcgacct gggccgcctg gcggcctgc tgaaactctg  13080 gctcaccgac gacccgcgca cggcgcggtt cggtgatgcc acgatcctcg ccctgctggc  13140
gaagatcgaa gagaagcagg acgagcttgg caaggtcatg atgggcgtgg tccgcccgag  13200
ggcagagcca tgactttttt agccgctaaa acggccgggg ggtgcgcgtg attgccaagc  13260
acgtccccat gcgctccatc aagaagagc acttcgcgga gctggtgaag tacatcaccg  13320
acgagcaagg caagaccgag cgccttgcg acgctcaccg gctggttgc cctcgccgct  13380 gggctggcgg ccgtctatgg ccctgcaaac gcgccagaaa cgccgtcgaa gccgtgtgcg  13440
agacaccgcg gccgccggcg ttgtggatac ctcgcgaaa acttggccct cactgacaga  13500
tgaggggcgg acgttgacac ttgaggggcc gactcacccg gcgcggcgtt gacagatgag  13560
gggcaggctc gatttcggcc ggcgacgtgg agctggccag cctcgcaaat cggcgaaaac  13620
gcctgatttt acgcgagttt cccacagatg atgtggacaa gctgggat aagtgccctg  13680 cggtattgac acttgagggg cgcgactact gacagatgag gggcgcgatc cttgacactt  13740
```

```
gagggggcaga gtgctgacag atgaggggcg cacctattga catttgaggg gctgtccaca   13800
ggcagaaaat ccagcatttg caagggtttc cgcccgtttt tcggccaccg ctaacctgtc   13860 tttttaacctg ctttttaaacc aatatttata aaccttgttt ttaaccaggg ctgcgccctg  13920
tgcgcgtgac cgcgcacgcc gaagggggt gcccccctt ctcgaaccct ccggccccgc     13980
taacgcgggc ctcccatccc cccaggggct gcgccctcg gccgcgaacg gcctcaccc    14040 aaaaatggca gcgctggcag tccttgccat tgccgggatc gggcagtaa cgggatgggc   14100 gatcagcccg agcgcgacgc ccggaagcat tgacgtgccg caggtgctgg catcgacatt   14160
cagcgaccag gtgccgggca gtgagggcgg cggcctgggt ggcggcctgc ccttcacttc   14220
ggccgtcggg gcattcacgg acttcatggc ggggccggca attttttacct tgggcattct  14280 tggcatagtg gtcgcgggtg ccgtgctcgt gttcggggt gcgataaacc cagcgaacca   14340
tttgaggtga taggtaagat tataccgagg tatgaaaacg agaattggac ctttacagaa   14400
ttactctatg aagcgccata tttaaaaagc taccaagacg aagaggatga agaggatgag   14460
gaggcagatt gccttgaata tattgacaat actgataaga taatatatct tttatataga   14520
agatatcgcc gtatgtaagg atttcagggg gcaaggcata ggcagcgcgc ttatcaatat   14580
atctatagaa tgggcaaagc ataaaaactt gcatggacta atgcttgaaa cccaggacaa   14640
taaccttata gcttgtaaat tctatcataa ttgggtaatg actccaactt attgatagtg   14700
ttttatgttc agataatgcc cgatgacttt gtcatgcagc tccaccgatt ttgagaacga   14760
cagcgacttc cgtcccagcc gtgccaggtg ctgcctcaga ttcaggttat gccgctcaat   14820
tcgctgcgta tatcgcttgc tgattacgtg cagctttccc ttcaggcggg attcatacag   14880
cggccagcca tccgtcatcc atatcaccac gtcaaagggt gacagcaggc tcataagacg   14940
ccccagcgtc gccatagtgc gttcaccgaa tacgtgcgca caaccgtct tccggagact   15000 gtcatacgcg taaaacagcc agcgctggcg cgatttagcc ccgacatagc cccactgttc   15060
gtccatttcc gcgcagacga tgacgtcact gcccggctgt atgcgcgagg ttaccgactg   15120
cggcctgagt ttttttaagtg acgtaaaatc gtgttgaggc caacgcccat aatgcgggct   15180
gttgcccggc atccaacgcc attcatggcc atatcaatga ttttctggtg cgtaccgggt   15240
tgagaagcgg tgtaagtgaa ctgcagttgc catgttttac ggcagtgaga gcagagatag   15300
cgctgatgtc cggcggtgct tttgccgtta cgcaccaccc cgtcagtagc tgaacaggag   15360
ggacagctga tagacacaga agccactgga gcacctcaaa aacaccatca tacactaaat   15420
cagtaagttg gcagcatcac ccataattgt ggtttcaaaa tcggctccgt cgatactatg   15480
ttatacgcca actttgaaaa caactttgaa aaagctgttt tctggtattt aaggttttag   15540
aatgcaagga acagtgaatt ggagttcgtc ttgttataat tagcttcttg gggtatcttt   15600
aaatactgta gaaaagagga aggaaataat aaatggctaa aatgagaata tcaccggaat   15660
tgaaaaaact gatcgaaaaa taccgctgcg taaaagatac ggaaggaatg tctcctgcta   15720
aggtatataa gctggtggga gaaaatgaaa acctatattt aaaaatgacg gacagccggt   15780
ataaagggac cacctatgat gtggaacggg aaaaggacat gatgctatgg ctggaaggaa   15840
agctgcctgt tccaaaggtc ctgcactttg aacggcatga tggctggagc aatctgctca   15900
tgagtgaggc cgatggcgtc ctttgctcgg aagagtatga agatgaacaa agccctgaaa   15960
agattatcga gctgtatgcg gagtgcatca ggctcttttca ctccatcgac atatcggatt   16020
gtccctatac gaatagctta gacagccgct tagccgaatt ggattactta ctgaataacg   16080
```

```
atctggccga tgtggattgc gaaaactggg aagaagacac tccatttaaa gatccgcgcg   16140
agctgtatga ttttttaaag acggaaaagc ccgaagagga acttgtcttt tcccacggcg   16200
acctgggaga cagcaacatc tttgtgaaag atggcaaagt aagtggcttt attgatcttg   16260
ggagaagcgg cagggcggac aagtggtatg acattgcctt ctgcgtccgg tcgatcaggg   16320
aggatatcgg ggaagaacag tatgtcgagc tattttttga cttactgggg atcaagcctg   16380
attgggagaa aataaaatat tatattttac tggatgaatt gttttagtac ctagatgtgg   16440
cgcaacgatg ccggcgacaa gcaggagcgc accgacttct tccgcatcaa gtgttttggc   16500
tctcaggccg aggcccacgg caagtatttg ggcaagtgcgt cgctggtatt cgtgcagggc   16560
aagattcgga ataccaagta cgagaaggac ggccagacgg tctacgggac cgacttcatt   16620
gccgataagg tggattatct ggacaccaag gcaccaggcg ggtcaaatca ggaataaggg   16680
cacattgccc cggcgtgagt cggggcaatc ccgcaaggag ggtgaatgaa tcggacgttt   16740
gaccggaagg catacaggca agaactgatc gacgcggggt tttccgccga ggatgccgaa   16800
accatcgcaa gccgcaccgt catgcgtgcg ccccgcgaaa ccttccagtc cgtcggctcg   16860
atggtccagc aagctacggc caagatcgag cgcgacagcg tgcaactggc tcccctgcc   16920 ctgcccgcgc atcggccgc cgtggagcgt tcgcgtcgtc tcgaacagga ggcggcaggt   16980
ttggcgaagt cgatgaccat cgacacgcga ggaactatga cgaccaagaa gcgaaaaacc   17040
gccggcgagg acctggcaaa acaggtcagc gaggccaagc aggccgcgtt gctgaaacac   17100
acgaagcagc agatcaagga aatgcagctt tccttgttcg atattgcgcc gtggccggac   17160
acgatgcgag cgatgccaaa cgacacggcc cgctctgccc tgttcaccac gcgcaacaag   17220
aaaatcccgc gcgaggcgct gcaaaacaag gtcattttcc acgtcaacaa ggacgtgaag   17280
atcacctaca ccgcgtcga gctgcgggcc gacgatgacg aactggtgtg gcagcaggtg   17340
ttggagtacg cgaagcgcac ccctatcggc gagccgatca ccttcacgtt ctacgagctt   17400
tgccaggacc tgggctggtc gatcaatggc cggtattaca cgaaggccga ggaatgcctg   17460
tcgcgcctac aggcgacggc gatgggcttc acgtccgacc gcgttgggca cctggaatcg   17520
gtgtcgctgt tgcaccgctt ccgcgtcctg gaccgtggca agaaaacgtc ccgttgccag   17580
gtcctgatcg acgaggaaat cgtcgtgctg tttgctggcg accactacac gaaattcata   17640
tgggagaagt accgcaagct gtcgccgacg gcccgacgga tgttcgacta tttcagctcg   17700
caccgggagc cgtacccgct caagctggaa accttccgcc tcatgtgcgg atcggattcc   17760
acccgcgtga agaagtggcg cgagcaggtc ggcgaagcct gcgaagagtt gcgaggcagc   17820
ggcctggtgg aacacgcctg ggtcaatgat gacctggtgc attgcaaacg ctagggcctt   17880
gtggggtcag ttccggctgg gggttcagca gccagcgctt tactggcatt tcaggaacaa   17940
gcgggcactg ctcgacgcac ttgcttcgct cagtatcgct cgggacgcac ggcgcgctct   18000
acgaactgcc gataaacaga ggattaaaat tgacaattgt gattaaggct cagattcgac   18060
ggcttggagc ggccgacgtg caggatttcc gcgagatccg attgtcggcc ctgaagaaag   18120
ctccagagat gttcgggtcc gtttacgagc acgaggagaa aaagcccatg gaggcgttcg   18180
ctgaacggtt gcgagatgcc gtggcattcg gcgcctacat cgacggcgag atcattgggc   18240
tgtcggtctt caaacaggag gacggcccca aggacgctca caaggcgcat ctgtccggcg   18300
ttttcgtgga gcccgaacag cgaggccgag gggtcgccgg tatgctgctg cgggcgttgc   18360
cggcgggttt attgctcgtg atgatcgtcc gacagattcc aacgggaatc tggtggatgc   18420
gcatcttcat cctcggcgca cttaatattt cgctattctg gagcttgttg tttatttcgg   18480
```

-continued

```
tctaccgcct gccgggcggg gtcgcggcga cggtaggcgc tgtgcagccg ctgatggtcg    18540
tgttcatctc tgccgctctg ctaggtagcc cgatacgatt gatggcggtc ctgggggcta    18600
tttgcggaac tgcgggcgtg gcgctgttgg tgttgacacc aaacgcagcg ctagatcctg    18660
tcggcgtcgc agcgggcctg gcgggggcgg tttccatggc gttcggaacc gtgctgaccc    18720
gcaagtggca acctcccgtg cctctgctca cctttaccgc ctggcaactg gcggccggag    18780
gacttctgct cgttccagta gctttagtgt ttgatccgcc aatcccgatg cctacaggaa    18840
ccaatgttct cggcctggcg tggctcggcc tgatcggagc gggtttaacc tacttcctttt   18900 ggttccgggg gatctcgcga ctcgaaccta cagttgtttc cttactgggc tttctcagcc    18960
ccagatctgg ggtcgatcag ccggggatgc atcaggccga cagtcggaac ttcgggtccc    19020
cgacctgtac cattcggtga gcaatggata ggggagttga tatcgtcaac gttcacttct    19080
aaagaaatag cgccactcag cttcctcagc ggctttatcc agcgatttcc tattatgtcg    19140
gcatagttct caagatcgac agcctgtcac ggttaagcga gaaatgaata agaaggctga    19200
taattcggat ctctgcgagg gagatgatat ttgatcacag gcagcaacgc tctgtcatcg    19260
ttacaatcaa catgctaccc tccgcgagat catccgtgtt tcaaacccgg cagcttagtt    19320
gccgttcttc cgaatagcat cggtaacatg agcaaagtct gccgccttac aacggctctc    19380
ccgctgacgc cgtcccggac tgatgggctg cctgtatcga gtggtgattt tgtgccgagc    19440
tgccggtcgg ggagctgttg gctggctggt ggcaggatat attgtggtgt aaacaaattg    19500
acgcttagac aacttaataa cacattgcgg acgtttttaa tgtactgggg tggtttttct    19560
tttcaccagt gagacgggca acagctgatt gcccttcacc gcctggccct gagagagttg    19620
cagcaagcgg tccacgctgg tttgccccag caggcgaaaa tcctgtttga tggtggttcc    19680
gaaatcggca aaatcccctta taaatcaaaa gaatagcccg agataggtt gagtgttgtt    19740 ccagtttgga acaagagtcc actattaaag aacgtggact ccaacgtcaa agggcgaaaa    19800
accgtctatc agggcgatgg cccactacgt gaaccatcac ccaaatcaag ttttttgggg    19860
tcgaggtgcc gtaaagcact aaatcggaac cctaaaggga gcccccgatt tagagcttga    19920
cggggaaagc cggcgaacgt ggcgagaaag gaagggaaga aagcgaaagg agcgggcgcc    19980
attcaggctg cgcaactgtt gggaagggcg atcggtgcgg gcctcttcgc tattacgcca    20040
gctggcgaaa gggggatgtg ctgcaagcg attaagttgg gtaacgccag ggttttccca    20100
gtcacgacgt tgtaaaacga cggccagtga attcgagctc ggtacccccc               20150
```

METHOD FOR DECREASING THE ALKALOID CONTENT OF A TOBACCO PLANT

CROSS REFERENCE TO RELATED APPLICATIONS

This is a U.S. National Phase application claiming priority to PCT/GB2020/050153, filed Jan. 23, 2020, the entire contents of which are hereby expressly incorporated by reference in its entirety including, without limitation, the specification, claims, and abstract, as well as any figures, tables, or drawings thereof.

REFERENCE TO SEQUENCE LISTING SUBMITTED ELECTRONICALLY

The instant application contains a Sequence Listing which has been submitted electronically in ST.25 format and is herein incorporated by reference in its entirety. Said ASCII plain text copy, created on Sep. 13, 2023, is named "P13640US00_ST25" and is 115,127 bytes in size.

FIELD OF THE INVENTION

The present invention relates to methods of modulating the alkaloid content e.g. nicotine content of a plant or part thereof. The invention also extends to methods of modulating the expression and/or activity of polypeptides which modulate alkaloid content within plants. Alternatively, the invention provides methods of modulating the expression and/or activity of genes which encode polypeptides which modulate alkaloid content within plants. The invention also extends to constructs, which can be used to modulate the polypeptides. The invention further relates to plant cells and plants modified to achieve a modulation in alkaloid content. The invention also relates to a processed and harvested leaf from such modulated plants and use thereof in a tobacco industry product, including combustible smoking articles.

BACKGROUND

Alkaloids are a group of naturally occurring compounds which mostly contain basic nitrogen atoms and are produced by a large variety of organisms including bacteria, fungi, plants and animals.

Alkaloids may be classified according to the similarity of the carbon skeleton e.g. indole-, isoquinoline- and pyridine-like. Pyridine derivatives are one class of monomeric alkaloids; this class includes simple derivatives of pyridine, polycyclic condensed and noncondensing pyridine derivatives and sesquiterpene pyridine derivatives. Examples are nicotine, nornicotine, anabasine, myosmine and anatabine.

Most of the known biological functions of alkaloids are related to protection. Neuroactive molecules, like caffeine, cocaine, morphine, and nicotine, act as defense compounds against invading predators. The accumulation of these alkaloids is the result of signal transduction cascades that monitor gene expression, enzyme activities, and alkaloid concentrations. The fine-tuning of alkaloid content in the plant involves negative feedback loops and degradative pathways.

Nicotine occurs naturally in several varieties of plants but is found at the highest level in the tobacco plant. Cultivated tobacco produces 2-4% alkaloids of total dry weight. Nicotine is produced in wild and cultivated *Nicotiana* species and plays an important role in plant defense against herbivores and insects (Voelckel et al. (2001) Oecologia 127(2): 274-280, incorporated herein by reference). It accounts for ~90% of the total alkaloid content. The remaining 10% of the alkaloid pool is mostly constituted by the structurally related compounds nornicotine, anatabine, anabasine and pseudoxynicotine (PON).

The regulation of alkaloid content in tobacco is complex. Several factors including genotype, environment, fertilization and agronomic practices (e.g. topping) affect alkaloid levels in tobacco plants. Some key regulators of nicotine biosynthesis are well characterized, for example putrescine N-methyltransferase (PMT), which plays a pivotal role in this pathway, is activated by members of the ethylene responsive factor (ERF) superfamily, the largest transcription factor family in the tobacco genome (Rushton et al. (2008) Plant Physiol. 147(1): 280-295 incorporated herein by reference). Other transcription factors that induce alkaloid biosynthesis belong to the MYC2-like basic helix-loop-helix (bHLH) family. MYC2-like bHLHs regulate alkaloid levels directly, through the Gbox-mediated binding and activation of alkaloid structural genes, and indirectly, through the activation of ERFs.

Modifying alkaloid content in plants (e.g. tobacco) can have several commercial advantages. For example, decreasing total alkaloid content in plants can increase the value of said plant as a biomass resource. For example, modifying alkaloid content may comprise reducing the alkaloid content e.g. nicotine content of tobacco plants. Tobacco plants and products with reduced nicotine may be desirable in view of the potential regulation of "nicotine ceilings" i.e. average upper limits of nicotine in tobacco products. Alternatively, increasing alkaloid content in plants e.g. tobacco plants, can help to protect plants against insects and herbivores. There remains a need for plants with modulated alkaloid content, for example with modulated nicotine content, with improved commercially desirable traits and methods for making the same.

During the post-harvest leaf curing, reactions between pyridine alkaloids and nitrosating species leads to the formation of tobacco-specific nitrosamines (TSNAs). Nornicotine and PON are the precursors of the TSNAs NNN and NNK respectively. Reducing the production and accumulation of nornicotine and PON is of high importance. The CYP82E family of nicotine demethylase genes is one of the primary regulators of nicotine to nornicotine conversion, and altering their activity or accumulation may result in a decrease in NNN levels. However, no enzymes or genes responsible for producing PON have been identified thus far.

As described in the Examples, the inventors sought to investigate genes responsible for alkaloid synthesis, with the aim of modulating alkaloid content in plants, e.g. decreasing nicotine content in tobacco plants.

SUMMARY OF THE INVENTION

It has been surprisingly found that by modulating the activity or expression of a gene encoding a SOUL haem-binding protein the alkaloid content and/or TSNA content or precursor of TSNA content of plants can be modulated. The SOUL haem-binding protein(s) as taught herein, for example Nitab4.5_0013616g0010.2, is a regulator of nicotine, nornicotine, anabasine, PON, myosmine and anatabine in cultivated tobacco. Nitab4.5_0013616g0010.2 encodes a SOUL haem-binding protein according to the present invention. Nitab4.5_0000652g0130.2, Nitab4.5_0001140g0220.2, Nitab4.5_0003235g0060.2, Nitab4.5_0004868g0020.2, Nitab4.5_0006614g0010.2, Nitab4.5_0006991g0050.2 and Nitab4.5_0009023g0010.2 encode homologues of Nitab4.5_0013616g0010.2 according to the present invention. SOUL haem-binding proteins according to the present invention contain a conserved three-dimensional structure termed a SOUL motif. SOUL haem-binding proteins according the present invention bind to haem.

According to the present invention, tobacco products with modulated alkaloid content and commercially desirable traits sought after by consumers of tobacco products can be produced. In some instances, consumers may desire a product with low levels of alkaloid content e.g. low levels of TSNAs or low nicotine content.

The present invention may be particularly useful in the field of plant molecular farming, where plants (such as tobacco and other *Nicotiana* spp.) are used for the production of proteins, peptides, and metabolites e.g. for the production of therapeutics and pharmaceuticals such as antibiotics, virus like particles, or neutraceuticals or small molecules. Tobacco has been used for the development of an HIV-neutralising antibody in an EU-funded project called PharmPlant and *Medicago* Inc., Canada have worked on a tobacco-based platform for the production of virus-like particles for flu vaccine manufacture.

Thus, a plant according to the present invention may be used for molecular farming to reduce or eliminate the presence of nicotine, nornicotine, PON and/or other nicotinic alkaloids, such as anabasine or anatabine or myosmine. The use of a low nicotine plant or rootsock is beneficial in molecular farming and would reduce downstream processing costs associated with purification.

In other instances, it may be desirable to produce plants with high alkaloid levels e.g. high levels of nicotine content so that nicotine may be purified from the tobacco plant to produce a pure nicotine product for example for use in devices which utilize liquid containing nicotine (e.g. e-cigarettes) or within tobacco heating devices. For example, the production of plants with leaves containing high levels of nicotine could reduce costs of nicotine extraction for the production of e-liquids for e-cigarettes.

The present inventors have surprisingly determined a method for modulating the alkaloid content, e.g. nicotine content, of a plant (e.g. a tobacco plant) by modulating the activity or expression of a gene encoding a SOUL haem-binding protein. The alkaloid content (e.g. the content of one or more of nicotine, nornicotine, anabasine, PON, myosmine or anatabine) of a plant (e.g. tobacco plant) may be decreased by decreasing the activity or expression of a gene encoding a SOUL haem-binding protein or may be increased by increasing the activity or expression of gene encoding a SOUL haem-binding protein (for example by increasing the haem-binding affinity of a SOUL haem-binding protein). Prior to the present invention it had not been known that modulation of the activity or expression of a gene encoding a SOUL haem-binding protein as described herein could be used to modulate alkaloid content.

In one aspect, there is provided a method of modulating (e.g. decreasing) the alkaloid content of a plant or a part thereof, or a cell or cell culture, the method comprising modifying said plant or a cell or cell culture by modulating the activity or expression of at least one gene encoding a SOUL haem-binding protein.

In one aspect, there is provided a method of decreasing the alkaloid content of a plant or a part thereof, or a cell or cell culture, the method comprising modifying said plant or a cell or cell culture by decreasing the activity or expression of at least one SOUL haem-binding protein.

In another aspect, there is provided a method of modulating (e.g. decreasing) the content of a tobacco specific nitrosamine (TSNA) or a precursor of a TSNA in a tobacco plant or plant part thereof, or cell, the method comprising modifying said plant or a cell or cell culture by modulating the activity or expression of at least one gene encoding a SOUL haem-binding protein.

In another aspect, there is provided a method of decreasing the content of a tobacco specific nitrosamine (TSNA) or a precursor of a TSNA in a tobacco plant or plant part thereof, or cell, the method comprising modifying said plant or a cell or cell culture by decreasing the activity or expression of at least one SOUL haem-binding protein.

In a further aspect there is provided the use of at least one gene encoding a SOUL haem-binding protein for modulating alkaloid content of a cell or plant or part thereof or a cell or cell culture.

In yet another aspect, there is provided a method for producing a plant or part thereof, a cell or cell culture, a plant propagation material, a leaf, a cut harvested leaf, a processed leaf or a cut and processed leaf which has modulated (e.g. decreased) alkaloid content, the method comprising modifying said plant or cell or cell culture to modulate the activity or expression of at least one gene encoding a SOUL haem-binding protein.

Suitably, the alkaloid content may be modulated (e.g. decreased) in comparison to a plant or cell or cell culture which has not been modified to modulate the activity or expression of the at least one gene encoding a SOUL haem-binding protein.

In a further aspect, there is provided a plant or part thereof or a cell or cell culture which has been modified to achieve a modulation (e.g. decrease) in alkaloid content in comparison to an unmodified plant or unmodified cell or cell culture, wherein the modification is the reduction of the activity or expression of at least one gene encoding a SOUL haem-binding protein.

In a further aspect, there is provided a plant propagation material obtainable from a plant according to the present invention or from a plant or cell or cell culture produced by the method according to the present invention.

In a further aspect, there is provided a method or use according to the present invention, or a plant or part thereof or a cell or cell culture according to the present invention, or a plant propagation material according to the present invention, wherein the alkaloid content of the plant is decreased in comparison to a plant or cell or cell culture which has not been modified to modulate the activity or expression of at least one gene encoding a SOUL haem-binding protein.

Suitably, the activity or expression of at least one gene encoding a SOUL haem-binding protein may be decreased in comparison to a plant or cell or cell culture which has not been modified to modulate the activity or expression of the at least one gene encoding a SOUL haem-binding protein.

Suitably, the alkaloid content of the plant or cell or cell culture may be increased in comparison to a plant which has not been modified to modulate the activity or expression of the at least one gene encoding a SOUL haem-binding protein.

Suitably, the plant may be modified to increase the activity or expression of at least one gene encoding a SOUL haem-binding protein and the plant or cell or cell culture exhibits increased alkaloid content in comparison to a plant or cell or cell culture which has not been modified to modulate the activity or expression of the at least one gene encoding a SOUL haem-binding protein.

Suitably, the total alkaloid content of the plant or cell or cell culture may be modulated (e.g. decreased).

Suitably, the content of one or more alkaloids may be selected from nicotine, nornicotine, PON, anabasine, myosmine and anatabine is modulated (e.g. decreased), preferably the content of nicotine, nornicotine and/or PON is modulated (e.g. decreased). In some embodiments two or more (or three or more) alkaloids selected from nicotine, nornicotine, PON, anabasine, myosmine and anatabine is modulated (e.g. decreased). In some embodiments the total alkaloid content of the plant or cell is modulated (e.g. decreased).

In one aspect, the plant or plant cell is from the Solanaceae family.

Suitably, the plant or plant cell may be from the *Nicotiana* genus.

Suitably, the nicotine content may be modulated. Suitably, the nicotine content may be decreased.

In one aspect there is provided a method or use according to the present invention, a plant or part thereof or a cell or cell culture according to the present invention, or a plant propagation material according to the present invention wherein the at least one gene encoding a SOUL haem-binding protein encodes a polypeptide which comprises an amino acid sequence as set out in SEQ ID No. 1, 4, 7, 10, 13, 16, 19 or 22 or a functional variant or functional fragment or orthologue thereof; or wherein the at least one gene encoding a SOUL haem-binding protein encodes a polypeptide which comprises an amino acid sequence which has at least 80% identity to SEQ ID NO. 1, 4, 7, 10, 13, 16, 19 or 22; or
- wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue thereof; or
- wherein the at least one gene encoding a SOUL haem-binding protein comprises a nucleotide sequence which has at least 80% identity to SEQ ID No. 2, 3, 5, 6, 8, 9, 11, 12, 14, 15, 17, 18, 20, 21, 23 or 24.

In a further aspect there is provided a method or use according to the present invention, a plant or part thereof or cell or cell culture according to the present invention, or a plant propagation material according to the present invention wherein an additional gene encoding a SOUL haem-binding protein is also modulated, wherein the additional gene encodes a polypeptide which comprises an amino acid sequence as set out in SEQ ID No. 1, 4, 7, 10, 13, 16, 19 or 22 or a functional variant or functional fragment or orthologue thereof; or
- wherein the additional gene encodes a polypeptide which comprises an amino acid sequence which has at least 80% identity to SEQ ID NO. 1, 4, 7, 10, 13, 16, 19 or 22; or
- wherein the additional gene comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue thereof; or
- wherein the additional gene comprises a nucleotide sequence which has at least 80% identity to SEQ ID No. 2, 3, 5, 6, 8, 9, 11, 12, 14, 15, 17, 18, 20, 21, 23 or 24.

In one aspect there is provided the use of a plant or part thereof or cell or cell culture according to the present invention, or of a plant produced by the method according to the present invention to breed a plant.

In another aspect there is provided the use of a plant or part thereof or a cell or cell culture according to the present invention, or of a plant produced by the method according to the present invention for production of a product.

In yet another aspect there is provided the use of a plant or part thereof according to the present invention, or of a plant produced by the method according to the present invention to grow a crop.

In another aspect there is provided the use of a plant or part thereof according to the present invention, or of a plant produced by the method according to the present invention to produce a leaf.

In another aspect there is provided a harvested leaf of a plant according to the present invention, or obtainable from a plant propagated from a propagation material according to the present invention, or obtainable from a plant obtained by a use according to the present invention, or obtainable from a plant produced by the method according to the present invention.

Suitably, the harvested may be a cut harvested leaf.

In another aspect there is provided a processed leaf, preferably a processed tobacco leaf, preferably a non-viable processed tobacco leaf:
- obtainable from a plant obtainable from a use according to the present invention; obtainable by processing a plant according to the present invention;
- obtainable from a plant propagated from a plant propagation material according to the present invention; or
- obtainable by processing a harvested leaf of a plant according to the present invention; or
- obtainable from a plant produced by the method according to the present invention.

Suitably, the leaf may be processed by curing, fermenting, pasteurising or a combination thereof.

Suitably, the processed leaf may be a cut processed leaf.

In another aspect there is provided cured tobacco material made from a plant or a part thereof according to the present invention or an extract thereof.

In another aspect there is provided a tobacco blend comprising said cured tobacco material according to the present invention.

In another aspect there is provided a tobacco industry product prepared from:
- a tobacco plant according to the present invention, or a part thereof or a tobacco cell or cell culture according to the present invention;
- a tobacco plant or part thereof propagated from a tobacco plant propagation material according to the present invention;
- a harvested leaf of a plant according to the present invention, wherein the plant is tobacco;
- a processed leaf according to the present invention, wherein the plant is tobacco; or
- a plant produced by the method according to the present invention.

Suitably, the tobacco product may be a combustible smoking article.

Suitably, the tobacco product may be a smokeless tobacco product.

Suitably, the tobacco product may be a non-combustible aerosol provision system such as a tobacco heating device or an aerosol-generating device.

In one aspect there is provided the use of a tobacco cell according to the present invention for modulating alkaloid content in cell cultures.

In another aspect there is provided a combustible smoking article, non-combustible aerosol provisioning system, smokeless tobacco product or tobacco heating device comprising a plant or a part thereof according to the present invention or an extract (e.g. a tobacco extract) thereof or a tobacco cell or cell culture according to the present invention; or a cured tobacco material according to the present invention; or a tobacco blend according to the present invention.

In one aspect there is provided the use of a nucleotide sequence of at least one gene encoding a SOUL haem-binding protein to select a plant having modulated (e.g. decreased) alkaloid content and/or modulated (e.g. decreased) content of tobacco specific nitrosamine (TSNA) or a precursor of a TSNA, preferably wherein the sequence of the SOUL haem-binding protein is selected from SEQ ID No. 1, 4, 7, 10, 13, 16, 19 or 22 or a functional variant or functional fragment or orthologue thereof; or wherein the sequence of the SOUL haem-binding protein is a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue thereof; or wherein the at least one gene encoding a SOUL haem-binding protein comprises a nucleotide sequence which has at least 80% identity to SEQ ID No. 2, 3, 5, 6, 8, 9, 11, 12, 14, 15, 17, 18, 20, 21, 23 or 24.

In another aspect there is provided a mutant of a plant carrying a heritable mutation in a nucleotide sequence of at least one gene encoding a SOUL haem-binding protein, preferably wherein the gene is selected from SEQ ID No. 2, 3, 5, 6, 8, 9, 11, 12, 14, 15, 17, 18, 20, 21, 23 or 24 or a functional variant or functional fragment or orthologue thereof; or wherein the gene is selected from a sequence which has at least 80% identity to SEQ ID No. 2, 3, 5, 6, 8, 9, 11, 12, 14, 15, 17, 18, 20, 21, 23 or 24; wherein said heritable mutation modulates (e.g. decreases) the activity or expression of the at least one gene encoding a SOUL haem-binding protein and wherein the mutant plant has modulated (e.g. decreased) alkaloid content and/or modulated content of a tobacco specific nitrosamine (TSNA) or a precursor of a TSNA relative to a comparable plant which does not carry said heritable mutation.

In another aspect there is provided progeny or seed of a mutant plant which carries the heritable mutation according to the present invention.

In another aspect there is provided a harvested leaf, a processed leaf or cured tobacco material produced from a plant comprising a modification in a nucleotide sequence of at least one gene encoding a SOUL haem-binding protein, wherein the at least one gene is selected from SEQ ID No. 2, 3, 5, 6, 8, 9, 11, 12, 14, 15, 17, 18, 20, 21, 23 or 24 or a functional variant or functional fragment or orthologue thereof; or wherein the at least one gene is selected from a sequence which has at least 80% identity to SEQ ID No. 2, 3, 5, 6, 8, 9, 11, 12, 14, 15, 17, 18, 20, 21, 23 or 24; wherein said modification modulates (e.g. decreases) the activity or expression of the at least one gene encoding a SOUL haem-binding protein and wherein said plant has modulated (e.g. decreased) alkaloid content and/or modulated content of a tobacco specific nitrosamine (TSNA) or a precursor of a TSNA relative to a comparable plant which does not carry said modification in the at least one gene encoding a SOUL haem-binding protein.

In another aspect there is provided a method, a leaf, a plant, a plant propagation material, a harvested leaf, a processed tobacco, a tobacco product, a use or a combination thereof as described herein with reference to the description and drawings.

BRIEF DESCRIPTION OF THE DRAWINGS

Embodiments of the invention will now be described, by way of example only, with reference to the accompanying drawings, in which:

FIG. 5 shows the amino acid sequence of Nitab4.5_0013616g0010.2—SEQ ID No. 1—a SOUL haem-binding protein from *Nicotiana tabacum* according to the present invention.

FIG. 6 shows the genomic sequence of Nitab4.5_0013616g0010.2—SEQ ID No. 2—encoding a SOUL haem-binding protein from *Nicotiana tabacum* according to the present invention.

FIG. 7 shows the coding sequence of Nitab4.5_0013616g0010.2—SEQ ID No. 3—encoding a SOUL haem-binding protein from *Nicotiana tabacum* according to the present invention.

FIG. 8 shows the amino acid sequence of Nitab4.5_0000652g0130.2—SEQ ID No. 4—a SOUL haem-binding protein from *Nicotiana tabacum* according to the present invention.

FIG. 9 shows the genomic sequence of Nitab4.5_0000652g0130.2—SEQ ID No. 5—encoding a SOUL haem-binding protein from *Nicotiana tabacum* according to the present invention.

FIG. 10 shows the coding sequence of Nitab4.5_0000652g0130.2—SEQ ID No. 6—encoding a SOUL haem-binding protein from *Nicotiana tabacum* according to the present invention.

FIG. 11 shows the amino acid sequence of Nitab4.5_0001140g0220.2—SEQ ID No. 7—a SOUL haem-binding protein from *Nicotiana tabacum* according to the present invention.

FIG. 12 shows the genomic sequence of Nitab4.5_0001140g0220.2—SEQ ID No. 8—encoding a SOUL haem-binding protein from *Nicotiana tabacum* according to the present invention.

FIG. 13 shows the coding sequence of Nitab4.5_0001140g0220.2—SEQ ID No. 9—encoding a SOUL haem-binding protein from *Nicotiana tabacum* according to the present invention.

FIG. 14 shows the amino acid sequence of Nitab4.5_0003235g0060.2—SEQ ID No. 10—a SOUL haem-binding protein from *Nicotiana tabacum* according to the present invention.

FIG. 15 shows the genomic sequence of Nitab4.5_0003235g0060.2—SEQ ID No. 11—encoding a SOUL haem-binding protein from *Nicotiana tabacum* according to the present invention.

FIG. 16 shows the coding sequence of Nitab4.5_0003235g0060.2—SEQ ID No. 12—encoding a SOUL haem-binding protein from *Nicotiana tabacum* according to the present invention.

FIG. 17 shows the amino acid sequence of Nitab4.5_0004868g0020.2—SEQ ID No. 13—a SOUL haem-binding protein from *Nicotiana tabacum* according to the present invention.

FIG. 18 shows the genomic sequence of Nitab4.5_0004868g0020.2—SEQ ID No. 14—encoding a SOUL haem-binding protein from *Nicotiana tabacum* according to the present invention.

FIG. 19 shows the coding sequence of Nitab4.5_0004868g0020.2—SEQ ID No. 15—encoding a SOUL haem-binding protein from *Nicotiana tabacum* according to the present invention.

FIG. 20 shows the amino acid sequence of Nitab4.5_0006614g0010.2—SEQ ID No. 16—a SOUL haem-binding protein from *Nicotiana tabacum* according to the present invention.

FIG. 21 shows the genomic sequence of Nitab4.5_0006614g0010.2—SEQ ID No. 17—encoding a SOUL haem-binding protein from *Nicotiana tabacum* according to the present invention.

FIG. 22 shows the coding sequence of Nitab4.5_0006614g0010.2—SEQ ID No. 18—encoding a SOUL haem-binding protein from *Nicotiana tabacum* according to the present invention.

FIG. 23 shows the amino acid sequence of Nitab4.5_0006991g0050.2—SEQ ID No. 19—a SOUL haem-binding protein from *Nicotiana tabacum* according to the present invention.

FIG. 24 shows the genomic sequence of Nitab4.5_0006991g0050.2—SEQ ID No. 20—encoding a SOUL haem-binding protein from *Nicotiana tabacum* according to the present invention.

FIG. 25 shows the coding sequence of Nitab4.5_0006991g0050.2—SEQ ID No. 21—encoding a SOUL haem-binding protein from *Nicotiana tabacum* according to the present invention.

FIG. 26 shows the amino acid sequence of Nitab4.5_0009023g0010.2—SEQ ID No. 22—a SOUL haem-binding protein from *Nicotiana tabacum* according to the present invention.

FIG. 27 shows the genomic sequence of Nitab4.5_0009023g0010.2—SEQ ID No. 23—encoding a SOUL haem-binding protein from *Nicotiana tabacum* according to the present invention.

FIG. 28 shows the coding sequence of Nitab4.5_0009023g0010.2—SEQ ID No. 24—encoding a SOUL haem-binding protein from *Nicotiana tabacum* according to the present invention.

FIG. 29 shows SEQ ID No. 25, a 300-nucleotide cDNA fragment used in Example 2.

FIG. 30 shows SEQ ID No. 26, sequence TRV1 used in Example 2.

FIG. 31 shows SEQ ID No. 27, sequence TRV2 used in Example 2.

SEQUENCE LISTING

Figure 1:
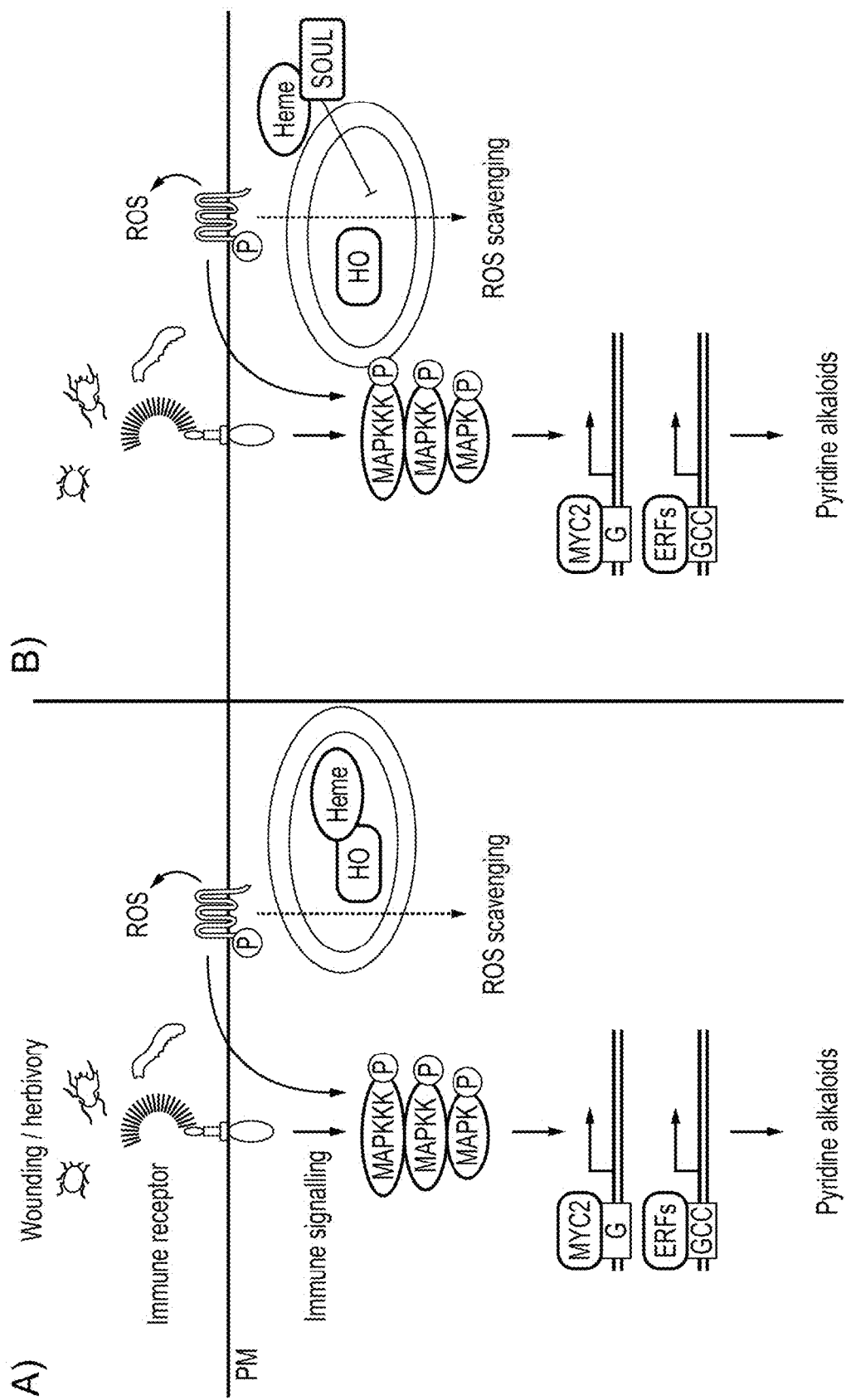
FIG. 1 depicts, without wishing to be bound by theory, the effect of overexpressing SOUL haem-binding protein on pyridine alkaloid biosynthesis. (A) Upon perception of wounding or herbivory by surface-localised receptors, immune signalling is induced via phosphorylation of MAPKs and production of reactive oxygen species (ROS). This activates jasmonic acid (JA)-responsive genes and upregulates pyridine alkaloid production. Intracellular ROS levels are kept under tight regulation through haem oxygenase (HO)-mediated haem catabolism. (B) SOUL overexpression reduces the available haem to be broken down by HO. This leads to an increase in intracellular ROS, which upregulates the nicotine biosynthetic pathway. PM: plasma membrane.

A summary of sequence identifiers used throughout the subject specification and the corresponding sequence listing is provided wherein:

SEQ ID No. 1 corresponds to the amino acid sequence of Nitab4.5_0013616g0010.2.

SEQ ID No. 2 corresponds to the genomic sequence of Nitab4.5_0013616g0010.2.

SEQ ID No. 3 corresponds to the coding sequence of Nitab4.5_0013616g0010.2.

SEQ ID No. 4 corresponds to the amino acid sequence of Nitab4.5_0000652g0130.2.

SEQ ID No. 5 corresponds to the genomic sequence of Nitab4.5_0000652g0130.2.

SEQ ID No. 6 corresponds to the coding sequence of Nitab4.5_0000652g0130.2.

SEQ ID No. 7 corresponds to the amino acid sequence of Nitab4.5_0001140g0220.2.

SEQ ID No. 8 corresponds to the genomic sequence of Nitab4.5_0001140g0220.2.

SEQ ID No. 9 corresponds to the coding sequence of Nitab4.5_0001140g0220.2.

SEQ ID No. 10 corresponds to the amino acid sequence of Nitab4.5_0003235g0060.2.

SEQ ID No. 11 corresponds to the genomic sequence of Nitab4.5_0003235g0060.2.

SEQ ID No. 12 corresponds to the coding sequence of Nitab4.5_0003235g0060.2.

SEQ ID No. 13 corresponds to the amino acid sequence of Nitab4.5_0004868g0020.2.

SEQ ID No. 14 corresponds to the genomic sequence of Nitab4.5_0004868g0020.2.

SEQ ID No. 15 corresponds to the coding sequence of Nitab4.5_0004868g0020.2.

SEQ ID No. 16 corresponds to the amino acid sequence of Nitab4.5_0006614g0010.2.

SEQ ID No. 17 corresponds to the genomic sequence of Nitab4.5_0006614g0010.2.

SEQ ID No. 18 corresponds to the coding sequence of Nitab4.5_0006614g0010.2.

SEQ ID No. 19 corresponds to the amino acid sequence of Nitab4.5_0006991g0050.2.

SEQ ID No. 20 corresponds to the genomic sequence of Nitab4.5_0006991g0050.2.

SEQ ID No. 21 corresponds to the coding sequence of Nitab4.5_0006991g0050.2.

SEQ ID No. 22 corresponds to the amino acid sequence of Nitab4.5_0009023g0010.2.

SEQ ID No. 23 corresponds to the genomic sequence of Nitab4.5_0009023g0010.2.

SEQ ID No. 24 corresponds to the coding sequence of Nitab4.5_0009023g0010.2.

SEQ ID No. 25 is a 300-nucleotide cDNA fragment used in Example 2.

SEQ ID No. 26 is sequence TRV1 used in Example 2.

SEQ ID No. 27 is sequence TRV2 used in Example 2.

Some sequences disclosed herein contain "X" or "N" in nucleotide sequences. "X" or "N" can be any nucleotide or a deletion or insertion of one or more nucleotides. For example, in some cases a string of "X"s or "N"s are shown. The number of "X"s or "N"s does not necessarily correlate with the actual number of nucleotides at that position. There may be more or fewer nucleotides than shown as "X" or "N" in the sequence.

DETAILED DESCRIPTION

For the first time the present inventors have shown that by modulating the activity or expression of at least one gene encoding a SOUL haem-binding protein in a plant (e.g. a tobacco plant), the alkaloid and/or TSNA content of the plant (or processed plant) can be modulated.

The present invention provides a method of modulating (e.g. decreasing) the alkaloid content of a plant or a part thereof, the method comprising modifying said plant by modulating (e.g. decreasing) the activity or expression of at least one gene encoding a SOUL haem-binding protein.

Also provided is a method of modulating (e.g. decreasing) the content of a tobacco specific nitrosamine (TSNA) or a precursor of a TSNA in a tobacco plant or plant part thereof, the method comprising modifying said plant by modulating (e.g. decreasing) the activity or expression of at least one gene encoding a SOUL haem-binding protein.

The at least one gene encoding a SOUL haem-binding protein may be selected from at least one gene encoding a SOUL haem-binding protein which comprises an amino acid sequence as set out in SEQ ID No. 1, 4, 7, 10, 13, 16, 19 or 22, or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

Suitably, the SOUL haem-binding protein may comprise a SOUL motif.

Suitably, more than one SOUL haem-binding proteins may be modified. In one embodiment at least one SOUL haem-binding protein gene is modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least two SOUL haem-binding protein genes are modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least three SOUL haem-binding protein genes are modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least four SOUL haem-binding protein genes modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least five SOUL haem-binding protein genes are modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least six SOUL haem-binding protein genes are modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least seven SOUL haem-binding protein genes are modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

In one embodiment at least eight SOUL haem-binding protein genes are modified selected from the group comprising genes encoding polypeptides comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

Suitably, the SOUL haem-binding protein of the present invention may comprise a SOUL motif.

In one aspect, the at least one SOUL haem-binding protein gene encodes a polypeptide which comprises an amino acid sequence as set out in: SEQ ID No. 1 or a functional variant or functional fragment or orthologue thereof, or a sequence which has at least 80% identity to SEQ ID No. 1; or wherein the at least one gene encoding a SOUL haem-binding protein comprises a nucleotide sequence as set out in SEQ ID No. 2 or 3 or a functional variant or functional fragment or orthologue of SEQ ID No. 2 or 3; or a nucleic acid sequence which has at least 80% identity to SEQ ID No. 2 or 3. Suitably, the SOUL haem-binding protein may comprise a SOUL motif.

In one aspect, the activity or expression of at least one further gene is modulated. Suitably, at least two (or at least three or at least four or at least five or at least six or at least seven or at least eight or at least nine) additional genes selected from SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24 may also be modulated. Suitably, the SOUL haem-binding protein may comprise a SOUL motif.

The "activity" of a gene encoding a SOUL haem-binding protein may refer to the ability of the SOUL haem-binding protein produced by the gene to bind other molecules, such as other proteins. Suitably, the "activity" of a gene encoding a SOUL haem-binding protein refers to the ability of the SOUL haem-binding protein produced by the gene to bind haem.

The "expression" of a gene encoding a SOUL haem-binding protein may refer to the level of transcription, translation i.e. protein expression.

Measurement of the level or amount of a gene product may be carried out by any suitable method, for example comparison of mRNA transcript levels, protein or peptide levels, and/or phenotype of a plant, between a modified plant and comparable plant which has not been modified according to the present invention.

The term "a comparable product" as defined herein would be one derived from a plant (e.g. a tobacco plant) which had not been modified according to the present invention, but in which all other relevant features were the same (e.g. plant species, growing conditions, method of processing the plant, e.g. tobacco, etc.). The comparable product according to the present invention may mean a plant (e.g. a tobacco plant) or a part thereof, such as a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf) or plant propagation material (e.g. tobacco plant propagation material), or a product comprising said plant or part therefore, e.g. a tobacco product or combinations thereof obtainable or obtained from a plant which has not been modified in accordance with the present invention, e.g. to modulate the activity or expression of gene encoding a SOUL haem-binding protein. In one embodiment a comparable product is one which does not comprise gene encoding a SOUL haem-binding protein whose activity or expression has been modulated.

The term "modifying" or "modified" as used herein means a plant (e.g. a tobacco plant) or nucleic acid sequence that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis e.g. ethyl methanesulfonate (EMS) mutagenesis and modern population analysis approaches.

The term "unmodified plant" as defined herein would be a plant (e.g. a tobacco plant) which had not been modified according to the present invention, e.g. to modulate the activity or expression of a gene encoding a SOUL haem-binding protein or to modify the nucleic acid sequence of at least one gene encoding a SOUL haem-binding protein; and in which all other relevant features were the same (e.g. plant species, growing conditions, method of processing tobacco, etc.). In one embodiment an unmodified plant is one which does not comprise a gene encoding an SOUL haem-binding protein whose activity or expression has been modulated. In one embodiment, an unmodified plant is one which does not comprise a modified nucleic acid sequence which encodes at least one gene encoding a SOUL haem-binding protein.

SOUL Haem-Binding Protein

A "SOUL haem-binding protein" as used herein has its usual meaning in the art and refers to a protein which comprises a SOUL motif, which is a hydrophobic cleft flanked by an α-helix and a β-loop.

SOUL haem-binding proteins are found in bacteria, plants and animals. SOUL haem-binding proteins bind tetrapyrroles such as haem (Takahashi et al. (2008) Photochem. Photobiol. Sci. 7, 1216-1224). It has been suggested that SOUL proteins in plants may be involved in transporting haem to other haem-containing proteins such as cytochrome P450s and in binding free haem (Freire et al. (2009) Acta Cryst. F65, 723-726).

The three-dimensional structure of a SOUL haem-binding protein from mouse has been determined. The murine SOUL structure consists of a nine-stranded twisted β-barrel, two α-helices and a hydrophobic cleft. The hydrophobic cleft is flanked by one of the α-helices and the β8-9 loop, forming a conserved "SOUL motif", which is essential for haem-binding (Dias et al. (2006) J. Biol. Chem. 276, 18161-18168). A similar structure is predicted for *Arabidopsis* SOUL haem-binding proteins (Takahashi et al. (2008) Photochem. Photobiol. Sci. 7, 1216-1224).

In one embodiment the SOUL haem-binding protein comprises a SOUL motif. As used herein the term "SOUL motif" refers to a conserved structural motif. SOUL haem-binding proteins and SOUL motifs may be identified by comparison of the predicted structure of a protein with known protein structures. For example, SOUL haem-binding proteins and SOUL motifs may be identified by comparison of the predicted structure of a protein against the predicted structure of SEQ ID No. 1, wherein the presence of a hydrophobic cleft flanked by an α-helix and β-loop identifies the protein as a SOUL haem binding protein.

In one embodiment, a SOUL motif is a region of a protein which corresponds to a hydrophobic cleft flanked by an α-helix and β-loop. The SOUL motif may be involved in haem-binding.

Without wishing to be bound by theory, it is hypothesized that increasing content of a SOUL haem-binding protein in a plant cell or increasing activity, such as haem-binding activity, of a SOUL haem-binding protein in a plant would lead to increased binding of free haem. The reduction in free haem levels would mean a reduction in haem degradation by haem oxygenase, leading to reduced scavenging of reactive oxygen species (ROS). ROS stimulate activation of nicotine biosynthesis genes. Increased activity or expression of a SOUL haem-binding protein thereby leads to increased levels of pyridine alkaloids. Conversely, according to this hypothesis, decreased levels or activity, such as haem-binding activity, of a SOUL haem-binding protein in a plant cell would increase the amount of free haem, leading to increased ROS scavenging and therefore reduced activation of nicotine biosynthesis genes, thereby decreasing levels of pyridine alkaloids in the cell. This hypothesis is depicted diagrammatically in FIG. 1.

In one embodiment a SOUL haem-binding protein comprises an amino acid sequence shown as SEQ ID No. 1 or a sequence which has at least 80% identity thereto, or a homologue thereof.

Suitably, the SOUL haem-binding protein may comprise a SOUL motif. Suitably, a homologue of SEQ ID No. 1 may be selected from the group comprising: SEQ ID No. 4, 7, 10, 13, 16, 19 or 22, or a sequence which has at least 80% identity thereto. Suitably, a homologue of SEQ ID No. 1 may be selected from the group comprising: SEQ ID No. 4, 7, 10, 13, 16, 19 or 22 wherein said sequence comprises a SOUL motif, or a sequence which has at least 80% identity to SEQ ID No. 4, 7, 10, 13, 16, 19 or 22 and comprises a SOUL motif.

In one embodiment a SOUL haem-binding protein comprises an amino acid sequence shown as SEQ ID No. 1, 4, 7, 10, 13, 16, 19 or 22, or a sequence which has at least 80% identity thereto (preferably at least 85%, at least 90%, at least 95%, at least 97%, or at least 99% identity thereto). In one embodiment a SOUL haem-binding protein comprises an amino acid sequence shown as SEQ ID No. 1, 4, 7, 10, 13, 16, 19 or 22, or a sequence which has at least 80% identity thereto (preferably at least 85%, at least 90%, at least 95%, at least 97%, or at least 99% identity thereto) and comprises a SOUL motif.

Suitably, a SOUL haem-binding protein according to the present invention may comprise an amino acid sequence shown as SEQ ID No. 1, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 4, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 7, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 10, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 13, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 16, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 19, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, a SOUL haem-binding protein according to the present invention may comprise an amino acid sequence shown as SEQ ID No. 22, or a sequence which has at least 80% identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

In one embodiment the SOUL haem-binding protein according to the present invention comprises or consists of an amino acid sequence selected from: SEQ ID No. 1, 4, 7, 10, 13, 16, 19 or 22.

Suitably, the protein may be from *Nicotiana tabacum*.

In one embodiment the SOUL haem-binding protein is encoded by a polynucleotide sequence wherein the gene (prior to mutation) comprises the sequence shown as SEQ ID No. 2, 3, 5, 6, 8, 9, 11, 12, 14, 15, 17, 18, 20, 21, 23 or 24; or a sequence which has at least 80% sequence identity thereto. Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 2, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 3, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 5, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 6, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 8, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 9, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 11, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 12, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 14, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 15, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 17, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 18, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 20, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 21, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 23, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

Suitably, the SOUL haem-binding protein for use according to the present invention may be encoded by a polynucleotide sequence wherein the gene (prior to mutation) comprises the sequence shown as SEQ ID No. 24, or a sequence which has at least 80% sequence identity thereto (preferably at least 85%, preferably at least 90%, preferably at least 93%, preferably at least 95%, at least 97%, or at least 99% identity thereto). Suitably, the SOUL haem-binding protein may comprise a SOUL motif.

In one embodiment the SOUL haem-binding protein is encoded by a polynucleotide sequence wherein the gene (prior to mutation) is selected from: SEQ ID No. 2, 3, 5, 6, 8, 9, 11, 12, 14, 15, 17, 18, 20, 21, 23 or 24.

Suitably, the protein for use according to the present invention may be encoded by a polynucleotide sequence from *Nicotiana tabacum*.

In one aspect the present invention provides a method of decreasing the alkaloid content of a plant or part thereof or cell (e.g. plant cell), the method comprising modifying said plant by decreasing or inhibiting the activity or expression of at least one gene encoding a SOUL haem-binding protein.

In one aspect the present invention provides a method of decreasing the alkaloid content of a plant or part thereof or plant cell, the method comprising modifying said plant by decreasing or inhibiting the activity or expression of at least one gene encoding a SOUL haem-binding protein comprising the amino acid sequence shown as SEQ ID No. 1, 4, 7, 10, 13, 16, 19 or 22, or a sequence which has at least 80% identity thereto or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24, or a nucleic acid sequence which has at least 80% identity to SEQ ID No. 2, 3, 5, 6, 8, 9, 11, 12, 14, 15, 17, 18, 20, 21, 23 or 24. Suitably, the SOUL haem-binding protein may comprise a SOUL motif.

In one aspect the present invention provides a method of decreasing the content of a tobacco specific nitrosamine (TSNA) or a precursor of a TSNA a plant or part thereof (e.g. leaf), the method comprising modifying said plant by decreasing or inhibiting the activity or expression of at least one gene encoding a SOUL haem-binding protein.

In one aspect the present invention provides a method of decreasing the content of a tobacco specific nitrosamine (TSNA) or a precursor of a TSNA in a plant or part thereof (e.g. leaf), the method comprising modifying said plant by decreasing or inhibiting the activity or expression of at least one gene encoding a SOUL haem-binding protein comprising the amino acid sequence shown as SEQ ID No. 2, 3, 5, 6, 8, 9, 11, 12, 14, 15, 17, 18, 20, 21, 23 or 24, or a sequence which has at least 80% identity thereto, or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24, or a nucleic acid sequence which has at least 80% identity to SEQ ID No. 2, 3, 5, 6, 8, 9, 11, 12, 14, 15, 17, 18, 20, 21, 23 or 24.

The term "decreasing" or "inhibiting" (e.g. inhibiting the activity or expression of gene encoding a SOUL haem-binding repeat protein) as used herein means that the activity or expression of the gene encoding the SOUL haem-binding repeat protein is lower or decreased compared with the activity or expression of the gene in a comparable product.

In one aspect the present invention provides a method of increasing the alkaloid content of a plant or part thereof or cell (e.g. plant cell), the method comprising modifying said plant by increasing or enhancing the activity or expression of at least one gene encoding a SOUL haem-binding protein.

In one aspect the present invention provides a method of increasing the alkaloid content of a plant or part thereof or plant cell, the method comprising modifying said plant by increasing or enhancing the activity or expression of at least one gene encoding a SOUL haem-binding protein comprising the amino acid sequence shown as SEQ ID No. 1, 4, 7, 10, 13, 16, 19 or 22, or a sequence which has at least 80% identity thereto or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24, or a nucleic acid sequence which has at least 80% identity to SEQ ID No. 2, 3, 5, 6, 8, 9, 11, 12, 14, 15, 17, 18, 20, 21, 23 or 24. Suitably, the SOUL haem-binding protein may comprise a SOUL motif.

In one aspect the present invention provides a method of increasing the content of a tobacco specific nitrosamine (TSNA) or a precursor of a TSNA a plant or part thereof (e.g. leaf), the method comprising modifying said plant by increasing or enhancing the activity or expression of at least one gene encoding a SOUL haem-binding protein.

In one aspect the present invention provides a method of increasing the content of a tobacco specific nitrosamine (TSNA) or a precursor of a TSNA in a plant or part thereof (e.g. leaf), the method comprising modifying said plant by increasing or enhancing the activity or expression of at least one gene encoding a SOUL haem-binding protein comprising the amino acid sequence shown as SEQ ID No. 2, 3, 5, 6, 8, 9, 11, 12, 14, 15, 17, 18, 20, 21, 23 or 24, or a sequence which has at least 80% identity thereto, or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24, or a nucleic acid sequence which has at least 80% identity to SEQ ID No. 2, 3, 5, 6, 8, 9, 11, 12, 14, 15, 17, 18, 20, 21, 23 or 24.

The term "increasing" or "enhancing" (e.g. increasing the activity or expression of gene encoding a SOUL haem-binding repeat protein) as used herein means that the activity or expression of the gene encoding the SOUL haem-binding repeat protein is higher or increased compared with the activity or expression of the gene in a comparable product.

According to the present invention, the activity or expression of a gene encoding a SOUL haem-binding protein is modulated.

In one aspect the present invention provides a method of modulating (i.e. increasing or decreasing) the alkaloid content of a plant or part thereof or cell (e.g. plant cell), the method comprising modifying said plant by modulating (i.e. increasing or decreasing) the activity of at least one gene encoding a SOUL haem-binding protein.

The term "activity" refers to any functionality of the SOUL haem-binding protein encoded by the at least one gene. Examples of activity include enzymatic activity or localization of the SOUL haem-binding protein. Suitably, the activity is the ability of the SOUL haem-binding protein to interact with another molecule or molecules. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of a SOUL haem-binding protein to interact with another molecule.

Suitably, the ability of the SOUL haem-binding protein to interact with the other molecule is the ability to bind the other molecule. The other molecule may be a protein. The other molecule may be a tetrapyrrole. The other molecule may be haem. In some embodiments the invention provides a method of modulating (i.e. increasing or decreasing) the alkaloid content of a plant or part thereof or cell (e.g. plant cell), the method comprising modifying said plant by modulating (i.e. increasing or decreasing) the ability of a SOUL haem-binding protein to bind haem.

Suitably, the other molecule is more than one molecule, such as one or more molecules, such as two or more molecules, such as three or more molecules. Where the other molecule is more than one molecule, the other molecules may be the same molecule or may be different molecules. Where the other molecule is more than one molecule, at least one of the other molecules may be haem.

Modulation of the activity of a gene encoding a SOUL haem-binding protein may entail increasing or decreasing the activity of the SOUL haem-binding protein.

Increasing the activity of a SOUL haem-binding protein refers to enhancing or improving the ability of the SOUL haem-binding protein to carry out a particular function in comparison to a SOUL haem-binding protein in a plant that has not been modified in accordance with the invention.

Decreasing the activity of a SOUL haem-binding protein refers to reducing, inhibiting or disrupting the ability of the SOUL haem-binding protein to carry out a particular function in comparison to a SOUL haem-binding protein in a plant that has not been modified in accordance with the invention. The activity of a SOUL haem-binding protein may be reduced to such an extent that the activity is prevented or eliminated.

In some embodiments the activity of a SOUL haem-binding protein may be modulated (i.e. increased or decreased) by at least about 10% 20% 30%, or 40%, suitably at least about 50%, 60%, 70%, more suitably at least about 80%, 90%, 95% or 100% in comparison to the activity of a gene encoding a SOUL haem-binding protein in a plant (e.g. a tobacco plant) which has not been modified in accordance with the present invention.

In some embodiments the modulated SOUL haem-binding protein exhibits increased or decreased activity compared to an unmodified SOUL haem-binding protein. The modulated SOUL haem-binding protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased or decreased activity compared to an unmodified SOUL haem-binding protein.

Suitably, the modulation of activity is an increase or decrease in the ability of the SOUL haem-binding protein to interact with (such as bind) another molecule or molecules (such as haem).

In some embodiments the invention provides a method of modulating the alkaloid content of a plant or part thereof or cell, the method comprising modifying said plant by modulating the ability of a SOUL haem-binding protein to bind haem. Suitably the ability of a SOUL haem-binding protein to bind haem is increased. Suitably the ability of a SOUL haem-binding protein to bind haem is decreased. An increase or decrease in the ability of the SOUL haem-binding protein to bind another molecule may be expressed as an increase or decrease in the binding affinity of the SOUL haem-binding protein. In some embodiments the invention provides a method of modulating the alkaloid content of a plant or part thereof or cell, the method comprising modifying said plant by modulating the binding affinity of a SOUL haem-binding protein for haem.

Techniques are known in the art for measuring protein activities. For example, assays are known for measuring the enzymatic activity of a protein and the localization of a protein can be identified using microscopy techniques.

In particular, the ability of a SOUL haem-binding protein to bind another molecule may be measured using techniques known in the art. Examples of such techniques include immunoprecipitation, isothermal calorimetry, surface plasmon resonance and microsclae thermophoresis. For example, the ability of a modulated or mutated SOUL haem-binding protein to bind other molecules may be determined for example by performing co-immunoprecipitation experiments using a modulated or mutated SOUL haem-binding protein and a corresponding unmodified or unmutated SOUL haem-binding protein. If the modulation or mutation in the SOUL haem-binding protein reduces, inhibits or eliminates the ability of the SOUL haem-binding protein bind other molecules, the co-immunoprecipitation will show that the modulated or mutated SOUL haem-binding protein binds fewer other molecules.

According to the present invention, the activity or expression of a SOUL haem-binding protein is modulated.

In one aspect the present invention provides a method of modulating (i.e. increasing or decreasing) the alkaloid content of a plant or part thereof or cell (e.g. plant cell), the method comprising modifying said plant by modulating (i.e. increasing or decreasing) the expression of at least one gene encoding a SOUL haem-binding protein.

The "expression" of a gene refers to the degree to which the information encoded in the gene is converted to a functionality. The level of expression of a gene may be equated with the amount of the product of that gene present in a cell or organism. A modification that modulates (i.e. increases or decreases) the expression of a gene is one that increases the amount of the product of that gene in a plant or cell in comparison to an unmodified plant or cell.

In some embodiments the expression of a SOUL haem-binding protein is modulated (i.e. increased or decreased) in comparison to the expression of a gene encoding a SOUL haem-binding protein in a plant (e.g. a tobacco plant) which has not been modified in accordance with the present invention.

In some embodiments the expression of a SOUL haem-binding protein may be modulated (i.e. increased or decreased) by at least about 10% 20% 30%, or 40%, suitably at least about 50%, 60%, 70%, more suitably at least about 80%, 90%, 95% or 100% in comparison to the expression of a gene encoding a SOUL haem-binding protein in a plant (e.g. a tobacco plant) which has not been modified in accordance with the present invention.

In some embodiments the modulated SOUL haem-binding protein exhibits increased or decreased expression compared to an unmodified SOUL haem-binding protein. The modulated SOUL haem-binding protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased or decreased expression compared to an unmodified SOUL haem-binding protein.

Typically, genes are transcribed to mRNA, which is translated to protein, the final gene product.

Proteins may be sequestered in cellular stores and/or degraded. The expression of a gene may be modulated by modulating any or all of these steps. Accordingly, in some embodiments the modification modulates expression of at least one SOUL haem-binding protein gene in one of the following ways:
  modulating transcription from the at least one SOUL haem-binding protein gene;
  modulating translation of the mRNA from the at least one SOUL haem-binding protein gene;
  modulating release of the SOUL haem-binding protein from intracellular stores; and/or
  modulating the rate of degradation of the SOUL haem-binding protein.

The expression of specific genes encoding SOUL haem-binding proteins can be measured by measuring transcription and/or translation of the gene. Methods for measuring transcription are well known in the art and include, amongst others, northern blot, RNA-Seq, in situ hybridization, DNA microarrays and RT-PCR. Alternatively, the expression of a gene may be measured indirectly by measuring the level of the gene product for example the protein encoded by said gene. For example, the expression of a SOUL haem-binding protein may be determined by measuring the presence of the protein using an antibody specific for the SOUL haem-binding protein (for example antibodies specific for a SOUL motif) by western blot.

Modifying

The term "modifying" as used herein refers to alteration of the genetic material of a plant or cell. The plant or cell may be modified in any way that modulates activity or expression of at least one gene encoding a SOUL haem-binding protein. Types of modifications to plants and cells that modulate activity or expression of genes, as well as techniques to achieve those modifications, are known in the art.

In some embodiments the present invention provides a method of decreasing the alkaloid content of a plant or part thereof or cell (e.g. plant cell), the method comprising modifying said plant by decreasing or inhibiting the activity or expression of at least one gene encoding a SOUL haem-binding protein.

In some embodiments the present invention provides a method of decreasing the content of a tobacco specific nitrosamine (TSNA) or a precursor of a TSNA in a tobacco plant or plant part thereof, the method comprising modifying said plant or a cell or cell culture by decreasing the activity or expression of at least one gene encoding a SOUL haem-binding protein.

Any method known in the art for decreasing or inhibiting the activity or expression of a gene may be used in the methods according to the present invention.

Suitably, the activity or expression of the SOUL haem-binding protein gene may be reduced, partly inactivated, inhibited, eliminated, knocked out or lost such that the protein activity, expression or function of the SOUL haem-binding protein gene is not detectable.

In one aspect, the at least one SOUL haem-binding protein gene is knocked out. In other words, the SOUL haem-binding protein gene has been rendered completely inoperative.

By way of example, the present method may comprise:
  providing a mutation in a nucleic acid sequence which encodes a protein comprising the amino acid sequence shown as SEQ ID No. 1, 4, 7, 10, 13, 16, 19 or 22 or an amino acid sequence which has at least 80% sequence identity thereto;
  providing a mutation in a regulatory region (e.g. a promoter or an enhancer) which contributes to controlling the expression of a protein comprising the amino acid sequence shown as SEQ ID No. 1, 4, 7, 10, 13, 16, 19 or 22, or an amino acid sequence which has at least 80% sequence identity thereto;
  providing an antisense RNA, siRNA or miRNA which reduces the level of nucleic acid sequence encoding a protein comprising the amino acid sequence shown as SEQ ID No. 1, 4, 7, 10, 13, 16, 19 or 22, or an amino acid sequence which has at least 80% sequence identity thereto.

Each of the above approaches results in the reduction or prevention of activity or expression of a protein comprising the amino acid sequence shown as SEQ ID No. 1, 4, 7, 10, 13, 16, 19 or 22, or an amino acid sequence which has at least 80% sequence identity thereto or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

As used herein, the term "mutation" encompasses a natural genetic variant or an engineered variant. In particular, the term "mutation" refers to a variation in the nucleotide sequence encoding the amino acid sequence or in the amino acid sequence compared to the sequence shown as SEQ ID No 1, 4, 7, 10, 13, 16, 19 or 22, or an amino acid sequence which has at least 80% (preferably at least 85%, preferably at least 90%, preferably at least 93%, preferably at least 95%, preferably at least 98%, preferably at least 99%) sequence identity thereto.

In one embodiment the mutation decreases the alkaloid content of a plant. In another embodiment, the mutation decreases the content of at least one TSNA or a precursor of a TSNA in tobacco.

In one embodiment, a method according to the present invention may comprise providing a nucleic acid sequence to a plant or part thereof or plant cell, wherein said nucleic acid results in the reduction or elimination of the activity or expression of at least one gene encoding a SOUL haem-binding protein.

In one embodiment, a method according to the present invention may comprise providing a nucleic acid sequence to a plant or part thereof or plant cell, wherein said nucleic acid results in the modification of the nucleic acid sequence of at least one gene encoding a SOUL haem-binding protein.

Suitably said nucleic acid sequence may be introduced to the plant or part thereof or cell. Suitably an endogenous nucleic acid sequence in the plant or part thereof or cell may be modified to encode the polypeptide according to the present invention (e.g. by gene editing). For example, an endogenous nucleotide sequence may be modified to decrease the activity or expression of at least one gene encoding a SOUL haem-binding protein.

In a preferred embodiment, each copy of a nucleic acid sequence encoding a protein comprising a sequence shown as SEQ ID No. 1, 4, 7, 10, 13, 16, 19 or 22, or a sequence which has at least 80% sequence identity thereto or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24 which is present in the plant is modified e.g. mutated as defined herein (e.g. each genomic copy of a gene encoding said protein in a plant is mutated). For example, each copy of the gene in the allotetraploid genome of *Nicotiana tabacum* may be mutated.

In a preferred embodiment, some or all of the homologues of the SOUL haem-binding protein described herein are modified e.g. inhibited or mutated. Suitably, some or all of SEQ ID No. 1, 4, 7, 10, 13, 16, 19 or 22, or corresponding sequences which have at least 80% sequence identity thereto are modified e.g. inhibited or mutated.

In some embodiments the plant or plant cell according to the present invention is homozygous.

Suitably, the plant or plant cell may be homozygous for the modification e.g. inhibition or mutation.

In some embodiments the plant or plant cell according to the present invention expresses only the modified e.g. mutated nucleic acid encoding the SOUL haem-binding protein. In other words, in some embodiments no endogenous (or endogenous and functional protein) is present in the plant according to the present invention. In other words, if any endogenous protein is present it is preferably in an inactive form.

In one embodiment the present method may comprise providing a mutation in the nucleic acid sequence shown as SEQ ID No. 2, 3, 5, 6, 8, 9, 11, 12, 14, 15, 17, 18, 20, 21, 23 or 24, or a nucleic acid sequence which has at least 80% identity thereto.

The mutation may alter the plant genome such that a nucleic acid sequence encoding a protein comprising the amino acid sequence shown as SEQ ID No. 1, 4, 7, 10, 13, 16, 19 or 22 or an amino acid sequence which has at least 80% sequence identity thereto is completely or partially deleted or otherwise modified to inhibit or eliminate the ability of the SOUL haem-binding protein to interact with other molecules, such as bind to other molecules, in comparison with a protein shown as SEQ ID No. 1, 4, 7, 10, 13, 16, 19 or 22 or a sequence which has at least 80% sequence identity thereto. In some embodiments the mutation does not alter the level or expression of the protein but reduces inhibits or eliminates the ability of the SOUL haem-binding protein to interact with other molecules, such as bind to other molecules, in comparison with a protein shown as SEQ ID No. 1, 4, 7, 10, 13, 16, 19 or 22, or a sequence which has at least 80% sequence identity thereto. Suitably, the mutation inhibits or eliminates ability of the SOUL haem-binding protein to interact with other proteins. Suitably, the mutation inhibits or eliminates the ability of the SOUL haem-binding protein to bind other molecules. Suitably, the mutation inhibits or eliminates the ability of the SOUL haem-binding protein to bind other proteins.

Suitably, the mutation inhibits or eliminates the ability of the SOUL haem-binding protein to bind a tetrapyrrole or tetrapyrroles. Suitably, the mutation inhibits or eliminates the ability of the SOUL haem-binding protein to bind haem. The expression "inhibits or eliminates" means that the interaction between the SOUL haem-binding protein and the other molecule is reduced, suitably to the extent that the interaction is prevented (i.e. the SOUL haem-binding protein does not interact with the other molecule at all). Suitably inhibition or elimination of binding of the SOUL haem-binding protein to another molecule means a decrease in the binding affinity of the SOUL haem-binding protein for the other molecule. In some embodiments, the mutation reduces the binding affinity of the SOUL haem-binding protein for haem.

Suitably, the mutation may be in a domain of the SOUL haem-binding protein that mediates interaction with other molecules. The mutation may be in a domain of the SOUL haem-binding protein that mediates binding to haem. The mutation may be in the SOUL motif of the SOUL haem-binding protein. In some embodiments, the SOUL motif may be mutated thereby modifying the ability of the SOUL haem-binding protein to interact with other molecules. In other words, the SOUL motif may be mutated, resulting in a modification of the binding affinity of the SOUL haem-binding protein for other molecules. Suitably, the SOUL motif is mutated such that the binding affinity of the SOUL haem-binding protein for other molecules is increased. Suitably, the SOUL motif is mutated such that the binding affinity of the SOUL haem-binding protein for other molecules is decreased.

The mutation may interrupt the nucleic acid sequence which encodes a protein comprising the amino acid sequence shown as SEQ ID No. 1, 4, 7, 10, 13, 16, 19 or 22, or an amino acid sequence which has at least 80% sequence identity thereto.

The interruption may cause the nucleic acid sequence to not be transcribed and/or translated.

The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutation or a non-tolerated amino acid substitution in the open reading frame.

A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutation inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the method according to the present invention. For example, homologous recombination may be used, in which a vector is created in which the relevant nucleic acid sequence(s) are mutated and used to transform plants or plant cells. Recombinant plants or plant cells expressing the mutated sequence may then be selected.

In one embodiment the mutation introduces a non-tolerated amino acid substitution in a protein comprising an amino acid sequence shown as SEQ ID No. 1, 4, 7, 10, 13, 16, 19 or 22, or a sequence which has at least 80% sequence identity thereto.

In some embodiments, the SOUL motif may contain a mutation which decreases the expression of the at least one gene encoding a SOUL haem-binding protein.

The mutation may be a deletion, a splice mutant or codon encoding a non-tolerated amino acid substitution.

In one embodiment, the nucleic acid sequence encoding the SOUL haem-binding protein may be wholly or partially deleted. The deletion may be continuous, or may comprise a plurality of sections of sequence. The deletion preferably removes a sufficient amount of nucleotide sequence such that the nucleic acid sequence no longer encodes a functional SOUL haem-binding protein. The deletion may be total, in which case 100% of the coding portion of the nucleic acid sequence is absent, when compared to the corresponding genome of a comparable unmodified plant. The deletion may, for example, remove at least 50, 60, 70, 80 or 90% of the coding portion of the nucleic acid sequence. Suitably, at least part of the protein may be deleted. The deletion may, for example, remove at least 10, 20, 30, 40, 50, 60, 70, 80 or 90% of the coding portion of the protein.

The deletion may remove at least part of the SOUL motif.

The deletion may, for example, remove at least 10, 20, 30, 40, 50, 60, 70, 80 or 90% of the SOUL motif.

Suitably, the deletion may remove at least 5 amino acids, at least 10 amino acids, at least 15, at least 20, at least 25, at least 30 amino acids from the SOUL motif. Suitably, the deletion may remove at least 5 amino acids, at least 10 amino acids, at least 15, at least 20, at least 25, at least 30 amino acids from the SOUL motif.

In one embodiment, the deletion may remove at least 100 amino acids, at least 150, at least 200, at least 250, at least 300, at least 350 amino acids from the C terminus of the SOUL haem-binding protein.

Suitably, the mutated protein may be a truncated protein which lacks at least about 100 amino acids, at least about 150 amino acids corresponding to the amino acids from the C-terminal of SEQ ID No. 1 or a sequence which has at least 80% (preferably at least 85%, at least, at least 90%, at least 95%, at least 98%) sequence identity thereto to a truncated protein which lacks at least about 100 amino acids, at least about 150 amino acids corresponding to the amino acids from the C-terminal of SEQ ID No. 1.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Plant cells transformed with a vector as described herein may be grown and maintained in accordance with well-known tissue culturing methods such as by culturing the cells in a suitable culture medium supplied with the necessary growth factors such as amino acids, plant hormones, vitamins, etc.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA, Cas9/gRNA, or other CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KeyBase® or TALENs).

Alternatively, mutagenesis systems such as TILLING (Targeting Induced Local Lesions IN Genomics; McCallum et al. (2000) Nat. Biotech. 18:455, and McCallum et al. (2000) Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis, which produces random mutations) followed by high-throughput screening for mutations. Thus, plants, seeds, cells and tissues comprising a gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Fast neutron deletion mutagenesis may be used in a reverse genetics sense (i.e. with PCR) to identify plant lines carrying a deletion in the endogenous gene. See for example Ohshima et al. (1998) Virology 213:472-481; Okubara et al. (1994) Genetics 137:867-874; and Quesada et al. (2000) Genetics 154:421-4315 which are incorporated herein by reference.

In another approach, dominant mutants may be used to trigger RNA silencing due to gene inversion and recombination of a duplicated gene locus. See for example Kusaba et al. (2003) Plant Cell 15:1455-1467 (incorporated herein by reference).

Modified plants may be distinguished from non-modified plants, i.e., wild type plants, by molecular methods, such as the mutation(s) present in the DNA, and by the modified phenotypic characteristics. The modified plants may be homozygous or heterozygous for the modification.

Preferably modified plants are homozygous for the modification.

In one embodiment the method of reducing or preventing the activity or expression of a protein comprising the amino acid sequence shown as SEQ ID No. 1, 4, 7, 10, 13, 16, 19 or 22, or an amino acid sequence which has at least 80% sequence identity thereto does not comprise treating the plant with a chemical (e.g. an agrochemical).

Other ways of reducing or preventing the expression will be apparent to one skilled in the art and include the use of virus-induced gene silencing (VIGs), micro RNA silencing, RNAi, antisense, tDNA insertions, or dominant negative constructs (or antimorphic mutations).

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by virus-induced gene silencing.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by microRNAs.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by RNAi.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by antisense suppression.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by sense suppression.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by tDNA insertions.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by dominant negative constructs (or antimorphic mutations).

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by a targeted mutagenesis based system.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by CRISPR based system.

In one embodiment the expression of a protein comprising the amino acid sequence shown as SEQ ID No. 1, 4, 7, 10, 13, 16, 19 or 22, or an amino acid sequence which has at least 80% sequence identity thereto may be reduced or eliminated by zinc finger nuclease, TALENs, meganucleases, mutagenic oligonucleotides or TILLING.

In some embodiments the present invention provides a method of increasing the alkaloid content of a plant or part thereof or cell (e.g. plant cell), the method comprising modifying said plant by increasing or enhancing the activity or expression of at least one gene encoding a SOUL haem-binding protein.

Any method known in the art for increasing or enhancing the activity or expression of a gene may be used in the methods according to the present invention.

In some embodiments the method may comprise overexpressing at least one gene encoding a SOUL haem-binding protein. Suitably the method may comprise expressing one or more additional copies of the at least one gene encoding a SOUL haem-binding protein in the plant or cell. Suitably the method may comprise modifying the endogenous copy of the at least one gene encoding a SOUL haem-binding protein such that its expression is increased. The method may comprise mutating the coding sequence of the at least one gene encoding a SOUL haem-binding protein. The method may comprise mutating a regulatory sequence that regulates expression of the at least one gene encoding a SOUL haem-binding protein.

Suitably the method may comprise transforming a cell of a plant (e.g. a tobacco plant) with a genetic construct which encodes at least one SOUL haem-binding protein comprising an amino acid sequence as set out in SEQ ID No. 1, 4, 7, 10, 13, 16, 19 or 22, or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24; or which comprises a nucleotide sequence which encodes a protein which is capable of promoting or augmenting at least one endogenous SOUL haem-binding protein gene. It will be appreciated that each of these options would result in an increased activity and expression of the polypeptide encoded by the at least one SOUL haem-binding protein gene. The method may comprise regenerating the plant from the transformed cell.

There is provided use of genetic construct which is capable of increasing the activity and/or expression of a polypeptide encoded by at least one SOUL haem-binding protein gene for increasing the alkaloid content (e.g. nicotine content) and or TSNA content (or precursor thereto) in a plant or part there of or cell transformed with the construct.

The genetic construct may encode a polypeptide comprising the amino acid SEQ ID No. 1, 4, 7, 10, 13, 16, 19 or 22, or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24, or a nucleic acid sequence which has at least 80% identity to SEQ ID No. 2, 3, 5, 6, 8, 9, 11, 12, 14, 15, 17, 18, 20, 21, 23 or 24.

In another embodiment, the invention relates to a method of increasing the alkaloid content of a plant or part thereof and/or TSNA content (or precursor thereto) in a plant or plant part thereof, comprising modifying said plant by increasing the activity of at least one gene encoding a SOUL haem-binding protein.

In one embodiment the activity of at least one gene encoding a SOUL haem-binding protein may be increased by introducing (or providing) a mutation to at least one gene encoding an SOUL motif.

Suitably, the activity of at least one gene encoding a SOUL haem-binding protein may be increased by introducing a mutation to at least one gene encoding a SOUL haem-binding protein which comprises an amino acid sequence as set out in SEQ ID No. 1, 4, 7, 10, 13, 16, 19 or 22; or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24, or a nucleic acid sequence which has at least 80% identity to SEQ ID No. 2, 3, 5, 6, 8, 9, 11, 12, 14, 15, 17, 18, 20, 21, 23 or 24.

In some embodiments a modification which increases the activity or expression of at least one SOUL haem-binding protein gene and thereby increases alkaloid content and/or TSNA content (or precursor thereof) by one of the following:
- modulating transcription from the at least one SOUL haem-binding protein gene;
- modulating translation of the mRNA from the at least one SOUL haem-binding protein gene;
- modulating release of the SOUL haem-binding protein from intracellular stores; and/or
- modulating the rate of degradation of the SOUL haem-binding protein.

Alkaloid Content

In one embodiment the present invention provides a method of modulating the alkaloid content of a plant (e.g. a tobacco plant) or a part thereof, the method comprising modifying said plant by modulating the activity or expression of at least one gene encoding a SOUL haem-binding protein.

The term "modulating" is used herein to mean either increasing or decreasing.

The term "increasing alkaloid content" is used herein to mean that the alkaloid content in the product of the present invention (e.g. plant, part thereof (e.g. leaf), processed leaf or a product made from the plant (e.g. a tobacco product)) is higher compared with a comparable product which has not been modified in accordance with the present invention.

The term "decreasing alkaloid content" is used herein to mean that alkaloid content in the product of the present invention (e.g. plant, part thereof (e.g. leaf), processed leaf or a product made from the plant (e.g. a tobacco product)) is lower compared with a comparable product which has not be modified in accordance with the present invention.

In some embodiments, the modulation of alkaloid content refers to an increase in alkaloid content wherein the activity or expression of at least one SOUL haem-binding protein gene is increased (or in other words the protein is overexpressed).

In some embodiments, the modulation of alkaloid content refers to a decrease in alkaloid content wherein the expression of at least one gene encoding a SOUL haem-binding protein is decreased or inhibited or eliminated.

In a further aspect, the alkaloid content is measured from leaves. In one aspect the alkaloid content is measured from green leaves. In a further aspect, the alkaloid content is measured from cured leaves, e.g. air-cured, flue-cured, fire-cured or sun-cured leaves. In a further aspect, the alkaloid content is measured from flue-cured leaves. In a further aspect, the alkaloid content is measured from air-cured leaves.

The term "alkaloid content" is used herein to mean the concentration and/or total amount of the entire group of compounds classified as alkaloids or the concentration and/or total amount of one or more compounds classified as alkaloids. Alkaloids typically present in tobacco include nicotine, nornicotine, PON, anatabine, anabasine and myosmine. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is modulated. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is increased. In some embodiments the content of one or more alkaloids, such as two or more alkaloids, such as three or more alkaloids, such as four or more alkaloids, such as five or more alkaloids, such as all six alkaloids, selected from nicotine, nornicotine, PON, anatabine, anabasine and myosmine is decreased. In some embodiments the total alkaloid content of the plant or cell is modulated. In some embodiments the total alkaloid content is increased. In some embodiments the total alkaloid content is increased.

Suitably nicotine content may be modulated. In one embodiment, the nicotine content is reduced. In another embodiment the nicotine content is not modulated but the content of one or more alkaloids selected from nornicotine, PON, anatabine, anabasine and myosmine is modulated. In another embodiment the nicotine content is not modulated but the content of one or more alkaloids selected from nornicotine, PON, anatabine and anabasine is modulated.

Any method known in the art for determining the concentration and/or total content of alkaloids may be used. One preferred method for analysing alkaloid content involves the analysis by gas chromatography-flame ionization detection method (GC-FID).

In one embodiment there is provided a method for producing a plant (e.g. a tobacco plant) or part thereof, a plant propagation material (e.g. a tobacco plant propagation material), a cell (e.g. a tobacco cell), a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf), a cut and processed leaf (e.g. a cut and processed tobacco leaf), a product comprising said plant or part thereof (e.g. a tobacco product) or combinations thereof obtainable or obtained by a plant of the invention which has modulated alkaloid content, the method comprising modifying said plant to modulate the activity or expression of a gene encoding an SOUL haem-binding protein. The modulated alkaloid content may be determined by comparing the alkaloid content in the plant (e.g. tobacco plant) or part thereof, plant propagation material (e.g. tobacco plant propagation material), a cell (e.g. a tobacco cell), leaf (e.g. tobacco leaf), harvested leaf (e.g. a harvested tobacco leaf), cut harvested leaf (e.g. a cut harvested tobacco leaf), processed leaf (e.g. processed tobacco leaf), cut and processed leaf (e.g. cut and processed tobacco leaf), a product comprising a plant or part thereof of the present invention, e.g. a tobacco product, or combinations thereof with a comparable product.

Suitably the alkaloid content may be modulated in a plant, e.g. a tobacco plant e.g. modified tobacco plant. Suitably the alkaloid content may be modulated in a leaf (e.g. a tobacco leaf e.g. a tobacco leaf from a modified tobacco plant). Suitably the alkaloid content may be modulated in a harvested leaf (e.g. a harvested tobacco leaf from a modified tobacco plant). Suitably the alkaloid content may be modulated in a cut harvested leaf (e.g. a cut harvested tobacco leaf from a modified tobacco plant). Suitably the alkaloid content may be modulated in a processed leaf (e.g. a processed tobacco leaf e.g. a processed tobacco leaf from a modified tobacco plant). Suitably the alkaloid content may be modulated in a cut and processed leaf (e.g. a cut and processed tobacco leaf e.g. a cut and processed tobacco leaf from a modified tobacco plant). Suitably the alkaloid content may be modulated in a cured leaf (e.g. cured a tobacco leaf from a modified tobacco plant). Suitably the alkaloid content may be modulated in an extract of a green leaf (e.g. a green tobacco leaf from a modified tobacco plant). Suitably the alkaloid content may be modulated in a product comprising the plant of the present invention or part thereof (e.g. a tobacco product, for example a tobacco product produced from a modified tobacco plant or part thereof). Suitably the alkaloid content may be modulated in any one of the above products or combinations thereof. Suitably the modulation of alkaloid content described above may be an increase in alkaloid content. Suitably the modulation of alkaloid content described above may be a decrease in alkaloid content (e.g. a decrease in nicotine content).

In one embodiment the content of one or more alkaloids selected from nicotine, nornicotine, PON, anatabine, anabasine and myosmine is decreased. In one embodiment the content of one or more alkaloids selected from nicotine, nornicotine, PON, anatabine and anabasine is decreased.

Suitably the modulation of alkaloid content described above may be a decrease in nicotine content. Suitably the modulation of alkaloid content described above may be a decrease in the content of one or more alkaloids selected from nornicotine, PON, anatabine, anabasine and myosmine but not a decrease in the content of nicotine. Suitably the modulation of alkaloid content described above may be a decrease in the content of one or more alkaloids selected from nornicotine, PON, anatabine and anabasine but not a decrease in the content of nicotine.

In one embodiment the nicotine content of a modified plant (e.g. tobacco plant), plant propagation material (e.g. tobacco plant propagation material), leaf (e.g. tobacco leaf), harvested leaf (e.g. harvested tobacco leaf), cut harvested leaf (e.g. cut harvested tobacco leaf), processed leaf (e.g. processed tobacco leaf), cut and processed leaf (e.g. cut and processed tobacco leaf) or tobacco product from a modified tobacco plant is decreased.

In one embodiment the alkaloid content of a plant (e.g. tobacco plant) or part thereof may be modulated by at least 0.5, 1.5 or 2 fold when compared to the alkaloid content of a plant (e.g. tobacco plant) or part thereof, respectively, which has not been modified to modulate the activity or expression of at least one gene encoding a SOUL haem-binding protein and which has been grown under similar growth conditions. Suitably the alkaloid content may be modulated by about 0.5 fold to about 2 fold. Suitably the modification may be an increase or a decrease in alkaloid content. Suitably the modulation may be of one or more alkaloids selected from nicotine, nornicotine, PON, anatabine, anabasine and myosmine. Suitably the modulation may be of one or more alkaloids selected from nicotine, nornicotine, PON, anatabine and anabasine. Suitably, the nicotine content is modulated.

In one embodiment of the invention the alkaloid content of a plant (e.g. a tobacco plant) or part thereof may be modulated by at least 1%, 2%, 5%, 8%, 10%, 12%, 15%, 20%, 25%, 30%, 40%, 50%, 60%, 70%, 80%, 90% or 100% in comparison to a plant (e.g. a tobacco plant) or part thereof which has not been modified according to the present invention. In one embodiment the alkaloid content may be modulated by at least 30% in comparison to an unmodified plant or part thereof. In one embodiment the alkaloid content may be modulated by at least 40% in comparison to an unmodified plant or part thereof. In one embodiment the alkaloid content may be modulated by at least 50% in comparison to an unmodified plant or part thereof. In one embodiment the alkaloid content may be modulated by at least 60% in comparison to an unmodified plant or part thereof. The modulation may be an increase or a decrease in alkaloid content when compared to an unmodified plant (e.g. a tobacco plant) or part thereof. Suitably the modulation may be of total alkaloid content. Suitably the modulation may be of one or more alkaloids selected from nicotine, nornicotine, PON, anatabine, anabasine and myosmine.

Suitably the modulation may be of one or more alkaloids selected from nicotine, nornicotine, PON, anatabine and anabasine. Suitably the modulation is of nicotine content, such as decrease in nicotine content. Suitably the modulation is of nornicotine content, such as decrease in nornicotine content. Suitably the modulation is of anabasine content, such as decrease in anabasine content. Suitably the modulation is of PON content, such as decrease in PON content. Suitably the modulation is of anatabine content, such as decrease in anatabine content. Suitably the modulation is of more than one alkaloid, such as two or more alkaloids, such as three or more alkaloids, such as four or more alkaloids, such as five or more alkaloids, such as all six alkaloids, selected from nicotine, nornicotine, PON, anatabine, anabasine and myosmine.

In some embodiments the alkaloid content of the plant may be modulated by between about 5% and about 100%, by between about 10% and about 90%, by between about 20% and about 80%, by between about 30% and about 70%, by between about 40% and 60%, or by between about 40% and 50%.

In one embodiment the alkaloid content of the plant may be modulated by between about 50% and about 100%, preferably between about 60% and 90%, preferably 80% or more.

Tobacco-Specific Nitrosamine (TSNA) Content

In one embodiment the present invention provides a method of modulating (i.e. increasing or reducing) the content of tobacco-specific nitrosamine (TSNA) or a precursor of a TSNA in a plant (e.g. a tobacco plant) or a part thereof. Suitably, the method may comprise modifying said plant by modulating the activity or expression of at least one gene encoding a SOUL haem-binding protein. Suitably, the content of TSNA or a precursor of a TSNA may be reduced.

Suitably, the total TSNA content of the plant or part thereof may be modulated.

The TSNA may be measured in a processed tobacco, e.g. cured tobacco or reconstituted tobacco. In one embodiment the TSNA content is measured and/or modified (e.g. reduced) in a cured tobacco plant or part thereof (e.g. in cured tobacco leaf).

The term "tobacco-specific nitrosamine" or "TSNA" as used herein has its usual meaning in the art, namely a nitrosamine which is found only in tobacco products or other nicotine-containing products. Suitably the at least one tobacco-specific nitrosamine may be 4-(methylnitrosamino)-1-(3-pyridyl)-1-butanone (NNK), N'-nitrosonornicotine (NNN), N'-nitrosoanatabine (NAT) or N-nitrosoanabasine (NAB).

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production. Suitably the term "precursor thereto" may refer to nitrate, nitrite or nitric oxide.

The term "modulating" is used herein to mean either increasing or decreasing.

In one embodiment the TSNA is N'nitrosonornicotine (NNN) and/or the precursor is nornicotine.

In one embodiment the TSNA may be one or more of group selected from: N'-nitrosonornicotine (NNN), N'-nitrosoanatabine (NAT), N'-nitrosoanabasine (NAB) and 4-(methyl nitrosamino)-1-(3-pyridyl)-1-butanone (NNK). Suitably the at least one tobacco-specific nitrosamine may be NNK or NNN. In one embodiment the tobacco-specific nitrosamine is NNN.

In one embodiment the precursor of the TSNA is one or more of the group selected from nornicotine, anabasine, anatabine, and an oxidised derivative of nicotine such as pseudooxynicotine (PON).

In a preferred embodiment the precursor of the TSNA is nornicotine.

In one embodiment, the precursor of the TSNA may be PON. The precursor of the TSNA (e.g. NNN, NNK, NAB and/or NAT) may be measured in green tobacco leaf, e.g. prior to processing, e.g. prior to curing. In one embodiment the precursor of the TSNA (e.g. NNN, NNK, NAB and/or NAT) is measured and/or modified (e.g. reduced) in a green tobacco leaf, e.g. prior to processing, e.g. prior to curing.

In one embodiment carrying out a method and or use of the invention results in a reduction of at least one TSNA or a precursor thereto in the modified tobacco plant (or part thereof) when compared to a tobacco plant (or part thereof) which has not been modified in accordance with the present invention.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco industry product would be derived from a tobacco plant which had not been modified according to the present invention, but in which all other relevant features were the same (e.g. plant species, growing conditions, method of processing tobacco, etc.).

Any method known in the art for determining the concentration and/or levels of at least one TSNA or precursor thereto may be used. In particular a method such may comprise the addition of deuterium labelled internal standard, an aqueous extraction and filtration, followed by analysis using reversed phase high performance liquid chromatography with tandem mass spectrometry (LC-MS/MS) may be used. Other examples for determining the concentration and/or level of a precursor to a tobacco-specific nitrosamine include a method such as the one detailed in CORESTA recommended method CRM-72: Determination of Tobacco Specific Nitrosamines in Tobacco and Tobacco Products by LC-MS/MS; CRM being developed into ISO/DIS 21766 or Wagner et al. (2005) Analytical Chemistry 77(4), 1001-1006 all of which are incorporated herein by reference.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable or obtained by a method and/or use of the invention) when compared to the concentration and/or level of the at least one tobacco-specific nitrosamine(s) or precursor thereto in a tobacco plant which has not been modified in accordance with present invention.

The concentration and/or total content of the at least one tobacco-specific nitrosamine(s) or precursor thereto may be reduced in a tobacco leaf, harvested leaf, processed tobacco leaf, tobacco industry product or combinations thereof obtainable or obtained from a tobacco plant (or part of a tobacco plant or a tobacco cell or cell culture) of the invention when compared with a tobacco leaf, harvested leaf, processed tobacco leaf, tobacco industry product or combinations thereof obtainable or obtained from a tobacco plant (or part of a tobacco plant or a tobacco cell or cell culture) which has not been modified in accordance with the present invention.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco industry product.

In one embodiment the at least one tobacco-specific nitrosamine or precursor thereto may be reduced by at least about 1%, at least about 3%, at least about 5%, at least about 10%, at least about 20%, at least about 30%, at least about 40% or at least about 50%. In some embodiments the at least one tobacco-specific nitrosamine or precursor thereto may be reduced by between about 5% and about 50%, by between about 10% and about 50%, by between about 20% and about 50%, by between about 30% and about 50%, or by between about 40% and 50%.

In relation to processed (e.g. cured) tobacco leaf (e.g. cured or reconstituted), the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

Biomass Production

In one aspect, the present invention provides a method of producing a biomass comprising: growing a cell which has been engineered to modulate (e.g. decrease) the activity or expression of a gene encoding a SOUL haem-binding protein under conditions to produce a biomass.

In one embodiment, the present invention provides a method of producing a biomass having modified (e.g. decreased) concentration and/or total content of nicotine, comprising growing a cell which has been engineered to decrease the activity or expression of at least one gene encoding a SOUL haem-binding protein comprising an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24, or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24.

The cell may be engineered by any method known in the art to modify the activity or expression of at least one gene encoding a SOUL haem-binding protein. Suitably, the cell may be engineered to express an exogenous gene encoding a SOUL haem-binding protein. Suitably, the cell may be engineered to overexpress a gene encoding a SOUL haem-binding protein.

Suitably, the cell may be engineered to decrease the activity or expression of a gene encoding a SOUL haem-binding protein.

Suitably, the biomass may contain a lower concentration and/or total content of nicotine compared with the biomass produced by a comparable cell which has not been modified in accordance with the present invention.

Suitably the cell for use in biomass production may be a plant cell, such as a tobacco cell.

Suitably the cell for use in biomass production may be a yeast cell.

In one embodiment the cell (e.g. yeast cell) may be further modified to comprise one or more sequences that increases nicotinic alkaloid biosynthesis. Suitably these one or more sequences may be incorporated into a nucleic acid construct that is suitable for cell (e.g. yeast cell) transformation. The one or more sequences may be overexpressed in the cell (e.g. yeast cell).

The sequences may be selected from one or more of the following genes: MPO (or Methylputrescine Oxidase or MPO1 or MPO2); A622 (or Isoflavone reductase-like protein or Isoflavone reductase homolog or Isoflavone reductase-like protein); BBL (or Berberine bridge enzyme or Berberine bridge enzyme-like or BBE or NBB1); PMT (or Putrescine N-Methyltransferase or putrescine methyltransferase or S-adenosyl-L-methionine:putrescine N-methyltransferase or PMT or PMT1 or PMT2 or PMT3 or PMT4) and QPT (or quinolinate phosphoribosyltransferase). In one embodiment the sequences may be selected from one or more of the following genes: BBL, A622, PMT and MPO (MPO1 or MPO2). Genes suitable for modification in this way may be taught in US2016032299 for example, which is incorporated herein by reference.

Commercially Desirable Traits

In one embodiment the plants of the present invention have modified (i.e. increased or decreased) total alkaloid content and/or modified (i.e. increased or decreased) content of one or more alkaloids selected from nicotine, nornicotine, anabasine, myosmine and anatabine and/or reduced nicotine, whilst the flavour characteristics and/or other commercially desirable traits are at least maintained. In one embodiment the plants of the present invention produce leaves of a similar grade and/or quality to plants which have not been modified according to the invention.

In one embodiment the plants of the present invention have reduced nicotine content without a significant change in the flavour characteristics of the plant (e.g. compared with the same plant which has not been modified in accordance with the present invention).

In one embodiment the plants of the present invention have modified (i.e. increased or decreased) alkaloid and/or TSNA content without a significant change (e.g. decrease) in other commercially desirable traits of the plant (e.g. compared with the same plant which has not been modified in accordance with the present invention). In particular the yield of the modified plant is preferably not reduced compared with the same plant which has not been modified in accordance with the present invention.

Therefore in one embodiment the methods and uses of the present invention relate to modifying (i.e. increasing or reducing) total alkaloid content and/or modifying (i.e. increasing or reducing) one or more alkaloids selected from nicotine, nornicotine, anabasine and anatabine and/or modifying (i.e. increasing or reducing) nicotine content and/or TSNA content, whilst maintaining the flavour characteristics and/or other commercially desirable traits (e.g. yield).

The term "commercially desirable traits" as used herein will include traits such as yield, mature plant height, harvestable leaf number, average node length, cutter leaf length, cutter leaf width, quality (e.g. leaf quality, suitably cured leaf quality), abiotic (for instance drought) stress tolerance, herbicide tolerance and/or biotic (for instance insect, bacteria or fungus) stress tolerance.

Leaf quality may be measured based on colour, texture and aroma of the cured leaf, for example according to United States Department of Agriculture (USDA) grades and standards.

Tobacco grades are evaluated based on factors including, but not limited to, the leaf stalk position, leaf size, leaf colour, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

Leaf grade can be determined using standard methods known in the art, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida ShadeGrown Cigar-Wrapper Tobacco (U.S. Type 62), Effective April 1971. A USDA grade index value can be determined according to an industry accepted grade index. See e.g. Bowman et al. (1988) Tobacco Science, 32:39-40; Legacy Tobacco Document Library (Bates Document #523267826-523267833, Jul. 1, 1988, Memorandum on the Proposed Burley Tobacco Grade Index); and Miller et al. (1990) Tobacco Intern., 192:55-57 (all foregoing references are incorporated herein in their entirety).

In one aspect, a USDA grade index is a 0-100 numerical representation of federal grade received and is a weighted average of all stalk positions. A higher grade index indicates higher quality. Alternatively, leaf grade may be determined via hyper-spectral imaging. See e.g. WO 2011/027315 (which is incorporated herein by reference).

In one embodiment, a tobacco plant of the present invention provides tobacco of commercially acceptable grade.

Suitably, the tobacco plant of the present invention provides cured tobacco of commercially acceptable grade.

In one embodiment, a tobacco plant of the present invention is capable of producing leaves having a USDA grade index value of at least about 70% of the USDA grade index value of leaves of a comparable plant when grown in similar growth conditions. Suitably, tobacco plants disclosed herein may be capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions. Suitably, tobacco plants disclosed herein may be capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a comparable plant.

In one aspect, the tobacco plant of the present invention is capable of producing leaves having a USDA grade index value of at least 50. Suitably, tobacco plants disclosed herein may be capable of producing leaves having a USDA grade index value of 55 or more, 60 or more, 65 or more, 70 or more, 75 or more, 80 or more, 85 or more, 90 or more, and 95 or more.

Unless specified otherwise, used herein, tobacco yield refers to cured leaf yield which is calculated based on the weight of cured tobacco leaves per acre under standard field conditions following standard agronomic and curing practice.

In one aspect, a plant (e.g. a tobacco plant) of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the plant (e.g. a tobacco plant) yield of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions.

In another aspect, the yield of a tobacco plant of the present invention is comparable to the yield of the flue cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Plant Breeding

In one embodiment the present invention provides a method of producing a plant having a modified alkaloid content and/or modified content of a tobacco specific nitrosamine (TSNA) or a precursor of a TSNA, comprising:
  a. crossing a donor plant having modified nicotine content and/or modified content of a tobacco specific nitrosamine (TSNA) or a precursor of a TSNA and wherein the activity or expression of at least one gene encoding a SOUL haem-binding protein according to the present invention has been modulated in the donor plant in accordance with the present invention with a recipient tobacco plant that does not have modified nicotine content or modified content of a tobacco specific nitrosamine (TSNA) or a precursor of a TSNA and possesses commercially desirable traits;
  b. isolating genetic material from a progeny of said donor plant crossed with said recipient plant; and
  c. performing molecular marker-assisted selection with a molecular marker comprising:

i. identifying an introgressed region comprising a mutation in a polynucleotide sequence encoding a protein defined in a.

Suitably, the activity or expression of a protein comprising an amino acid sequence as set out in SEQ ID No. 1, 4, 7, 10, 13, 16, 19 or 22, or a functional variant or functional fragment or orthologue thereof, or a sequence which has at least 80% identity to SEQ ID No. 2, 3, 5, 6, 8, 9, 11, 12, 14, 15, 17, 18, 20, 21, 23 or 24; or a protein encoded by a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24 is modulated in the donor plant when compared to a comparable plant.

The molecular marker assisted selection may comprise performing PCR to identify an introgressed nucleic acid sequence comprising a mutation which modulates the activity or expression of a protein comprising the amino acid sequence shown as SEQ ID No. 1, 4, 7, 10, 13, 16, 19 or 22 or an amino acid sequence which has at least 80% identity thereto.

Plants

Suitable plants according to the invention include the Solanaceae family of plants which include, for example jimson weed, eggplant, mandrake, deadly nightshade (*belladonna*), *capsicum* (paprika, chilli pepper), potato and tobacco.

In one embodiment a suitable genus of Solanaceae is *Nicotiana*, e.g. *Nicotiana tabacum* or *Nicotiana rustica*.

A suitable species of *Nicotiana* may be *Nicotiana tabacum*. Species of *Nicotiana* may be referred to herein as a tobacco plant, or simply tobacco.

Tobacco Plants

The present invention provides methods, uses directed to plants (e.g. tobacco plants) as well as a cell (e.g. a tobacco cell), a plant (e.g. a tobacco plant) and a plant propagation material.

The term "tobacco plant" as used herein refers to a plant in the genus *Nicotiana* that is used in the production of tobacco products. Non-limiting examples of suitable "tobacco" plants include *N. tabacum* and *N. rustica* (for example, *N. tabacum* L., LA B21, LN KY171, TI 1406, Basma, Galpao, Perique, Beinhart 1000-1, and Petico).

The tobacco material can be derived or obtained from varieties of *Nicotiana tabacum* types, commonly known as Burley varieties, flue or bright varieties and dark varieties. In some embodiments, the tobacco material is derived from a Burley, Virginia or a dark tobacco plant.

The tobacco plant may be selected from Burley tobacco, rare tobacco, speciality tobacco, expanded tobacco or the like.

The use of tobacco cultivars and elite tobacco cultivars is also contemplated herein. The tobacco plant for use herein may therefore be a tobacco variety or elite tobacco cultivar.

Particularly useful *Nicotiana tabacum* varieties include Flue-cured Virginia type, Burley type, and Oriental type.

In some embodiments, the tobacco plant may be, for example, selected from one or more of the following varieties: L. cultivar T.I. 1068, AA 37-1, B 13P, Xanthi (Mitchell-Mor), KT D #3 Hybrid 107, Bel-W3, 79-615, Samsun Holmes N N, F4 from cross BU21 x Hoja Parado, line 97, KTRDC #2 Hybrid 49, KTRDC #4 Hybrid 1 10, Burley 21, PM016, KTRDC #5 KY 160 SI, KTRDC #7 FCA, KTRDC #6 TN 86 SI, PM021, K 149, K 326, K 346, K 358, K 394, K 399, K 730, KY 10, KY 14, KY 160, KY 17, KY 8959, KY 9, KY 907, MD 609, McNair 373, NC 2000, PG 01, PG 04, P01, P02, P03, RG 11, RG 17, RG 8, Speight G-28, TN 86, TN 90, VA 509, AS44, Banket A1, Basma Drama B84/31, Basma I Zichna ZP4/B, Basma Xanthi BX 2A, Batek, Besuki Jember, C104, Coker 319, Coker 347, Criollo Misionero, PM092, Delcrest, Djebel 81, DVH 405, Galpao Comum, HB04P, Hicks Broadleaf, Kabakulak Elassona, PM102, Kutsage E1, KY 14 x L8, KY 171, LA BU 21, McNair 944, NC 2326, NC 71, NC 297, NC 3, PVH 03, PVH 09, PVH 19, PVH 21 10, Red Russian, Samsun, Saplak, Simmaba, Talgar 28, PM132, Wislica, Yayaldag, NC 4, TR Madole, Prilep HC-72, Prilep P23, Prilep PB 156/1, Prilep P12-2/1, Yaka JK-48, Yaka JB 125/3, T-1068, KDH-960, TI-1070, TW136, PM204, PM205, Basma, TKF 4028, L8, TKF 2002, TN 90, GR141, Basma xanthi, GR149, GR153, and Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC, Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVHO3, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 1 1, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant may be a Burley, Flue-cured Virginia, or Oriental.

In one embodiment the plant propagation material may be obtainable from a plant (e.g. a tobacco plant) of the invention.

A "plant propagation material" as used herein refers to any plant matter taken from a plant from which further plants may be produced. Suitably, a plant propagation material may be selected from a seed, plant calli and plant clumps. Suitably the plant propagation material may be a seed. Suitably, the plant propagation material may be plant calli. Suitably the plant propagation material may be plant clumps.

In one embodiment the cell (e.g. tobacco cell), tobacco plant and/or plant propagation material may be obtainable (e.g. obtained) by a method according to the invention.

Suitably a tobacco plant according to the present invention may have modulated (e.g. decreased) nicotine content when compared to an unmodified tobacco plant, wherein the tobacco plant has been modified to modulate (e.g. decrease) the activity or expression of at least on one gene encoding a SOUL haem-binding protein.

Suitably a tobacco plant according to the present invention may have modulated (e.g. reduced) content of a tobacco specific nitrosamine (TSNA) or a precursor of a TSNA when compared to an unmodified tobacco plant, wherein the tobacco plant has been modified to modulate (e.g. increase) the activity or expression of at least on one gene encoding a SOUL haem-binding protein.

In one embodiment the tobacco plant in accordance with the present invention comprises a tobacco cell of the invention.

In another embodiment the plant propagation material may be obtainable (e.g. obtained) from a tobacco plant of the invention.

In one embodiment there is provided the use of a tobacco plant as described herein to breed a tobacco plant.

The present invention also provides in another embodiment the use of a tobacco plant of the foregoing embodiments for the production of a tobacco industry product.

In another embodiment there is provided the use of a tobacco plant of the invention to grow a crop.

In one embodiment there is provided the use of a cell as provided for in the foregoing embodiments for production of a tobacco industry product.

In one embodiment the present invention provides a plant cell or cell culture (e.g. in in vitro culture).

The tobacco cell culture may be a cell suspension culture. These cells cultured in vitro may be incorporated into a tobacco industry product, e.g. as a substitute for conventional tobacco particles, shreds, fine cut or long cut tobacco lamina, as an additive ingredient or as both a substitute and an additive. Suitably, the cell culture may produce nicotine.

In one embodiment there is provided the use of a cell culture, e.g. a harvested and/or processed cell culture according to the present invention for the production of a tobacco industry product.

The tobacco cells harvested from an in vitro culture may be dried, e.g. freeze-dried, for example to produce a powder.

In one embodiment the plant cell is a tobacco plant cell.

In one embodiment, the cell culture is a tobacco cell culture. The skilled person will be aware of known methods for establishing in vitro cultures of tobacco cells. By way of example only, the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell or cell culture may be further processed, e.g. dried, such as air-dried and/or freeze-dried. The harvested tobacco cell or cell culture or dried harvested tobacco cell or cell culture or an extract therefrom may be incorporated into tobacco industry products according to the present invention.

In one embodiment, the present invention provides a plant (e.g. tobacco plant) or part thereof for use in molecular farming. Suitably, a plant or part thereof modified in accordance with the present invention may be used in the manufacture of proteins such as therapeutics e.g. antibiotics, virus like particles, neutraceuticals or small molecules.

In one embodiment, the present invention provides a method for the production of proteins (e.g. therapeutic proteins), the method comprising modifying a plant or part thereof capable of producing said protein (e.g. therapeutic protein) by modulating the activity or expression of at least one SOUL haem-binding protein gene encoding an amino acid sequence as set out in SEQ ID No. 1, 4, 7, 10, 13, 16, 19 or 22 or a functional variant or functional fragment or orthologue thereof, or a sequence which has at least 80% identity to SEQ ID No. 1, 4, 7, 10, 13, 16, 19 or 22; or wherein the at least one gene encoding a SOUL haem-binding protein comprises a nucleotide sequence as set out in SEQ ID No. 2, 3, 5, 6, 8, 9, 11, 12, 14, 15, 17, 18, 20, 21, 23 or 24 or a functional variant or functional fragment or orthologue of SEQ ID No. 2, 3, 5, 6, 8, 9, 11, 12, 14, 15, 17, 18, 20, 21, 23 or 24 or a nucleic acid sequence which has at least 80% identity to SEQ ID No. 2, 3, 5, 6, 8, 9, 11, 12, 14, 15, 17, 18, 20, 21, 23 or 24; and culturing the plant under conditions sufficient to allow the production of said protein (e.g. therapeutic protein).

Products

The present invention also provides for products obtainable or obtained from plants according to the present invention. Products are provided which are obtainable or obtained from a plant in which the activity or expression of gene encoding a SOUL haem-binding protein has been modulated.

In one embodiment, the product may comprise a construct of the invention which modulates the activity or expression of at least one gene encoding a SOUL haem-binding protein protein as defined herein. In one embodiment, the product may comprise a construct of the invention which modifies the nucleic acid sequence of at least one gene encoding a SOUL haem-binding protein as defined herein.

The present invention also provides for products obtainable or obtained from tobacco according to the present invention.

In one embodiment there is provided the use of a tobacco plant of the invention to produce a tobacco leaf.

Suitably the tobacco leaf may be subjected to downstream applications such as processing.

Thus in one embodiment the use of the foregoing embodiment may provide a processed tobacco leaf. Suitably the tobacco leaf may be subjected to curing, fermenting, pasteurising or combinations thereof. In another embodiment the tobacco leaf may be cut. In some embodiments the tobacco leaf may be cut before or after being subjected to curing, fermenting, pasteurising or combinations thereof.

In one embodiment the present invention provides a harvested leaf of a tobacco plant of the invention.

In a further embodiment the harvested leaf may be obtainable (e.g. obtained) from a tobacco plant propagated from a propagation material of the present invention.

In another embodiment there is provided a harvest leaf obtainable from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf.

The processed tobacco leaf may be obtainable from a tobacco plant of the invention. Suitably the processed tobacco leaf may be obtainable from a tobacco plant obtained in accordance with any of the methods and/or uses of the present invention.

In another embodiment the processed tobacco leaf may be obtainable from a tobacco plant propagated form a tobacco plant propagation material according to the present invention.

The processed tobacco leaf of the present invention may be obtainable by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active.

Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising.

Suitably the processed tobacco leaf may be processed by curing.

Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smoulder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco industry product, most preferably snus.

Tobacco leaf pasteurisation may be carried out by any method known in the art. For example pasteurisation may be carried out as detailed in J Foulds, L Ramstrom, M Burke, K Fagerstrom.

Effect of smokeless tobacco (snus) on smoking and public health in Sweden Tobacco Control (2003) 12: 349-359, the teaching of which is incorporated herein by reference.

During the production of snus, pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In one embodiment, the use of the foregoing embodiment may provide reconstituted tobacco.

In one embodiment, there is provided reconstituted tobacco.

"Reconstituted" as used herein may also be referred to as recon, recycled or homogenized sheet tobacco and refers to tobacco material generated from remnants of tobacco leaf after processing. Reconstituted tobacco allows the production of a consistent, high quality blend and allows the adjustment of the ratio of individual components.

Reconstituted tobacco may be nano fibre recon (nanofibers can be extracted in solid or liquid form), paper making recon (which uses stems, scraps, and midribs, etc. as the raw material) or slurry type recon (which uses a mixture of fines and tobacco stems, ground to power, mixed with water and vegetable binding agent; the soluble residue is formed to sheets by extracting the water).

Any method known in the art may be used for making reconstituted tobacco, for example see CORESTA Congress, Sapporo, 2012, Smoke Science/Product Technology Groups, SSPT 12 (incorporated herein by reference).

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention.

In another aspect, the present invention provides a tobacco blend comprising tobacco material made from a tobacco plant or part thereof according to the present invention, or from a tobacco cell or cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell or cell culture according to the present invention. Suitably, the tobacco blend may comprise approximately 10% tobacco from a tobacco plant or part thereof according to the present invention, or from a tobacco cell or cell culture according to the present invention. Suitably, the tobacco blend may comprise approximately 20% tobacco from a tobacco plant or part thereof according to the present invention, or from a tobacco cell or cell culture according to the present invention. Suitably, the tobacco blend may comprise approximately 30% tobacco from a tobacco plant or part thereof according to the present invention, or from a tobacco cell or cell culture according to the present invention. Suitably, the tobacco blend may comprise approximately 40% tobacco from a tobacco plant or part thereof according to the present invention, or from a tobacco cell or cell culture according to the present invention. Suitably, the tobacco blend may comprise approximately 50% tobacco from a tobacco plant or part thereof according to the present invention, or from a tobacco cell or cell culture according to the present invention. Suitably, the tobacco blend may comprise approximately 60% tobacco from a tobacco plant or part thereof according to the present invention, or from a tobacco cell or cell culture according to the present invention.

Suitably, the tobacco blend may comprise approximately 70% tobacco from a tobacco plant or part thereof according to the present invention, or from a tobacco cell or cell culture according to the present invention. Suitably, the tobacco blend may comprise approximately 80% tobacco from a tobacco plant or part thereof according to the present invention, or from a tobacco cell or cell culture according to the present invention. Suitably, the tobacco blend may comprise approximately 90% tobacco from a tobacco plant or part thereof according to the present invention, or from a tobacco cell or cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell or cell culture according to the present invention.

Suitably, the cured tobacco material may be air cured. Suitably, the cured tobacco material may be flue cured. Suitably, the cured tobacco material may be sun cured. Suitably, the cured tobacco material may be fire cured.

A tobacco industry product or smoking article according to the present invention may comprise the tobacco material (e.g. cured tobacco material or reconstituted tobacco material) according to the present invention.

In another aspect the present invention provides a tobacco industry product.

In one embodiment the tobacco industry product according to the present invention may be a blended tobacco industry product. Suitably, the tobacco blend may comprise cured tobacco material according to the present invention.

In one embodiment the tobacco industry product may be prepared from a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Suitably, the "part thereof" may be a leaf, root or stem of a tobacco plant or the flowers. Suitably, the "part thereof" may be a leaf, root or stem of a tobacco plant.

Tobacco Industry Product

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco industry products such as snus and snuff, which aerosol-free delivery articles may or may not deliver nicotine.

In one embodiment the tobacco industry product may be prepared from (e.g. may comprise) a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco industry product may be prepared from a harvested leaf of the invention.

In a further embodiment the tobacco industry product may be prepared from a processed tobacco leaf of the invention.

Suitably the tobacco industry product may be prepared from a tobacco leaf processed by one or more of: curing, fermenting and/or pasteurising.

Suitably the tobacco industry product may comprise a cut tobacco leaf, optionally processed as per the foregoing embodiment.

In another embodiment, the tobacco industry product may be prepared from a tobacco cell or cell culture according to the present invention.

In another embodiment, the tobacco industry product may be prepared from (e.g. may comprise) a cured tobacco material according to the present invention.

In another embodiment, the tobacco industry product may be prepared from (e.g. may comprise) a tobacco blend according to the present invention.

In one embodiment the tobacco industry product may be a smoking article.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco industry product may be a smokeless tobacco industry product.

The term "smokeless tobacco industry product" as used herein refers to a tobacco industry product that is not intended to be smoked and/or subjected to combustion.

Smokeless tobacco industry products (including heat-not-burn materials) may contain tobacco in any form, including dried particles, shreds, granules, powders, or slurry, deposited on, mixed in, surrounded by, or combined with other ingredients in any format, such as flakes, films, tabs, foams, or beads.

In one embodiment a smokeless tobacco industry product may include snus, snuff, chewing tobacco or the like.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In a further embodiment the tobacco industry product may be a tobacco heating device or hybrid device or e-cigarette or the like.

Typically in tobacco heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device.

Preferably the tobacco heating device may be a heat-not-burn device. Heat-not-burn devices are known in the art and release compounds by heating, but not burning, tobacco.

An example of a suitable, heat-not-burn device may be one taught in WO2013/034459 or GB2515502 which are incorporated herein by reference.

In one embodiment the aerosol-forming substrate of a tobacco heating device may be a tobacco industry product in accordance with the present invention.

In one embodiment the tobacco heating device may be a hybrid device.

Polynucleotides/Polypeptides/Constructs

In certain embodiments of the present invention, constructs which modulate activity or expression at least gene encoding a SOUL haem-binding protein may be transformed into plant cells, suitably under the direction of a promoter.

In certain embodiments of the present invention, constructs which decrease (i.e. inhibit) the activity or expression of at least one gene encoding a SOUL haem-binding protein may be transformed into plant cells under the direction of a promoter. For example, the genetic construct may be a gene editing construct or may comprise an RNAi molecule, which may comprise a small interfering RNA (siRNA) molecule, or a short hairpin loop (shRNA) molecule.

In certain embodiments of the present invention, constructs which increase activity or expression of gene encoding a SOUL haem-binding protein may be transformed into plant cells, suitably under the direction of a promoter e.g. constructs which encode a gene encoding a SOUL haem-binding protein such as an endogenous SOUL haem-binding protein.

Constructs may be introduced into plants according to the present invention by means of suitable vector, e.g. plant transformation vectors. A plant transformation vector may comprise an expression cassette comprising 5'-3' in the direction of transcription, a promoter sequence, a construct sequence targeting gene encoding a SOUL haem-binding protein and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application No. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest, e.g. the gene the promoter is going to direct, for instance a gene encoding a SOUL haem-binding protein according to the invention, a coding sequence used in the present invention or may be derived from a different gene, from *Nicotiana tabacum*, or another organism, for example from a plant of the family Solanaceae, or from the subfamily Cestroideae.

The expression cassette may be incorporated into a basic plant transformation vector, such as pBIN 19 Plus, pBI 101, pKYLX71:3552, pCAMBIA2300 or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "expression vector or plant transformation vector" means a construct capable of in vivo or in vitro expression. Preferably, the expression vector is incorporated in the genome of the organism. In one embodiment the vector of the present invention expresses a protein e.g. a SOUL haem-binding protein as described herein. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christon (AgroFood-Industry Hi-Tech March/April 1994 17-27), which are incorporated herein by reference.

Typically, in *Agrobacterium*-mediated transformation a binary vector carrying a foreign DNA of interest, i.e. a construct according to the present invention, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 December; 16(6):735-43, which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher et al. (1980) Tissue Culture Methods for Plant Pathologists, eds.: D. S. Ingrams and J. P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation and production of fertile transgenic maize plants by silicon carbide whisker-mediated transformation is taught in Frame et al. (1994) The Plant Journal 6(6): 941-948, which is incorporated herein by reference, and viral transformation techniques is taught in, for example, Meyer et al. (1992) Mol. Gen. Genet. 231(3): 345-352, which is incorporated herein by reference. The use of cassava mosaic virus as a vector system for plants is taught in Meyer et al. (1992) Gene 110: 213-217, which is incorporated herein by reference. Further teachings on plant transformation may be found in EP-A-0449375, incorporated herein by reference.

In a further aspect, the present invention relates to a vector system which carries a construct and introducing it into the genome of an organism, such as a plant, suitably a tobacco plant. The vector system may comprise one vector, but it may comprise two vectors. In the case of two vectors, the vector system is normally referred to as a binary vector system. Binary vector systems are described in further detail in Gynheung et al. (1980) Binary Vectors, Plant Molecular Biology Manual A3, 1-19, which is incorporated herein by reference.

One extensively employed system for transformation of plant cells uses the Ti plasmid from *Agrobacterium tumefaciens* or a Ri plasmid from *Agrobacterium rhizogenes* described by An et al. (1986) Plant Physiol. 81, 301-305 and Butcher et al. (1980) Tissue Culture Methods for Plant Pathologists eds.: D. S. Ingrams and J. P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema (1985) The Binary Plant Vector System, Offset-drukkerij Kanters B. B., Amsterdam Chapter V; Fraley et al. Crit. Rev. Plant Sci. 4:1-46; and An et al. (1985) EMBO J 4: 277-284, all incorporated herein by reference.

Plant cells transformed with construct(s) which modulate the activity or expression of at least one gene encoding a SOUL haem-binding protein may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a construct which modulates the activity or expression of at least one gene encoding a SOUL haem-binding protein according to the invention. Accordingly a transgenic plant is a plant which has been transformed with a construct according to the invention. Preferably the transgenic plant exhibits modulated alkaloid content and/or modulated TSNA content (or precursor thereof) according to the present invention. The term "transgenic plant" does not cover native nucleotide coding sequences in their natural environment when they are under the control of their native promoter which is also in its natural environment.

In one aspect, a gene encoding a SOUL haem-binding protein, a construct, a plant transformation vector or a plant cell according to the present invention is in an isolated form.

The term "isolated" means that the sequence is at least substantially free from at least one other component with which the sequence is naturally associated in nature and as found in nature.

In one aspect, a gene encoding a SOUL haem-binding protein, a construct, plant transformation vector or a plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention, i.e. the gene encoding a SOUL haem-binding protein, includes the native nucleotide sequence when in its natural environment and when it is linked to its naturally associated sequence(s) that is/are also in its/their natural environment. For ease of reference, we shall call this preferred embodiment the "native nucleotide sequence". In this regard, the term "native nucleotide sequence" means an entire nucleotide sequence that is in its native environment and when operatively linked to an entire promoter with which it is naturally associated, which promoter is also in its native environment.

The nucleotide sequence for use in the present invention may be present in a vector in which the nucleotide sequence is operably linked to regulatory sequences capable of providing for the expression of the nucleotide sequence by a suitable host organism. The constructs for use in the present invention may be transformed into a suitable host cell as described herein to provide for expression of a polypeptide of the present invention. The choice of vector e.g. a plasmid, cosmid, or phage vector will often depend on the host cell into which it is to be introduced.

Vectors may be used in vitro, for example for the production of RNA or used to transfect, transform, transduce or infect a host cell.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of gene encoding a SOUL haem-binding protein as described herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals. The term "promoter" is used in the normal sense of the art, e.g. an RNA polymerase binding site. The nucleotide sequence within a construct which encodes gene encoding a SOUL haem-binding protein may be operably linked to at least a promoter.

The term "construct"—which is synonymous with terms such as "cassette" or "vector"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The construct may even contain or express a marker, which allows for the selection of the genetic construct.

In some embodiments, a promoter may be operably linked to nucleotide sequence in a construct or vector which is used to modulate the concentration and/or total content of nicotine in a cell or cell culture or tobacco plant or part thereof.

In some embodiments the promoter may be selected from the group consisting of: a constitutive promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, Longstaff M (1986) (CaMV/35S), figwort mosaic virus 35S promoter. The sequence of carnation etched ring virus DNA:

comparison with cauliflower mosaic virus and retroviruses. EMBO Journal, 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

The promoter may be a tissue specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Tissue specific promoters include the phaseolin-promoter, legumin b4-promoter, usp-promoter, sbp-promoter, ST-LS1 promoter, B33 (patatin class I promoter).

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator (such as auxin and salicylic acid which activate the OCS promoter), or a toxic element, a physiological stress such as heat, light (such as the soybean SSU promoter), wounding (e.g. the nos, nopaline synthase promoter), or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. ((1993) Plant J. 3 191-201), temperature response as disclosed by Benfey & Chua (1989) (Benfey, P. N., and Chua, N-H. ((1989) Science 244 174-181), and chemically induced, as described by Gatz ((1995) Methods in Cell Biol. 50 411-424).

A nucleotide sequence encoding either a protein which has the specific properties as gene encoding a SOUL haem-binding protein as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

In a yet further alternative, the nucleotide sequence encoding the SOUL haem-binding protein may be prepared synthetically by established standard methods, e.g. the phosphoroamidite method described by Beucage et al. (1981) Tetrahedron Letters 22, 1859-1869 which is incorporated herein by reference, or the method described by Matthes et al. (1984) EMBO J. 3, 801-805 which is incorporated herein by reference. In the phosphoroamidite method, oligonucleotides are synthesised, e.g. in an automatic DNA synthesiser, purified, annealed, ligated and cloned in appropriate vectors.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The present invention also encompasses the use of sequences having a degree of sequence identity or sequence homology with amino acid sequence(s) of a polypeptide having the specific properties defined herein or of any nucleotide sequence i.e. a SOUL haem-binding protein gene encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the SOUL haem-binding protein gene. Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity. Homologous sequences typically retain functional domains or motifs. Suitably, homologues of SOUL haem-binding proteins may contain a haem-binding site.

In one embodiment, a homologous sequence is taken to include an amino acid sequence or nucleotide sequence which has one, two or several additions, deletions and/or substitutions compared with the subject sequence.

Sequence Identity

Sequence identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. (1999) Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should gap penalties be used when determining sequence identity, then preferably the following parameters are used for pairwise alignment:

| FOR BLAST | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 50 contiguous nucleotides, preferably over at least 60 contiguous nucleotides, preferably over at least 70 contiguous nucleotides, preferably over at least 80 contiguous nucleotides, preferably over at least 90 contiguous nucleotides, preferably over at least 100 contiguous nucleotides, preferably over at least 150 contiguous nucleotides, preferably over at least 200 contiguous nucleotides, preferably over at least 250 contiguous nucleotides, preferably over at least 300 contiguous nucleotides, preferably over at least 350 contiguous nucleotides, preferably over at least 400 contiguous nucleotides, preferably over at least 450 contiguous nucleotides, preferably over at least 500 contiguous nucleotides, preferably over at least 550 contiguous nucleotides, preferably over at least 600 contiguous nucleotides, preferably over at least 650 contiguous nucleotides, or preferably over at least 700 contiguous nucleotides.

Suitably, the degree of identity with regard to a nucleotide, cDNA, cds or amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone"*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues.

A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon et al. (1992) PNAS 89(20), 9367-9371 and Horwell (1995) Trends Biotechnol. 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein). Preferably, hybridisation is determined under stringency conditions (e.g. 50° C. and 0.2×SSC {1×SSC=0.15 M NaCl, 0.015 M Na$_3$citrate pH 7.0}). More preferably, hybridisation is determined under high stringency conditions (e.g. 65° C. and 0.1×SSC {1×SSC=0.15 M NaCl, 0.015 M Na$_3$citrate pH 7.0}).

A review of the general techniques used for transforming plants may be found in articles such as Potrykus et al. (1991) Annu Rev Plant Physiol. Plant Mol. Biol. 42:205-225 and Christou et al. (1994) Agro-Food-Industry Hi-Tech March/April 17-27, which are incorporated herein by reference. Further teachings on plant transformation may be found in EP-A-0449375, incorporated herein by reference.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

Advantages

It has been surprisingly found that by modulating the activity or expression of at least one gene encoding a SOUL haem-binding protein as taught herein which acts as a positive regulator of nicotine in tobacco, the alkaloid content (e.g. nicotine and/or nornicotine and/or PON and/or anatabine and/or anabasine and/or myosmine content or total alkaloid content) and/or TSNA content of plants can be modulated. Thereby tobacco products with modulated alkaloid (e.g. nicotine and/or nornicotine and/or PON and/or anatabine and/or anabasine and/or myosmine content or total alkaloid content) and/or TSNA content and commercially desirable traits sought after by consumers of tobacco products can be produced.

The present inventors have surprisingly determined a method for modulating the alkaloid content (e.g. nicotine and/or nornicotine and/or PON and/or anatabine and/or anabasine and/or myosmine content content or total alkaloid content), and/or TSNA content of a plant (e.g. tobacco plant) by modulating the activity or expression of a gene encoding a SOUL haem-binding protein. Alkaloid (e.g. nicotine and/or nornicotine and/or PON and/or anatabine and/or anabasine and/or myosmine content or total alkaloid content) or TSNA content of a plant (e.g. tobacco plant) may be decreased by decreasing or inhibiting the activity or expression of a gene encoding a SOUL haem-binding protein. Alkaloid (e.g. nornicotine or nicotine content) or TSNA content of a plant (e.g. tobacco plant) may be increased by increasing the activity or expression of gene encoding a SOUL haem-binding protein. Prior to the present invention it had not been known that modulation of the activity or expression of a gene encoding a SOUL haem-binding protein as described herein could be used to modulate alkaloid (e.g. nicotine and/or nornicotine and/or PON and/or anatabine and/or anabasine and/or myosmine content or total alkaloid content) and/or TSNA content of a plant (e.g. a tobacco plant).

The present inventors have determined that the inhibition of the activity or expression of a gene encoding a SOUL haem-binding protein can reduce the alkaloid content (e.g. nicotine and/or nornicotine and/or PON and/or anatabine and/or anabasine and/or myosmine content or total alkaloid content or total alkaloid content) of the modified plant to a surprisingly low level.

The publications discussed herein are provided solely for their disclosure prior to the filing date of the present application. Nothing herein is to be construed as an admission that such publications constitute prior art to the claims appended hereto.

EXAMPLES

Figure 2:
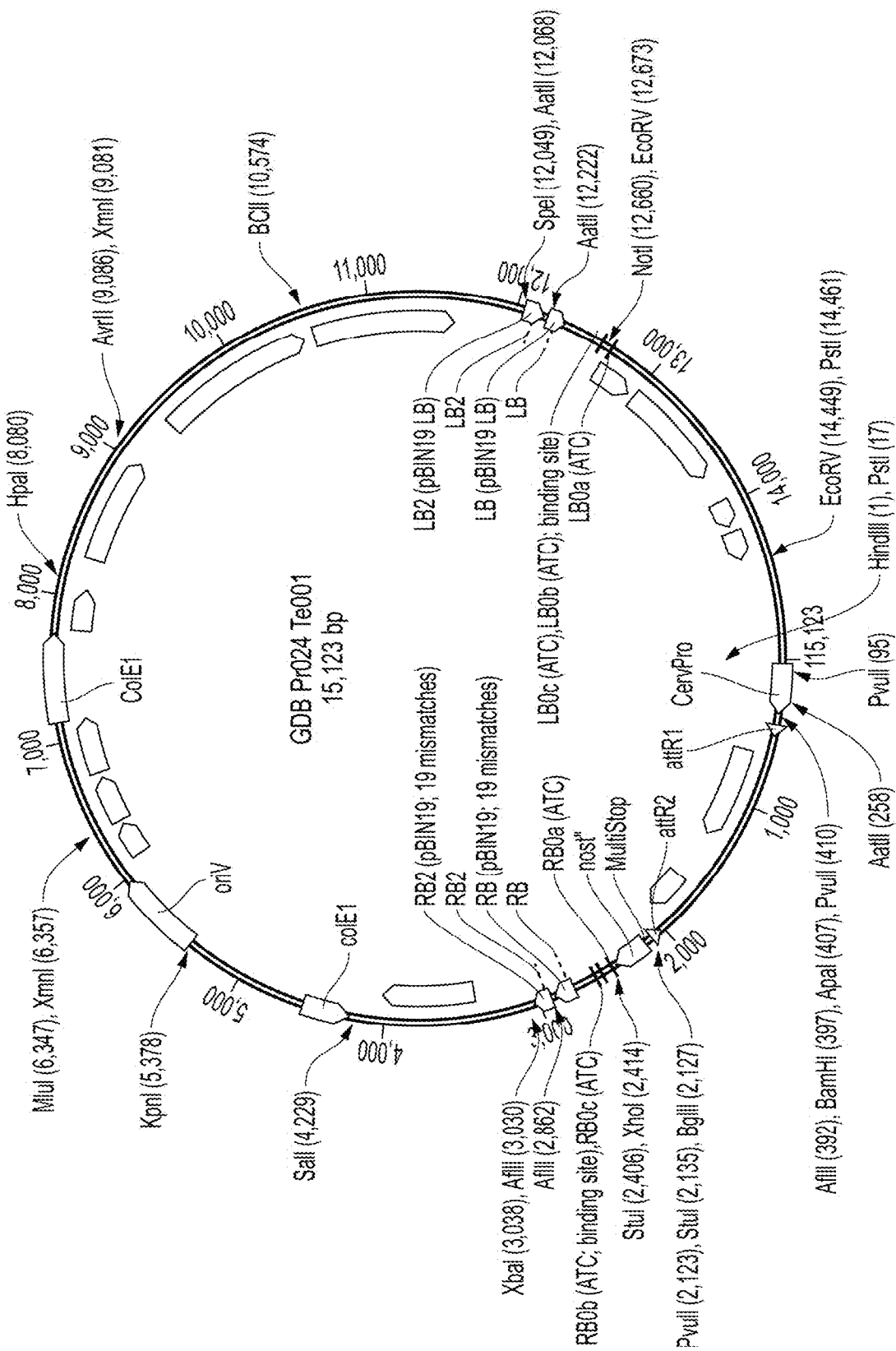
FIG. 2 shows the vector used to transiently overexpress a SOUL haem-binding protein in tobacco.

Example 1—Transient Overexpression of a SOUL Haem-Binding Protein Increases Alkaloid Content in Leaves Methods and Materials
Cloning
SOUL Haem-Binding Protein Expression Vector The SOUL haem-binding protein gene sequence (SEQ ID No. 3) was amplified from a Gateway™ compatible cDNA library using primers located outside restriction sites flanking the gene sequence. The gene sequence was then transferred to an expression vector, depicted in FIG. 2.

The resulting plasmid was sequenced and transformed into Agrobacterium tumefaciens GV3101pMP90 by heat shock and transiently expressed in TN90 leaves.

Transient Gene Expression

Agrobacterium tumefaciens GV3101 strains carrying the construct of interest were grown overnight in Luria-Bertani (LB) medium supplemented with appropriate antibiotics. Cultures were spun down and re-suspended in buffer containing 10 mM MgCl2, 10 mM MES pH 5.6 and 100 µM acetosyringone to OD600=0.6 and incubated for one hour at room temperature.

Infiltration was performed with a needleless syringe into TN90 leaves. Samples are taken 5 days post-infiltration.

Tests were performed in three biological replicates.

Alkaloid Measurement

Relative content of pyridine alkaloids was determined by reversed phase high performance liquid chromatography with tandem mass spectrometry (LC-MS/MS). Chromatographic separation was achieved using a Gemini-NX column (100 mm×3.0 mm, particle size 3 µm, Phenomenex) and gradient chromatographic separation using 6.5 mM ammonium acetate buffer (aq) (pH10) and Methanol.

Mass Spectrometer operates in electrospray (ESI) positive mode using scheduled MRM data acquisition. Two MRM transitions were monitored for each analyte and one for the isotope labelled internal standard.

| Analyte | Precursor Ion | Daughter Ion (quant/confirm) |
| --- | --- | --- |
| Nicotine | 163.1 | 130/106 |
| Nicotine d4 | 167.1 | 134.1 |
| Anabasine | 163.1 | 80/120 |
| Anatabine | 161.1 | 144/80 |
| Nornicotine | 149.1 | 80/130 |
| Nornicotine d4 | 153.1 | 84.1 |
| PON | 176.1 | 106.0/148 |
| PON d4 | 183.1 | 110.0 |

Statistical Analysis

Statistical significances based on one-way ANOVA analyses was performed with Prism 5.01 software (GraphPad Software).

Results

Figure 3:
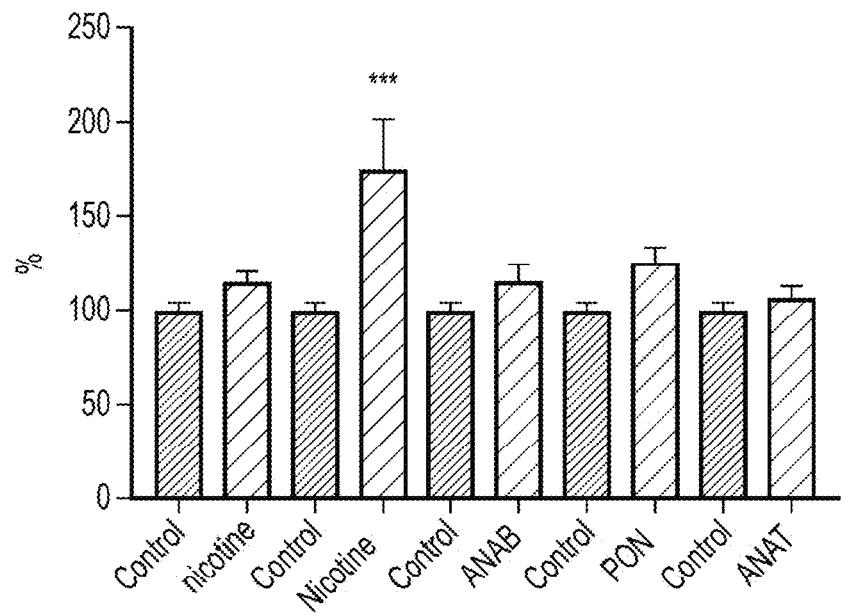
FIG. 3 shows the alkaloid (nicotine, nornicotine, anabasine, PON and anatabine) content of 5-week-old TN90 leaves expressing Nitab4.5_0013616g0010.2 (SEQ ID No. 3). Alkaloid content is represented relative to a control and comprises three biological replicates analysed by t-test. Values are shown as means±SEM. Asterisks indicate statistical significance of P value≤0.001.

Alkaloid content of 5-week-old TN90 leaves expressing the Nitab4.5_0013616g0010.2 construct is shown in FIG. 3. Nicotine, Nornicotine and PON content is represented relative to control and comprises three biological replicates analysed by one-way ANOVA and Tukey's multiple-comparison post-test. Values are shown as means±SEM. Asterisks indicate statistical significance of P value≤0.001.

Overexpression of Nitab4.5_0013616g0010.2 leads to a significant increase in nornicotine content in leaves.

Conclusions

Nitab4.5_0013616g0010.2 is a positive regulator of alkaloid content, in particular nornicotine and content in leaves and is a regulator of pyridine alkaloids in tobacco.

Example 2—Virus-Induced Gene Silencing (VIGS) of a SOUL Haem-Binding Protein Decreases Alkaloid Content in Leaves Virus-Induced Gene Silencing (VIGS)

For virus induced gene silencing, a 300-nucleotide cDNA fragment (SEQ ID No. 25) was synthesized and cloned with In-Fusion cloning kit into pTV00. The plasmid was then transformed into *A. tumefaciens* GV3101.

The TRV vector comprising both TRV RNA1 (SEQ ID No. 26) and TRV RNA2 (SEQ ID No. 27) comprising the targeted nucleotide sequence were separately propagated in *A. tumefaciens*. These cultures were mixed (1:1) and syringe-infiltrated into 2-week-old TN90 plants. The silencing effect was assessed five weeks post-virus infection by assessing the expression level of the target gene.

Silencing

VIGS assays were performed as previously described (Ratcliff et al. (2001) The Plant Journal 25: 237-245, incorporated herein by reference). Briefly, independent cultures of *A. tumefaciens* GV3101 carrying TRV2 and TRV1 plasmids were propagated overnight in LB medium supplemented with appropriate antibiotics. Cultures were resuspended in VIGS buffer (10 mM morpholineethanesulfonic acid pH 5.6, 10 mM $MgCL_2$, and 100 μM acetocyringone) adjusting optical density to $OD_{600}$=1, and incubated overnight at room temperature in the dark. These cultures were mixed (1:1) and syringe-infiltrated into 2-week-old TN90 plants. The silencing effect was assessed two weeks post-virus infection by assessing the expression level of the target gene. TRV-Luciferase was used as a negative control and TRV-PDS (reduced chlorophyll content of the silenced leaves) was used as a phenotypic silencing control.

Results

Figure 4:
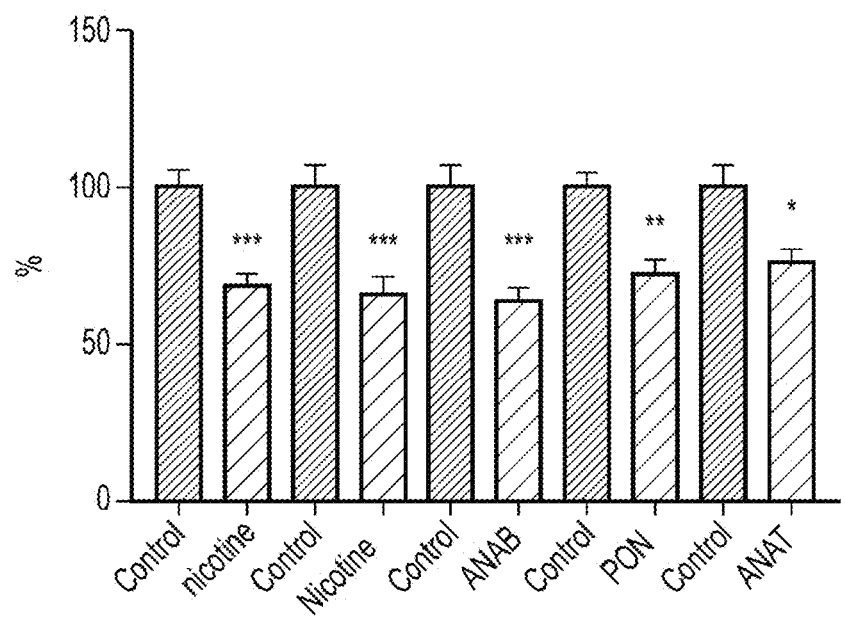
FIG. 4 shows the alkaloid (nicotine, nornicotine, anabasine, PON and anatabine) content of 5-week-old TN90 leaves expressing a construct which silences Nitab4.5_0013616g0010.2 (SEQ ID No. 3) by virus-induced gene silencing (VIGS). Alkaloid content is represented relative to control and comprises three biological replicates analysed by t-test. Values are shown as means±SEM. Asterisks indicate statistical significance of P value≤0.001

Nicotine, nornicotine, anabasine, PON and anatabine content of 5-week-old TN90 leaves expressing the indicated constructs which silence Nitab4.5_0013616g0010.2 are shown in FIG. 4. Content is represented relative to control and comprises three biological replicates analysed by t-test. Values are shown as means±SEM. Asterisks indicate statistical significance of P value≤0.001

Silencing Nitab4.5_0013616g0010.2 leads to a decrease in nicotine, nornicotine, anabasine, PON and anatabine content in leaves.

Conclusions

Nitab4.5_0013616g0010.2 is a positive regulator of alkaloid content, in particular nicotine, nornicotine, anabasine, PON and anatabine content in leaves and is a regulator of pyridine alkaloids in tobacco.

Example 3—Homologue Testing

The effects of the homologues of SEQ ID No. 1, namely SEQ ID Nos 4, 7, 10, 13, 16, 19 or 22 are tested in transient assays as described in Example 2.

Figure 33:
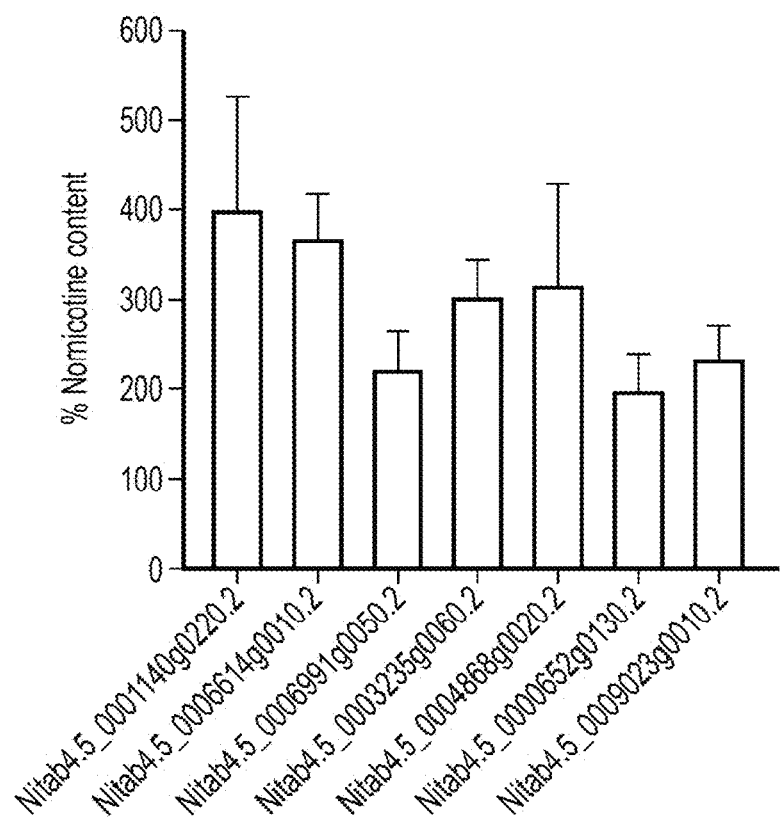
FIG. 33 shows the nornicotine content of 5-week-old TN90 leaves transiently expressing constructs which encode the indicated homologue sequences (see Example 3). Content is represented as percentage relative to control (100%) and comprises two biological replicates analysed by t-test. Values are shown as means±SEM.

The transient expression of SOUL haem-binding binding protein expression vectors for homologues SEQ ID Nos 4, 7, 10, 13, 16, 19 and 22 are shown in FIG. 33.

Transient overexpression of all tested homologues led to a significant increase in nornicotine content.

Example 4—Nitab4.5_0013616q0010.2 Antisense Leads to a Significant Reduction in Nornicotine Content Nitab4.5_0013616g0010.2_AS expression vector A Nitab4.5_0013616g0010.2_AS (antisense) construct was generated by two-step amplification and Gateway™ cloning, using the Nitab4.5_0013616g0010.2 expression vector as template, a first set of gene-specific primers and a second set of Gateway™ compatible primers. The amplification product was inserted into the Gateway™ pDONR™/Zeo vector (ThermoFisher Scientific). The sequence was then transferred to the expression vector.

The resulting plasmid was sequenced and transformed into *Agrobacterium tumefaciens* GV3101pMP90 by heat shock and transiently expressed in TN90 leaves.

Results

Figure 32:
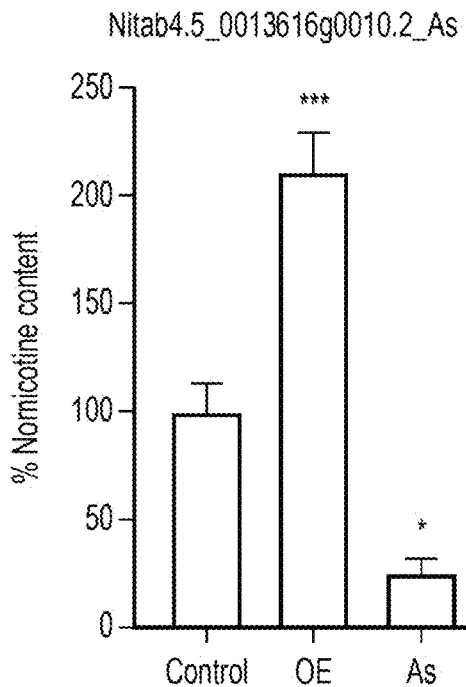
FIG. 32 shows the nornicotine content of 5-week-old TN90 leaves transiently expressing the indicated constructs: OE=expressing Nitab4.5_0013616g0010.2; or As=an antisense construct which silences Nitab4.5_0013616g0010.2. Content is represented relative to control and comprises three biological replicates analysed by one-way ANOVA and Tukey's multiple-comparison post-test. Values are shown as means±SEM. Asterisks indicate statistical significance of P value≤0.001.

Nornicotine content of 5-week-old TN90 leaves expressing the indicated constructs which silence Nitab4.5_0013616g0010.2 is shown in FIG. 32. Content is represented relative to control and comprises three biological replicates analysed by one-way ANOVA and Tukey's multiple-comparison post-test. Values are shown as means±SEM. Asterisks indicate statistical significance of P value ≤0.001.

Conclusion

Nitab4.5_0013616g0010.2 is a positive regulator of nornicotine content in leaves.

Example 5—Stable T1 Line Overexpressing Nitab4.5_0013616q0010.2 Greenhouse

We also validated the function of Nitab4.5_0013616g0010.2 with stable transformation assays.

Twenty-four TN90 T1 plants overexpressing Nitab4.5_0013616g0010.2 were grown in the greenhouse. At the 12 leaf stage the nornicotine content was measured as described above.

Results

Figure 34:
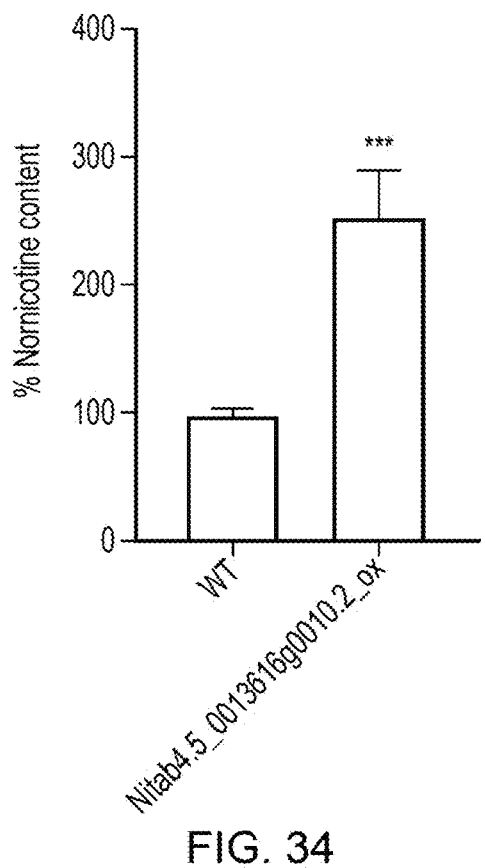
FIG. 34 shows the nornicotine content of greenhouse-grown TN90 plants at 12 leaf stage overexpressing Nitab4.5_0013616g0010.2 or control plants. (n=24).

Nornitcotine content of greenhouse-grown TN90 plants at 12 leaf stage overexpressing Nitab4.5_001316g0010.2 is shown in FIG. 34.

Example 6—Field-Grown T1 Plants Overexpressing Nitab4.5_0013616q0010.2

Twenty-four TN90 T1 plants overexpressing Nitab4.5_0013616g0010.2 were grown in the greenhouse. At the 12 leaf stage the nornicotine content was measured as described above.

Results

Figure 35:
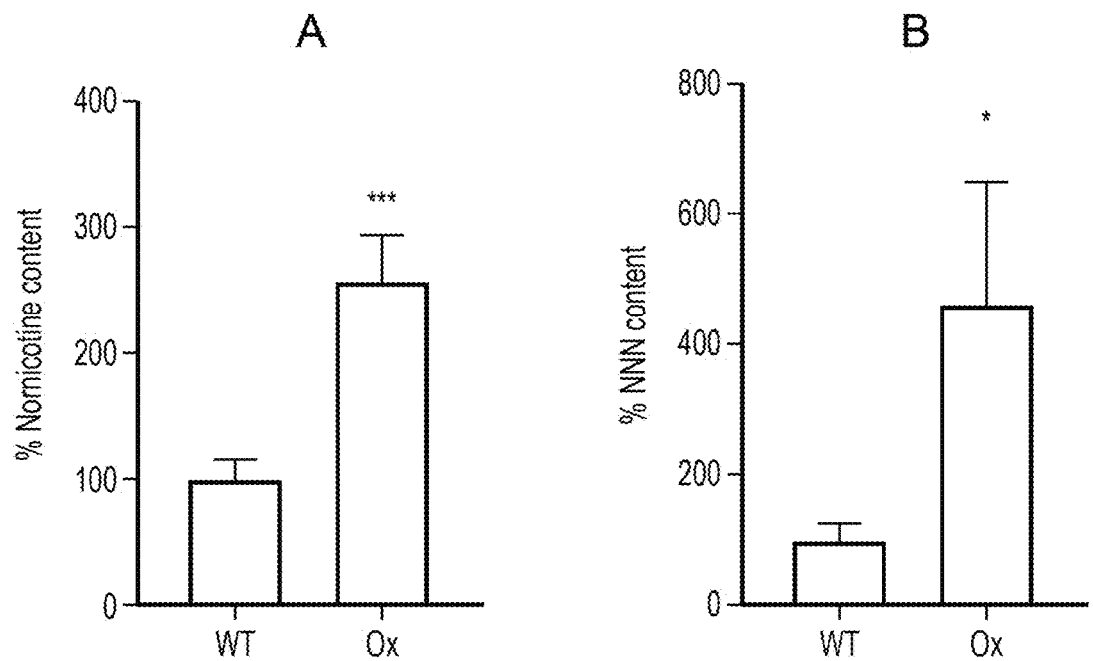
FIG. 35 shows in panel (A) the nornicotine content of field-grown control (wild type WT) TN90 leaves and Nitab4.5_0013616g0010.2 overexpressors (OX). Content is represented relative to control. Results were analysed by t-test. Values are shown as means±SEM. Asterisks indicate statistical significance of P value≤0.001. In panel (B) the NNN content of field-grown control (WT) TN90 leaves and Nitab4.5_0013616g0010.2 overexpressors. Content is represented relative to control. Results were analysed by t-test. Values are shown as means±SEM. Asterisks indicate statistical significance of P value≤0.01.

Nornicotine content of leaves of field-grown TN90 overexpressing Nitab4.5_0013616g0010.2 is shown in FIG. 35A. Content is represented relative to control. Results were analysed by t-test. Values are shown as means±SEM. Asterisks indicate statistical significance of P value≤0.001.

NNN content of leaves of field-grown TN90 leaves overexpressing Nitab4.5_0013616g0010.2 is shown in FIG. 35B. Content is represented relative to control. Results were analysed by t-test. Values are shown as means±SEM. Asterisks indicate statistical significance of P value≤0.01.

Conclusion

Overexpression of Nitab4.5_0013616g0010.2 in T1 plants increases nornicotine content and NNN content.

Nitab4.5_0013616g0010.2 is a positive regulator of nornicotine content in leaves.

The invention claimed is:

1. A method of decreasing the alkaloid content of a *Nicotiana* plant or a part thereof, or a *Nicotiana* cell or cell culture, the method comprising modifying said plant or cell or cell culture by decreasing the activity or expression of a gene encoding a SOUL haem-binding protein wherein the gene encoding a SOUL haem-binding protein encodes a polypeptide which comprises an amino acid sequence as set out in SEQ ID NO: 1, 4, 7, 10, 13, 16, 19 or 22,
wherein the content of one or more alkaloids selected from nicotine, nornicotine, pseudoxynicotine (PON), anabasine and anatabine is decreased in comparison to a plant or cell or cell culture which has not been modified to modulate the activity or expression of the gene encoding a SOUL haem-binding protein, and
wherein the activity or expression of the gene encoding a SOUL haem-binding protein is decreased in comparison to a plant or cell or cell culture which has not been modified to modulate the activity or expression of gene encoding a SOUL haem-binding protein.

2. A *Nicotiana* plant or part thereof or *Nicotiana* plant propagation material obtained therefrom or a *Nicotiana* cell or cell culture which has been modified to achieve a decrease in the content of one or more alkaloids selected from nicotine, nornicotine, pseudoxynicotine (PON), anabasine, and anatabine in comparison to an unmodified *Nicotiana* plant or unmodified *Nicotiana* cell or *Nicotiana* cell culture, wherein the modification is the reduction of the activity or expression of a gene encoding a SOUL haem-binding protein wherein the gene encoding a SOUL haem-binding protein encodes a polypeptide which comprises an amino acid sequence as set out in SEQ ID NO: 1, 4, 7, 10, 13, 16, 19 or 22.

3. The *Nicotiana* plant or part thereof or plant propagation material obtained therefrom or a *Nicotiana* cell or cell culture according to claim 2, wherein the total alkaloid content of the *Nicotiana* plant or cell or cell culture is decreased.

4. The *Nicotiana* plant or part thereof or *Nicotiana* plant propagation material obtained therefrom or a *Nicotiana* cell or cell culture according to claim 2, wherein the content of nicotine, nornicotine and/or PON is decreased.

5. The *Nicotiana* plant or part thereof or *Nicotiana* plant propagation material or a *Nicotiana* cell or cell culture according to claim 2, wherein the nicotine content is decreased.

6. The *Nicotiana* plant or part thereof or *Nicotiana* plant propagation material obtained therefrom or a *Nicotiana* cell or cell culture according to claim 2, wherein the gene encoding a SOUL haem-binding protein comprises a nucleotide sequence as set out in SEQ ID NO: 2, 3, 5, 6, 8, 9, 11, 12, 14, 15, 17, 18, 20, 21, 23 or 24.

7. A harvested *Nicotiana* leaf or a cut harvested *Nicotiana* leaf of the *Nicotiana* plant according to claim 2.

8. A processed *Nicotiana* leaf or a cut processed *Nicotiana* leaf obtained by processing the *Nicotiana* plant or a part thereof according to claim 2 or a *Nicotiana* plant propagated from a *Nicotiana* propagation material according to claim 2, wherein said *Nicotiana* plant propagation material comprises the modification.

9. The processed *Nicotiana* leaf or the cut processed *Nicotiana* leaf according to claim 8, wherein the *Nicotiana* leaf is processed by curing, fermenting, pasteurising or a combination thereof.

10. Cured tobacco material, a tobacco blend comprising said cured tobacco material, or a tobacco industry product made from the *Nicotiana* plant or a part thereof according to claim 2.

11. The tobacco industry product according to claim 10, wherein the tobacco product is a combustible smoking article, a smokeless tobacco product, or a non-combustible aerosol provision system such as a tobacco heating device or an aerosol-generating device.

12. A mutant *Nicotiana* plant carrying a heritable mutation in a nucleotide sequence of a gene encoding a SOUL haem-binding protein wherein said gene is selected from SEQ ID NO: 2, 3, 5, 6, 8, 9, 11, 12, 14, 15, 17, 18, 20, 21, 23, or 24, wherein said heritable mutation decreases the activity or expression of the gene encoding a SOUL haem-binding protein relative to a comparable plant which does not carry said heritable mutation and wherein the mutant plant has decreased content of one or more alkaloids selected from nicotine, nornicotine, pseudoxynicotine (PON), anabasine, and anatabine relative to a comparable plant which does not carry said heritable mutation.

13. Progeny or seed of a mutant *Nicotiana* plant which carries the heritable mutation according to claim 12.

14. A harvested *Nicotiana* leaf, a processed *Nicotiana* leaf or cured tobacco material produced from the *Nicotiana* plant according to claim 12.

15. The processed *Nicotiana* leaf or cut processed *Nicotiana* leaf of claim 8, wherein said processed *Nicotiana* leaf or cut processed *Nicotiana* leaf is a non-viable processed tobacco leaf.

* * * * *